(12) United States Patent
Haginoya et al.

(10) Patent No.: US 10,442,797 B2
(45) Date of Patent: Oct. 15, 2019

(54) PYRIDONE DERIVATIVES HAVING TETRAHYDROPYRANYLMETHYL GROUPS

(71) Applicant: DAIICHI SANKYO COMPANY, LIMITED, Tokyo (JP)

(72) Inventors: Noriyasu Haginoya, Tokyo (JP); Takashi Suzuki, Tokyo (JP); Miho Hayakawa, Tokyo (JP); Masahiro Ota, Tokyo (JP); Tomoharu Tsukada, Tokyo (JP); Katsuhiro Kobayashi, Tokyo (JP); Yosuke Ando, Tokyo (JP); Takeshi Jimbo, Tokyo (JP); Koichi Nakamura, Tokyo (JP)

(73) Assignee: DAIICHI SANKYO COMPANY, LIMITED, Tokyo (JP)

(*) Notice: Subject to any disclaimer, the term of this patent is extended or adjusted under 35 U.S.C. 154(b) by 0 days.

(21) Appl. No.: 15/036,981

(22) PCT Filed: Jul. 6, 2015

(86) PCT No.: PCT/JP2015/069976
§ 371 (c)(1),
(2) Date: May 16, 2016

(87) PCT Pub. No.: WO2016/006706
PCT Pub. Date: Jan. 14, 2016

(65) Prior Publication Data
US 2017/0183329 A1 Jun. 29, 2017
US 2018/0148436 A2 May 31, 2018

(30) Foreign Application Priority Data

Jul. 7, 2014 (JP) .................. 2014-139628

(51) Int. Cl.

| | |
|---|---|
| *C07D 405/14* | (2006.01) |
| *C07D 409/14* | (2006.01) |
| *A61K 31/444* | (2006.01) |
| *A61K 31/496* | (2006.01) |
| *A61K 31/497* | (2006.01) |
| *A61K 31/501* | (2006.01) |

(Continued)

(52) U.S. Cl.
CPC .......... *C07D 409/14* (2013.01); *A61K 31/444* (2013.01); *A61K 31/496* (2013.01); *A61K 31/497* (2013.01); *A61K 31/501* (2013.01); *A61K 31/506* (2013.01); *A61K 31/5377* (2013.01); *C07B 59/002* (2013.01); *C07C 309/04* (2013.01); *C07C 309/35* (2013.01); *C07D 405/14* (2013.01); *C07B 2200/05* (2013.01); *C07B 2200/13* (2013.01)

(58) Field of Classification Search
CPC .................................. C07D 405/14
USPC ........................ 546/261; 514/333
See application file for complete search history.

(56) References Cited

U.S. PATENT DOCUMENTS

| 8,933,103 B2 | 1/2015 | Ohki et al. |
|---|---|---|
| 2007/0142402 A1 | 6/2007 | Ding et al. |

(Continued)

FOREIGN PATENT DOCUMENTS

| CN | 101796048 A | 8/2010 |
|---|---|---|
| CN | 101910158 A | 12/2010 |

(Continued)

OTHER PUBLICATIONS

Johnson et al., Relationships between drug activity in NCI preclinical in vitro and in vivo models and early clinical trials, British Journal of Cancer (2001) 64(10): 1424-1431.*

(Continued)

*Primary Examiner* — Patricia L Morris
(74) *Attorney, Agent, or Firm* — Dorsey & Whitney LLP

(57) ABSTRACT

The present disclosure provides novel compounds or salts thereof, or crystals of the compounds or the salts, which inhibit Axl and are useful in the treatment of a disease caused by hyperfunction of Axl, the treatment of a disease associated with hyperfunction of Axl, and/or the treatment of a disease involving hyperfunction of Axl.

The present disclosure provides pyridone derivatives having a tetrahydropyranylmethyl group represented by the following formula (I) having various substituents, or salts thereof, or crystals of the compounds or the salts, wherein $R_1$, $R_2$, $R_3$, $R_4$, $R_5$, W, X, Y, and Z are each as defined in the specification:

Formula (I)

(I)

5 Claims, 11 Drawing Sheets

(51) Int. Cl.
A61K 31/506 (2006.01)
A61K 31/5377 (2006.01)
C07B 59/00 (2006.01)
C07C 309/04 (2006.01)
C07C 309/35 (2006.01)

(56) References Cited

U.S. PATENT DOCUMENTS

| | | | |
|---|---|---|---|
| 2009/0111816 | A1 | 4/2009 | Singh et al. |
| 2009/0274693 | A1 | 11/2009 | Gilmer et al. |
| 2010/0069369 | A1 | 3/2010 | Ding et al. |
| 2010/0168416 | A1 | 7/2010 | Goff et al. |
| 2010/0204221 | A1 | 8/2010 | Vankayalapati et al. |
| 2013/0281428 | A1 | 10/2013 | Ohki et al. |

FOREIGN PATENT DOCUMENTS

| | | | |
|---|---|---|---|
| CN | 102459179 | A | 5/2012 |
| JP | 2010-533159 | A | 10/2010 |
| JP | 2011-500778 | A | 1/2011 |
| JP | 2011-500801 | A | 1/2011 |
| WO | WO 2001/070726 | A1 | 9/2001 |
| WO | WO 2007/030680 | A2 | 3/2007 |
| WO | WO 2007/057399 | A2 | 5/2007 |
| WO | WO 2007/066187 | A2 | 6/2007 |
| WO | WO 2007/070872 | A1 | 6/2007 |
| WO | WO 2008/025820 | A1 | 3/2008 |
| WO | WO 2008/045978 | A1 | 4/2008 |
| WO | WO 2008/074997 | A1 | 6/2008 |
| WO | WO 2008/083353 | A1 | 7/2008 |
| WO | WO 2008/083354 | A1 | 7/2008 |
| WO | WO 2008/083356 | A1 | 7/2008 |
| WO | WO 2008/083357 | A1 | 7/2008 |
| WO | WO 2008/083367 | A2 | 7/2008 |
| WO | WO 2008/128072 | A2 | 10/2008 |
| WO | WO 2009/007390 | A2 | 1/2009 |
| WO | WO 2009/007749 | A2 | 1/2009 |
| WO | WO 2009/024825 | A1 | 2/2009 |
| WO | WO 2009/047514 | A1 | 4/2009 |
| WO | WO 2009/053737 | A2 | 4/2009 |
| WO | WO 2009/054864 | A1 | 4/2009 |
| WO | WO 2009/058801 | A1 | 5/2009 |
| WO | WO 2009/094417 | A1 | 7/2009 |
| WO | WO 2009/094427 | A1 | 7/2009 |
| WO | WO 2009/127417 | A1 | 10/2009 |
| WO | WO 2009/138799 | A1 | 11/2009 |
| WO | WO 2010/005876 | A2 | 1/2010 |
| WO | WO 2010/005879 | A1 | 1/2010 |
| WO | WO 2010/090764 | A1 | 8/2010 |
| WO | WO 2010/126914 | A1 | 11/2010 |
| WO | WO 2011/045084 | A1 | 4/2011 |
| WO | WO 2012/121939 | A2 | 9/2012 |
| WO | WO 2013/115280 | A1 | 8/2013 |
| WO | WO 2013/162061 | A1 | 10/2013 |

OTHER PUBLICATIONS

Simone, Oncology: Introduction, Cecil Textbook of Medicine, 20th Edition, vol. 1, pp. 1004-1010, 1996.*
Gura, Systems for identifying New Drugs Are Often Faulty, Cancer Models, Science, vol. 278, No. 5340, pp. 1041-1042, Nov. 1997.*
Golub et al, Science, vol. 286, Oct. 15, 1999, pp. 531-537.*
Arcangeli et a;l., "Novel persepectives, etc.," Drug Resistance Updates( 21-22) 11-19 (Year: 2015).*
Chambers et al., Dissemination and Growth of Cancer Cells in Metastatic Sites, Nature Reviews, vol. 2, pp. 663-672. (Year: 2002).*
Wells et al., "The dormancy, etc.," Cancer Res., 3811-3816. (Year: 2013).*
Angelillo-Scherrer, A., et al., "Deficiency or inhibition of Gas6 causes platelet dysfunction and protects mice against thrombosis," Nature Medicine, (2001), 7(2):215-221.

Berclaz, G., et al., "Estrogen dependent expression of the receptor tyrosine kinase axl in normal and malignant human breast," Annals of Oncology, (2001), 12:819-824.
Chung, B.I., et al., "Expression of the Proto-Oncogene Axl in Renal Cell Carcinoma," DNA and Cell Biology, (2003), 22(8):533-540.
Craven, R.J., et al., "Receptor Tyrosine Kinases Expressed in Metastatic Colon Cancer," Int. J. Cancer, (1995), 60:791-797.
Illig, C.R., et al., "Discovery of novel FMS kinase inhibitors as anti-inflammatory agents," Bioorganic & Medicinal Chemistry Letters, (2008), 18:1642-1648.
Ito, T., et al., "Expression of the Axl Receptor Tyrosine Kinase in Human Thyroid Carcinoma," Thyroid, (1999), 9(6):563-567.
Kim, K.S., et al., "Discovery of Pyrrolopyridine—Pyridone Based Inhibitors of Met Kinase: Synthesis, X-ray Crystallographic Analysis, and Biological Activities," J. Med. Chem., (2008), 51:5330-5341.
Ksantini, M, et al., "Homozygous mutation in MERTK causes severe autosomal recessive retinitis pigmentosa," Eur. J. Ophthalmol., (2012), 22(4):647-653.
Lai, D., et al., "9,10-Secosteroids, protein kinase inhibitors from the Chinese gorgonian Astrogorgia sp.," Bioorganic & Medicinal Chemistry, (2011), 19:6873-6880.
Linger, R.M.A., et al., "Taking aim at Mer and Axl receptor tyrosine kinases as novel therapeutic targets in solid tumors," Expert Opinion Ther. Targets, (2010), 14(10):1073-1090.
Lu, Q., et al., "Tyro-3 family receptors are essential regulators of mammalian spermatogenesis," Nature, (1999), 398:723-728.
Lu, Q., et al., "Homeostatic Regulation of the Immune System by Receptor Tyrosine Kinases of the Tyro 3 Family," Science, (2001), 293:306-311.
Mackay, D., et al., "Novel mutations in MERTK associated with childhood onset rod-cone dystrophy," Molecular Vision, (2010), 16:369-377.
Mahadevan, D., et al., "A novel tyrosine kinase switch is a mechanism of imatinib resistance in gastrointestinal stromal tumors," Oncogene, (2007), 26:3909-3919.
Mollard, A., et al., "Design, Synthesis, and Biological Evaluation of a Series of Novel AXL Kinase Inhibitors," ACS Med. Chem. Lett., (2011), 2:907-912.
Nakano, T., et al., "Vascular Smooth Muscle Cell-derived, Gla-containing Growth-potentiating Factor for $Ca^{2+}$-mobilizing Growth Factors," The Journal of Biological Chemistry, (1995), 270(11):5702-5705.
Nemoto, T., et al., "Overexpression of Protein Tyrosine Kinases in Human Esophageal Cancer," Pathobiology, (1997), 65:195-203.
O'Bryan, J.P., et al., "axl, a Transforming Gene Isolated from Primary Human Myeloid Leukemia Cells, Encodes a Novel Receptor Tyrosine Kinase," Molecular and Cellular Biology, (1991), 11(10):5016-5031.
Quong, R.Y.Y., et al., "Protein kinases in normal and transformed melanocytes," Melanoma Research, (1994), 4:313-319.
Sawabu, T., et al., "Growth Arrest-Specific Gene 6 and Axl Signaling Enhances Gastric Cancer Cell Survival via Akt Pathway," Molecular Carcinogenesis, (2007), 46:155-164.
Schroeder, G.M., et al., "Discovery of N-(4-(2-Amino-3-chloropyridin-4-yloxy)-3-fluorophenyl)-4-ethoxy-1-(4-fluorophenyl)-2-oxo-1,2-dihydropyridine-3-carboxamide (BMS-777607), a Selective and Orally Efficacious Inhibitor of the Met Kinase Superfamily," J. Med. Chem., (2009), 52:1251-1254.
Son, B., et al., "Gas6/Axl-PI3K/Akt pathway plays a central role in the effect of statins on inorganic phosphate-induced calcification of vascular smooth muscle cells," European Journal of Pharmacology, (2007), 556:1-8.
Sun, W.S., et al., "Coexpression of growth arrest-specific gene 6 and receptor tyrosine kinases Axl and Sky in human uterine endometrial cancers," Annals of Oncology, (2003), 14:898-906..
Sun, W., et al., "Coexpression of Gas6/Axl in Human Ovarian Cancers," Oncology, (2004), 66:450-457.
Yanagita, M., et al., "Essential role of Gas6 for glomerular injury in nephrotoxic nephritis," The Journal of Clinical Investigation, (2002), 110(2):239-246.

(56) References Cited

OTHER PUBLICATIONS

Zhang, Y., et al., "AXL Is a Potential Target for Therapeutic Intervention in Breast Cancer Progression," *Cancer Research*, (2008), 68(6):1905-1915.
English translation of International Search Report dated Oct. 6, 2015, in PCT Application No. PCT/JP2015/069976, 5 pages.
Supplementary European Search Report dated Dec. 21, 2017, in European Application No. 15818440.8, 7 pages.
Poster presented at the 22nd Japanese Foundation for Cancer Research—International Symposium on Cancer Chemotherapy (JFCR-ISCC), Dec. 12-13, 2017, Tokyo, Japan, 1 page.

\* cited by examiner

[Figure 1]
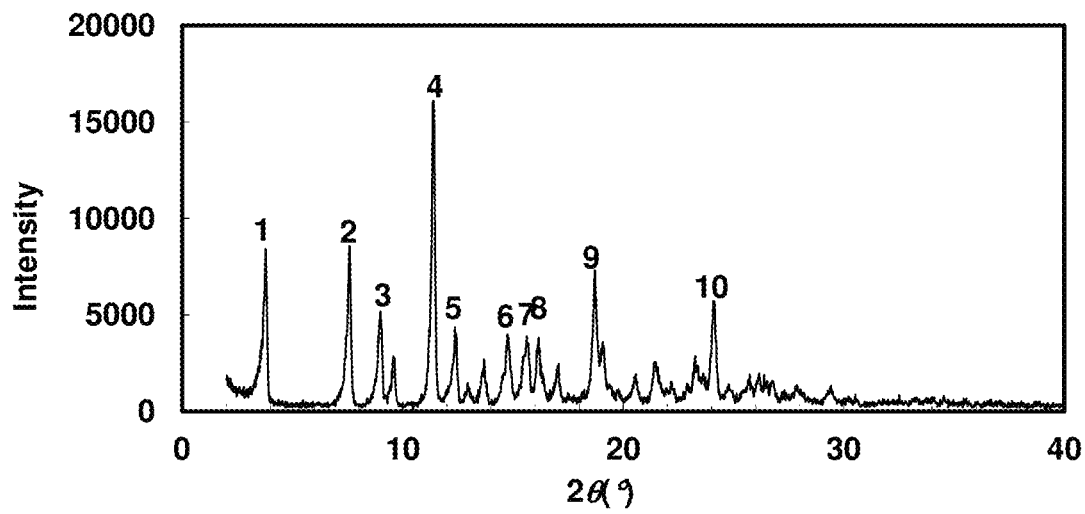
[Figure 2]
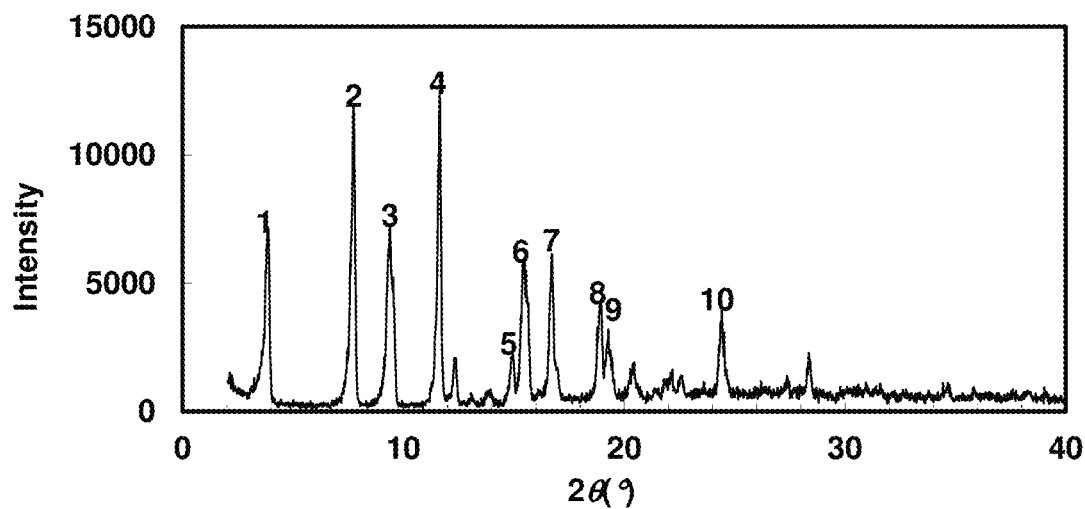

[Figure 3]
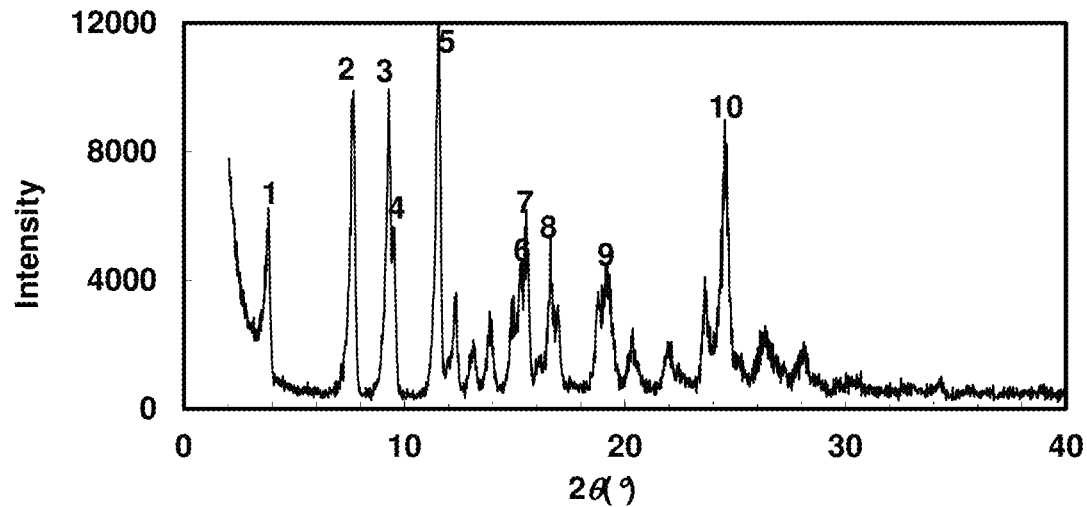
[Figure 4]
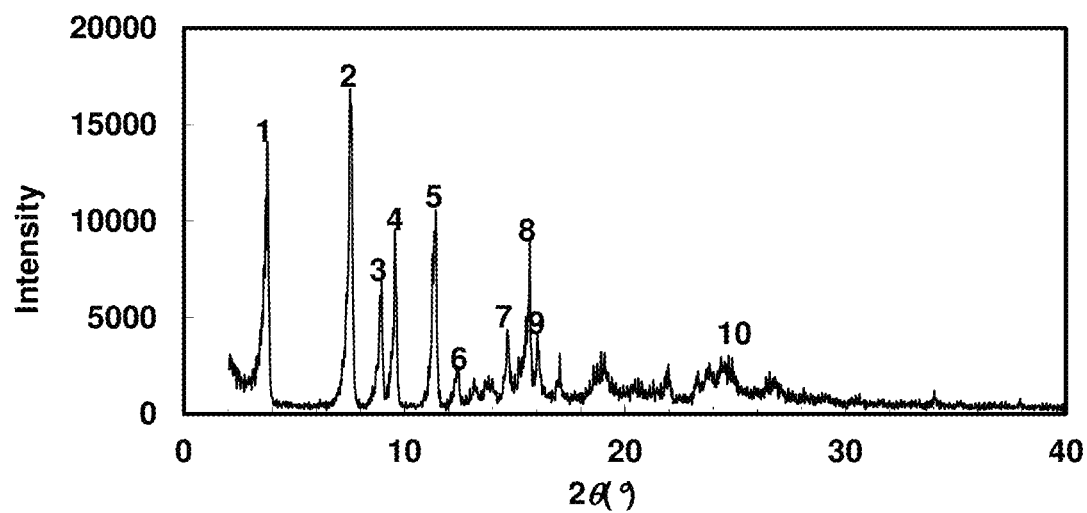

[Figure 5]
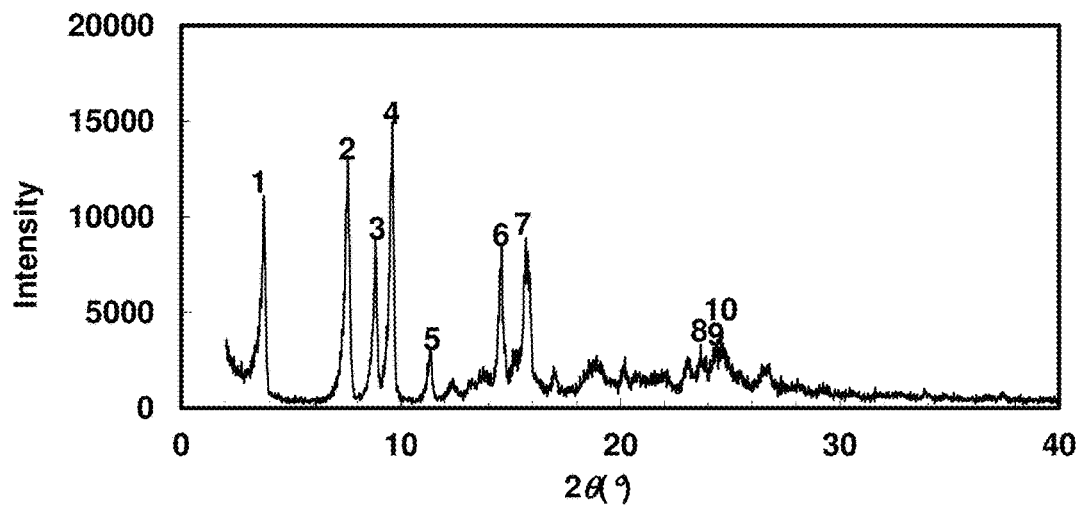
[Figure 6]
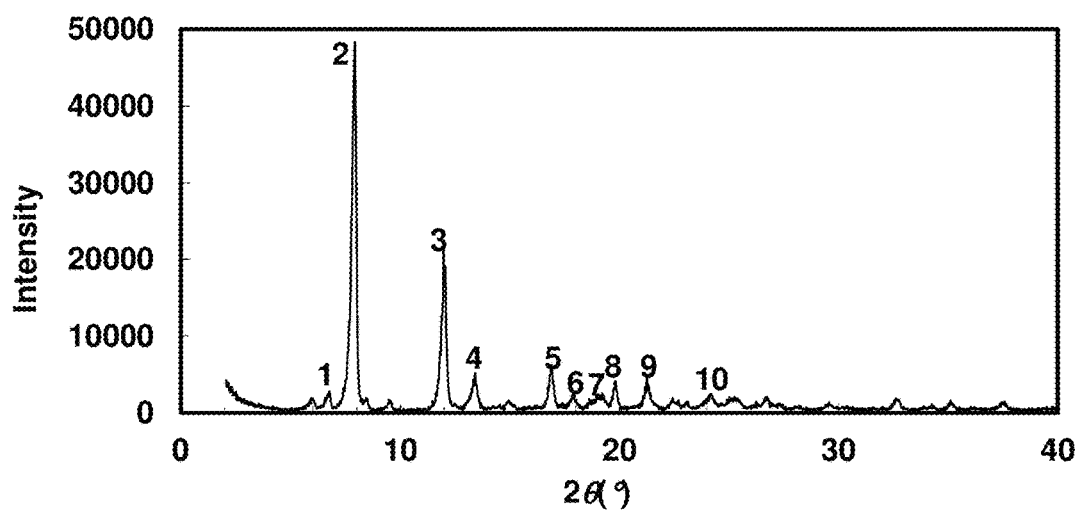

[Figure 7]
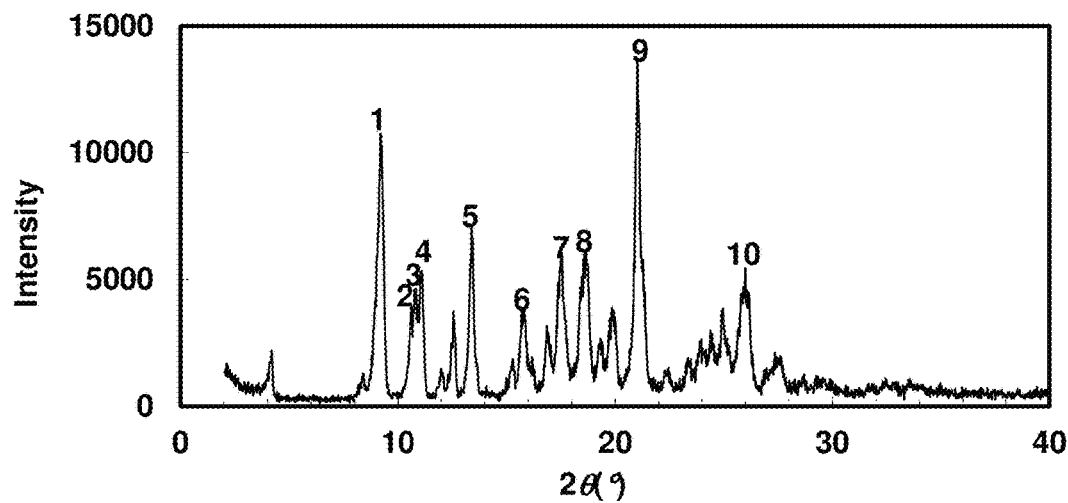
[Figure 8]
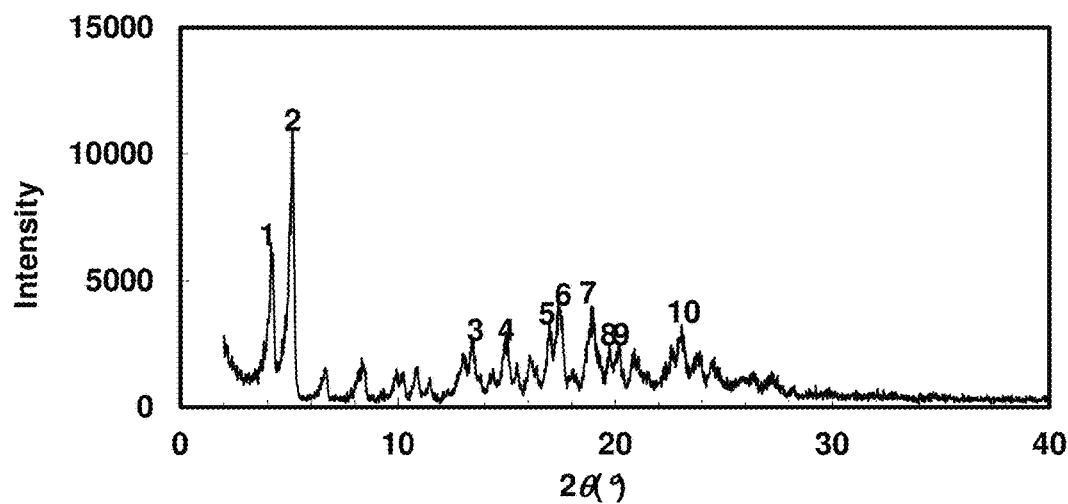

[Figure 9]
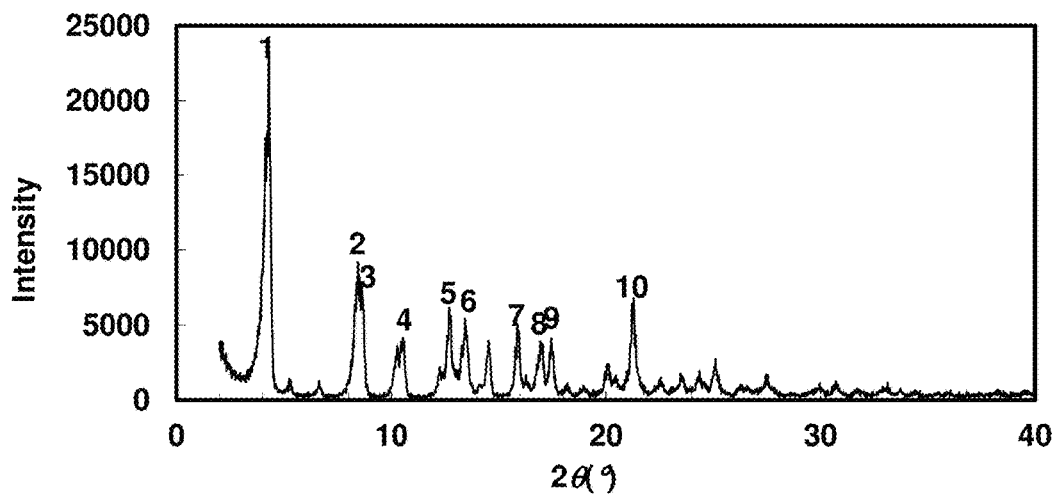
[Figure 10]
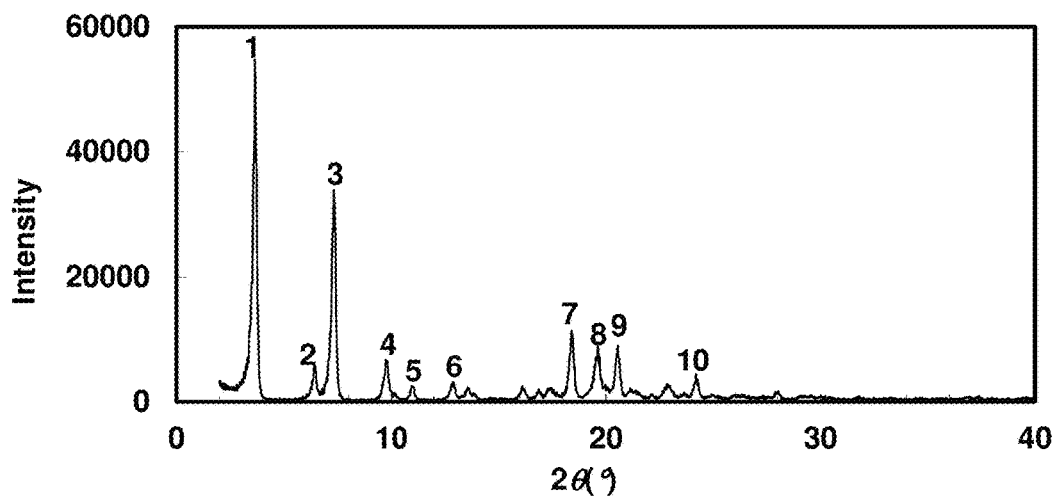

[Figure 11]
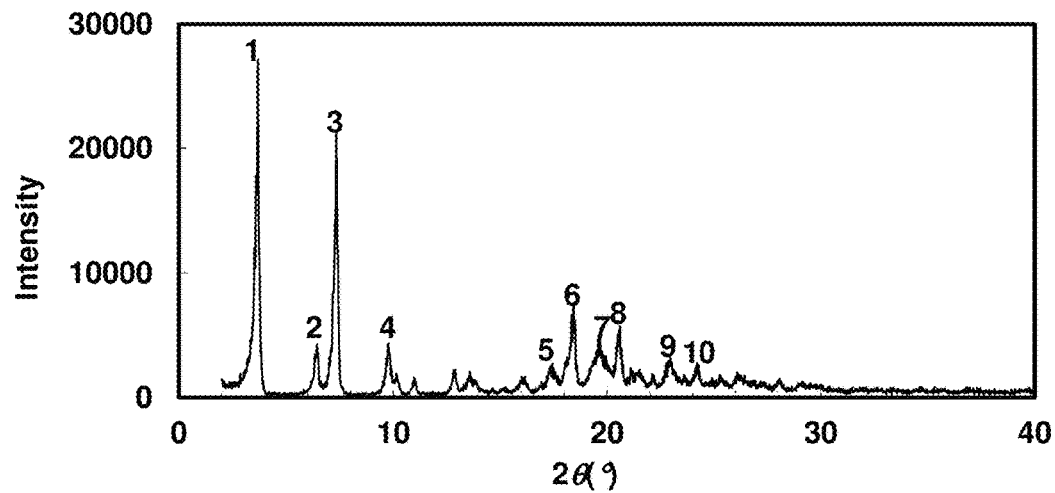
[Figure 12]
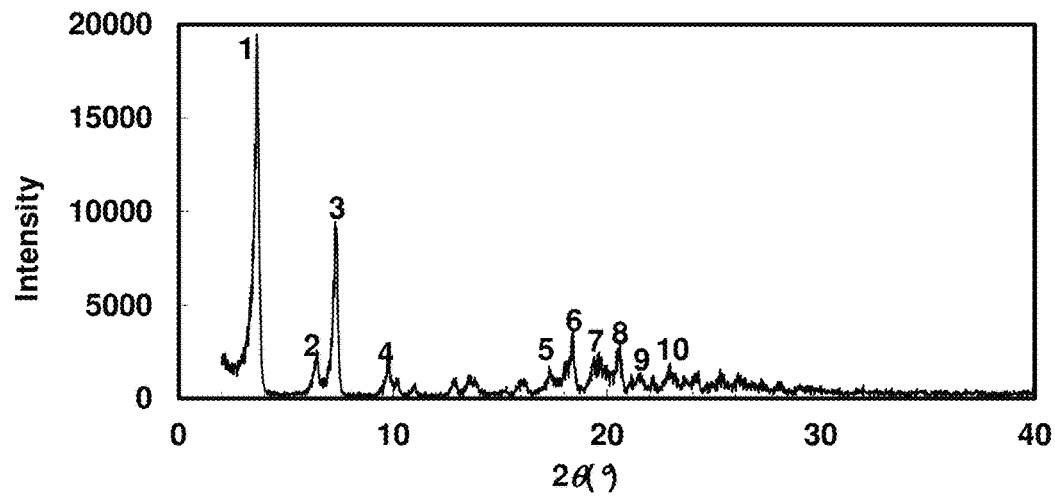

[Figure 13]
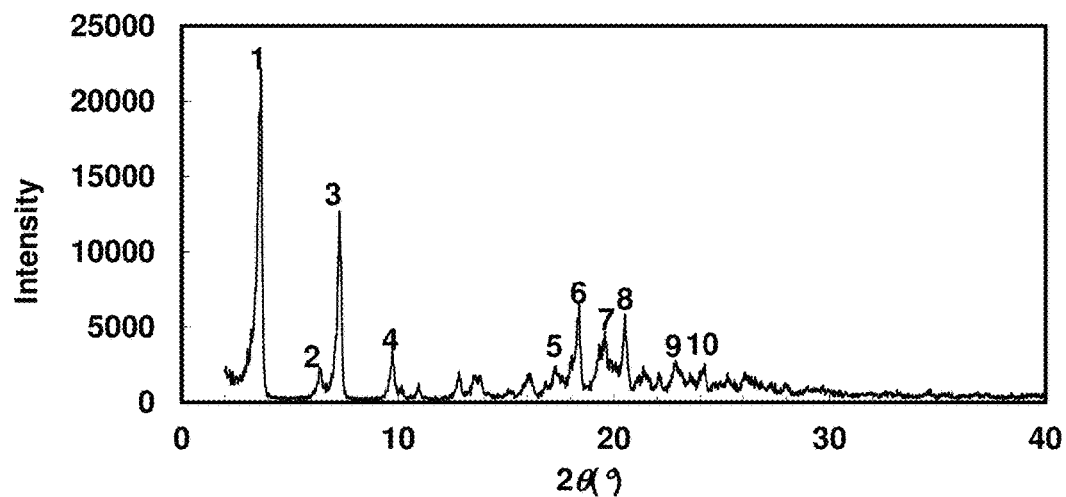
[Figure 14]
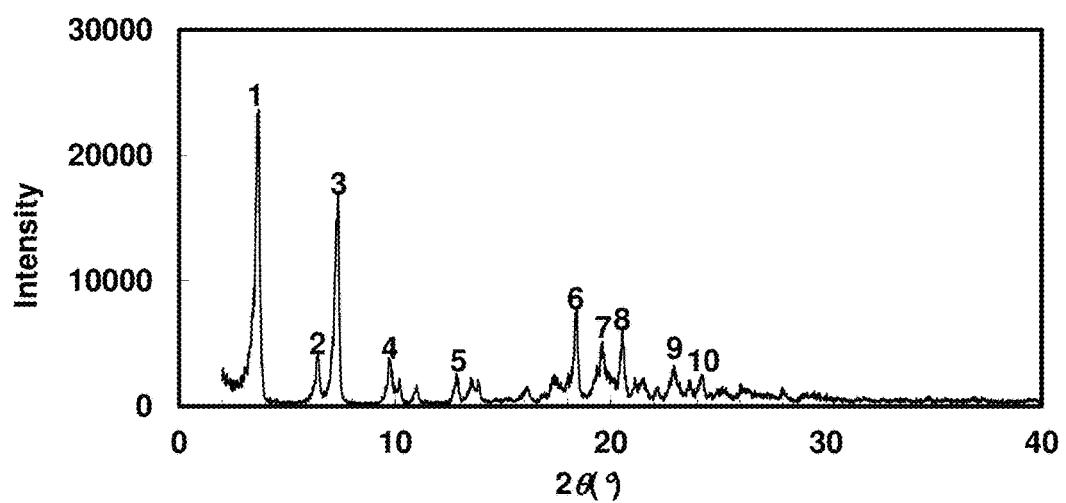

[Figure 15]
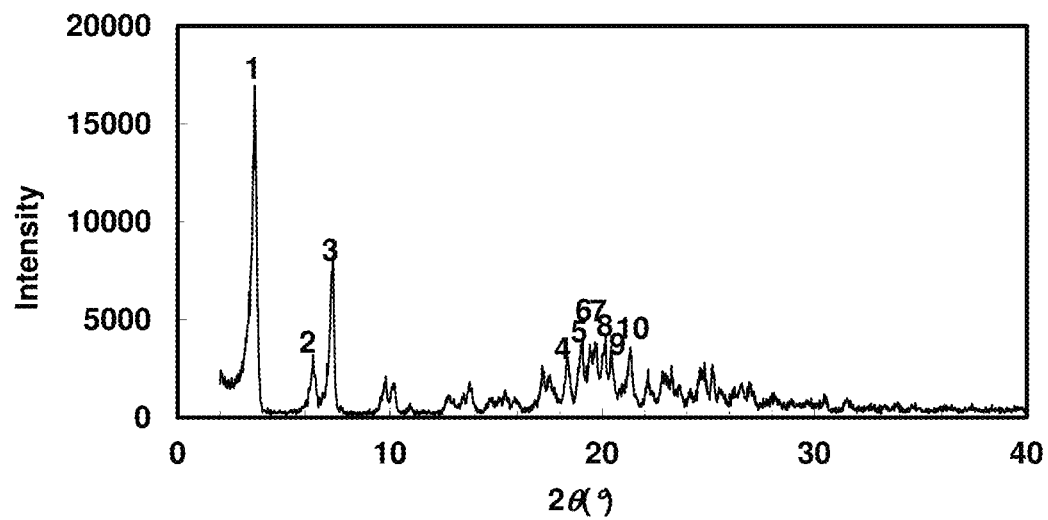
[Figure 16]
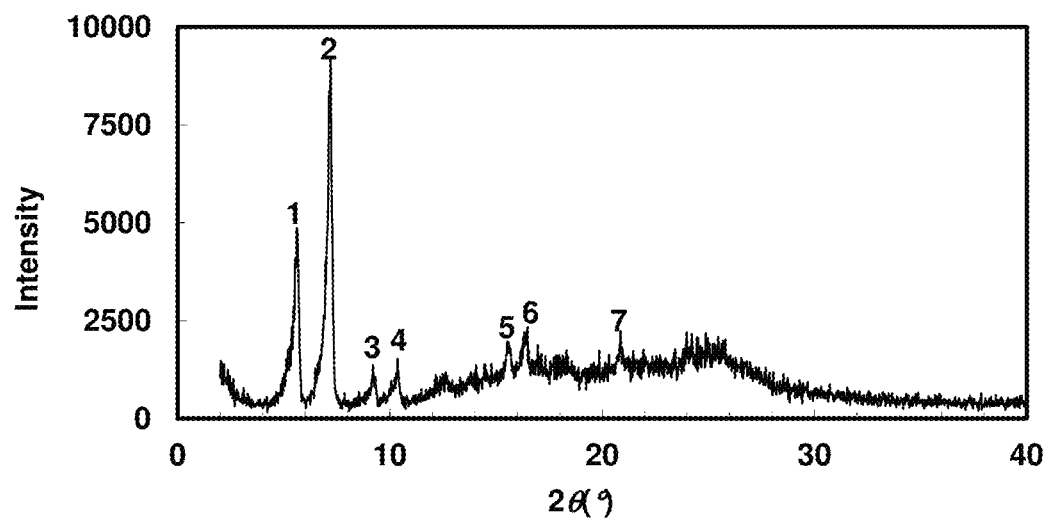

[Figure 17]
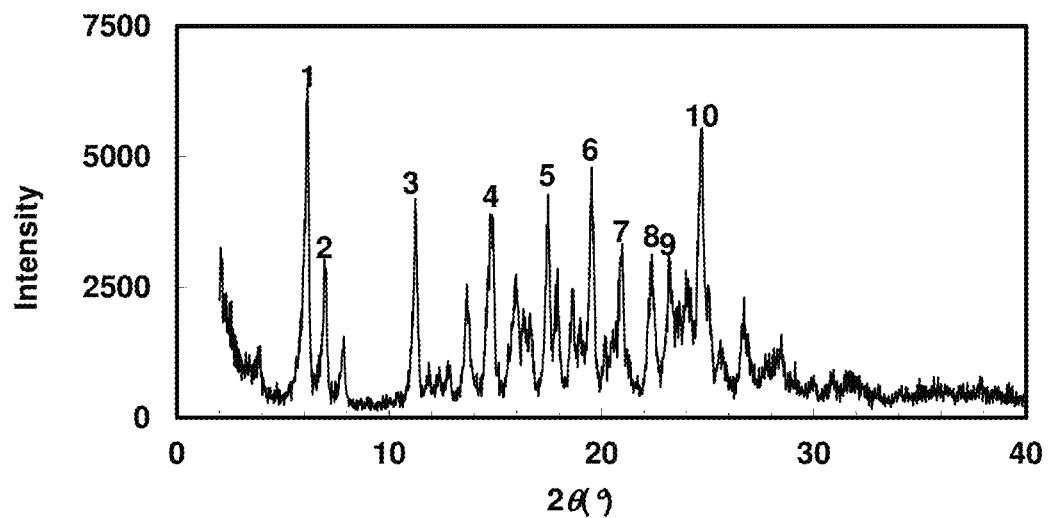
[Figure 18]
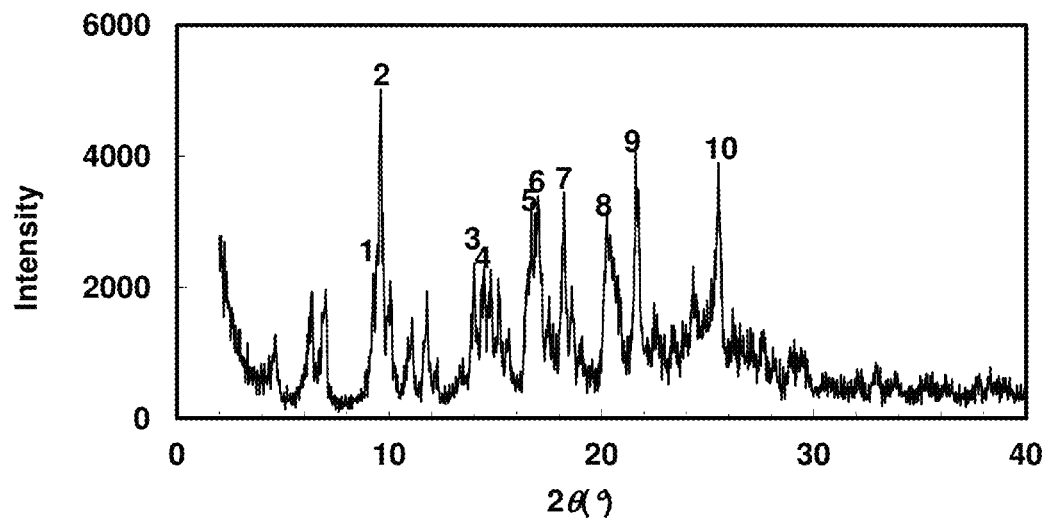

[Figure 19-1]
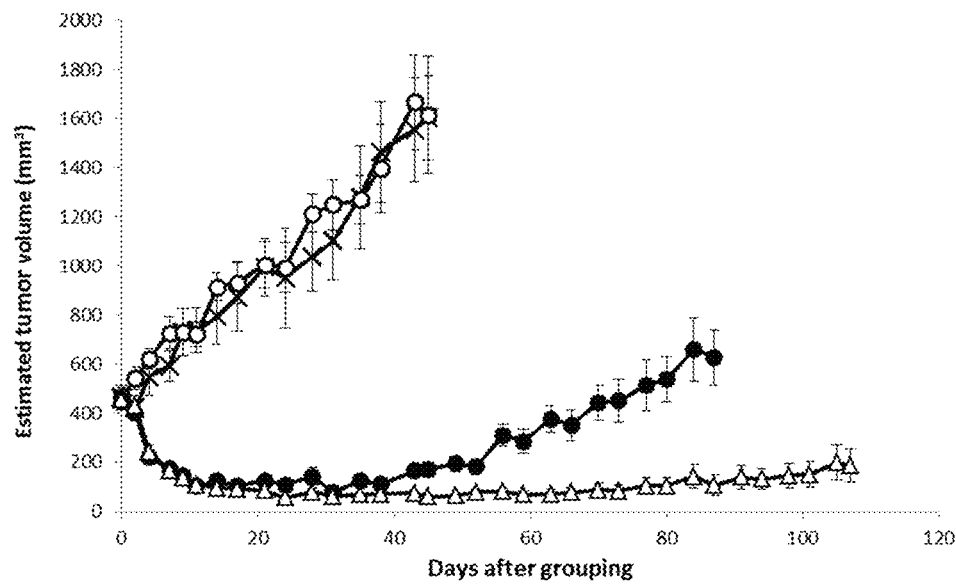
[Figure 19-2]
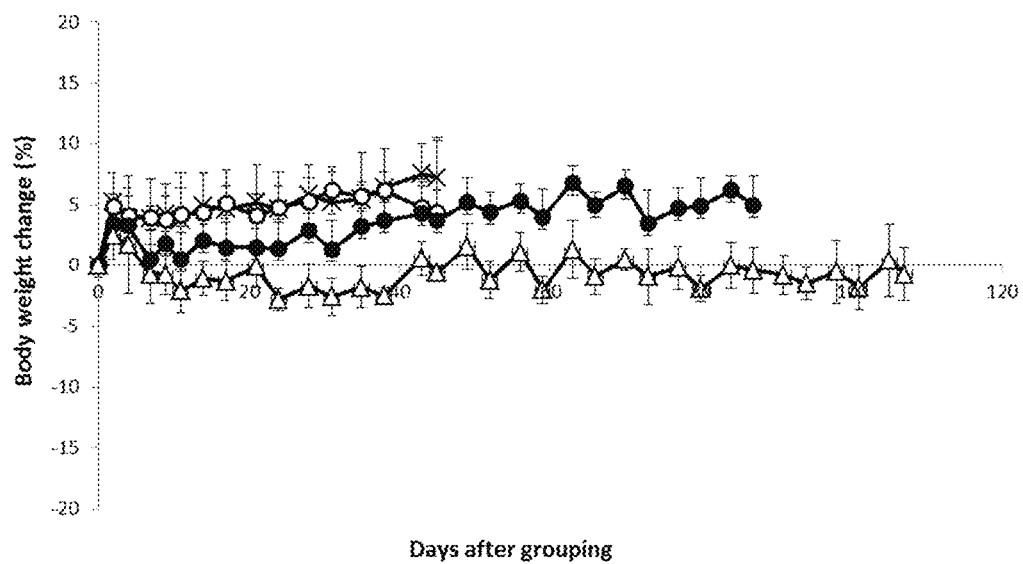

[Figure 20-1]
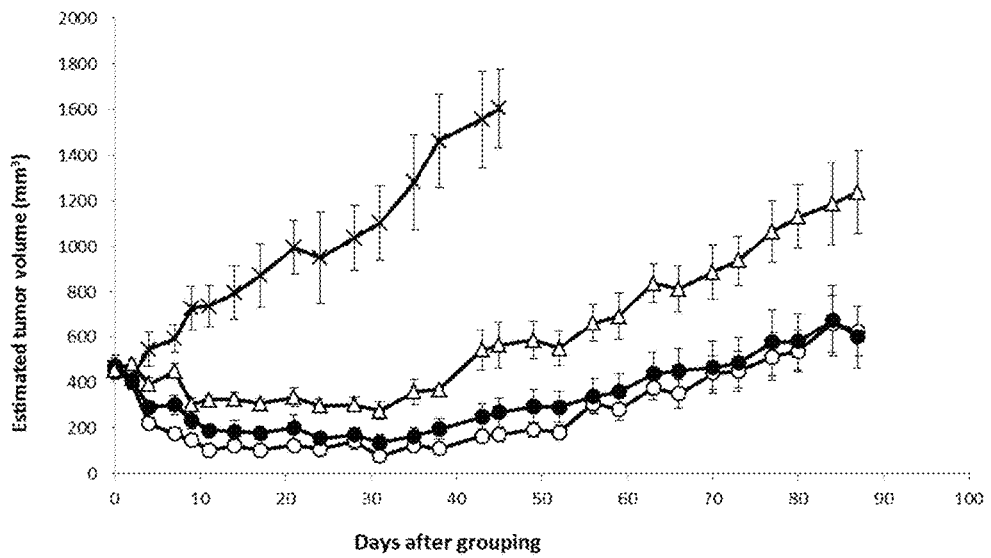
[Figure 20-2]
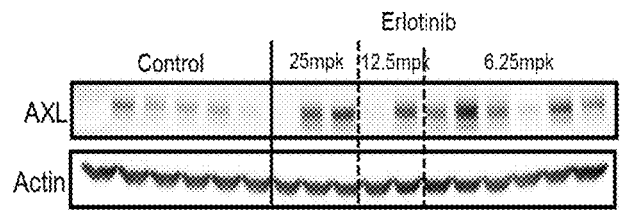
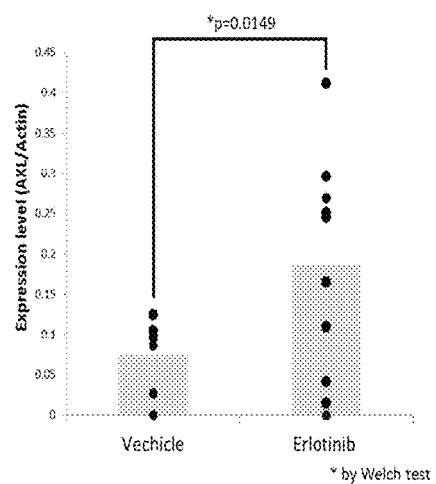

PYRIDONE DERIVATIVES HAVING TETRAHYDROPYRANYLMETHYL GROUPS

This application is a national stage application under 35 U.S.C. § 371 of International Application No. PCT/JP2015/069976, filed Jul. 6, 2015, entitled "PYRIDONE DERIVATIVE HAVING TETRAHYDROPYRANYL METHYL GROUP," which claims priority to Japanese Patent Application No. 2014-139628, filed Jul. 7, 2014.

TECHNICAL FIELD

The present invention relates to a compound or a salt thereof having Axl inhibitory activity.

BACKGROUND ART

Axl is a receptor tyrosine kinase belonging to the Tyro3-Axl-Mer (TAM) receptor tyrosine kinase family whose ligand is a protein encoded by growth arrest-specific gene 6 (Gas6). The gene of this kinase was originally identified as a transforming gene in chronic myelogenous leukemia (Non Patent Document 1).

The Gas6/Axl signalling system has been reported to regulate diverse cellular responses such as cell survival, cell division, autophagy, cell migration, angiogenesis, platelet aggregation, and NK cell differentiation (Non Patent Document 2) Also, many reports show the overexpression of Axl in tissues of cancers such as primary colon cancer (Non Patent Document 3), gastric cancer (Non Patent Document 4), esophagus cancer (Non Patent Document 5), melanoma (Non Patent Document 6), ovary cancer (Non Patent Document 7), kidney cancer (Non Patent Document 8), endometrial cancer (Non Patent Document 9), and thyroid gland cancer (Non Patent Document 10). The presence of Axl has been found to be closely related to the lymph node involvement and stage of lung cancer and ER expression in breast cancer (Non Patent Document 11).

Axl has been further found to play a role in immunity (Non Patent Document 12), platelet functions (Non Patent Document 13), spermatogenesis (Non Patent Document 14), vascular calcification (Non Patent Document 15), thrombin-induced vascular smooth muscle cell (VSMC) proliferation (Non Patent Document 16), and various kidney diseases, for example, acute and chronic glomerulonephritis, diabetic nephropathy, and chronic allograft rejection (Non Patent Document 17). Axl inhibitors are expected to provide therapeutic benefits to many diseases including cancers (including solid tumors such as carcinoma and sarcoma, leukemia, and lymphoid malignant diseases) as well as vascular diseases (including, but not limited to, thrombosis, atherosclerosis, and restenosis), kidney diseases (including, but not limited to, acute and chronic glomerulonephritis, diabetic nephropathy, and graft rejection), and diseases in which the disorganized formation of blood vessels has serious consequences (including, but not limited to, diabetic retinopathy, retinopathy, psoriasis, rheumatoid arthritis, atheroma, Kaposi's sarcoma, and angioma).

Meanwhile, Mer, another member of the TAM receptor tyrosine kinase family to which Axl belongs, has been reported to cause autosomal recessive retinitis pigmentosa through its homozygous mutation (Non Patent Document 24). A certain mutation in Mer has been further reported to be related to childhood-onset rod-cone dystrophy (Non Patent Document 25).

Compounds having a sulfonamide structure (Patent Document 3), compounds having a pyrrolopyrimidine structure (Patent Documents 4 and 5), compounds having pyridine and pyrazine structures (Patent Document 6), compounds having a pyrazine structure (Patent Document 7), compounds having a pyrazinylbenzimidazole structure (Patent Document 8), compounds having an indolinone structure (Patent Document 9), compounds having triazolopyridine and triazolopyrimidine structures (Patent Document 10), compounds having an imidazole structure (Patent Document 11), compounds having a triazole structure (Patent Documents 12, 13, 14, 15, 16, 17, 20, 24, 25, 26, 27, and 28), compounds having a pyrimidinediamine structure (Patent Document 18), compounds having a pyrimidine structure (Patent Document 19 and Non Patent Documents 18 and 22), compounds having a quinolinyloxyphenylsulfonamide structure (Patent Document 21), compounds having a quinoline structure (Patent Documents 22 and 30 and Non Patent Document 21), compounds having a pyridine structure (Patent Documents 23 and 33 and Non Patent Document 19), compounds having an urea structure (Patent Document 29), compounds having a 2,4-disubstituted arylamide structure (Non Patent Document 20), compounds having a secosteroid structure (Non Patent Document 23), compounds having a bicyclic pyrimidine structure (Patent Documents 31, 32, and 34), and the like have been reported as compounds inhibiting Axl.

CITATION LIST

Patent Documents

[Patent Document 1] International Publication No. WO2008/025820
[Patent Document 2] International Publication No. WO02008/074997
[Patent Document 3] International Publication No. WO2008/128072
[Patent Document 4] US Patent Application Publication No. 20100204221
[Patent Document 5] International Publication No. WO2010/090764
[Patent Document 6] International Publication No. WO2009/053737
[Patent Document 7] International Publication No. WO2009/007390
[Patent Document 8] International Publication No. WO2009/024825
[Patent Document 9] International Publication No. WO2007/057399
[Patent Document 10] International Publication No. WO2009/047514
[Patent Document 11] International Publication No. WO2009/058801
[Patent Document 12] International Publication No. WO2008/083367
[Patent Document 13] International Publication No. WO2008/083353
[Patent Document 14] International Publication No. WO2010/005879
[Patent Document 15] International Publication No. WO2008/083357
[Patent Document 16] International Publication No. WO2008/083356
[Patent Document 17] International Publication No. WO2008/083354
[Patent Document 18] International Publication No. WO2008/045978
[Patent Document 19] International Publication No. WO2007/070872
[Patent Document 20] International Publication No. WO2007/030680
[Patent Document 21] International Publication No. WO2011/045084
[Patent Document 22] International Publication No. WO2009/127417

[Patent Document 23] International Publication No. WO2007/066187
[Patent Document 24] International Publication No. WO2009/054864
[Patent Document 25] International Publication No. WO2010/005876
[Patent Document 26] International Publication No. WO2009/054864
[Patent Document 27] US Patent Application Publication No. 20090111816
[Patent Document 28] US Patent Application Publication No. 20100168416
[Patent Document 29] International Publication No. WO2009/138799
[Patent Document 30] US Patent Application Publication No. 20090274693
[Patent Document 31] US Patent Application Publication No. 20100069369
[Patent Document 32] US Patent Application Publication No. 20070142402
[Patent Document 33] International Publication No. WO2013/115280
[Patent Document 34] International Publication No. WO2013/162061

Non Patent Documents

[Non Patent Document 1] O'Bryan et al., Mol. Cell. Biol., 11, 5031 (1991)
[Non Patent Document 2] Rachel M A Linger et al., Expert Opin. Ther. Targets, 14, 1073 (2010)
[Non Patent Document 3] Craven et al., Int. J. Cancer., 60, 791 (1995)
[Non Patent Document 4] Sawabu et al., Mol. Carcinog., 46, 155 (2007)
[Non Patent Document 5] Nemoto et al., Pathobiology, 65, 195 (1997)
[Non Patent Document 6] Quong et al., Melanoma Res., 4, 313 (1994)
[Non Patent Document 7] Sun et al., Oncology, 66, 450 (2004)
[Non Patent Document 8] Chung et al., DNA Cell Biol., 22, 533 (2003)
[Non Patent Document 9] Sun et al., Ann. Oncol., 14, 898 (2003)
[Non Patent Document 10] Ito et al., Thyroid, 9, 563 (1999)
[Non Patent Document 11] Berclaz et al., Ann. Oncol., 12, 819 (2001)
[Non Patent Document 12] Lu et al., Science, 293, 306 (2001)
[Non Patent Document 13] Angelillo-Scherrer et al., Nat. Med., 7, 215 (2001)
[Non Patent Document 14] Lu et al., Nature, 398, 723 (1999)
[Non Patent Document 15] Son et al., Eur. J. Pharmacol., 556, 1 (2007)
[Non Patent Document 16] Nakano et al., J. Biol. Chem., 270, 5702 (1995)
[Non Patent Document 17] Yanagita et al., J. Clin. Invest., 110, 239 (2002)
[Non Patent Document 18] AlexisMollard et al., Med. Chem. Lett., 2, 907 (2011)
[Non Patent Document 19] Gretchen M. Schroeder et al., J. Med. Chem., 52, 1251 (2009)
[Non Patent Document 20] Carl R. Illig et al., Bioorg. Med. Chem. Lett., 18, 1642 (2008)
[Non Patent Document 21] Yi-Xiang Zhang et al., Cancer Res., 68, 1905 (2008)
[Non Patent Document 22] D Mahadevan et al., Oncogene, 26, 3909 (2007)
[Non Patent Document 23] Daowan Lai et al., Bioorg. Med. Chem., 19, 6873 (2011)
[Non Patent Document 24] Ksantini M., Eur J Ophthalmol., 22, 647 (2012)
[Non Patent Document 25] Mackay et al., Molecular Vision., 16, 369 (2010)

SUMMARY OF INVENTION

Technical Problem

An object of the present invention is to provide an Axl-inhibiting compound having high inhibitory specificity for Axl and higher safety. Another object of the present invention is to provide a therapeutic agent for a disease caused by hyperfunction of Axl, a therapeutic agent for a disease associated with hyperfunction of Axl, and/or a therapeutic agent for a disease involving hyperfunction of Axl, for example, an anticancer agent, comprising an Axl-inhibiting compound.

Solution to Problem

The compound of Example 9 of Patent Document 33 (hereinafter, referred to as Compound A) has high Axl inhibitory activity, but has been confirmed to cause irreversible retinal photoreceptor degeneration in a long-term administration test using mice. The inactivation of Mer, a member of the TAM family, as with Axl, is reportedly related to retinal cell degeneration, and the compound of Example 9 of Patent Document 33 also has inhibitory activity against Mer. In consideration of these facts, the present inventors have considered that the inhibition of Mer by this compound leads to retinal toxicity.

As a result of conducting diligent studies, the present inventors have found that a compound having a structure represented by the general formula (I) given below or a salt thereof has high Axl inhibitory specificity and low inhibitory activity against Mer, and further found that this compound or salt thereof induces no retinal toxicity in a long-term administration test using mice.

Specifically, the present invention relates to the following [1] to [53]:

[1] A compound represented by the general formula (I) or a pharmaceutically acceptable salt thereof:

[Formula 1]

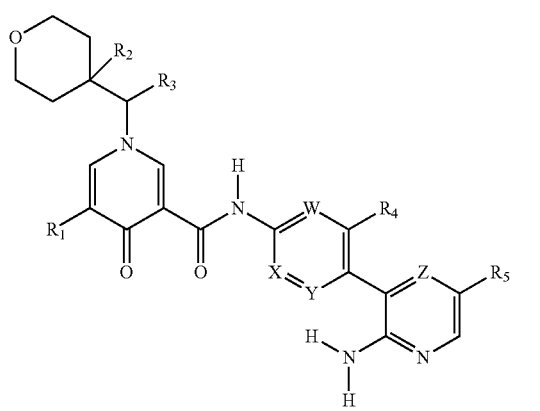

(I)

wherein
W, X, and Y each independently represent a nitrogen atom, C—H, C—F, or C—Cl, Z represents a nitrogen atom, C—H, C—F, C—Cl, C—$C_1$-$C_6$ alkyl, or C—$C_1$-$C_6$ alkoxy group, $R_1$ represents a group represented by the following formula (II-1) or (II-2):

[Formula 2]

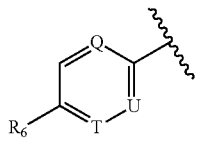
(II-1)

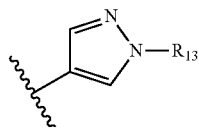
(III-2)

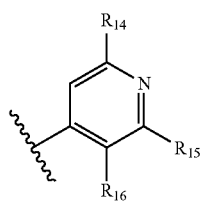
(III-3)

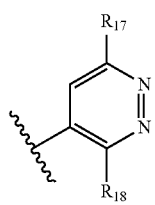
(III-4)

(II-2)

wherein in the formula (II-1),

Q represents a nitrogen atom, C—H, or C—F,

T represents a nitrogen atom or C—H,

U represents a nitrogen atom or C—H, and $R_6$ represents a halogen atom, a $C_1$-$C_6$ alkyl group, a $C_3$-$C_6$ cycloalkyl group, a cyano group, or a trifluoromethoxy group, and in the formula (II-2), V represents a sulfur atom or an oxygen atom, and $R_7$ represents a $C_1$-$C_6$ alkyl group, $R_2$ represents a hydrogen atom, a halogen atom, a $C_1$-$C_6$ alkyl group, a $C_1$-$C_6$ alkoxy group, or a cyano group, $R_3$ represents a hydrogen atom or a $C_1$-$C_6$ alkyl group, $R_4$ represents a hydrogen atom, a halogen atom, or a $C_1$-$C_6$ alkyl group, and $R_5$ represents a hydrogen atom or a group represented by the following formula (III-1), (III-2), (III-3), or (III-4):

[Formula 3]

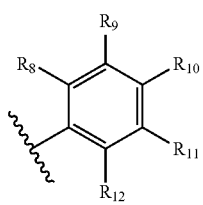
(III-1)

wherein in the formula (III-1), $R_8$ and $R_{12}$ each independently represent a hydrogen atom or a deuterium atom, $R_9$ represents a hydrogen atom, a halogen atom, or a $C_1$-$C_6$ alkoxy group, $R_{10}$ represents a hydrogen atom, a $C_1$-$C_6$ alkyl group optionally substituted by a heterocycloalkyl group, or a $C_1$-$C_6$ alkoxy group optionally substituted by a heterocycloalkyl group optionally substituted by a $C_1$-$C_6$ alkyl group, and $R_{11}$ represents a hydrogen atom, a $C_1$-$C_6$ alkoxy group, or a deuterium-substituted $C_1$-$C_6$ alkoxy group, in the formula (III-2), $R_{13}$ represents a $C_1$-$C_6$ alkyl group optionally substituted by a heterocycloalkyl group, or a heterocycloalkyl group, in the formula (III-3), $R_{14}$ represents a hydrogen atom or a $C_1$-$C_6$ alkyl group, $R_{15}$ represents a hydrogen atom, a $C_1$-$C_6$ alkyl group, or a $C_1$-$C_6$ alkoxy group, and $R_{16}$ represents a hydrogen atom or a halogen atom, and in the formula (III-4), $R_{17}$ represents a $C_1$-$C_6$ alkoxy group, and $R_{18}$ represents a $C_1$-$C_6$ alkoxy group.

[2] N-[4-(2-Amino-5-{4-[(2R)-1,4-dioxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide represented by the following formula:

[Formula 4]

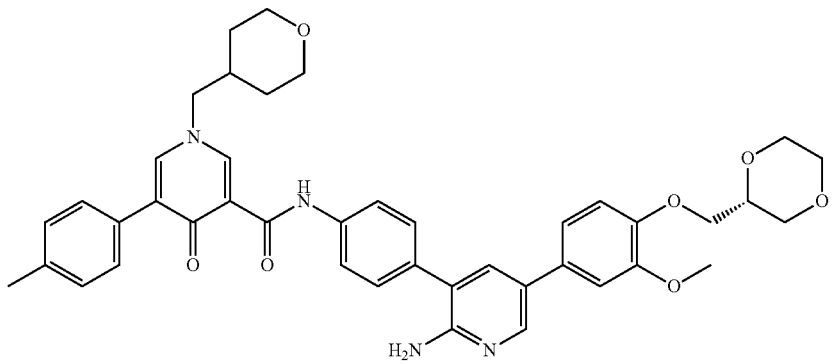

or a pharmaceutically acceptable salt thereof.

[3] N-[4-(2-Amino-5-{4-[(2S)-1,4-dioxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide represented by the following formula:

[Formula 5]

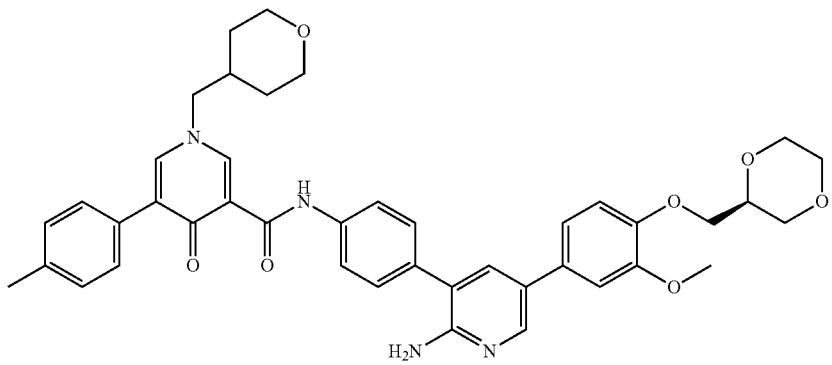

or a pharmaceutically acceptable salt thereof.

[4] N-{4-[2-Amino-5-(3,4-dimethoxyphenyl)pyridin-3-yl]phenyl}-5-(4-methylphenyl)-4-oxo-1-(tetrahydro-2H-pyran-4-ylmethyl)-1,4-dihydropyridine-3-carboxamide represented by the following formula:

[Formula 6]

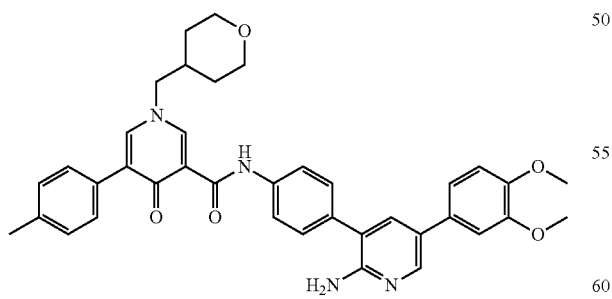

or a pharmaceutically acceptable salt thereof.

[5] N-[4-(2-Amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide represented by the following formula:

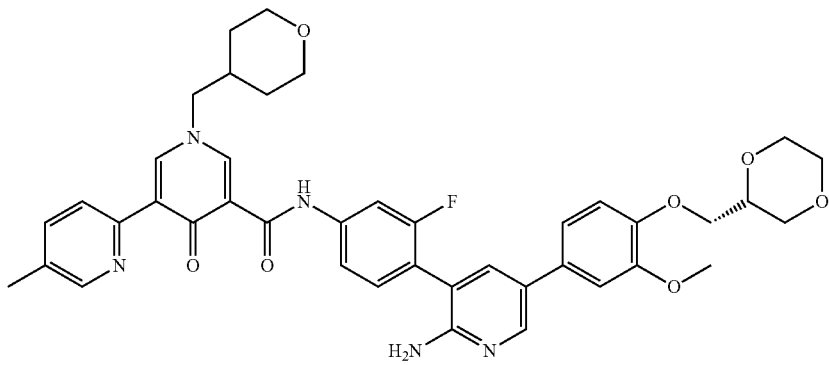

or a pharmaceutically acceptable salt thereof.

[6] N-[4-(2-Amino-5-{4-[(2S)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide represented by the following formula:

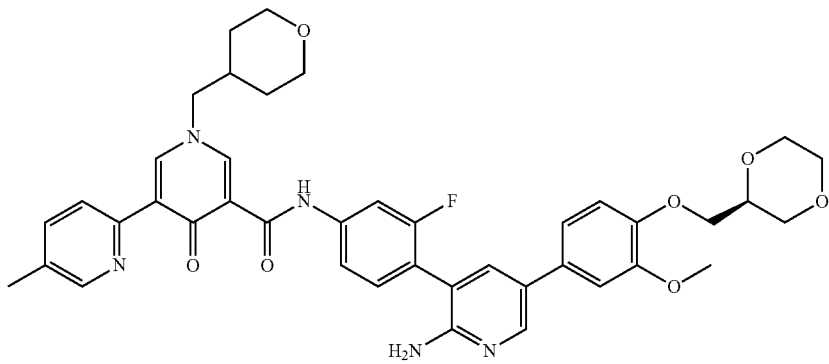

or a pharmaceutically acceptable salt thereof.

[7] N-{4-[2-Amino-5-(1-ethyl-1H-pyrazol-4-yl)pyridin-3-yl]-3-fluorophenyl}-5-(4-methylphenyl)-4-oxo-1-(tetrahydro-2H-pyran-4-ylmethyl)-1,4-dihydropyridine-3-carboxamide represented by the following formula:

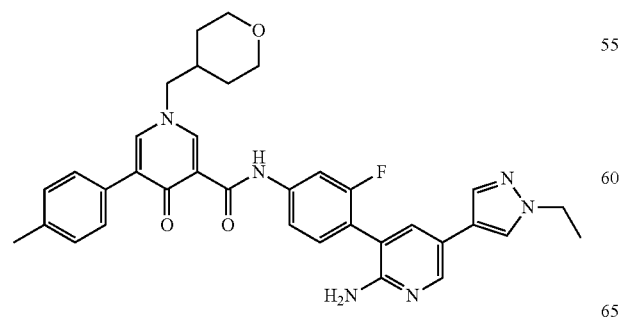

or a pharmaceutically acceptable salt thereof.

[8] N-(4-{2-Amino-5-[1-(tetrahydro-2H-pyran-4-yl)-1H-pyrazol-4-yl]pyridin-3-yl}-3-fluorophenyl)-5-(4-methylphenyl)-4-oxo-1-(tetrahydro-2H-pyran-4-ylmethyl)-1,4-dihydropyridine-3-carboxamide represented by the following formula:

[Formula 10]

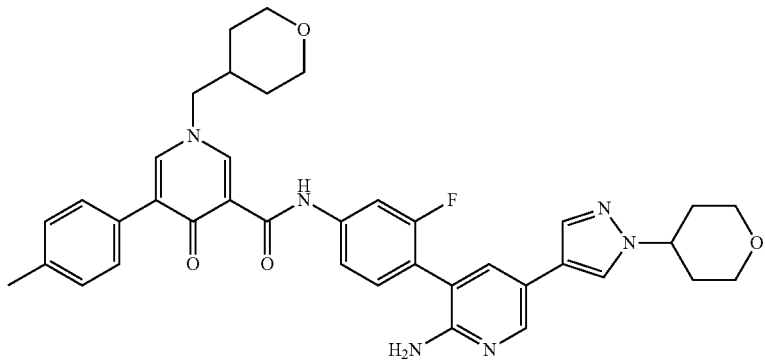

or a pharmaceutically acceptable salt thereof.

[9] N-[6-(2-Amino-5-{4-[(2R)-1,4-dioxan-2-ylmethoxy]-3-methoxyphenyl}pyridin-3-yl)pyridazin-3-yl]-5-(5-methylthiophen-2-yl)-4-oxo-1-(tetrahydro-2H-pyran-4-ylmethyl)-1,4-dihydropyridine-3-carboxamide represented by the following formula:

[Formula 11]

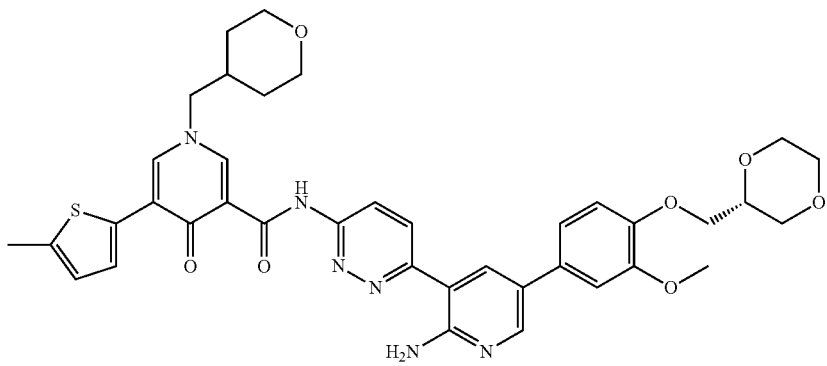

or a pharmaceutically acceptable salt thereof.

[10] N-[6-(2-Amino-5-{3-methoxy-4-[2-(morpholin-4-yl)ethoxy]phenyl}pyridin-3-yl)pyridazin-3-yl]-5-(4-methylphenyl)-4-oxo-1-(tetrahydro-2H-pyran-4-ylmethyl)-1,4-dihydropyridine-3-carboxamide represented by the following formula:

[Formula 12]

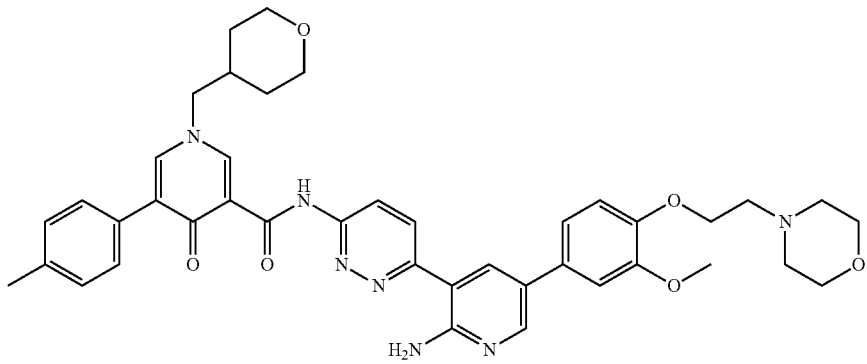

or a pharmaceutically acceptable salt thereof.

[11] A hydrobromide, nitrate, sulfate, phosphate, methanesulfonate, ethanesulfonate, benzenesulfonate, or p-toluenesulfonate of a compound according to [2].

[12] A methanesulfonate of a compound according to [4].

[13] A methanesulfonate, phosphate, naphthalene-1,5-disulfonate, or sulfate of a compound according to [5].

[14] A crystal of a methanesulfonate according to [11], wherein the crystal exhibits characteristic peaks at diffraction angles 2θ=3.74, 7.56, 8.96, 11.38, 12.36, 14.78, 15.60, 16.16, 18.70, and 24.10 in a powder X-ray diffraction pattern obtained by irradiation with copper Kα radiation (wavelength λ=1.54 angstroms).

[15] A crystal of a hydrobromide according to [11], wherein the crystal exhibits characteristic peaks at diffraction angles 2θ=3.84, 7.72, 9.40, 11.62, 14.92, 15.48, 16.70, 18.88, 19.32, and 24.40 in a powder X-ray diffraction pattern obtained by irradiation with copper Kα radiation (wavelength λ=1.54 angstroms).

[16] A crystal of a nitrate according to [11], wherein the crystal exhibits characteristic peaks at diffraction angles 2θ=3.82, 7.66, 9.28, 9.52, 11.54, 15.26, 15.54, 16.62, 19.24, and 24.56 in a powder X-ray diffraction pattern obtained by irradiation with copper Kα radiation (wavelength λ=1.54 angstroms).

[17] A crystal of a sulfate according to [11], wherein the crystal exhibits characteristic peaks at diffraction angles 2θ=3.74, 7.56, 8.92, 9.58, 11.36, 12.38, 14.68, 15.64, 16.06, and 24.38 in a powder X-ray diffraction pattern obtained by irradiation with copper Kα radiation (wavelength λ=1.54 angstroms).

[18] A crystal of a phosphate according to [11], wherein the crystal exhibits characteristic peaks at diffraction angles 2θ=3.74, 7.56, 8.80, 9.56, 11.34, 14.56, 15.74, 23.68, 24.34, and 24.68 in a powder X-ray diffraction pattern obtained by irradiation with copper Kα radiation (wavelength λ=1.54 angstroms).

[19] A crystal of an ethanesulfonate according to [11], wherein the crystal exhibits characteristic peaks at diffraction angles 2θ=6.72, 7.90, 12.02, 13.40, 16.90, 17.88, 19.00, 19.80, 21.26, and 24.18 in a powder X-ray diffraction pattern obtained by irradiation with copper Kα radiation (wavelength λ=1.54 angstroms).

[20] A crystal of a benzenesulfonate according to [11], wherein the crystal exhibits characteristic peaks at diffraction angles 2θ=9.22, 10.60, 10.82, 11.10, 13.40, 15.78, 17.50, 18.66, 21.02, and 26.10 in a powder X-ray diffraction pattern obtained by irradiation with copper Kα radiation (wavelength λ=1.54 angstroms).

[21] A crystal of a p-toluenesulfonate according to [11], wherein the crystal exhibits characteristic peaks at diffraction angles 2θ=4.18, 5.12, 13.44, 14.98, 16.96, 17.44, 18.92, 19.72, 20.16, and 23.04 in a powder X-ray diffraction pattern obtained by irradiation with copper KG radiation (wavelength λ=1.54 angstroms).

[22] A crystal of a phosphate according to [13], wherein the crystal exhibits characteristic peaks at diffraction angles 2θ=4.28, 8.42, 8.64, 10.54, 12.72, 13.48, 15.90, 17.00. 17.46, and 21.26 in a powder X-ray diffraction pattern obtained by irradiation with copper Kα radiation (wavelength λ=1.54 angstroms).

[23] A crystal of a sulfate according to [13], wherein the crystal exhibits characteristic peaks at diffraction angles 2θ=3.66, 6.42, 7.32, 9.76, 11.00, 12.88, 18.42, 19.62, 20.54, and 24.22 in a powder X-ray diffraction pattern obtained by irradiation with copper Kα radiation (wavelength λ=1.54 angstroms).

[24] A crystal of a sulfate according to [13], wherein the crystal exhibits characteristic peaks at diffraction angles 2θ=3.64, 6.40, 7.32, 9.76, 17.38, 18.42, 19.64, 20.56, 22.90, and 24.20 in a powder X-ray diffraction pattern obtained by irradiation with copper Kα radiation (wavelength λ=1.54 angstroms).

[25] A crystal of a sulfate according to [13], wherein the crystal exhibits characteristic peaks at diffraction angles 2θ=3.64, 6.40, 7.30, 9.76, 17.34, 18.38, 19.34, 20.56, 21.52, and 22.94 in a powder X-ray diffraction pattern obtained by irradiation with copper Kα radiation (wavelength λ=1.54 angstroms).

[26] A crystal of a sulfate according to [13], wherein the crystal exhibits characteristic peaks at diffraction angles 2θ=3.62, 6.38, 7.28, 9.74, 17.30, 18.36, 19.54, 20.52, 22.86, and 24.14 in a powder X-ray diffraction pattern obtained by irradiation with copper Kα radiation (wavelength λ=1.54 angstroms).

[27] A crystal of a sulfate according to [13], wherein the crystal exhibits characteristic peaks at diffraction angles 2θ=3.64, 6.40, 7.30, 9.76, 12.86, 18.40, 19.62, 20.54, 22.92, and 24.20 in a powder X-ray diffraction pattern obtained by irradiation with copper Kα radiation (wavelength λ=1.54 angstroms).

[28] A crystal of a sulfate according to [13], wherein the crystal exhibits characteristic peaks at diffraction angles 2θ=3.64, 6.36, 7.30, 18.36, 19.04, 19.42, 19.70, 20.12, 20.42, and 21.32 in a powder X-ray diffraction pattern obtained by irradiation with copper Kα radiation (wavelength λ=1.54 angstroms).

[29] A crystal of a sulfate according to [13], wherein the crystal exhibits characteristic peaks at diffraction angles 2θ=5.62, 7.18, 9.22, 10.36, 15.56, 16.40, and 20.86 in a powder X-ray diffraction pattern obtained by irradiation with copper Kα radiation (wavelength λ=1.54 angstroms).

[30] A crystal of a naphthalene-1,5-disulfonate according to [13], wherein the crystal exhibits characteristic peaks at diffraction angles 2θ=6.14, 6.98, 11.24, 14.84, 17.48, 19.54, 20.94, 22.38, 23.20, and 24.70 in a powder X-ray diffraction pattern obtained by irradiation with copper KG radiation (wavelength λ=1.54 angstroms).

[31] A crystal of a naphthalene-1,5-disulfonate according to [13], wherein the crystal exhibits characteristic peaks at diffraction angles 2θ=9.24, 9.58, 14.00, 14.46, 16.70, 17.02, 18.22, 20.24, 21.64, and 25.52 in a powder X-ray diffraction pattern obtained by irradiation with copper KG radiation (wavelength λ=1.54 angstroms).

[32] An Axl inhibitor comprising a compound according to any one of [1] to [10] or a pharmaceutically acceptable salt thereof.

[33] A medicament comprising a compound according to any one of [1] to [10] or a pharmaceutically acceptable salt thereof as an active ingredient.

[34] A medicament for the treatment of a disease caused by hyperfunction of Axl kinase, a disease associated with hyperfunction of Axl kinase, and/or a disease involving hyperfunction of Axl kinase, comprising a compound according to any one of [1] to [10] or a pharmaceutically acceptable salt thereof as an active ingredient.

[35] A medicament for the treatment of a hyperproliferative disease, comprising a compound according to any one of [1] to [10] or a pharmaceutically acceptable salt thereof as an active ingredient.

[36] A medicament for the treatment of a cancer, comprising a compound according to any one of [1] to [10] or a pharmaceutically acceptable salt thereof as an active ingredient.

[37] A medicament for the prevention of cancer metastasis, comprising a compound according to any one of [1] to [10] or a pharmaceutically acceptable salt thereof as an active ingredient.

[38] A medicament for overcoming drug resistance of a cancer, comprising a compound according to any one of [1] to [10] or a pharmaceutically acceptable salt thereof as an active ingredient.

[39] A medicament for the inhibition of drug resistance acquisition of a cancer, comprising a compound according to any one of [1] to [10] or a pharmaceutically acceptable salt thereof as an active ingredient.

[40] A medicament according to any one of [36] to [39], wherein the cancer is selected from breast cancer, colon cancer, prostate cancer, lung cancer, gastric cancer, ovary cancer, endometrial cancer, kidney cancer, hepatocellular cancer, thyroid gland cancer, uterus cancer, esophagus cancer, squamous cell cancer, leukemia, osteosarcoma, melanoma, glioblastoma, neuroblastoma, and pancreatic cancer.

[41] A pharmaceutical composition comprising a compound according to any one of [1] to [10] or a pharmaceutically acceptable salt thereof and a pharmaceutically acceptable carrier.

[42] A method for treating a disease caused by hyperfunction of Axl kinase, a disease associated with hyperfunction of Axl kinase, and/or a disease involving hyperfunction of Axl kinase, comprising using a compound according to any one of [1] to [10] or a pharmaceutically acceptable salt thereof.

[43] A method for treating a hyperproliferative disease, comprising using a compound according to any one of [1] to [10] or a pharmaceutically acceptable salt thereof.

[44] A method for treating a cancer, comprising using a compound according to any one of [1] to [10] or a pharmaceutically acceptable salt thereof.

[45] A method for preventing cancer metastasis, comprising using a compound according to any one of [1] to [10] or a pharmaceutically acceptable salt thereof.

[46] A method for overcoming drug resistance of a cancer, comprising using a compound according to any one of [1] to [10] or a pharmaceutically acceptable salt thereof.

[47] A method for inhibiting drug resistance acquisition of a cancer, comprising using a compound according to any one of [1] to [10] or a pharmaceutically acceptable salt thereof.

[48] A method according to any one of [44] to [49], wherein the cancer is selected from breast cancer, colon cancer, prostate cancer, lung cancer, gastric cancer, ovary cancer, endometrial cancer, kidney cancer, hepatocellular cancer, thyroid gland cancer, uterus cancer, esophagus cancer, squamous cell cancer, leukemia, osteosarcoma, melanoma, glioblastoma, and neuroblastoma.

[49] Use of a compound according to any one of [1] to [10] or a pharmaceutically acceptable salt thereof for the manufacture of a medicament.

[50] Use of a compound according to any one of [1] to [10] or a pharmaceutically acceptable salt thereof for the treatment of a cancer.

[51] Use of a compound according to any one of [1] to [10] or a pharmaceutically acceptable salt thereof for the prevention of cancer metastasis.

[52] Use of a compound according to any one of [1] to [10] or a pharmaceutically acceptable salt thereof for overcoming drug resistance of a cancer.

[53] Use of a compound according to any one of [1] to [10] or a pharmaceutically acceptable salt thereof for the inhibition of drug resistance acquisition of a cancer.

Advantageous Effects of the Invention

The present invention provides a compound represented by the formula (I) having Axl inhibitory activity. The compound is useful as a therapeutic agent for a disease caused by hyperfunction of Axl, a disease associated with hyperfunction of Axl, and/or a disease involving hyperfunction of Axl, for example, an anticancer agent.

BRIEF DESCRIPTION OF DRAWINGS

FIG. 1 shows a powder X-ray diffraction pattern of the crystal obtained in Example 130. In this drawing, the ordinate indicates diffraction intensity (Intensity) by count/sec (cps) unit, and the abscissa depicts values of diffraction angle 2θ.

FIG. 2 shows a powder X-ray diffraction pattern of the crystal obtained in Example 131. In this drawing, the FIG. 3 shows a powder X-ray diffraction pattern of the crystal obtained in Example 132. In this drawing, the ordinate indicates diffraction intensity (Intensity) by count/sec (cps) unit, and the abscissa depicts values of diffraction angle 2θ.

FIG. 4 shows a powder X-ray diffraction pattern of the crystal obtained in Example 133. In this drawing, the ordinate indicates diffraction intensity (Intensity) by count/sec (cps) unit, and the abscissa depicts values of diffraction angle 2θ.

FIG. 5 shows a powder X-ray diffraction pattern of the crystal obtained in Example 134. In this drawing, the ordinate indicates diffraction intensity (Intensity) by count/sec (cps) unit, and the abscissa depicts values of diffraction angle 2θ.

FIG. 6 shows a powder X-ray diffraction pattern of the crystal obtained in Example 135. In this drawing, the ordinate indicates diffraction intensity (Intensity) by count/sec (cps) unit, and the abscissa depicts values of diffraction angle 2θ.

FIG. 7 shows a powder X-ray diffraction pattern of the crystal obtained in Example 136. In this drawing, the ordinate indicates diffraction intensity (Intensity) by count/sec (cps) unit, and the abscissa depicts values of diffraction angle 2θ.

FIG. 8 shows a powder X-ray diffraction pattern of the crystal obtained in Example 137. In this drawing, the ordinate indicates diffraction intensity (Intensity) by count/sec (cps) unit, and the abscissa depicts values of diffraction angle 2θ.

FIG. 9 shows a powder X-ray diffraction pattern of the crystal obtained in Example 138. In this drawing, the ordinate indicates diffraction intensity (Intensity) by count/sec (cps) unit, and the abscissa depicts values of diffraction angle 2θ.

FIG. 10 shows a powder X-ray diffraction pattern of the crystal obtained in Example 139. In this drawing, the ordinate indicates diffraction intensity (Intensity) by count/sec (cps) unit, and the abscissa depicts values of diffraction angle 2θ.

FIG. 11 shows a powder X-ray diffraction pattern of the crystal obtained in Example 140. In this drawing, the ordinate indicates diffraction intensity (Intensity) by count/sec (cps) unit, and the abscissa depicts values of diffraction angle 2θ.

FIG. 12 shows a powder X-ray diffraction pattern of the crystal obtained in Example 141. In this drawing, the ordinate indicates diffraction intensity (Intensity) by count/sec (cps) unit, and the abscissa depicts values of diffraction angle 2θ.

FIG. 13 shows a powder X-ray diffraction pattern of the crystal obtained in Example 142. In this drawing, the ordinate indicates diffraction intensity (Intensity) by count/sec (cps) unit, and the abscissa depicts values of diffraction angle 2θ.

FIG. 14 shows a powder X-ray diffraction pattern of the crystal obtained in Example 143. In this drawing, the ordinate indicates diffraction intensity (Intensity) by count/sec (cps) unit, and the abscissa depicts values of diffraction angle 2θ.

FIG. 15 shows a powder X-ray diffraction pattern of the crystal obtained in Example 144. In this drawing, the ordinate indicates diffraction intensity (Intensity) by count/sec (cps) unit, and the abscissa depicts values of diffraction angle 2θ.

FIG. 16 shows a powder X-ray diffraction pattern of the crystal obtained in Example 145. In this drawing, the ordinate indicates diffraction intensity (Intensity) by count/sec (cps) unit, and the abscissa depicts values of diffraction angle 2θ.

FIG. 17 shows a powder X-ray diffraction pattern of the crystal obtained in Example 146. In this drawing, the ordinate indicates diffraction intensity (Intensity) by count/sec (cps) unit, and the abscissa depicts values of diffraction angle 2θ.

FIG. 18 shows a powder X-ray diffraction pattern of the crystal obtained in Example 147. In this drawing, the ordinate indicates diffraction intensity (Intensity) by count/sec (cps) unit, and the abscissa depicts values of diffraction angle 2θ.

FIG. 19-1 is a diagram showing an effect brought about by combined use of the Axl-inhibiting compound of the present application with erlotinib on tumors derived from HCC827 (which has a deletion mutation in EGFR gene exon 19 and exhibits high sensitivity to EGFR inhibitors) subcutaneously transplanted in mice. The symbol x represents a group given a vehicle three times a day (Tid). The symbol open circle represents a group given 50 mg/kg Compound B sulfate hydrate twice a day (bid). The symbol filled circle represents a group given 25 mg/kg erlotinib once a day (qd). The symbol open triangle represents a group given 50 mg/kg Compound B sulfate hydrate (bid) and 25 mg/kg erlotinib (qd). The abscissa depicts the number of days after the start of administration. The ordinate depicts an estimated tumor volume calculated from tumor axes.

FIG. 19-2 is a diagram showing a mean rate of change in the body weights of individuals in a test on the combined use of the Axl-inhibiting compound of the present application with erlotinib (the same legends as in FIG. 19-1 are used).

FIG. 20-1 is a diagram showing the antitumor effect of erlotinib on tumors derived from HCC827 subcutaneously transplanted in mice. The symbol x represents a vehicle administration group. The symbol open circle represents a group given 25 mg/kg erlotinib. The symbol filled circle represents a group given 12.5 mg/kg erlotinib. The symbol open triangle represents a group given 6.25 mg/kg erlotinib. The abscissa depicts the number of days after the start of administration. The ordinate depicts an estimated tumor volume calculated from tumor axes.

FIG. 20-2 is a diagram showing change in the expression level of the Axl protein when erlotinib was administered to tumors derived from HCC827 subcutaneously transplanted in mice.

DESCRIPTION OF EMBODIMENTS

In the present invention, Axl refers to a protein encoded by an Axl gene. "Axl" includes, for example, Axl proteins encoded by the full-length Axl gene or Axl proteins encoded by an Axl gene variant (including a deletion variant, a substitution variant, or an addition variant). In the present invention, "Axl" also includes homologs derived from various animal species.

In the present invention, "Axl inhibitor" refers to an inhibitor of a function of Axl as a tyrosine kinase.

In the present invention, the terms "tumor" and "cancer" are used interchangeably. In the present invention, tumor, malignant tumor, cancer, malignant neoplasm, carcinoma, sarcoma, etc., are also collectively referred to as "tumor" or "cancer".

In the present invention, a "$C_1$-$C_6$ alkyl group" means a linear or branched alkyl group having 1 to 6 carbon atoms. Examples of a "$C_1$-$C_6$ alkyl group" include a methyl group, an ethyl group, a propyl group, an isopropyl group, a butyl group, and a tert-butyl group.

A "$C_1$-$C_6$ alkoxy group" means an alkoxy group having a linear or branched alkyl group having 1 to 6 carbon atoms. Examples of a "$C_1$-$C_6$ alkoxy group" include a methoxy group, an ethoxy group, a propoxy group, an isopropoxy group, and a butoxy group.

Examples of a "halogen atom" include a fluorine atom, a chlorine atom, a bromine atom, and an iodine atom.

A "cycloalkyl group" means a cyclic alkyl group having 3 to 8 carbon atoms, unless otherwise specified. Examples thereof include a cyclopropyl group, a cyclobutyl group, a cyclopentyl group, and a cyclohexyl group.

A "heterocycloalkyl group" means a monovalent saturated heterocyclic group. Examples thereof include a saturated heterocyclic group having a nitrogen atom in the ring, and a saturated heterocyclic group having an oxygen atom in the ring and specifically include monovalent groups derived from pyrrolidine, imidazoline, piperidine, piperazine, azetidine, morpholine, dioxane, oxetane, tetrahydropyran, and quinuclidine.

A "cycloalkenyl group" refers to the aforementioned "cycloalkyl group" having one or more unsaturated bonds such as double bonds. Examples thereof include a cyclopentenyl group and a cyclohexenyl group.

A "heterocycloalkenyl group" refers to the aforementioned "heterocycloalkyl group" having one or more unsaturated bonds such as double bonds. Examples thereof include a tetrahydropyridinyl group and a dihydropyranyl group. Hereinafter, each substituent in the formula (I) will be described.

In the following general formula (I),

[Formula 13]

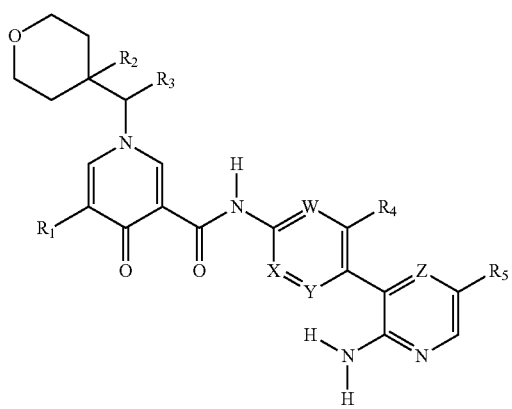

(I)

W, X, and Y each independently represent a nitrogen atom, C—H, C—F, or C—Cl.

Z represents a nitrogen atom, C—H, C—F, C—$C_1$-$C_6$ alkyl group, C—$C_1$-$C_6$ alkoxy group, or C—Cl.

$R_1$ represents a group represented by the following formula (II-1) or (II-2):

[Formula 14]

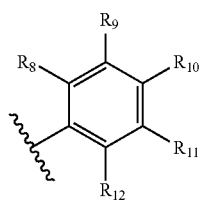

(II-1)

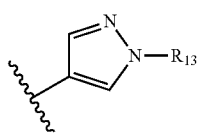

(II-2)

wherein in the formula (II-I), Q represents a nitrogen atom, C—H, or C—F, T represents a nitrogen atom or C—H, U represents a nitrogen atom or C—H, and $R_6$ represents a halogen atom, a $C_1$-$C_6$ alkyl group, a $C_3$-$C_6$ cycloalkyl group, a cyano group, or a trifluoromethoxy group, and in the formula (II-2), V represents a sulfur atom or an oxygen atom, and $R_7$ represents a $C_1$-$C_6$ alkyl group.

$R_2$ represents a hydrogen atom, a halogen atom, a $C_1$-$C_6$ alkyl group, a $C_1$-$C_6$ alkoxy group, or a cyano group. In this context, the $C_1$-$C_6$ alkyl group is preferably a methyl group, an ethyl group, or a propyl group. The $C_1$-$C_6$ alkoxy group is preferably a methoxy group or an ethoxy group.

$R_3$ represents a hydrogen atom or a $C_1$-$C_6$ alkyl group. The $C_1$-$C_6$ alkyl group is preferably a methyl group, an ethyl group, or a propyl group.

$R_4$ represents a hydrogen atom, a halogen atom, or a $C_1$-$C_6$ alkyl group. $R_4$ is preferably a hydrogen atom, a fluorine atom, a chlorine atom, a methyl group, or an ethyl group.

$R_5$ represents a hydrogen atom or a group represented by the following formula (III-1), (III-2), (III-3), or (III-4):

[Formula 15]

(III-1)

(III-2)

-continued

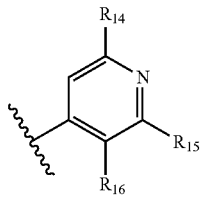
(III-3)

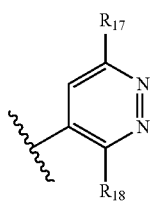
(III-4)

wherein in the formula (III-1),

R$_8$ and R$_{12}$ each independently represent a hydrogen atom or a deuterium atom, R$_9$ represents a hydrogen atom, a halogen atom, or a C$_1$-C$_6$ alkoxy group, R$_{10}$ represents a hydrogen atom, a C$_1$-C$_6$ alkyl group optionally substituted by a heterocycloalkyl group, or a C$_1$-C$_6$ alkoxy group optionally substituted by a heterocycloalkyl group optionally substituted by a C$_1$-C$_6$ alkyl group, and R$_{11}$ represents a hydrogen atom, a C$_1$-C$_6$ alkoxy group, or a deuterium-substituted C$_1$-C$_6$ alkoxy group, in the formula (III-2), R$_{13}$ represents a C$_1$-C$_6$ alkyl group optionally substituted by a heterocycloalkyl group, or a heterocycloalkyl group, in the formula (III-3), R$_{14}$ represents a hydrogen atom or a C$_1$-C$_6$ alkyl group, R$_{15}$ represents a hydrogen atom, a C$_1$-C$_6$ alkyl group, or a C$_1$-C$_6$ alkoxy group, and R$_{16}$ represents a hydrogen atom or a halogen atom, and in the formula (III-4), R$_{17}$ represents a C$_1$-C$_6$ alkoxy group, and R$_{18}$ represents a C$_1$-C$_6$ alkoxy group.

When R$_5$ is a group represented by the formula (III-1), the heterocycloalkyl group of R$_{10}$ is preferably a dioxanyl group, a morpholino group, a piperazinyl group, or a tetrahydropyranyl group, and the C$_1$-C$_6$ alkyl group is preferably a methoxy group or an ethoxy group. The C$_1$-C$_6$ alkoxy group of R$_{11}$ is preferably a methoxy group or an ethoxy group.

When R$_5$ is a group represented by the formula (III-2), the heterocycloalkyl group of R$_{13}$ is preferably a dioxanyl group, a morpholino group, a piperazinyl group, or a tetrahydropyranyl group, and the C$_1$-C$_6$ alkyl group of R$_{13}$ is preferably a methyl group or an ethyl group.

The compound represented by the general formula (I) or the pharmaceutically acceptable salt thereof is more preferably any of the following compounds or pharmaceutically acceptable salts thereof:

N-[4-(2-amino-5-{4-[(2R)-1,4-dioxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide represented by the following formula:

[Formula 16]

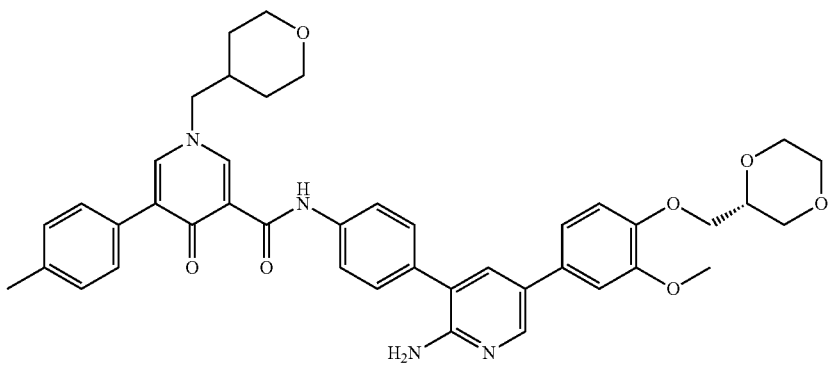

N-[4-(2-amino-5-{4-[(2S)-1,4-dioxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide represented by the following formula:

[Formula 17]

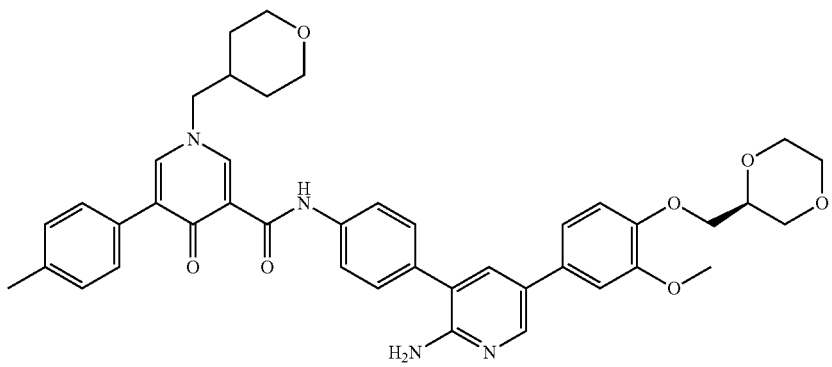

N-{4-[2-amino-5-(3,4-dimethoxyphenyl)pyridin-3-yl]phenyl}-5-(4-methylphenyl)-4-oxo-1-(tetrahydro-2H-pyran-4-ylmethyl)-1,4-dihydropyridine-3-carboxamide represented by the following formula:

[Formula 18]

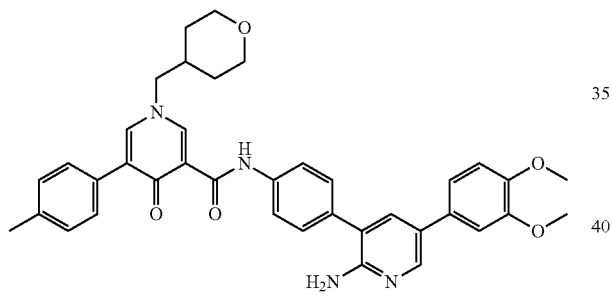

N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide represented by the following formula:

[Formula 19]

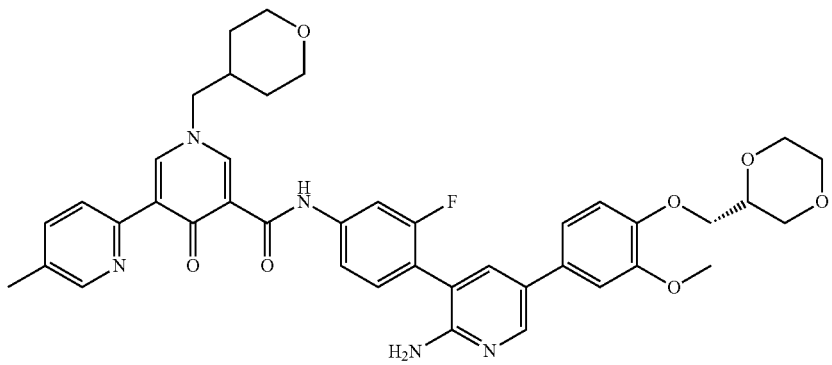

N-[4-(2-amino-5-{4-[(2S)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide represented by the following formula:

[Formula 20]

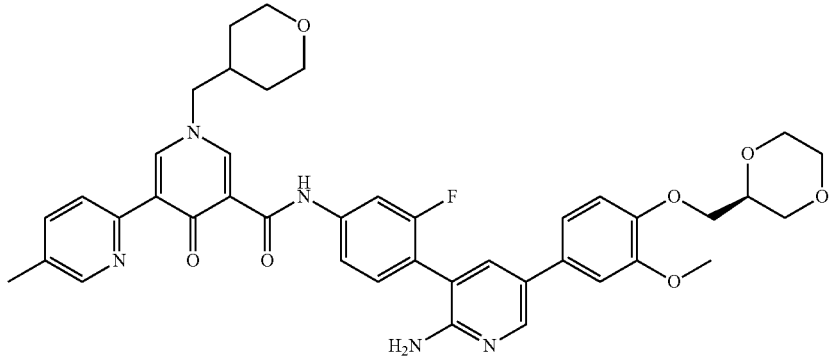

N-{4-[2-amino-5-(1-ethyl-1H-pyrazol-4-yl)pyridin-3-yl]-3-fluorophenyl}-5-(4-methylphenyl)-4-oxo-1-(tetrahydro-2H-pyran-4-ylmethyl)-1,4-dihydropyridine-3-carboxamide represented by the following formula:

[Formula 21]

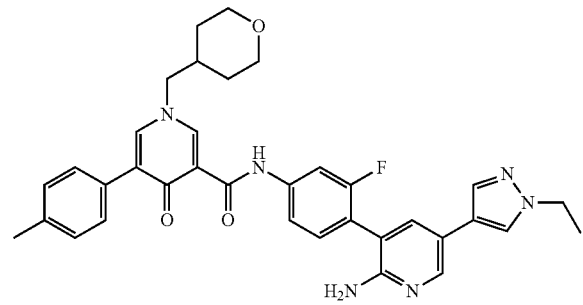

N-(4-{2-amino-5-[1-(tetrahydro-2H-pyran-4-yl)-1H-pyrazol-4-yl]pyridin-3-yl}-3-fluorophenyl)-5-(4-methylphenyl)-4-oxo-1-(tetrahydro-2H-pyran-4-ylmethyl)-1,4-dihydropyridine-3-carboxamide represented by the following formula:

[Formula 22]

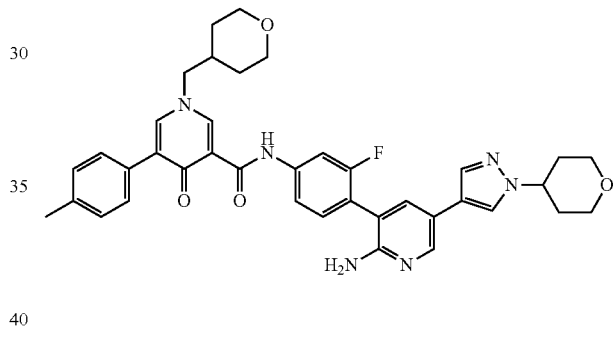

N-[6-(2-amino-5-{4-[(2R)-1,4-dioxan-2-ylmethoxy]-3-methoxyphenyl}pyridin-3-yl)pyridazin-3-yl]-5-(5-methylthiophen-2-yl)-4-oxo-1-(tetrahydro-2H-pyran-4-ylmethyl)-1,4-dihydropyridine-3-carboxamide represented by the following formula:

[Formula 23]

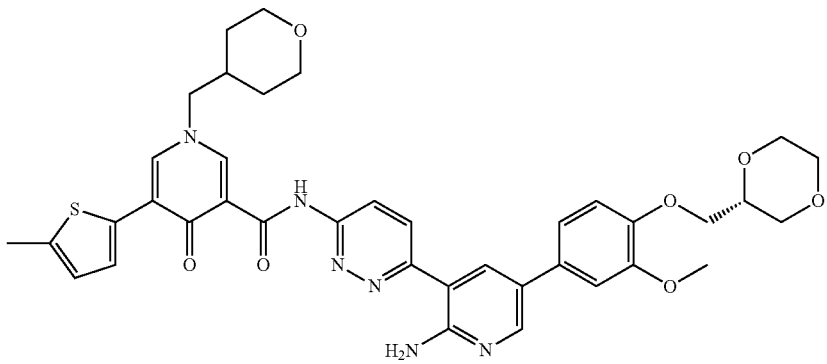

and

N-[6-(2-amino-5-{3-methoxy-4-[2-(morpholin-4-yl)ethoxy]phenyl}pyridin-3-yl)pyridazin-3-yl]-5-(4-methylphenyl)-4-oxo-1-(tetrahydro-2H-pyran-4-ylmethyl)-1,4-dihydropyridine-3-carboxamide represented by the following formula:

[Formula 24]

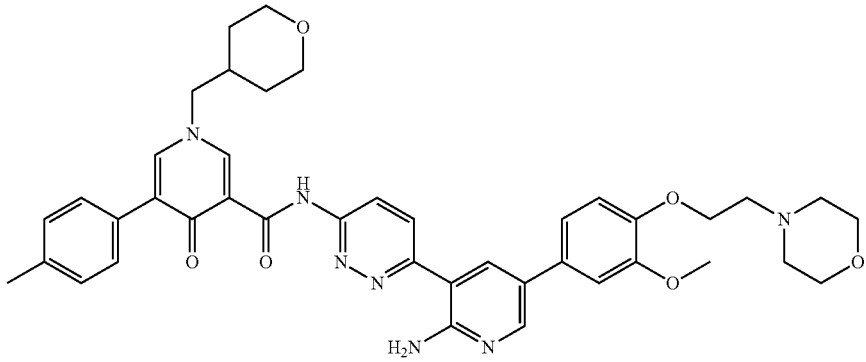

The compounds represented by formula (I) of the present invention may have stereoisomers or optical isomers derived from asymmetric carbon atoms. All of these stereoisomers and optical isomers, and mixtures thereof are included in the present invention.

The compounds represented by general formula (I) of the present invention can form a pharmaceutically acceptable salt, if desired, when having a basic group such as an amino group. Examples of such salts can include: hydrohalides such as hydrochlorides, hydrobromides, and hydroiodides; inorganic acid salts such as nitrates, perchlorates, sulfates, and phosphates; lower alkanesulfonates such as methanesulfonates, trifluoromethanesulfonates, and ethanesulfonates; arylsulfonates such as benzenesulfonates and p-toluenesulfonates; organic acid salts such as formates formic acid, acetates acetic acid, malates malic acid, fumarates, succinates, citrates, tartrates, oxalates, and maleates; and amino acid salts such as ornithine salts, glutamates, and aspartates. Hydrohalides and organic acid salts are preferred.

The compounds represented by general formula (I) of the present invention may generally form a base-addition salt when having an acidic group such as a carboxy group. Examples of such pharmaceutically acceptable salts can include: alkali metal salts such as sodium salts, potassium salts, and lithium salts; alkaline earth metal salts such as calcium salts and magnesium salts; inorganic salts such as ammonium salts; and organic amine salts such as dibenzylamine salts, morpholine salts, phenylglycine alkyl ester salts, ethylenediamine salts, N-methylglucamine salts, diethylamine salts, triethylamine salts, cyclohexylamine salts, dicyclohexylamine salts, N,N'-dibenzylethylenediamine salts, diethanolamine salts, N-benzyl-N-(2-phenylethoxy)amine salts, piperazine salts, tetramethyl ammonium salts, and tris(hydroxymethyl)aminomethane salts.

The compounds represented by general formula (I) of the present invention or salts thereof may exist in a free or solvate form. The compounds represented by general formula (I) of the present invention or salts thereof may exist in a hydrate form, for example, by absorbing moisture in the air. Solvates are not particularly limited as long as the solvate is pharmaceutically acceptable. Specifically, a solvate is preferably a hydrate, an ethanol solvate, or the like.

The compounds represented by general formula (I) of the present invention may be in an N-oxide form when containing a nitrogen atom. These solvate and N-oxide forms are also included in the scope of the present invention. Crystals of the compounds of the present invention or salts thereof are also included in the scope of the present invention.

More specifically, examples of the salt include a hydrobromide, nitrate, sulfate, phosphate, ethanesulfonate, benzenesulfonate, and p-toluenesulfonate of N-[4-(2-amino-5-{4-[(2R)-1,4-dioxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide.

Further examples thereof include a methanesulfonate of N-{4-[2-amino-5-(3,4-dimethoxyphenyl)pyridin-3-yl]phenyl}-5-(4-methylphenyl)-4-oxo-1-(tetrahydro-2H-pyran-4-ylmethyl)-1,4-dihydropyridine-3-carboxamide.

Further examples thereof include a methanesulfonate, phosphate, and sulfate of N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide.

In another aspect, the present invention relates to crystals of the compounds of the present invention or the salts. In this context, the crystals refer to a solid whose internal structure is formed by a three-dimensionally regular repetition of constituent atoms (or a group thereof), and are distinguished from an amorphous solid not having such a regular internal structure.

Crystals of the same compound having a plurality of different internal structures and physicochemical properties (crystal polymorphs) may be generated depending on the crystallization conditions. The crystals of the present invention may be any of these crystal polymorphs or may be a mixture of two or more crystal polymorphs.

The crystals of the present invention may absorb moisture or adsorb water when left to stand in the air or may be heated to 25 to 150° C. under normal atmospheric conditions, for example, to form a hydrate. The crystals of the present invention may also contain a crystallization solvent in the attached residual solvent or solvate.

In the present specification, the crystals of the present invention may be represented on the basis of powder X-ray diffraction data. The powder X-ray diffraction may be measured and analyzed by an approach conventionally used in the art and can be carried out by, for example, a method described in the Examples. Generally, in hydrates and dehydrates, attachment and detachment of water of crystallization may change their lattice constants and thus change diffraction angles (2θ) in powder X-ray diffraction. Also, the peak intensity may vary according to, for example, the difference in crystal growth surface or the like (crystal habit). Accordingly, when the crystals of the present invention are represented on the basis of powder X-ray diffraction data, crystals whose peak diffraction angles and powder X-ray diffraction patterns in the powder X-ray diffraction are identical to those of the crystals of the present invention as well as hydrates and dehydrates obtained from these crystals are also included in the scope of the present invention.

In a more specific aspect, the present invention relates to a crystal of a methanesulfonate of N-[4-(2-amino-5-{4-[(2R)-1,4-dioxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide. More preferably, the present invention relates to a crystal of a methanesulfonate of N-[4-(2-amino-5-{4-[(2R)-1,4-dioxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide, wherein the crystal exhibits characteristic peaks at diffraction angles 2θ=3.74, 7.56, 8.96, 11.38, 12.36, 14.78, 15.60, 16.16, 18.70, and 24.10 in a powder X-ray diffraction pattern obtained by irradiation with copper Kα radiation (wavelength λ=1.54 angstroms). The crystal exhibits the powder X-ray diffraction pattern of FIG. 1 by irradiation with copper Kα radiation (wavelength λ=1.54 angstroms).

In a more specific aspect, the present invention relates to a crystal of a hydrobromide of N-[4-(2-amino-5-{4-[(2R)-1,4-dioxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide. More preferably, the present invention relates to a crystal of a hydrobromide of N-[4-(2-amino-5-{4-[(2R)-1,4-dioxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide, wherein the crystal exhibits characteristic peaks at diffraction angles 2θ=3.84, 7.72, 9.40, 11.62, 14.92, 15.48, 16.70, 18.88, 19.32, and 24.40 in a powder X-ray diffraction pattern obtained by irradiation with copper Kα radiation (wavelength λ=1.54 angstroms). The crystal exhibits the powder X-ray diffraction pattern of FIG. 2 by irradiation with copper Kα radiation (wavelength λ=1.54 angstroms).

In a more specific aspect, the present invention relates to a crystal of a nitrate of N-[4-(2-amino-5-{4-[(2R)-1,4-dioxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide. More preferably, the present invention relates to a crystal of a nitrate of N-[4-(2-amino-5-{4-[(2R)-1,4-dioxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide, wherein the crystal exhibits characteristic peaks at diffraction angles 2θ=3.82, 7.66, 9.28, 9.52, 11.54, 15.26, 15.54, 16.62, 19.24, and 24.56 in a powder X-ray diffraction pattern obtained by irradiation with copper Kα radiation (wavelength λ=1.54 angstroms). The crystal exhibits the powder X-ray diffraction pattern of FIG. 3 by irradiation with copper Kα radiation (wavelength λ=1.54 angstroms).

In a more specific aspect, the present invention relates to a crystal of a sulfate of N-[4-(2-amino-5-{4-[(2R)-1,4-dioxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide. More preferably, the present invention relates to a crystal of a sulfate of N-[4-(2-amino-5-{4-[(2R)-1,4-dioxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide, wherein the crystal exhibits characteristic peaks at diffraction angles 2θ=3.74, 7.56, 8.92, 9.58, 11.36, 12.38, 14.68, 15.64, 16.06, and 24.38 in a powder X-ray diffraction pattern obtained by irradiation with copper Kα radiation (wavelength λ=1.54 angstroms). The crystal exhibits the powder X-ray diffraction pattern of FIG. 4 by irradiation with copper Kα radiation (wavelength λ=1.54 angstroms).

In a more specific aspect, the present invention relates to a crystal of a phosphate of N-[4-(2-amino-5-{4-[(2R)-1,4-dioxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide. More preferably, the present invention relates to a crystal of a phosphate of N-[4-(2-amino-5-{4-[(2R)-1,4-dioxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide, wherein the crystal exhibits characteristic peaks at diffraction angles 2θ=3.74, 7.56, 8.80, 9.56, 11.34, 14.56, 15.74, 23.68, 24.34, and 24.68 in a powder X-ray diffraction pattern obtained by irradiation with copper Kα radiation (wavelength λ=1.54 angstroms). The crystal exhibits the powder X-ray diffraction pattern of FIG. 5 by irradiation with copper Kα radiation (wavelength λ=1.54 angstroms).

In a more specific aspect, the present invention relates to a crystal of an ethanesulfonate of N-[4-(2-amino-5-{4-[(2R)-1,4-dioxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide. More preferably, the present invention relates to a crystal of an ethanesulfonate of N-[4-(2-amino-5-{4-[(2R)-1,4-dioxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide, wherein the crystal exhibits characteristic peaks at diffraction angles 2θ=6.72, 7.90, 12.02, 13.40, 16.90, 17.88, 19.00, 19.80, 21.26, and 24.18 in a powder X-ray diffraction pattern obtained by irradiation with copper KG radiation (wavelength λ=1.54 angstroms). The crystal exhibits the powder X-ray diffraction pattern of FIG. 6 by irradiation with copper Kα radiation (wavelength λ=1.54 angstroms).

In a more specific aspect, the present invention relates to a crystal of a benzenesulfonate of N-[4-(2-amino-5-{4-[(2R)-1,4-dioxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide. More preferably, the present invention relates to a crystal of a benzenesulfonate of N-[4-(2-amino-5-{4-[(2R)-1,4-dioxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide, wherein the crystal exhibits characteristic peaks at diffraction angles 2θ=9.22, 10.60, 10.82, 11.10, 13.40, 15.78, 17.50, 18.66, 21.02, and 26.10 in a powder X-ray diffraction pattern obtained by irradiation with copper KG radiation (wavelength λ=1.54 angstroms). The crystal exhibits the powder X-ray diffraction pattern of FIG. 7 by irradiation with copper Kα radiation (wavelength λ=1.54 angstroms).

In a more specific aspect, the present invention relates to a crystal of a p-toluenesulfonate of N-[4-(2-amino-5-{4-[(2R)-1,4-dioxan-2-ylmethoxy]-3-methoxyphenyl}pyridin-3-yl)phenyl]-5-(4-methylphenyl)-4-oxo-1-(tetrahydro-2H- pyran-4-ylmethyl)-1,4-dihydropyridine-3-carboxamide.

More preferably, the present invention relates to a crystal of a p-toluenesulfonate of N-[4-(2-amino-5-{4-[(2R)-1,4-dioxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide, wherein the crystal exhibits characteristic peaks at diffraction angles 2θ=4.18, 5.12, 13.44, 14.98, 16.96, 17.44, 18.92, 19.72, 20.16, and 23.04 in a powder X-ray diffraction pattern obtained by irradiation with copper Kα radiation (wavelength λ=1.54 angstroms). The crystal exhibits the powder X-ray diffraction pattern of FIG. 8 by irradiation with copper Kα radiation (wavelength λ=1.54 angstroms).

In a more specific aspect, the present invention relates to crystal of a phosphate of N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide. More preferably, the present invention relates to a crystal of a phosphate of N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide, wherein the crystal exhibits characteristic peaks at diffraction angles 2θ=4.28, 8.42, 8.64, 10.54, 12.72, 13.48, 15.90, 17.00, 17.46, and 21.26 in a powder X-ray diffraction pattern obtained by irradiation with copper KG radiation (wavelength λ=1.54 angstroms). The crystal exhibits the powder X-ray diffraction pattern of FIG. 9 by irradiation with copper Kα radiation (wavelength λ=1.54 angstroms).

In a more specific aspect, the present invention relates to a crystal of a sulfate of N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide. More preferably, the present invention relates to a crystal of a sulfate of N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide, wherein the crystal exhibits characteristic peaks at diffraction angles 2θ=3.66, 6.42, 7.32, 9.76, 11.00, 12.88, 18.42, 19.62, 20.54, and 24.22 in a powder X-ray diffraction pattern obtained by irradiation with copper KG radiation (wavelength λ=1.54 angstroms). The crystal exhibits the powder X-ray diffraction pattern of FIG. 10 by irradiation with copper Kα radiation (wavelength λ=1.54 angstroms). Also preferably, the present invention relates to a crystal of a sulfate of N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide, wherein the crystal exhibits characteristic peaks at diffraction angles 2θ=3.64, 6.40, 7.32, 9.76, 17.38, 18.42, 19.64, 20.56, 22.90, and 24.20 in a powder X-ray diffraction pattern obtained by irradiation with copper KG radiation (wavelength λ=1.54 angstroms). The crystal exhibits the powder X-ray diffraction pattern of FIG. 11 by irradiation with copper Kα radiation (wavelength λ=1.54 angstroms). Also preferably, the present invention relates to a crystal of a sulfate of N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide, wherein the crystal exhibits characteristic peaks at diffraction angles 2θ=3.64, 6.40, 7.30, 9.76, 17.34, 18.38, 19.34, 20.56, 21.52, and 22.94 in a powder X-ray diffraction pattern obtained by irradiation with copper KG radiation (wavelength λ=1.54 angstroms).

The crystal exhibits the powder X-ray diffraction pattern of FIG. 12 by irradiation with copper Kα radiation (wavelength λ=1.54 angstroms). Also preferably, the present invention relates to a crystal of a sulfate of N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide, wherein the crystal exhibits characteristic peaks at diffraction angles 2θ=3.62, 6.38, 7.28, 9.74, 17.30, 18.36, 19.54, 20.52, 22.86, and 24.14 in a powder X-ray diffraction pattern obtained by irradiation with copper KG radiation (wavelength λ=1.54 angstroms). The crystal exhibits the powder X-ray diffraction pattern of FIG. 13 by irradiation with copper Kα radiation (wavelength λ=1.54 angstroms). Also preferably, the present invention relates to a crystal of a sulfate of N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide, wherein the crystal exhibits characteristic peaks at diffraction angles 2θ=3.64, 6.40, 7.30, 9.76, 12.86, 18.40, 19.62, 20.54, 22.92, and 24.20 in a powder X-ray diffraction pattern obtained by irradiation with copper KG radiation (wavelength λ=1.54 angstroms). The crystal exhibits the powder X-ray diffraction pattern of FIG. 14 by irradiation with copper Kα radiation (wavelength λ=1.54 angstroms). Also preferably, the present invention relates to a crystal of a sulfate of N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide, wherein the crystal exhibits characteristic peaks at diffraction angles 2θ=3.64, 6.36, 7.30, 18.36, 19.04, 19.42, 19.70, 20.12, 20.42, and 21.32 in a powder X-ray diffraction pattern obtained by irradiation with copper KG radiation (wavelength λ=1.54 angstroms). The crystal exhibits the powder X-ray diffraction pattern of FIG. 15 by irradiation with copper Kα radiation (wavelength λ=1.54 angstroms). Also preferably, the present invention relates to a crystal of a sulfate of N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide, wherein the crystal exhibits characteristic peaks at diffraction angles 2θ=5.62, 7.18, 9.22, 10.36, 15.56, 16.40, and 20.86 in a powder X-ray diffraction pattern obtained by irradiation with copper Kα radiation (wavelength λ=1.54 angstroms). The crystal exhibits the powder X-ray diffraction pattern of FIG. 16 by irradiation with copper Kα radiation (wavelength λ=1.54 angstroms).

In a more specific aspect, the present invention relates to a crystal of a naphthalene-1,5-disulfonate of N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide. More preferably, the present invention relates to a crystal of a naphthalene-1,5-disulfonate of N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide, wherein the crystal exhibits characteristic peaks at diffraction angles 2θ=6.14, 6.98, 11.24, 14.84, 17.48, 19.54, 20.94, 22.38, 23.20, and 24.70 in a powder X-ray diffraction pattern obtained by irradiation with copper Kα radiation (wavelength λ=1.54 angstroms). The crystal exhibits the powder X-ray diffraction pattern of FIG. 17 by irradiation with copper Kα radiation (wavelength λ=1.54 angstroms). Also preferably, the present invention relates to a crystal of a naphthalene-1,5-disulfonate of N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide, wherein the crystal exhibits characteristic peaks at diffraction angles 2θ=9.24, 9.58, 14.00, 14.46, 16.70, 17.02, 18.22, 20.24, 21.64, and 25.52 in a powder X-ray diffraction pattern obtained by irradiation with copper Kα radiation (wavelength λ=1.54 angstroms). The crystal exhibits the powder X-ray diffraction pattern of FIG. 18 by irradiation with copper Kα radiation (wavelength λ=1.54 angstroms).

The compounds represented by general formula (I) of the present invention may exist as various isomers including geometric isomers such as cis and trans isomers, tautomers, or optical isomers such as d- and l-isomers depending on the types and combinations of the substituents. The compounds of the present invention also include all of these isomers and stereoisomers, and mixtures of any proportions of these isomers and stereoisomers, unless otherwise specified.

The compounds represented by general formula (I) of the present invention may also contain unnatural proportions of atomic isotopes at one or more of the atoms that constitute the compounds. Examples of the atomic isotopes include deuterium ($^2$H), also referred to as D in the present specification, tritium ($^3$H), iodine-125 ($^{125}$I), and carbon-14 ($^{14}$C). These compounds are useful as therapeutic or prophylactic agents, research reagents (e.g., assay reagents), and diagnostic agents (e.g., in vivo diagnostic imaging agents). All isotopic variants of the compounds represented by general formula (I) are included in the scope of the present invention, whether radioactive or not.

The present invention also encompasses compounds that are converted to the compounds represented by general formula (I) that serve as active ingredients in the pharmaceutical compositions of the present invention through reactions with an enzyme, gastric acid or the like under physiological conditions in vivo, i.e., "pharmaceutically acceptable prodrug compounds" that are converted to the compounds represented by general formula (I) by enzymatic oxidation, reduction, hydrolysis, etc., or are converted to the compounds represented by general formula (I) by hydrolysis, etc., by gastric acid or the like.

Examples of the prodrugs of the compounds represented by general formula (I) in which an amino group is present can include compounds in which the amino group is acylated, alkylated, or phosphorylated (e.g., compounds in which the amino group is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, or tert-butylated). Examples of the prodrugs of the compounds represented by general formula (I) in which a hydroxy group is present can include compounds in which the hydroxy group is acylated, alkylated, phosphorylated, or borated (e.g., compounds in which the hydroxy group is acetylated, palmitoylated, propanoylated, pivaloylated, succinylated, fumarylated, alanylated, or dimethylaminomethylcarbonylated). Examples of the prodrugs of the compounds represented by general formula (I) in which a carboxy group is present include compounds in which the carboxy group is esterified or amidated (e.g., compounds in which the carboxy group is ethyl esterified, phenyl esterified, carboxymethyl esterified, dimethylaminomethyl esterified, pivaloyloxymethyl esterified, ethoxycarbonyloxyethyl esterified, amidated, or methylamidated).

The prodrugs of the compounds of the present invention can be produced from the compounds represented by general formula (I) by methods known in the art. The prodrugs of the compounds of the present invention also include compounds that are converted to the compounds represented by general formula (I) under physiological conditions as described in "Iyakuhin No Kaihatsu" [Development of Pharmaceuticals], Vol. 7, Bunshi Sekkei [Molecular Design], Hirokawa Shoten, 1990, pp. 163-198.

Next, typical production processes for the compounds represented by general formula (I) will be described. The compounds of the present invention can be produced by various production processes. The production processes shown below are given merely for illustrative purposes, and the present invention should not be construed to be limited thereby. Each reaction can be performed with substituents protected with appropriate protecting groups as required, and the type of protecting group is not particularly limited.

[Formula 25]

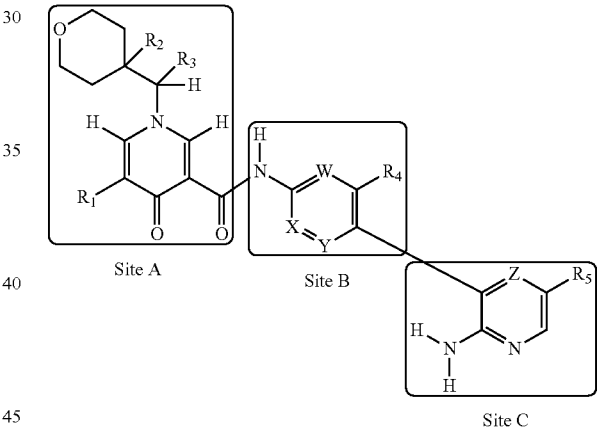

The compounds of general formula (I) can be assumed to be constituted by separate sites, i.e., site A, site B, and site C as described above. Examples of main synthesis procedures include, but are not particularly limited to, a method which involves first bonding compound (B) to compound (C-I) and bonding the complex to compound (A-I), a method which involves first bonding compound (A-I) to compound (B) and bonding the complex to compound (C-I), a method which involves first bonding compound (B) to compound (C-I), bonding the complex to compound (A-II), and then converting the bromine group to $R_1$, a method which involves converting the bromine group in compound (BC) to $R_5$ and then bonding the resulting compound to compound (A-I) or compound (A-II), a method which involves first bonding compound (A-I) to compound (BC) and then converting the bromine group to $R_5$, and a method which involves bonding a compound (A-I)-compound (B) complex to compound (C-II) and then converting the bromine group to $R_5$.

[Formula 26]

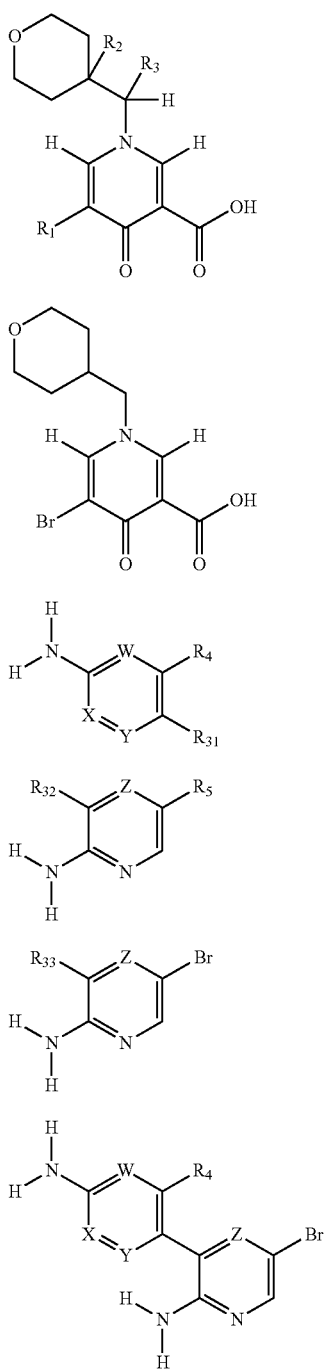

(A-I)

(B)

(BC)

wherein $R_1$ to $R_5$, W, X, Y, and Z are as defined above; $R_{31}$ is a substituent necessary for bonding compound (B) to compound (C-I) or compound (C-II) and represents a halogen group, a triflate group, boronic acid, or boronic acid ester; $R_{32}$ is a substituent necessary for bonding compound (B) to compound (C-I) and represents a halogen group, a triflate group, boronic acid, or boronic acid ester; and $R_{33}$ is a substituent necessary for bonding compound (B) to compound (C-II) and represents boronic acid or boronic acid ester.

First, the method for synthesizing compound (A-I) will be described.

[Production Process 1]

Compound (A-I) can be synthesized by, but not particularly limited to, a method as shown in the following reaction scheme 1:

Reaction scheme 1

[Formula 27]

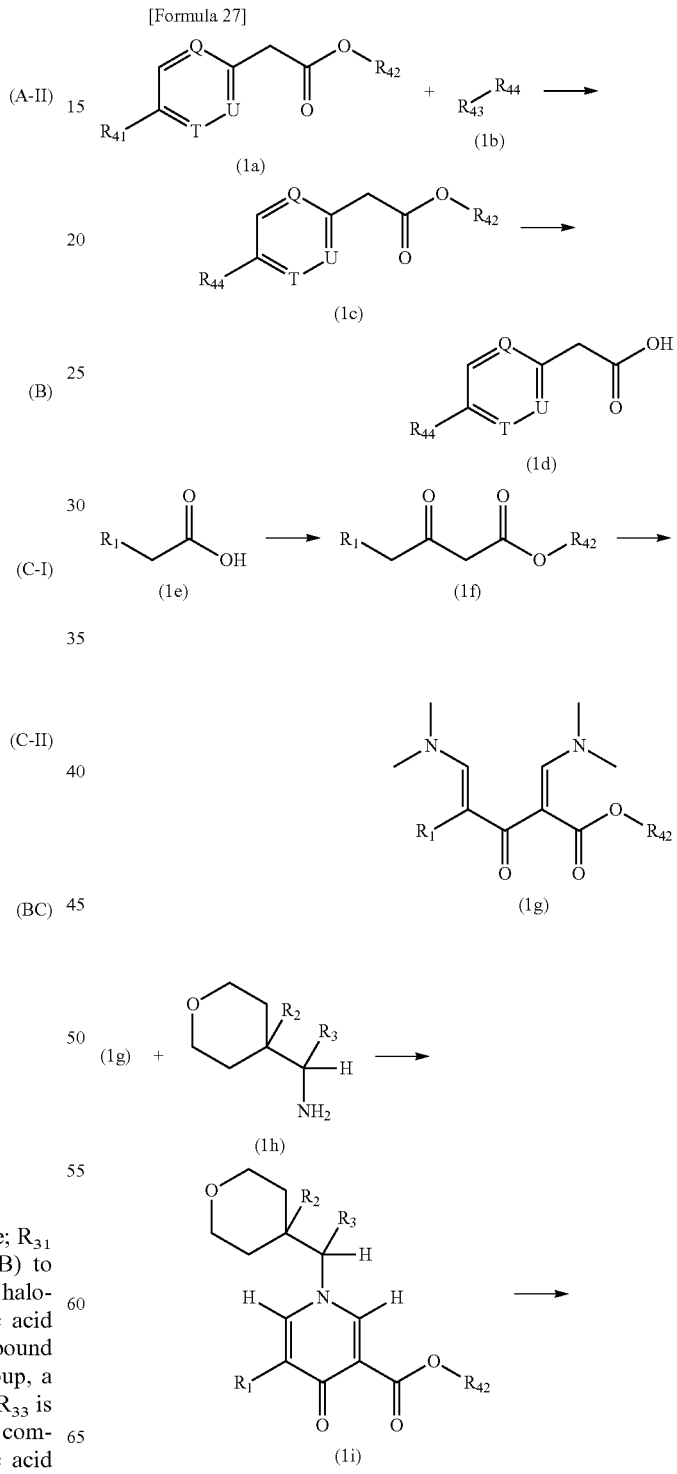

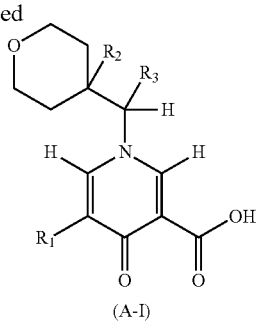

(A-I)

wherein $R_1$ to $R_3$, Q, T, and U are as defined above; $R_{41}$ represents a halogen group; $R_{42}$ is a protecting group for the carboxylic acid and represents a $C_1$-$C_6$ alkyl group; $R_{43}$ represents boronic acid or boronic acid ester; and $R_{44}$ represents a $C_1$-$C_6$ alkyl group or a cyclo-$C_3$-$C_6$ alkyl group. Compound (1d) is included in compound (1e).

Synthesis of Compound (1c)

Commercially available or appropriately synthesized compound (1a) can be subjected to a coupling reaction with commercially available compound (1b) or compound (1b) synthesized by a method shown in production process 4, production process 5, or production process 6 in the presence of an organic or inorganic base such as potassium carbonate, sodium carbonate, cesium carbonate, potassium acetate, potassium phosphate, tert-butoxide, or triethylamine, and a transition metal catalyst such as tris(dibenzylideneacetone)-dipalladium(0), tetrakis(triphenylphosphine)palladium(0), palladium(II) bis(triphenylphosphine)chloride, palladium(II) [1,1'-bis(diphenylphosphino)-ferrocene]chloride-dichloromethane complex, palladium(II) acetate, copper(I) iodide, or copper(I) chloride to obtain compound (1c). The reaction can also be carried out in the presence of a ligand such as triphenylphosphine, tricyclohexylphosphine, dibenzylideneacetone, 1,3-bis(diphenylphosphino)propane, 2-dicyclohexylphosphino-2',4',6'-triisopropylbiphenyl, or 4,5-bis(diphenylphosphino)-9,9-dimethylxanthene. The reaction can also be carried out using two or more types of transition metal catalysts in combination. Examples of the solvent include, but are not particularly limited to, 1,4-dioxane, 1,2-dimethoxyethane, methanol, toluene, water, and mixed solvents thereof. The reaction temperature is usually in the range of 0° C. to 200° C. or the boiling point of the solvent, preferably in the range of 0° C. to the boiling point of the solvent. The treatment mentioned above can also be carried out with a microwave in a sealed tube. The organic or inorganic base can be used at 1 to excess molar equivalents, preferably 1 to 5 molar equivalents, with respect to compound (1a). The transition metal catalyst or the ligand can be used at 0.001 to 1 molar equivalents, preferably 0.05 to 1 molar equivalents, with respect to compound (1c). The boronic acid ester can be used at 1 to excess molar equivalents, preferably 1 to 5 molar equivalents, with respect to compound (1c).

Synthesis of Compound (1d)

Compound (1c) can be hydrolyzed with an acid such as sulfuric acid or hydrochloric acid, or an alkali such as sodium hydroxide or potassium carbonate to obtain compound (1d). The base or the acid can be used at 1 to excess molar equivalents with respect to compound (1c). Examples of the solvent for use in the reaction include, but are not particularly limited to, methanol, ethanol, propanol, water, and mixed solvents thereof. The reaction temperature is usually in the range of 0° C. to 200° C. or the boiling point of the solvent, preferably in the range of 0° C. to the boiling point of the solvent.

Synthesis of Compound (1f)

Commercially available or appropriately synthesized compound (1e) can be activated and reacted with malonic acid monoester or a salt thereof in the presence of magnesium chloride to obtain compound (1f). Examples of the method for activating carboxylic acid can include a method using 1,1'-carbonyldiimidazole and a method mediated by acid chloride. A base can be added, if necessary, to the reaction system. Examples of the base can include triethylamine. The base can be used at 1 to excess molar equivalents, preferably 2 to 10 molar equivalents, with respect to compound (1e). Examples of the solvent for use in the reaction include, but are not particularly limited to, tetrahydrofuran, dioxane, acetonitrile, N,N-dimethylformamide, toluene, and mixed solvents thereof. The reaction temperature is usually in the range of −78° C. to 100° C. or the boiling point of the solvent, preferably in the range of approximately room temperature to 100° C.

Synthesis of Compound (1g)

Compound (1f) can be treated with N,N-dimethylformamide dimethyl acetal to obtain compound (1g). The N,N-dimethylformamide dimethyl acetal can be used at 2 to excess molar equivalents with respect to compound (1f). Examples of the solvent for use in the reaction include, but are not particularly limited to, toluene, xylene, dichloromethane, ethanol, N,N-dimethylformamide, ethyl acetate, and mixed solvents thereof. Alternatively, the reaction is carried out without the solvent. The reaction temperature is usually in the range of 0° C. to 300° C., preferably in the range of approximately room temperature to 130° C.

Synthesis of Compound (1i)

Compound (1g) can be treated with commercially available or appropriately synthesized compound (1h) to obtain compound (1i). Examples of the solvent for use in the reaction include, but are not particularly limited to, toluene, ethyl acetate, ethanol, 1,4-dioxane, and mixed solvents thereof. The reaction temperature is usually in the range of −78° C. to 130° C. or the boiling point of the solvent, preferably in the range of approximately room temperature to the boiling point of the solvent. The reaction can be carried out, if necessary, by the addition of an organic or inorganic base such as potassium carbonate, cesium carbonate, potassium tert-butoxide, or triethylamine, or an acid such as acetic acid, hydrogen chloride, hydrogen bromide, or sulfuric acid. The compound (1h), the base, or the acid can be used at 1 to excess molar equivalents, preferably 1 to 5 molar equivalents, with respect to compound (1g).

Synthesis of Compound (A-I)

Compound (A-I) can be obtained by the same operation as in the synthesis of compound (1d).

[Production Process 2]

Compound (1i) can also be synthesized by, but not particularly limited to, a method as shown in the following reaction scheme 2:

Reaction scheme 2

[Formula 28]

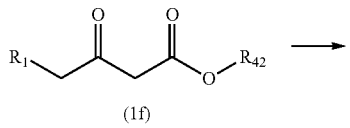

(1f)

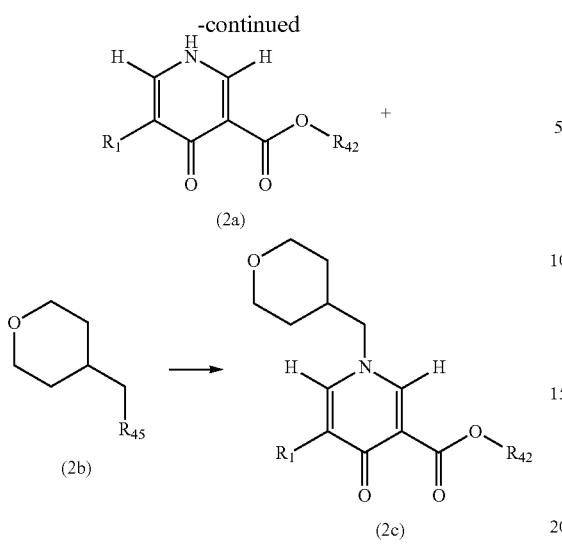

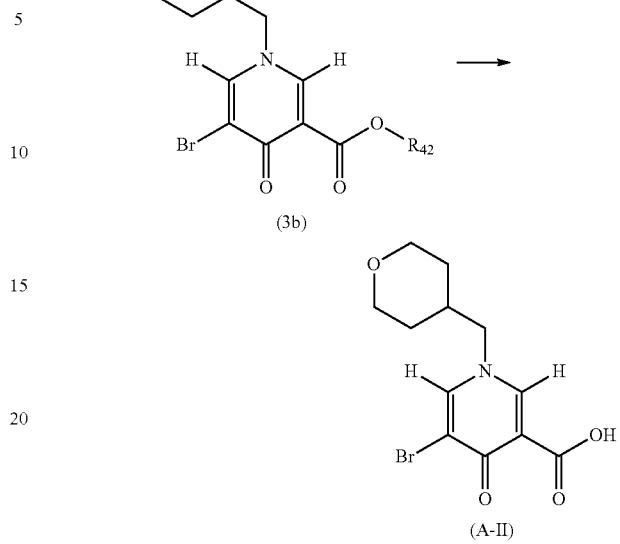

wherein $R_1$ and $R_{42}$ are as defined above; and $R_{45}$ represents a halogen group, a methanesulfonyloxy group, a trifluoromethanesulfonyloxy group, or a p-toluenesulfonyloxy group. Compound (2c) is included in compound (1i) Synthesis of compound (2a)

Compound (2a) is commercially available or can be synthesized from compound (1f) with reference to previous reports such as J. Heterocyclic Chem. 17, 359 (1980) and Chem. Pharm. Bull. 43, 450 (1995).

Synthesis of Compound (2c)

Compound (2a) can be treated with compound (2b) in the presence of an organic or inorganic base such as potassium carbonate, cesium carbonate, potassium tert-butoxide, or triethylamine to obtain compound (2c). Examples of the solvent for use in the reaction include, but are not particularly limited to, N,N-dimethylformamide, dimethyl sulfoxide, acetonitrile, and mixed solvents thereof. The reaction temperature is usually in the range of 0° C. to 200° C. or the boiling point of the solvent, preferably in the range of 0° C. to the boiling point of the solvent. The compound (2b) or the base can be used at 1 to excess molar equivalents, preferably 1 to 5 molar equivalents, with respect to compound (2a).

Next, the method for synthesizing compound (A-II) will be described.

[Production Process 3]

Compound (A-II) can be synthesized by, but not particularly limited to, a method as shown in the following reaction scheme 3:

Reaction scheme 3

[Formula 29]

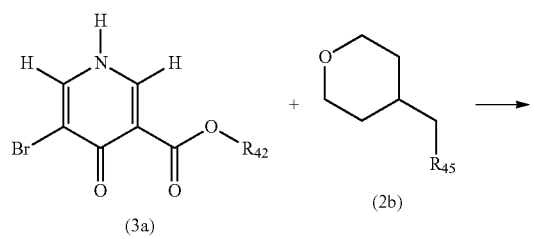

wherein $R_{42}$ and $R_{45}$ are as defined above.

Synthesis of Compound (3b)

Commercially available compound (3a) or compound (3a) that can be readily synthesized with reference to previous reports such as J. Med. Chem. 51, 5330 (2008) can be treated with compound (2b) in the presence of an organic or inorganic base such as potassium carbonate, cesium carbonate, potassium tert-butoxide, or triethylamine to obtain compound (3b). Examples of the solvent for use in the reaction include, but are not particularly limited to, N,N-dimethylformamide, dimethyl sulfoxide, acetonitrile, and mixed solvents thereof. The reaction temperature is usually in the range of 0° C. to 200° C. or the boiling point of the solvent, preferably in the range of 0° C. to the boiling point of the solvent. The compound (2b) or the base can be used at 1 to excess molar equivalents, preferably 1 to 5 molar equivalents, with respect to compound (3a).

Synthesis of Compound (A-II)

Compound (A-II) can be obtained by the same operation as in the synthesis of compound (A-I) in [Production process 1].

Next, the method for synthesizing compound (C-I) will be described.

When $R_5$ is a hydrogen atom, compound (C-I) is commercially available or can be readily synthesized from a commercially available product by a method known in the literature.

When $R_5$ is a group other than a hydrogen atom, compound (C-I) can be synthesized by a method as shown in production process 4 to production process 7 given below. Specifically, compound (4c), compound (5h), or compound (6c) constituting $R_5$ is synthesized by selecting any of the methods shown in production process 4 to production process 6. Then, compound (C-I) can be synthesized by production process 7 using the compound thus synthesized or a commercially available compound, though the synthesis method is not particularly limited thereto.

[Production Process 4]

Reaction scheme 4

[Formula 30]

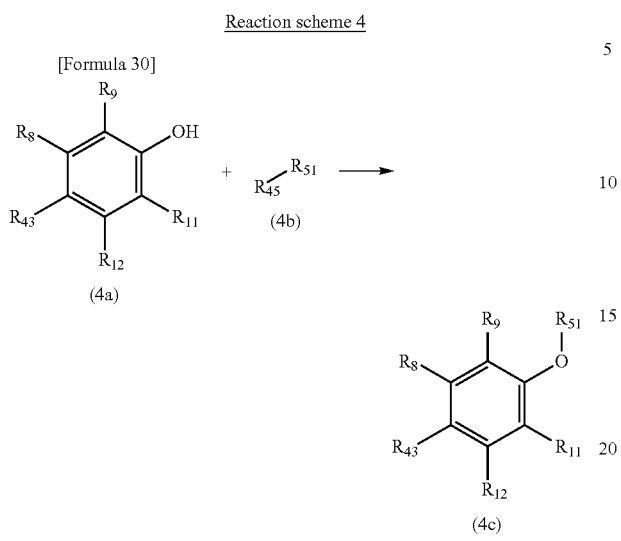

wherein $R_8$, $R_9$, $R_{11}$, $R_{12}$, $R_{43}$, and $R_{45}$ are as defined above; and $R_{51}$ represents a $C_1$-$C_6$ alkyl group optionally substituted by a heterocycloalkyl group.

Synthesis of Compound (4c)

Commercially available or appropriately synthesized compound (4a) can be treated with compound (4b) in the presence of an organic or inorganic base such as potassium carbonate, cesium carbonate, potassium tert-butoxide, or triethylamine to obtain compound (4c). Examples of the solvent for use in the reaction include, but are not particularly limited to, N,N-dimethylformamide, dimethyl sulfoxide, acetonitrile, and mixed solvents thereof. The reaction temperature is usually in the range of 0° C. to 200° C. or the boiling point of the solvent, preferably in the range of 0° C. to the boiling point of the solvent. The compound (4b) or the base can be used at 1 to excess molar equivalents, preferably 1 to 5 molar equivalents, with respect to compound (4a).

[Production Process 5]

Reaction scheme 5

[Formula 31]

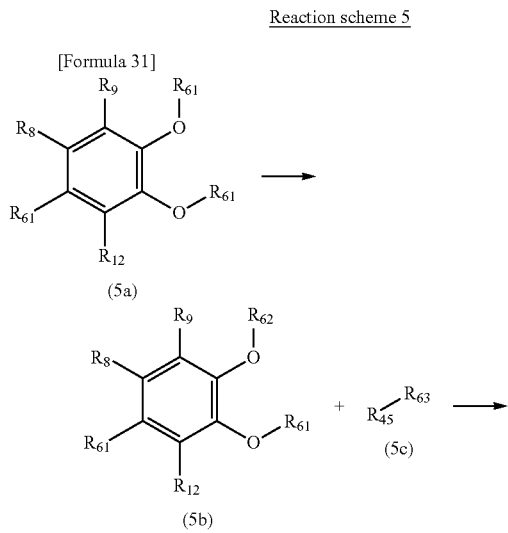

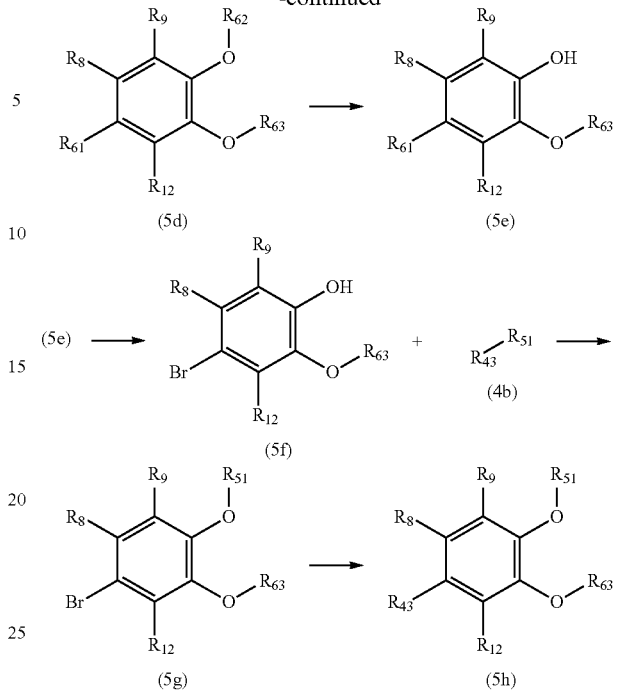

wherein $R_8$, $R_9$, $R_{12}$, $R_{43}$, $R_{45}$, and $R_{51}$ are as defined above; $R_{61}$ represents a deuterium or hydrogen atom; $R_{62}$ represents a hydroxy group or a deuterium-substituted protecting group for the hydroxy group, wherein examples of the protecting group include ether groups typified by a tetrahydropyranyl group, silyl groups typified by a t-butyldiphenylsilyl group, ester groups typified by an acetyl group, and carbonate groups typified by a vinyl carbonate group; and $R_{63}$ represents a deuterium-substituted $C_1$-$C_6$ alkyl group.

Synthesis of Compound (5b)

Only one of the two hydroxy groups in commercially available or appropriately synthesized compound (5a) can be protected to obtain compound (5b). For example, compound (5a) can be treated with 3,4-dihydro-2H-pyran in the presence of an acid such as p-toluenesulfonic acid pyridine salt to obtain compound (5b) with only one of the hydroxy groups protected with a tetrahydropyranyl group, though the method for protecting the hydroxy group is not particularly limited thereto. Examples of the solvent for use in the reaction include, but are not particularly limited to, dichloromethane, chloroform, toluene, and mixed solvents thereof. The reaction temperature is usually in the range of 0° C. to 200° C. or the boiling point of the solvent, preferably in the range of 0° C. to the boiling point of the solvent. Compound (4b) or the acid can be used at 0.01 to excess molar equivalents, preferably 0.01 to 1 molar equivalents, with respect to compound (5a).

Synthesis of Compound (5d)

Compound (5b) can be treated with compound (5c) in the presence of an organic or inorganic base such as potassium carbonate, cesium carbonate, potassium tert-butoxide, or triethylamine to obtain compound (5d). Examples of the solvent for use in the reaction include, but are not particularly limited to, N,N-dimethylformamide, dimethyl sulfoxide, acetonitrile, acetone, and mixed solvents thereof. The reaction temperature is usually in the range of 0° C. to 200° C. or the boiling point of the solvent, preferably in the range of 0° C. to the boiling point of the solvent. The compound (5c) or the base can be used at 1 to excess molar equivalents, preferably 1 to 5 molar equivalents, with respect to compound (5b).

Synthesis of Compound (5e)

Compound (5d) can be treated with an acid such as hydrochloric acid, acetic acid, or p-toluenesulfonic acid pyridine salt to obtain compound (5e). Examples of the solvent for use in the reaction include, but are not particularly limited to, ethanol, methanol, isopropanol, water, and mixed solvents thereof. The reaction temperature is usually in the range of 0° C. to 200° C. or the boiling point of the solvent, preferably in the range of 0° C. to the boiling point of the solvent. The compound (4b) or the acid can be used at 0.01 to excess molar equivalents, preferably 0.01 to 1 molar equivalents, with respect to compound (5d).

Synthesis of Compound (5f)

Compound (5e) can be treated with a brominating reagent such as N-bromosuccinimide or potassium bromate to obtain compound (5f). Examples of the solvent for use in the reaction include, but are not particularly limited to, N,N-dimethylformamide, a 30% solution of hydrobromic acid in acetic acid, acetic acid, and mixed solvents thereof. The reaction temperature is usually in the range of 0° C. to 200° C. or the boiling point of the solvent, preferably in the range of 0° C. to the boiling point of the solvent. The brominating reagent can be used at 0.1 to excess molar equivalents, preferably 0.1 to 5 molar equivalents, with respect to compound (5e).

Synthesis of Compound (5g)

Compound (5g) can be obtained by the same operation as in [Production process 4].

Synthesis of Compound (5h)

Compound (5g) can be treated with boronic acid ester such as bis(pinacolato)diboron or pinacol boron in the presence of an organic or inorganic base such as potassium carbonate, sodium carbonate, cesium carbonate, potassium acetate, potassium phosphate, tert-butoxide, or triethylamine, a transition metal catalyst such as tris(dibenzylideneacetone)-dipalladium(0), palladium(II) bis(triphenylphosphine)chloride, palladium(II) [1,1'-bis(diphenylphosphino)-ferrocene]chloride-dichloromethane complex, palladium(II) [1,1'-bis(diphenylphosphino)-ferrocene]chloride-dichloromethane complex, or nickel(II) 1,3-bis(diphenylphosphino)propane]chloride, and a ligand such as triphenylphosphine, tricyclohexylphosphine, dibenzylideneacetone, 1,3-bis(diphenylphosphino)propane, 2-dicyclohexylphosphino-2',4',6'-triisopropylbiphenyl, or 4,5-bis(diphenylphosphino)-9,9-dimethylxanthene to obtain compound (5h). Examples of the solvent include, but are not particularly limited to, 1,4-dioxane, 1,2-dimethoxyethane, methanol, toluene, and mixed solvents thereof. The reaction temperature is usually in the range of 0° C. to 200° C. or the boiling point of the solvent, preferably in the range of 0° C. to the boiling point of the solvent. The treatment mentioned above can also be carried out with a microwave in a sealed tube. The organic or inorganic base can be used at 1 to excess molar equivalents, preferably 1 to 5 molar equivalents, with respect to compound (5g). The transition metal catalyst or the ligand can be used at 0.001 to 1 molar equivalents, preferably 0.05 to 1 molar equivalents, with respect to compound (5g). The boronic acid ester can be used at 1 to excess molar equivalents, preferably 1 to 5 molar equivalents, with respect to compound (5g).

[Production Process 6]

Reaction scheme 6

[Formula 32]

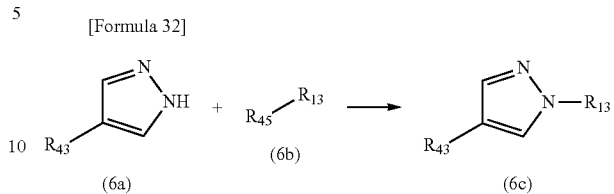

wherein $R_{13}$, $R_{43}$, and $R_{45}$ are as defined above.

Synthesis of Compound (6c)

Compound (6c) can be obtained by the same operation as in [Production process 4] using commercially available or appropriately synthesized compounds (6a) and (6b).

[Production Process 7]

Reaction scheme 7

[Formula 33]

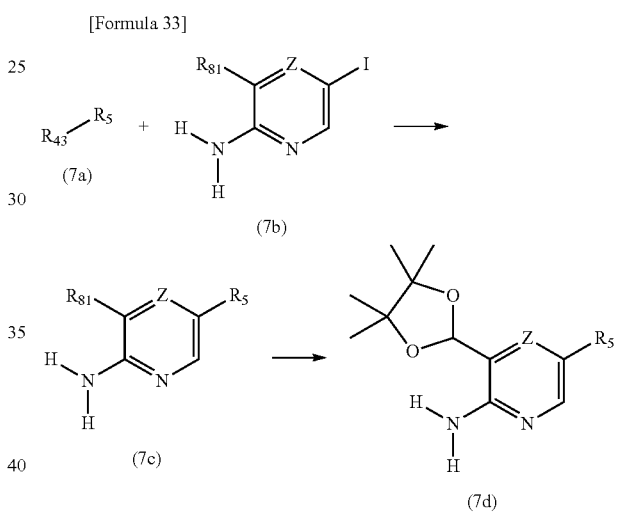

wherein $R_5$ and $R_{43}$ are as defined above; and $R_{81}$ represents a halogen group. Compound (7a) is a boronic acid or boronic acid ester compound containing compound (4c), compound (5h), or compound (6c). Compound (7c) and compound (7d) are included in compound (C-I).

Synthesis of Compound (7c)

Compound (7b) can be subjected to coupling reaction with commercially available compound (7a) or compound (7a) synthesized by a method shown in production process 4, production process 5, or production process 6 in the same way as in the synthesis of compound (1c) in [Production process 1] to obtain compound (7c).

Synthesis of Compound (7d)

Compound (7d) can be obtained by the same operation as in the synthesis of compound (5h) in [Production process 5]using commercially available or appropriately synthesized compound (7c).

Next, the method for synthesizing a compound (B)-compound (C-I) complex will be described.

The compound (B)-compound (C-I) complex can be synthesized by a method for converting the bromine group in compound (BC) to $R_5$ as shown in [Production process 8], though the synthesis method is not particularly limited thereto.

[Production Process 8]

Reaction scheme 8

[Formula 34]

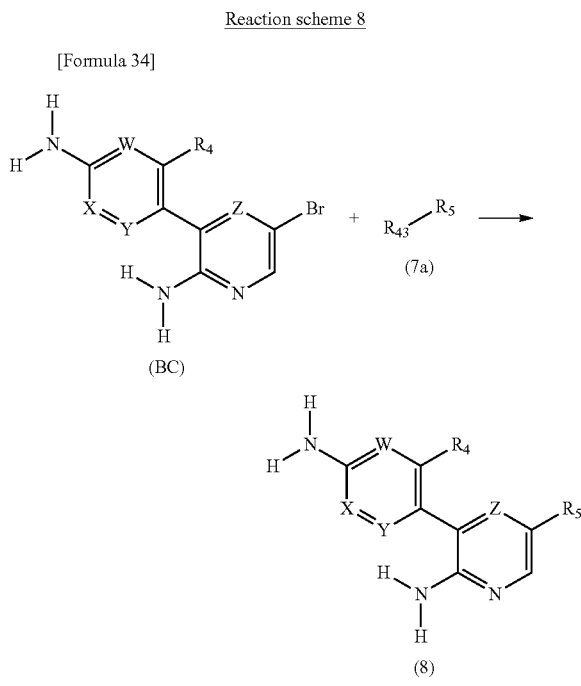

wherein $R_4$, $R_5$, W, X, Y, Z, and $R_{43}$ are as defined above. Compound (8) is included in the compound (B)-compound (C-I) complex.

Compound (8) can be obtained by the same operation as in the synthesis of compound (1c) in [Production process 1] using commercially available or appropriately synthesized compound (BC) or compound (8).

Compound (8) can also be synthesized by a method shown in [Production process 9] or [Production process 10], though the synthesis method is not particularly limited thereto.

[Production Process 9]

Reaction scheme 9

[Formula 35]

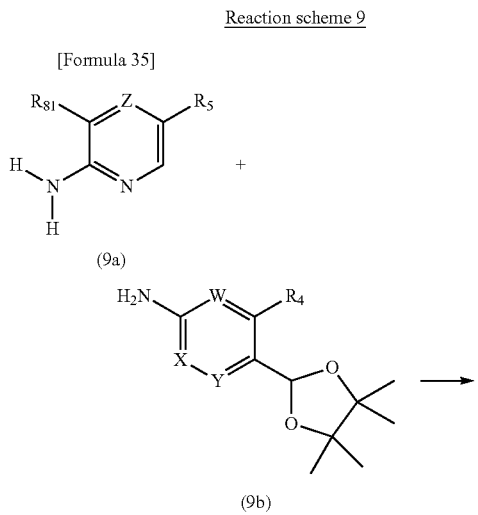

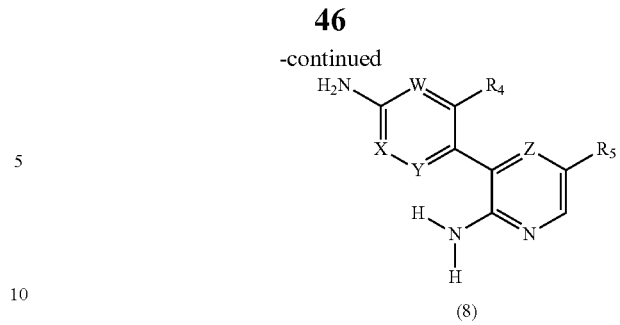

wherein $R_4$, $R_5$, W, X, Y, Z, and $R_{81}$ are as defined above. Compound (8) is included in the compound (B)-compound (C-I) complex.

Compound (8) can be obtained by the same operation as in the synthesis of compound (1c) in [Production process 1] using commercially available or appropriately synthesized compounds (9a) and (9b).

[Production Process 10]

Reaction scheme 10

[Formula 36]

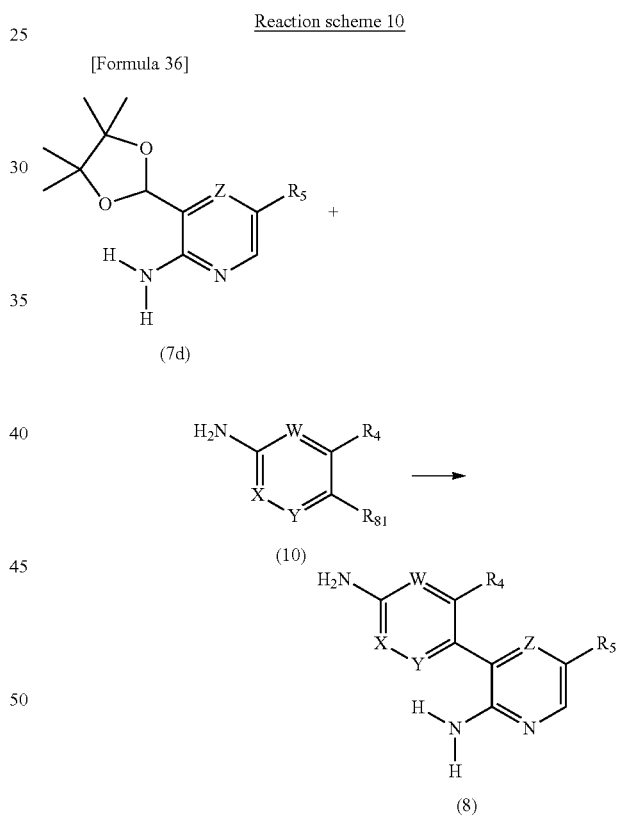

wherein $R_4$, $R_5$, W, X, Y, Z, and $R_{81}$ are as defined above. Compound (8) is included in the compound (B)-compound (C-I) complex.

Compound (8) can be obtained by the same operation as in the synthesis of compound (1c) in [Production process 1] using commercially available or appropriately synthesized compound (7d) and compound (10).

Next, the synthesis method for bonding the compound (B)-compound (C-I) complex to compound (A-I) will be described.

The compound (B)-compound (C-I) complex can be bonded to compound (A-I) according to the following production process 11 or production process 12:

[Production Process 11]

Compound (11) can be synthesized by, but not particularly limited to, a method as shown in the following reaction scheme 11:

Reaction scheme 11

[Formula 37]

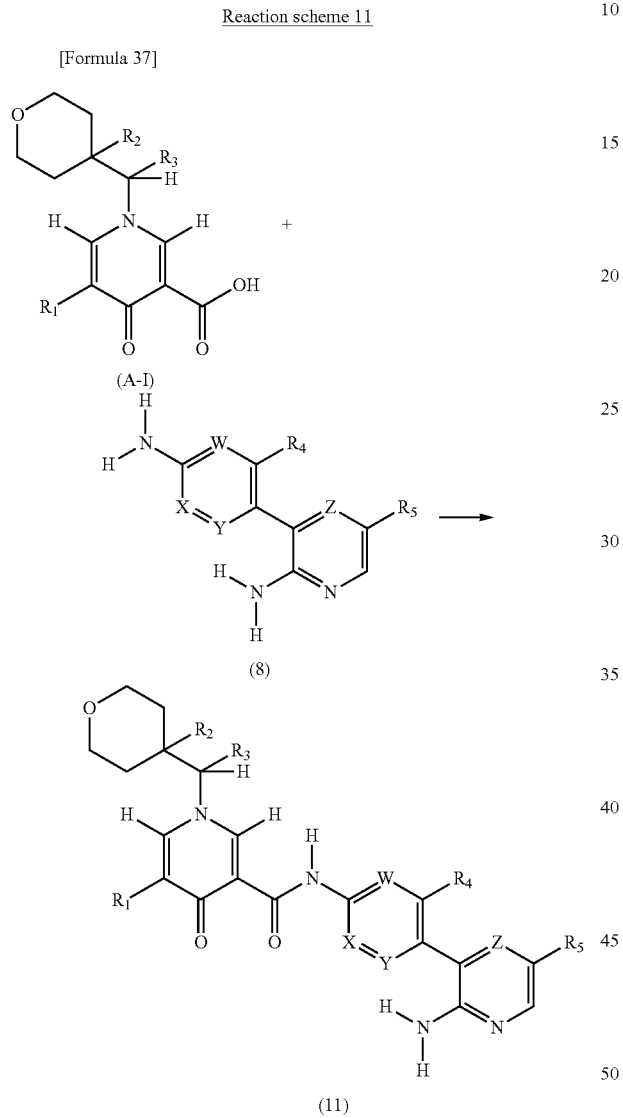

wherein $R_1$ to $R_5$, W, X, Y, and Z are as defined above. Compound (8) is included in the compound (B)-compound (C-I) complex.

Compound (A-I) can be reacted with compound (8) in the presence of a condensing agent to obtain compound (11). Examples of the condensing agent include, but are not limited to, N-[1-(cyano-2-ethoxy-2-oxoethylideneaminooxy)dimethylamino(morpholino)]uronium hexafluorophosphate (COMU). Examples of the solvent for use in the reaction include, but are not particularly limited to, N,N-dimethylformamide, dichloromethane, and mixed solvents thereof. The reaction temperature is usually in the range of −78° C. to 200° C. or the boiling point of the solvent, preferably in the range of 0° C. to 100° C. The condensing agent can be used at 1 to excess molar equivalents, preferably 1 to 5 molar equivalents, with respect to compound (A-I).

[Production Process 12]

Compound (11) can be synthesized by, but not particularly limited to, a method as shown in the following reaction scheme 12:

Reaction scheme 12

[Formula 38]

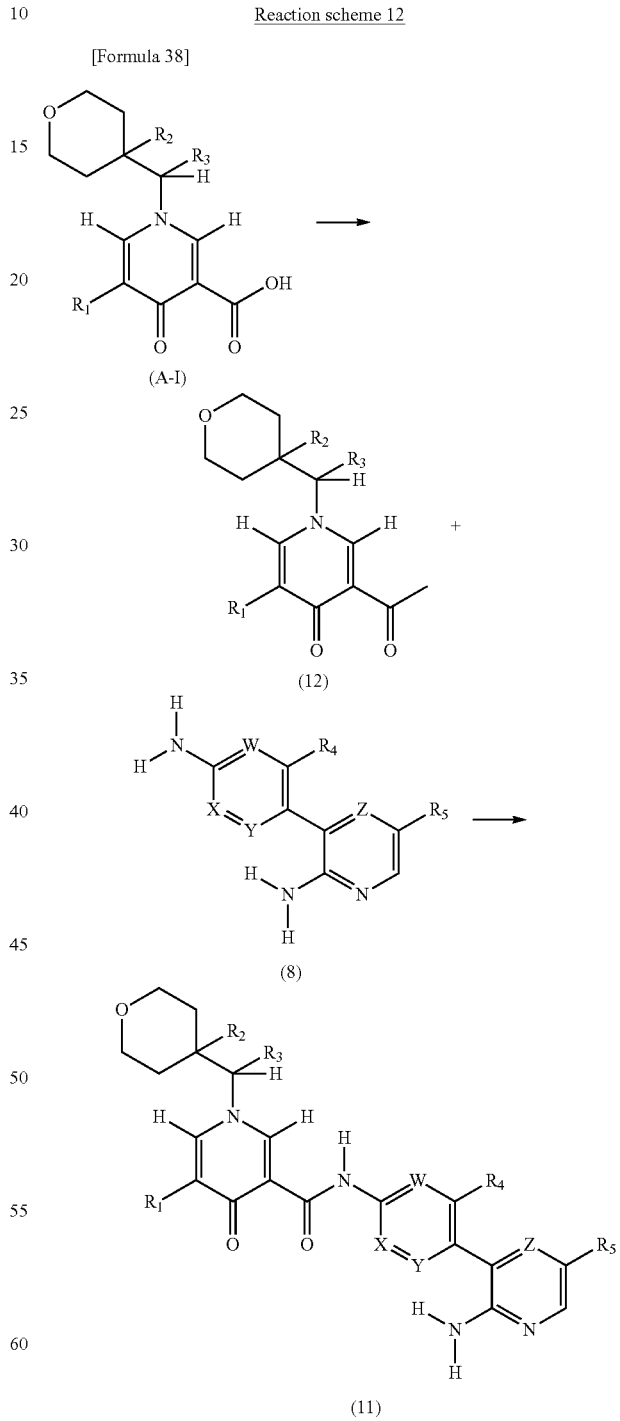

wherein $R_1$ to $R_5$, W, X, Y, and Z are as defined above. Compound (8) is included in the compound (B)-compound (C-I) complex.

Compound (A-I) can be treated with an acid halogenating reagent such as thionyl chloride or oxalyl chloride to obtain compound (12), which is then treated with compound (8) to obtain compound (11). Examples of the solvent for use in the reaction include, but are not particularly limited to, dichloromethane, dichloroethane, and mixed solvents thereof. The acid halogenating reagent can be used at 0.9 to excess molar equivalents, preferably 0.9 to 2 molar equivalents, with respect to compound (A-I).

Next, the method for synthesizing the compound (A-I)-compound (B) complex will be described.

[Production Process 13]

Compound (13) can be synthesized by, but not particularly limited to, a method as shown in the following reaction scheme 13.

Reaction scheme 13

[Formula 39]

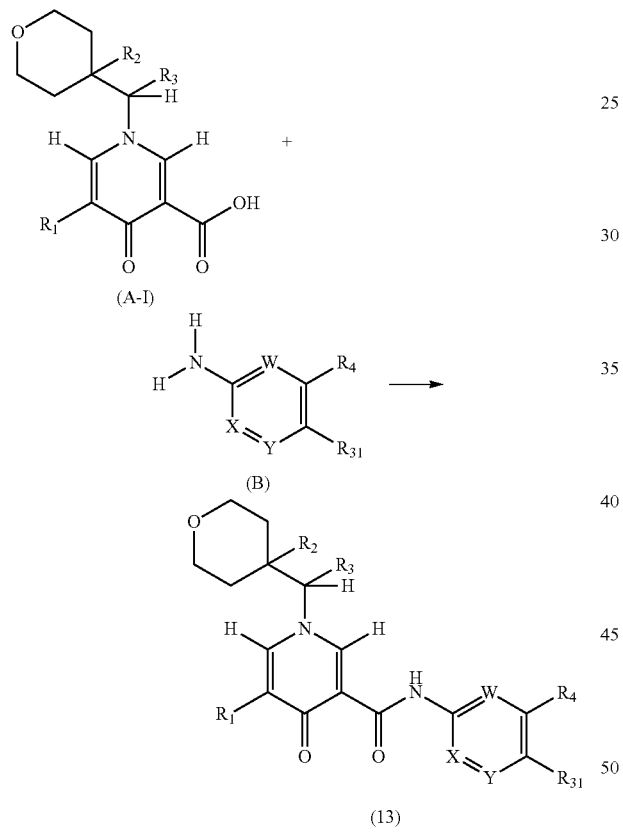

wherein $R_1$ to $R_4$, W, X, Y, and $R_{31}$ are as defined above. Compound (13) is included in the compound (A-I)-compound (B) complex.

Synthesis of Compound (13)

Compound (B) is commercially available or can be readily synthesized from a commercially available product by a method known in the literature. Compound (13) can be obtained by the same operation as in [Production process 11] using compound (A-I) and commercially available or appropriately synthesized compound (B).

Next, the synthesis method for bonding the compound (A-I)-compound (B) complex to compound (C-I) will be described.

[Production Process 14]

Compound (11) can be synthesized by, but not particularly limited to, a method as shown in the following reaction scheme 14:

Reaction scheme 14

[Formula 40]

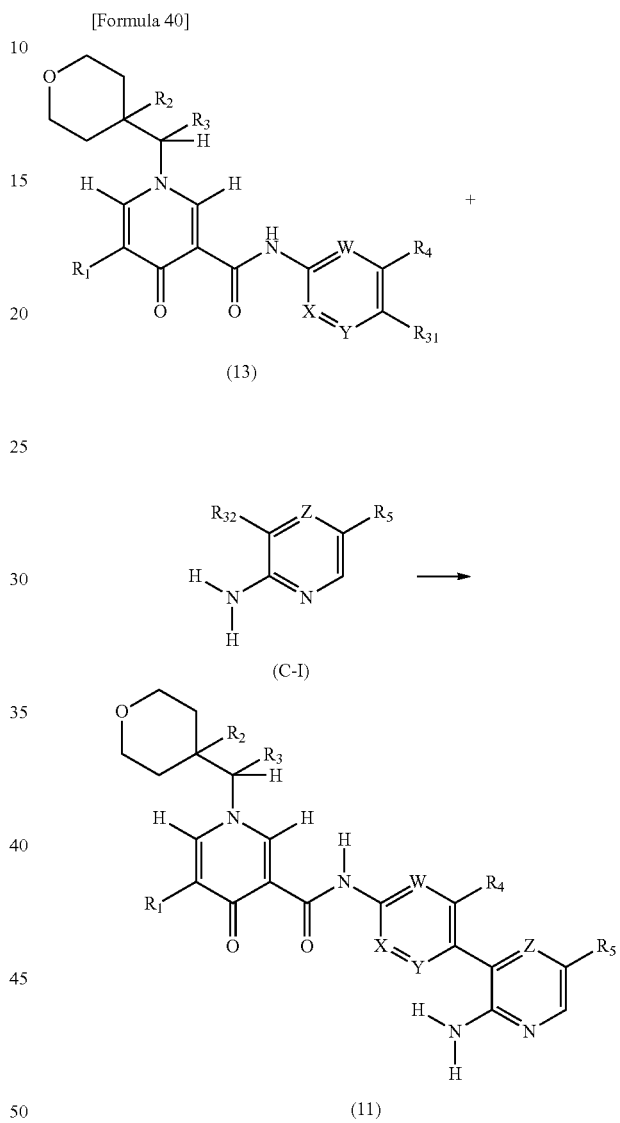

wherein $R_1$ to $R_5$, W, X, Y, and Z are as defined above; when $R_{31}$ is a halogen group, a triflate group, or the like, $R_{32}$ represents boronic acid or boronic acid ester; and when $R_{31}$ is boronic acid or boronic acid ester, $R_{32}$ represents a halogen group, a triflate group, or the like. Compound (13) is included in the compound (A-I)-compound (B) complex.

Synthesis of Compound (11)

Compound (11) can be obtained by the same operation as in the synthesis of compound (1c) in [Production process 1] using compound (13) and commercially available or appropriately synthesized compound (C-I).

Next, the synthesis method for bonding the compound (B)-compound (C-I) complex to compound (A-II) will be described.

[Production Process 15]

Compound (15) can be synthesized by, but not particularly limited to, a method as shown in the following reaction scheme 15:

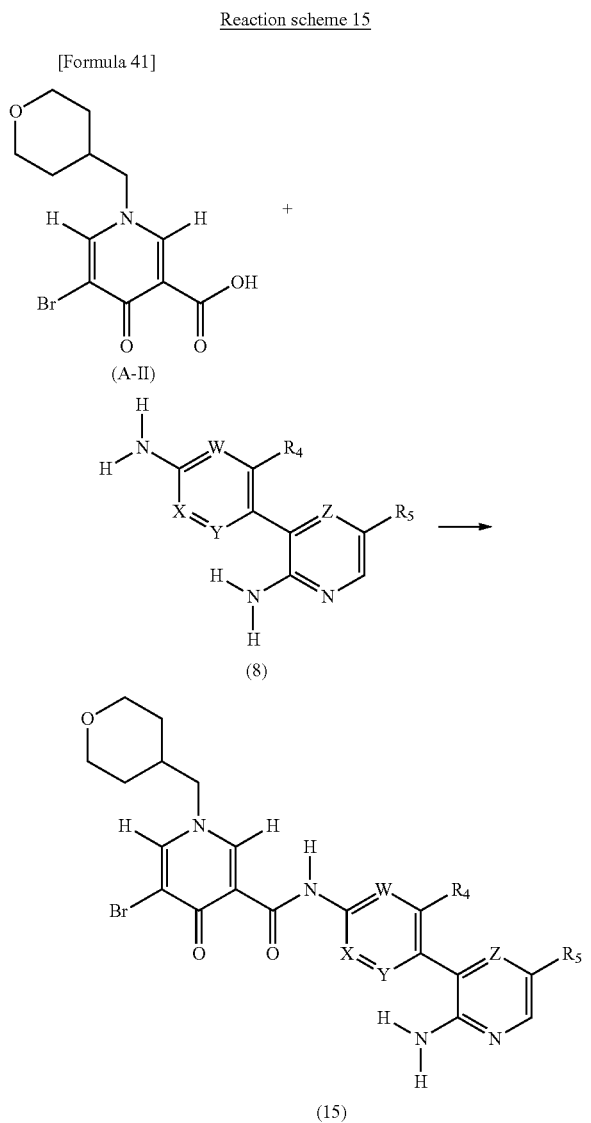

wherein $R_4$ to $R_5$, W, X, Y, and Z are as defined above. Compound (8) is included in the compound (B)-compound (C-I) complex.

Synthesis of Compound (15)

Compound (15) can be obtained by the same operation as in [Production process 11] using compound (A-II) and compound (8).

Next, the synthesis method for converting the bromine group in the compound (A-II)-compound (B)-compound (C-I) complex to $R_1$ will be described.

[Production Process 16]

Compound (16b) can be synthesized by, but not particularly limited to, a method as shown in the following reaction scheme 16:

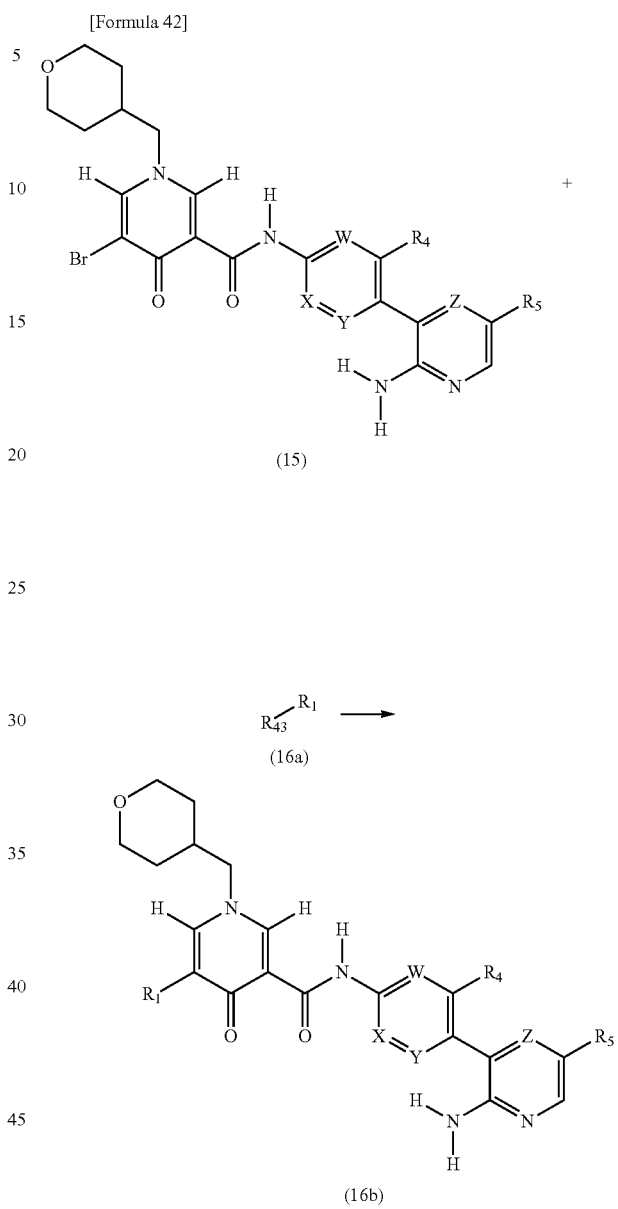

wherein $R_1$, $R_4$ to $R_5$, W, X, Y, Z, and $R_{43}$ are as defined above. Compound (15) is included in the compound (A-I)-compound (B)-compound (C-I) complex.

Synthesis of Compound (16b)

Compound (16b) can be obtained by the same operation as in the synthesis of compound (1c) in [Production process 1] using compound (15) and commercially available or appropriately synthesized compound (16a).

Next, the synthesis method for converting the halogen group in the compound (A-I)-compound (B)-compound (C-I) complex to an alkyl group will be described.

[Production Process 17]

Compound (17b) can be synthesized by, but not particularly limited to, a method as shown in the following reaction scheme 17:

Reaction scheme 17

[Formula 43]

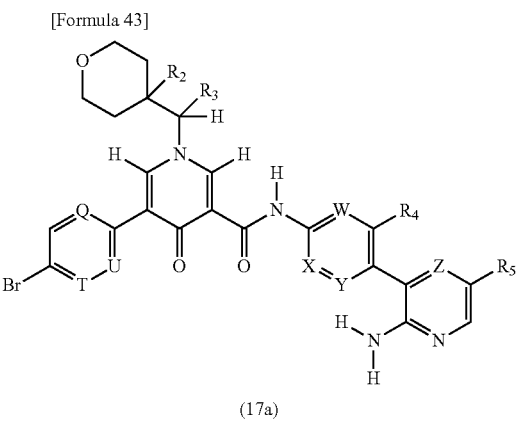

(17a)

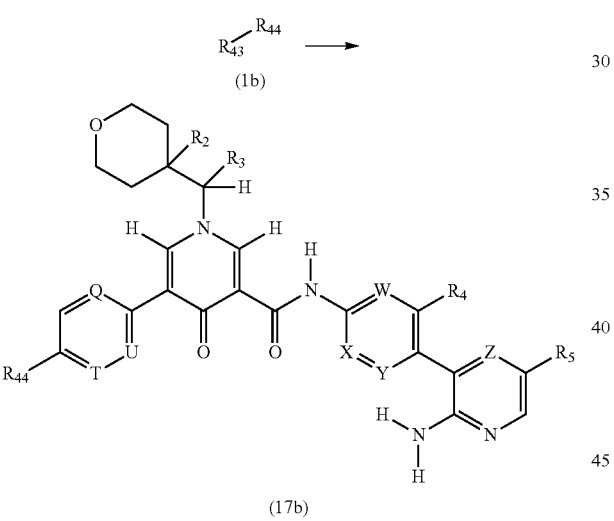

(17b)

wherein $R_2$ to $R_5$, Q, T, U, W, X, Y, Z, $R_{43}$, and $R_{44}$ are as defined above. Compound (17a) and compound (17b) are included in the compound (A-I)-compound (B)-compound (C-I) complex.

Synthesis of Compound (17b)

Compound (17b) can be obtained by the same operation as in the synthesis of compound (1c) in [Production process 1] using compound (17a) and commercially available or appropriately synthesized compound (1b).

Next, the synthesis method for bonding compound (A-I) to compound (BC) and then converting the bromine group to $R_5$ will be described.

[Production Process 18]

Compound (11) can be synthesized by, but not particularly limited to, a method as shown in the following reaction scheme 18:

Reaction scheme 18

[Formula 44]

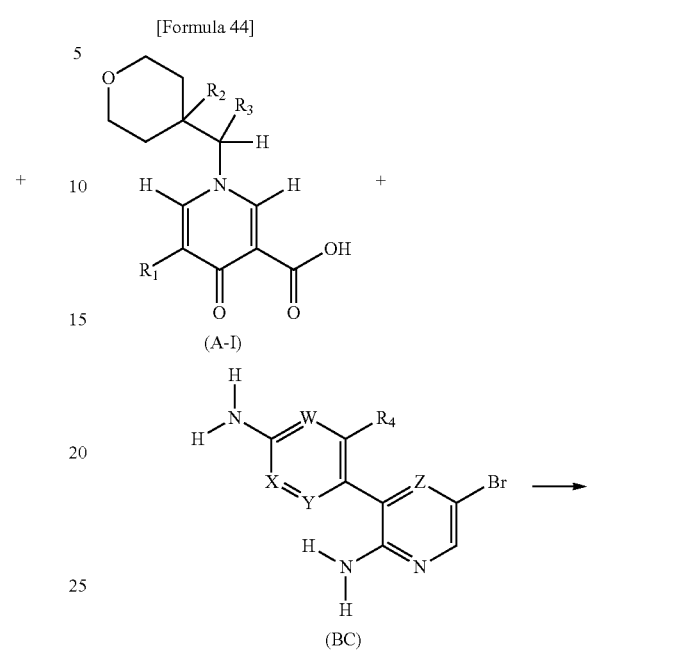

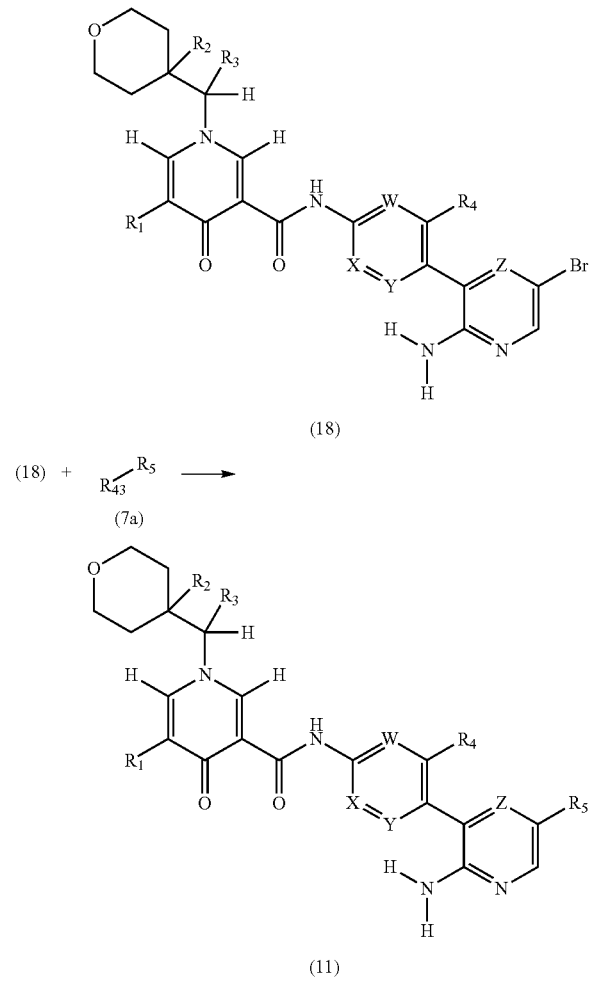

wherein $R_1$ to $R_5$, W, X, Y, Z, and $R_{43}$ are as defined above.

Synthesis of Compound (18)

Compound (18) can be obtained by the same operation as in [Production process 19] using compound (A-I) and compound

[Production Process 19]

Reaction scheme 19

[Formula 45]

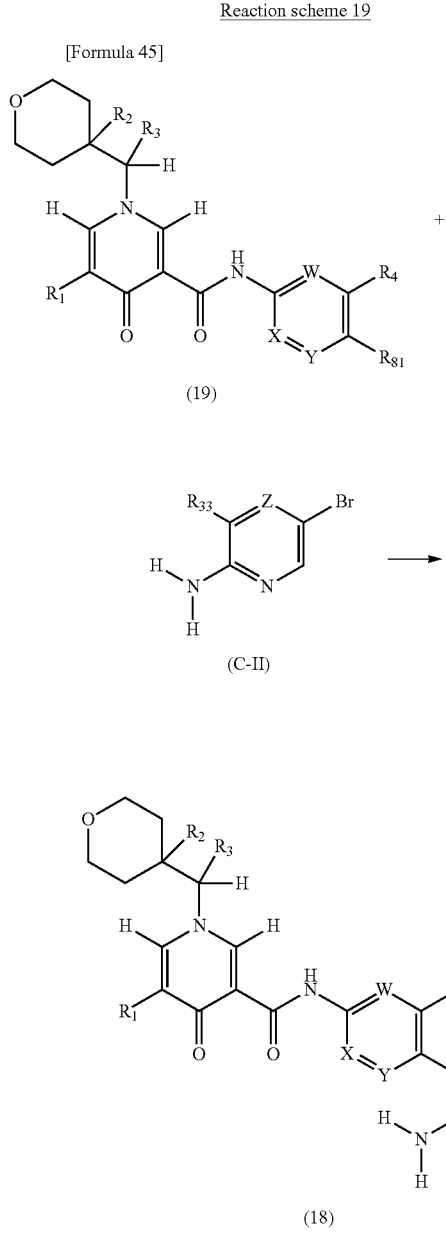

wherein $R_1$ to $R_4$, $R_{33}$, $R_{81}$, W, X, Y, and Z are as defined above. Compound (19) is included in compound (13).

Compound (C-II) is commercially available or can be readily synthesized from a commercially available product by a method known in the literature. Compound (18) can be obtained by the same operation as in the synthesis of compound (1c) in [Production process 1] using compound (19) and commercially available or appropriately synthesized compound (C-II).

Compound (11) can also be produced according to production process 20.

[Production Process 20]

Reaction scheme 20

[Formula 46]

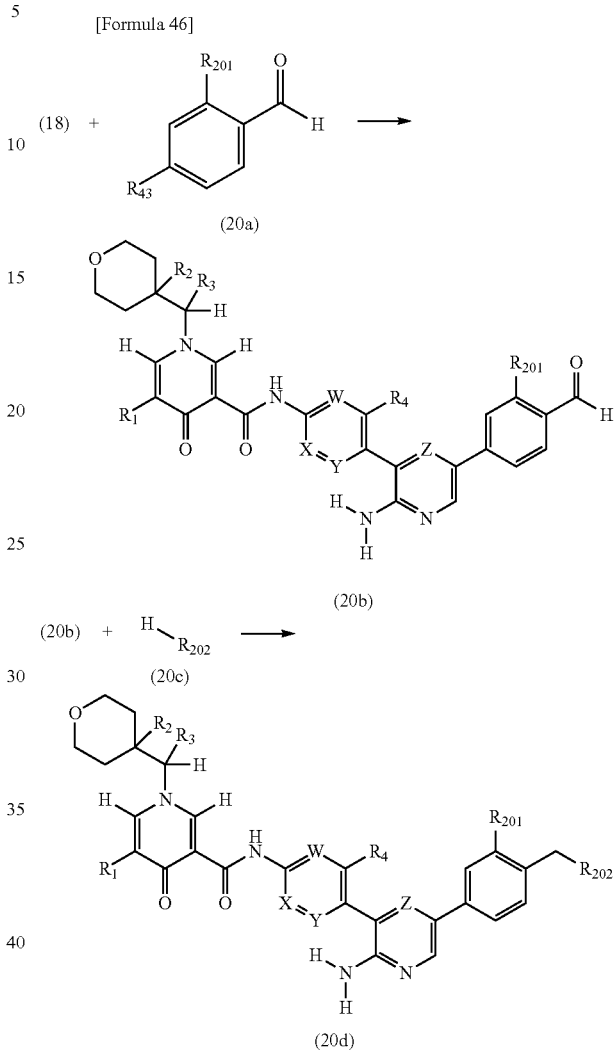

wherein $R_1$ to $R_4$, $R_{43}$, W, X, Y, and Z are as defined above, $R_{201}$ represents a hydrogen atom or a halogen group; and $R_{202}$ represents a $C_1$-$C_6$ alkylamino group optionally forming a ring or an oxy-$C_1$-$C_6$ alkylamino group optionally forming a ring. Compound (20d) is included in compound (11)

Synthesis of Compound (20b)

Compound (20b) can be obtained by the same operation as in the synthesis of compound (1c) in [Production process 1] using compound (18) and commercially available or appropriately synthesized compound (20a)

Synthesis of Compound (20d)

Compound (20b) can be reacted with commercially available or appropriately synthesized compound (20c) in the presence of a reducing agent to obtain compound (20d). Examples of the reducing agent used can include sodium triacetoxyborohydride, sodium cyanoborohydride, and sodium borohydride. Examples of the solvent used include, but are not particularly limited to, methanol, ethanol, water, tetrahydrofuran, dioxane, N,N-dimethylformamide, methylene chloride, acetic acid, and mixed solvents thereof. The reaction temperature is usually in the range of −78° C. to 100° C. or the boiling point of the solvent, preferably in the range of 0° C. to 100° C.

As mentioned above, the Gas6/Axl signalling system has been reported to regulate diverse cellular responses such as cell survival, cell division, autophagy, cell migration, angiogenesis, platelet aggregation, and NK cell differentiation (Non Patent Document 2). Therefore, Axl inhibitors are useful for treating a disease caused by hyperfunction of Axl kinase, a disease associated with hyperfunction of Axl kinase, and/or a disease involving hyperfunction of Axl kinase.

Particularly, the compounds of the present invention can be used more safely because the compounds of the present invention have high Axl inhibitory specificity and cause no retinal toxicity.

Examples of diseases caused by hyperfunction of Axl kinase, diseases associated with hyperfunction of Axl kinase, and diseases involving hyperfunction of Axl kinase include diseases having tissues containing overexpressed Axl genes and/or proteins, and diseases having tissues with an elevated phosphorylating activity of Axl.

Examples of the aforementioned diseases include hyperproliferative diseases. Examples of hyperproliferative diseases include, but are not limited to, endometrial hyperplasia, thrombin-induced vascular smooth muscle cell (VSMC) proliferation, benign tumor, malignant tumor (cancer), acute and chronic glomerulonephritis, and diabetic nephropathy.

Axl has been further found to play a role in immunity (Non Patent Document 12), platelet functions (Non Patent Document 13), spermatogenesis (Non Patent Document 14), vascular calcification (Non Patent Document 15), (Non Patent Document 16), and various kidney diseases and chronic allograft rejection (Non Patent Document 17). Thus, Axl inhibitors are useful in the treatment of many diseases including vascular diseases (including, but not limited to, thrombosis, atherosclerosis, and restenosis) and diseases in which the disorganized formation of blood vessels has serious consequences (including, but not limited to, diabetic retinopathy, retinopathy, psoriasis, rheumatoid arthritis, atheroma, Kaposi's sarcoma, and angioma).

The compounds of the present invention inhibit Axl and are therefore useful in the treatment of the diseases described above.

More preferably, the compounds of the present invention are useful in the treatment of various cancers. Examples of the cancers include, but are not limited to, breast cancer, colon cancer, prostate cancer, lung cancer, gastric cancer, ovary cancer, cervical cancer, endometrial cancer, uterine body cancer, kidney cancer, hepatocellular cancer, thyroid gland cancer, esophagus cancer, squamous cell cancer, leukemia, osteosarcoma, melanoma, glioblastoma, neuroblastoma, ovary cancer, head and neck cancer, testicular tumor, colorectal cancer, blood cancer, retinoblastoma, and pancreatic cancer.

Various reports on the relation of Axl to cancers have been made from the viewpoints of the inhibition of growth, the inhibition of metastasis, migration, or invasion, and the overcoming of drug resistance.

Axl dominant negative mutants have been reported to inhibit brain tumor growth (Vajkoczy et al., PNAS 2006, 103, 5799). Tumors in glioblastoma patient-derived tissues having the expression of Axl or the coexpression of Axl/Gas6 have been reported to grow significantly more rapidly and to render the lifetime of the patients short (Hutterer et al., Clin Cancer Res 14, 130 (2008)). Axl shRNA has been reported to inhibit the growth of breast cancer cells (Yi-Xiang et al., Cancer Res 68, 1905 (2008)). As is evident from these reports, Axl inhibitors are useful in the inhibition of cell growth in cancers.

On the other hand, Axl dominant negative mutants have been reported to inhibit cell migration and invasion (Zhang et al., Cancer Res 68, 1905 (2008); Vajkoczy et al., PNAS 103, 5799 (2006); and Holland et al., Cancer Res 65, 9294 (2005)). Axl shRNA has been reported to inhibit metastasis in vivo (Li et al., oncogene 28, 3442 (2009)). Anti-Axl antibodies and siRNA have been reported to inhibit tumor growth and metastasis in a mouse model (Li et al., Oncogene 28, 3442 (2009); Ye et al., Oncogene 29, 5254 (2010)). Axl has been reported to promote cell invasion (Tai et al., Oncogene 27, 4044 (2008)). R-428, an Axl inhibitor, has been reported to inhibit a diffusion model of metastatic breast cancer (Holland et al., Cancer Res 70, 1544 (2010)). Axl antibodies, Axl shRNA, and an Axl inhibitor NA80×1 have been reported to inhibit the migration and invasion of breast cancer cells (Yi-Xiang et al., Cancer Res 68, 1905 (2008)). Additionally, there have been a plurality of reports on the involvement of Axl in the metastasis and malignant progression of prostate cancer, spleen cancer, metastatic ovary cancer, thymic carcinoma, and the like. As is evident from these reports, Axl inhibitors are useful for, for example, inhibiting, treating, and preventing cancer metastasis, cell migration, and cell invasion.

Also, Axl inhibitors have been reported to overcome imatinib resistance in gastric cancer (Mahadevan et al., Oncogene 26, 3909 (2007)). Axl has been found to be induced in the resistance of acute myeloid leukemia to chemotherapeutic agents such as doxorubicin, VP16, and cisplatin (Hong et al., Cancer Letters 268, 314 (2008)). Axl is reportedly activated in lapatinib resistance in HER-2 positive breast cancer cells (Liu et al., Cancer Res 69, 6871 (2009)). Axl has been reported to participate in the PLX4032 (vemurafenib) resistance mechanism (Johannessen et al., Nature 468, 968 (2010)). Additionally, Axl has been reported to participate in resistance to temozolomide, carboplatin, and vincristine (AK Keeating et al., Mol Cancer Ther 9 (5), 1298 (2010)). As is evident from these reports, Axl inhibitors are useful in overcoming drug resistance, for example, overcoming resistance to various anticancer agents.

The Axl inhibitors of the present application, as shown in the Test Examples of the present application, inhibited the resistance of tumors to erlotinib through administration in combination with erlotinib. Significant induction of the Axl protein by erlotinib administration was observed, suggesting that Axl is involved in the acquisition of drug resistance by cancers.

The combined use with the Axl inhibitors of the present application for erlotinib-resistant tumors restored sensitivity to erlotinib, suggesting that Axl inhibitors are effective for overcoming drug resistance of cancers.

Axl has been further reported to participate in kidney diseases such as fibril formation in the kidney and diabetic nephropathy (National Publication of International Patent Application No. 2005-517412). Thus, Axl inhibitors are evidently useful in the treatment of these kidney diseases as well as fibrillization diseases such as idiopathic pulmonary fibrosis.

The Axl inhibitory activity of the compounds can be measured by, but not limited to, the methods described in, for example, the Test Examples of the present application.

Inhibitory activity against cell growth can be examined by use of a growth inhibition test method conventionally used by those skilled in the art. Inhibitory activity against cell growth can be determined by comparing the degree of growth of cells (e.g., tumor cells) in the presence of and in the absence of the test compound. The degree of growth can be examined using, for example, a test system for measuring live cells. Examples of the method for measuring live cells include the [$^3$H]-thymidine uptake test, BrdU method, and MTT assay.

In vivo antitumor activity can be examined by use of an antitumor test method conventionally used by those skilled in the art. The in vivo antitumor activity according to the present invention can be confirmed by, for example: transplanting various tumor cells into mice, rats, or the like; after confirmation of engraftment of the transplanted cells, administering a compound of the present invention through an oral route, an intravenous route, or the like to the animals; a few days to a few weeks later, comparing tumor growth in a vehicle group with tumor growth in the compound administration group.

Additionally, metastasis inhibitory activity, invasion inhibitory activity, migration inhibitory activity, and drug resistance-overcoming activity can be measured by test methods described above in the literature reporting the relation of Axl to each activity.

The pharmaceutical compositions of the present invention comprise a compound of the present invention and a pharmaceutically acceptable carrier and can be administered as various injections such as intravenous injections, intramuscular injections, or subcutaneous injections, or by various methods such as oral administration or transdermal administration. A pharmaceutically acceptable carrier means a pharmaceutically acceptable material (e.g., an excipient, a diluent, an additive, or a solvent) involved in the transport of the compound of the present invention or the composition comprising the compound of the present invention from an organ to another organ.

Formulations (e.g., oral formulations or injections) can be appropriately selected according to the administration method and prepared by methods conventionally used for preparing various formulations. Examples of oral formulations can include tablets, powders, granules, capsules, pills, troches, solutions, syrups, elixirs, emulsions, and oily or aqueous suspensions. These formulations may be orally administered either in free forms or in salt forms. Aqueous formulations can be prepared by forming acid adducts with pharmaceutically acceptable acids or by forming salts of alkali metals such as sodium. In the case of injections, stabilizers, preservatives, solubilizing agents, and the like may be used in the formulations. Solutions that may contain these adjuvants, etc., may be stored in containers and then lyophilized, for example, to form solid formulations to be prepared before use. One dose may be stored in one container, or multiple doses may be stored in one container.

Examples of solid formulations include tablets, powders, granules, capsules, pills, and troches. These solid formulations may contain pharmaceutically acceptable additives together with the compounds of the present invention. Examples of the additives include fillers, bulking agents, binders, disintegrants, dissolution promoters, wetting agents, and lubricants, which can be selected and mixed as necessary to prepare formulations.

Examples of liquid formulations include solutions, syrups, elixirs, emulsions, and suspensions. These liquid formulations may contain pharmaceutically acceptable additives together with the compounds of the present invention. Examples of the additives include suspending agents and emulsifiers, which can be selected and mixed as necessary to prepare formulations.

The compounds of the present invention can be used for treating cancers in mammals, particularly, humans. The dose and the dosing interval can be appropriately selected by the judgment of the physician according to the site of the disease and the height, body weight, sex, or medical history of the patient. When a compound of the present invention is administered to a human, the dose is in the range of approximately 0.01 mg/kg body weight to approximately 500 mg/kg body weight per day, preferably approximately 0.1 mg/kg body weight to approximately 100 mg/kg body weight per day. In administration to a human, the dose is preferably administered in either a single dose or two to four separate doses per day, and the administration is preferably repeated at appropriate intervals. The daily dose may exceed the aforementioned dose according to the judgment of the physician, if necessary.

The compounds of the present invention may be used in combination with an additional antitumor agent. Examples thereof include tyrosine kinase inhibitors (TKI) such as erlotinib listed above as well as antitumor antibiotics, antitumor plant components, BRM (biological response modifiers), hormones, vitamins, antitumor antibodies and other molecular target drugs, and other antitumor agents.

More specifically, examples of alkylating agents include: alkylating agents such as nitrogen mustard, nitrogen mustard N-oxide, and chlorambucil; aziridine alkylating agents such as carboquone and thiotepa; epoxide alkylating agents such as dibromomannitol and dibromodulcitol; nitrosourea alkylating agents such as carmustine, lomustine, semustine, nimustine hydrochloride, streptozocin, chlorozotocin, and ranimustine; and others such as busulfan, improsulfan tosylate, and dacarbazine.

Examples of various antimetabolites include: purine antimetabolites such as 6-mercaptopurine, 6-thioguanine, and thioinosine; pyrimidine antimetabolites such as fluorouracil, tegafur, tegafur uracil, carmofur, doxifluridine, broxuridine, cytarabine, and enocitabine; and antifolates such as methotrexate and trimetrexate.

Examples of antitumor antibiotics include: anthracycline antibiotic antitumor agents such as mitomycin C, bleomycin, peplomycin, daunorubicin, aclarubicin, doxorubicin, pirarubicin, THP-adriamycin, 4'-epidoxorubicin, and epirubicin; and others such as chromomycin A3 and actinomycin D.

Examples of antitumor plant components include: *vinca* alkaloids such as vindesine, vincristine, and vinblastine; taxanes such as paclitaxel and docetaxel; and epipodophyllotoxins such as etoposide and teniposide.

Examples of BRM include tumor necrosis factors and indomethacin.

Examples of hormones include hydrocortisone, dexamethasone, methylprednisolone, prednisolone, prasterone, betamethasone, triamcinolone, oxymetholone, nandrolone, metenolone, fosfestrol, ethynyl estradiol, chlormadinone, and medroxyprogesterone.

Examples of vitamins include vitamin C and vitamin A.

Examples of antitumor antibodies and molecular target drugs include trastuzumab, rituximab, cetuximab, nimotuzumab, denosumab, bevacizumab, infliximab, imatinib mesylate, gefitinib, erlotinib, sunitinib, lapatinib, sorafenib, dasatinib, nilotinib, vemurafenib, and tivantinib.

Examples of other antitumor agents include cisplatin, carboplatin, oxaliplatin, tamoxifen, camptothecin, ifosfamide, cyclophosphamide, melphalan, L-asparaginase, aceglatone, sizofiran, picibanil, procarbazine, pipobroman, neocarzinostatin, hydroxyurea, ubenimex, and krestin.

The present invention also includes a method for preventing and/or treating a cancer, comprising administering a compound of the present invention or a salt thereof.

The present invention further includes use of a compound of the present invention or a salt thereof, or a solvate of the compound or the salt for the manufacture of the aforementioned medicament.

The present invention will be specifically described with reference to the Examples illustrated below. However, the present invention is not limited by these Examples, and these Examples should not be construed as a limitation in any sense. Reagents, solvents, and starting materials described in the present specification are readily available from commercial sources, unless otherwise specified.

EXAMPLES

Abbreviations

DMF: N,N-dimethylformamide

THF: tetrahydrofuran

HATU: N,N,N',N-tetramethyl-O-(7-azabenzotriazol-1-yl)uronium hexafluorophosphate HOAt: 1-hydroxy-7-azabenzotriazole DIPEA: N,N-diisopropylethylamine COMU: (1-cyano-2-ethoxy-2-oxoethylideneaminooxy)dimethylamino-morpholino-carbenium hexafluorophosphate TFA: trifluoroacetic acid EDC.HCl: 1-ethyl-3-(3-dimethylaminopropyl)carbodiimide hydrochloride HOBt: 1-hydroxybenzotriazole DMAP: 4-dimethylaminopyridine PLC: preparative thin-layer chromatography HPLC: high-performance liquid chromatography (Intermediate 1a) 5-(4-Methylphenyl)-4-oxo-1-(tetrahydro-2H-pyran-4-ylmethyl)-1,4-dihydropyridine-3-carboxylic acid

[Formula 47]

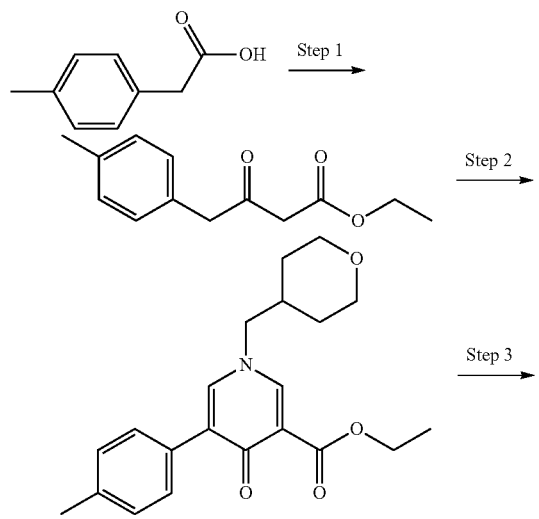

-continued

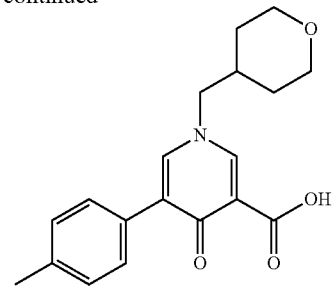

(Step 1) Ethyl 4-(4-methylphenyl)-3-oxobutanoate (4-Methylphenyl)acetic acid (75.0 g, 499 mmol) was dissolved in tetrahydrofuran (1.00 L). To the solution, carbonyldiimidazole (105 g, 649 mmol) was added, and the mixture was stirred at room temperature for 40 minutes. To the reaction mixture, malonic acid monoethyl ester potassium salt (111 g, 649 mmol) and anhydrous magnesium chloride (57.1 g, 599 mmol) were added, and the mixture was heated with stirring at 60° C. for 6 hours. The reaction mixture was cooled to room temperature, and ethyl acetate (2.00 L) was added thereto, followed by washing with 1 N hydrochloric acid (1.00 L). The organic layer was washed with a saturated aqueous solution of sodium bicarbonate and brine in this order. The organic layer was dried over anhydrous sodium sulfate, and then, the solvent was distilled off under reduced pressure. The oil obtained was subjected to azeotropic distillation with toluene under reduced pressure to obtain the title compound (86.8 g, yield: 78.8%) as an oil.

$^1$H-NMR (CDCl$_3$) g (47.18-7.07 (4H, m), 4.17 (2H, q, J=7.5 Hz), 3.78 (2H, s), 3.43 (2H, s), 2.33 (3H, s), 1.26 (3H, t, J=7.5 Hz).

MS (ESI) m/z: 221 [(M+H)$^+$].

(Step 2) Ethyl 5-(4-methylphenyl)-4-oxo-1-(tetrahydro-2H-pyran-4-ylmethyl)-1,4-dihydropyridine-3-carboxylate Ethyl 4-(4-methylphenyl)-3-oxobutanoate (43.0 g, 195 mmol) was dissolved in toluene (390 ml). To the solution, N,N-dimethylformamide dimethyl acetal (130 ml, 976 mmol) was added, and the mixture was heated with stirring at 100° C. for 5 hours while formed methanol was trapped in a Dean-Stark apparatus. The reaction mixture was cooled to room temperature and concentrated under reduced pressure. The residue was dissolved in ethanol (390 ml). To the solution, tetrahydro-2H-pyran-4-ylmethanamine (26.0 ml, 215 mmol) was added, and the mixture was heated with stirring at 60° C. for 9 hours. The reaction mixture was cooled to room temperature and concentrated under reduced pressure. The residue was purified by silica gel column chromatography (Shoko Scientific Co., Ltd., elution solvent: dichloromethane/ethyl acetate=75/25→20/80) to obtain the title compound (36.9 g, yield: 53.2%) as a caramel-like substance.

$^1$H-NMR (CDCl$_3$) δ: 8.10 (1H, d, J=2.4 Hz), 7.48 (2H, d, J=8.0 Hz), 7.32 (1H, d, J=2.4 Hz), 7.20 (2H, d, J=8.0 Hz), 4.38 (2H, q, J=7.0 Hz), 4.02 (2H, dd, J=11.5, 4.0 Hz), 3.74 (2H, d, J=7.3 Hz), 3.38 (2H, td, J=11.5, 2.0 Hz), 2.08-2.00 (1H, m), 1.63-1.56 (2H, m), 1.35-1.42 (5H, m).

MS (APCI) m/z: 356 [(M+H)$^+$].

(Step 3) 5-(4-Methylphenyl)-4-oxo-1-(tetrahydro-2H-pyran-4-ylmethyl)-1,4-dihydropyridine-3-carboxylic acid Ethyl 5-(4-methylphenyl)-4-oxo-1-(tetrahydro-2H-pyran-4-ylmethyl)-1,4-dihydropyridine-3-carboxylate (36.9 g, 104 mmol) was dissolved in methanol (519 ml). To the solution, a 1 N aqueous sodium hydroxide solution (311 ml, 311 mmol) was added, and the mixture was stirred at room temperature for 1 hour. The reaction mixture was concentrated under reduced pressure. To the residue, 1 N hydrochloric acid (400 ml) was added, followed by extraction with dichloromethane. The organic layer was dried over anhydrous sodium sulfate, and then, the solvent was distilled off under reduced pressure. The residue was washed with methanol by the slurry method to obtain the title compound (31.6 g, yield: 92.9%) as a solid.

$^1$H-NMR (CDCl$_3$) δ: 8.46 (1H, d, J=2.4 Hz), 7.56 (1H, d, J=2.4 Hz), 7.48 (2H, d, J=8.5 Hz), 7.28 (2H, d, J=8.5 Hz), 4.03 (2H, dd, J=11.3, 4.0 Hz), 3.89 (2H, d, J=7.5 Hz), 3.38 (2H, t, J=11.3 Hz), 2.40 (3H, s), 2.16-2.04 (1H, m), 1.62-1.53 (3H, m), 1.49-1.37 (2H, m).

MS (APCI) m/z: 328 [(M+H)$^+$].

Similarly, the intermediates of Table 1 were synthesized from the corresponding starting materials A and B.

TABLE 1

| Intermediate No. | Structural formula of intermediate Instrumental data on intermediate | Structural formula of starting material A | Structural formula of starting material B |
|---|---|---|---|
| Intermediate 1b | 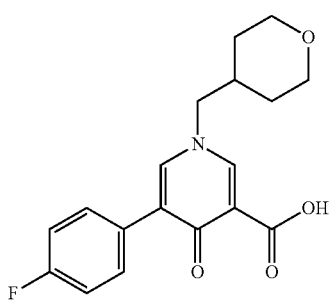 [SMILES: O=C(O)c1cn(CC2CCOCC2)cc(-c2ccc(F)cc2)c1=O] $^1$H-NMR (DMSO-D$_6$) δ: 8.78 (1H, d, J = 1.8 Hz), 8.42 (1H, d, J = 1.8 Hz), 7.76-7.72 (2H, m), 7.34-7.28 (2H, m), 4.14 (2H, d, J = 7.3 Hz), 3.85 (2H, dd, J = 11.5, 3.0 Hz), 3.28-3.21 (2H, m), 2.17-2.06 (1H, m), 1.46-1.40 (2H, m), 1.35-1.23 (2H, m). MS (ESI) m/z: 332 [(M + H)$^+$] | 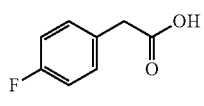 | 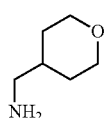 |
| Intermediate 1c | 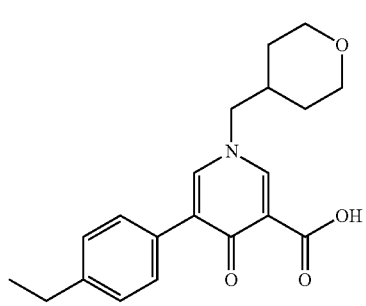 [SMILES: CCc1ccc(-c2cn(CC3CCOCC3)cc(C(=O)O)c2=O)cc1] 1H-NMR (CDCl$_3$) δ: 8.47 (1H, d, J = 2.4 Hz), 7.57 (1H, d, J = 2.4 Hz), 7.51 (2H, d, J = 8.0 Hz), 7.30 (2H, d, J = 8.0 Hz), 4.03 (2H, dd, J = 11.5, 4.0 Hz), 3.90 (2H, d, J = 7.5 Hz), 3.38 (2H, td, J = 11.5, 2.0 Hz), 2.70 (2H, q, J = 7.5 Hz), 2.16-2.04 (1H, m), 1.61-1.55 (2H, m), 1.49-1.37 (2H, m), 1.26 (3H, t, J = 7.5 Hz). MS (APCI) m/z: 342 [(M + H)$^+$]. | 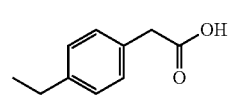 | 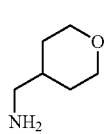 |

TABLE 1-continued

| Intermediate No. | Structural formula of intermediate Instrumental data on intermediate | Structural formula of starting material A | Structural formula of starting material B |
|---|---|---|---|
| Intermediate 1d | 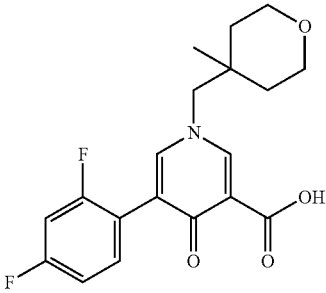 [SMILES: CC1(Cn2cc(C(=O)O)c(=O)c(-c3ccc(F)cc3F)c2)CCOCC1]<br>¹H-NMR (DMSO-D₆) δ: 8.73 (1H, d, J = 1.8 Hz), 8.30 (1H, d, J = 1.8 Hz), 7.55 (1H, td, J = 8.5, 7.3 Hz), 7.40 (1H, td, J = 10.0, 2.4 Hz), 7.22 (1H, td, J = 8.2, 2.4 Hz), 4.15 (2H, d, J = 9.7 Hz), 3.75-3.66 (2H, m), 3.55-3.45 (2H, m), 3.34 (1H, s), 1.60-1.49 (2H, m), 1.27-1.19 (2H, m),1.02 (3H, s).<br>MS (ESI) m/z: 364 [(M + H)⁺] | 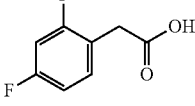 | 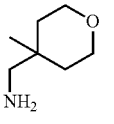 |
| Intermediate 1e | 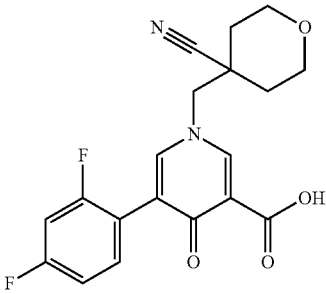 [SMILES: N#CC1(Cn2cc(C(=O)O)c(=O)c(-c3ccc(F)cc3F)c2)CCOCC1]<br>¹H-NMR (DMSO-D₆) δ: 8.89 (1H, d, J = 1.8 Hz), 8.37 (1H, d, J = 2.4 Hz), 7.57-7.49 (1H, m), 7.41 (1H, td, J = 10.0, 2.4 Hz), 7.24 (1H, td, J = 8.5, 2.4 Hz), 4.59 (2H, s), 3.99-3.91 (2H, m), 3.50-3.39 (2H, m), 3.34 (1H, s), 1.84-1.76 (4H, m).<br>MS (ESI) m/z: 375 [(M + H)⁺] | 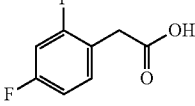 | 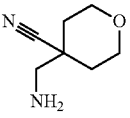 |
| Intermediate 1f | 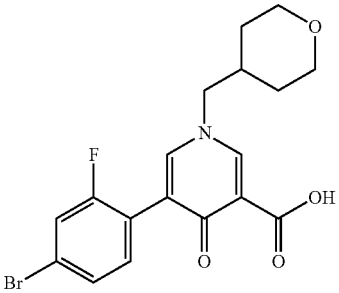 [SMILES: O=C(O)c1cn(CC2CCOCC2)cc(-c2ccc(Br)cc2F)c1=O]<br>1H-NMR (DMSO-D₆) δ: 8.83 (1H, d, J = 2.4 Hz), 8.39 (1H, d, J = 2.4 Hz), 7.69 (1H, dd, J = 9.7, 1.8 Hz), 7.55 (1H, dd, J = 7.9, 1.8 Hz), 7.49-7.45 (1H, m), 4.12 (2H, d, J = 7.3 Hz), 3.85 (2H, dd, J = 11.5, 3.0 Hz), 3.25 (2H, t, J = 11.5 Hz), 2.11-2.05 (1H, m), 1.44 (2H, br d, J = 10.9 Hz), 1.33-1.23 (2H, m).<br>MS (APCI) m/z: 410 [(M + H)⁺] . | 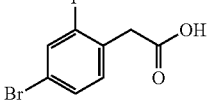 | 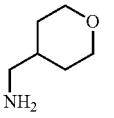 |

TABLE 1-continued

| Intermediate No. | Structural formula of intermediate Instrumental data on intermediate | Structural formula of starting material A | Structural formula of starting material B |
|---|---|---|---|
| Intermediate 1g | 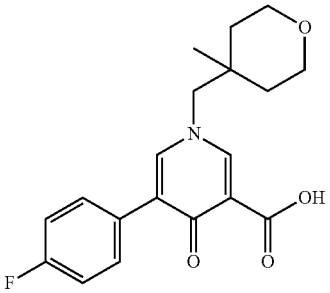 [SMILES: CC1(Cn2cc(C(=O)O)c(=O)c(-c3ccc(F)cc3)c2)CCOCC1]<br>1H-NMR (CDCl₃) δ: 8.43 (1H, d, J = 2.4 Hz), 7.59-7.51 (3H, m), 7.17 (2H, t, J = 8.5 Hz), 3.89-3.83 (4H, m), 3.63 (2H, td, J = 11.7, 2.0 Hz), 1.67 (2H, td, J = 12.7, 5.0 Hz), 1.36 (2H, d, J = 13.7 Hz), 1.16 (3H, s).<br>MS (APCI) m/z: 346 [(M + H)+]. | 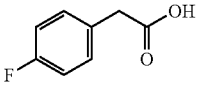 | 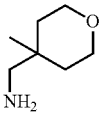 |
| Intermediate 1h | 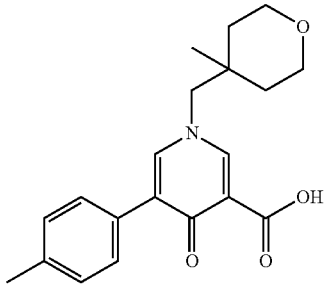 [SMILES: Cc1ccc(-c2cn(CC3(C)CCOCC3)cc(C(=O)O)c2=O)cc1]<br>1H-NMR (CDCl₃) δ: 8.41 (1H, d, J = 1.8 Hz), 7.52 (1H, d, J = 1.8 Hz), 7.47 (2H, d, J = 8.0 Hz), 7.28 (2H, d, J = 8.0 Hz), 3.89-3.81 (4H, m), 3.63 (2H, t, J = 11.0 Hz), 2.41 (3H, s), 1.70-1.61 (2H, m), 1.39-1.32 (2H, m), 1.15 (3H, s).<br>MS (APCI) m/z: 342 [(M + H)⁺]. | 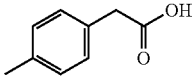 | 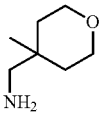 |
| Intermediate 1i | 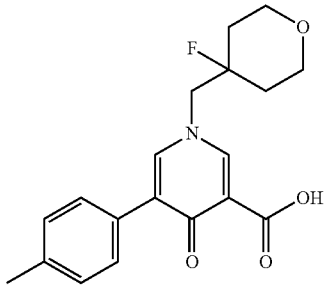 [SMILES: Cc1ccc(-c2cn(CC3(F)CCOCC3)cc(C(=O)O)c2=O)cc1]<br>1H-NMR (CDCl₃) δ: 8.47 (1H, d, J = 2.4 Hz), 7.65 (1H, d, J = 2.4 Hz), 7.48 (2H, d, J = 8.0 Hz), 7.27 (2H, d, J = 8.0 Hz), 4.13 (2H, d, J = 21.0 Hz), 3.92 (2H, dd, J = 12.0, 5.0 Hz), 3.70 (2H, td, J = 12.0, 3.0 Hz), 2.40 (3H, s), 1.92-1.65 (4H, m).<br>MS (APCI) m/z: 346 [(M + H)⁺]. | 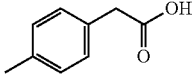 | 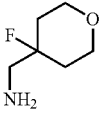 |

TABLE 1-continued

| Intermediate No. | Structural formula of intermediate Instrumental data on intermediate | Structural formula of starting material A | Structural formula of starting material B |
|---|---|---|---|
| Intermediate 1j | 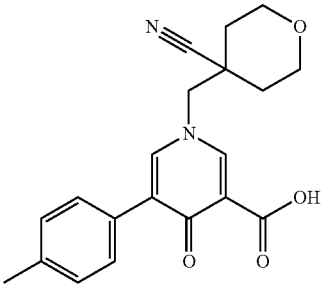 [SMILES: Cc1ccc(-c2cn(CC3(C#N)CCOCC3)cc(C(=O)O)c2=O)cc1]<br>¹H-NMR (DMSO-D₆) δ: 8.82 (1H, d, J = 2.4 Hz), 8.39 (1H, d, J = 1.8 Hz), 7.57 (2H, d, J = 7.9 Hz), 7.29 (2H, d, J = 8.5 Hz), 4.61 (2H, s), 3.99-3.91 (2H, m), 3.48-3.39 (2H, m), 3.34 (1H, s), 2.36 (3H, s), 1.87-1.74 (4H, m).<br>MS (ESI) m/z: 353 [(M + H)⁺]. | 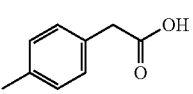 | 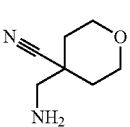 |
| Intermediate 1k | 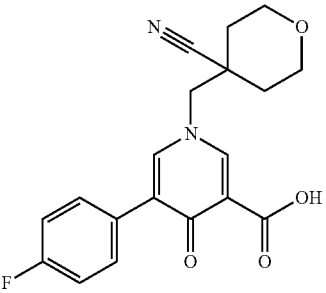 [SMILES: N#CC1(Cn2cc(C(=O)O)c(=O)c(-c3ccc(F)cc3)c2)CCOCC1]<br>¹H-NMR (DMSO-D₆) δ: 8.85 (1H, d, J = 2.4 Hz), 8.43 (1H, d, J = 2.4 Hz), 7.74-7.67 (2H, m), 7.38-7.30 (2H, m), 4.61 (2H, s), 3.99-3.91 (2H, m), 3.48-3.39 (2H, m), 3.34 (1H, s), 1.87-1.75 (4H, m).<br>MS (ESI) m/z: 357 [(M + H)⁺]. | 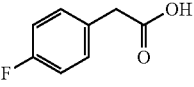 | 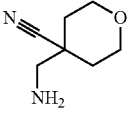 |
| Intermediate 1l | R-isomer<br>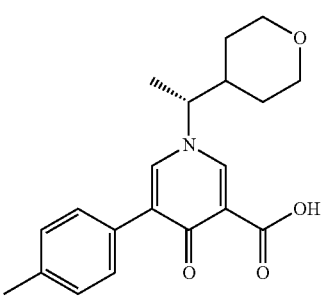 [SMILES: Cc1ccc(-c2cn([C@H](C)C3CCOCC3)cc(C(=O)O)c2=O)cc1]<br>MS (ESI) m/z: 342 [(M + H)⁺]. | 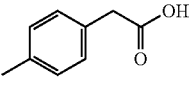 | 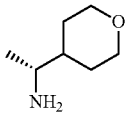 |

TABLE 1-continued

| Intermediate No. | Structural formula of intermediate Instrumental data on intermediate | Structural formula of starting material A | Structural formula of starting material B |
|---|---|---|---|
| Intermediate 1m | S-isomer 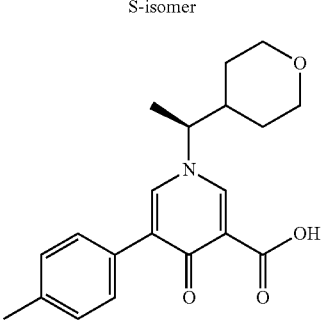 <br> ¹H-NMR (CDCl₃) δ: 8.49 (1H, d, J = 1.8 Hz), 7.59 (1H, d, J = 1.8 Hz), 7.49 (2H, d, J = 7.9 Hz), 7.28 (2H, d, J = 7.9 Hz), 4.07 (1H, dd, J = 11.8, 3.9 Hz), 4.00-3.94 (1H, m), 3.83-3.74 (1H, m), 3.35 (2H, tdd, J = 23.9, 12.1, 2.2 Hz), 2.41 (3H, s), 1.97-1.88 (1H, m), 1.75 (1H, d, J = 12.1 Hz), 1.62 (3H, d, J = 6.7 Hz), 1.49-1.22 (4H, m). <br> MS (ESI) m/z: 342 [(M + H)⁺] | 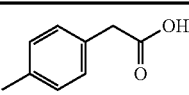 | 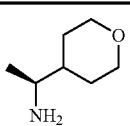 |
| Intermediate 1n | 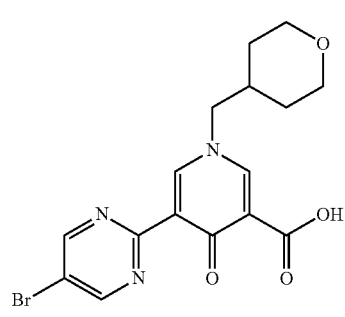 [SMILES: O=C(O)c1cn(CC2CCOCC2)cc(-c2ncc(Br)cn2)c1=O] <br> ¹H-NMR (DMSO-D₆) δ: 9.15-9.13 (2H, m), 8.84 (1H, d, J = 2.4 Hz), 8.66 (1H, d, J = 2.4 Hz), 4.18 (2H, d, J = 7.3 Hz), 3.88-3.81 (2H, m), 3.28-3.19 (3H, m), 2.12-1.99 (1H, m), 1.47-1.39 (2H, m), 1.34-1.22 (2H, m). <br> MS (ESI) m/z: 394 [(M + H)⁺] | 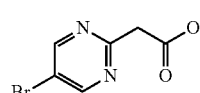 | 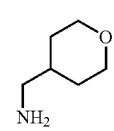 |
| Intermediate 1o | 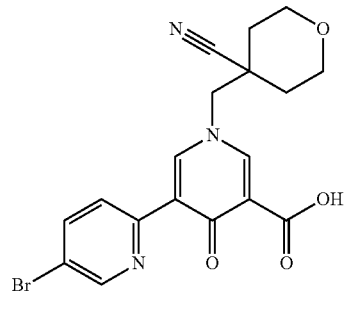 [SMILES: N#CC1(Cn2cc(C(=O)O)c(=O)c(-c3ccc(Br)cn3)c2)CCOCC1] <br> ¹H-NMR (DMSO-D₆) δ: 8.97 (1H, d, J = 2.4 Hz), 8.88 (1H, d, J = 2.4 Hz), 8.82 (1H, d, J = 2.4 Hz), 8.50 (1H, d, J = 8.5 Hz), 8.19 (1H, dd, J = 8.5, 2.4 Hz), 4.73 (2H, s), 3.97-3.92 (2H, m), 3.46-3.39 (2H, m), 1.86- 1.76 (4H, m). <br> MS (APCI) m/z: 418 [(M + H)⁺]. | 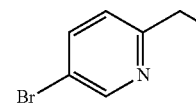 | 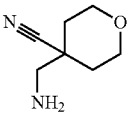 |

TABLE 1-continued

| Intermediate No. | Structural formula of intermediate Instrumental data on intermediate | Structural formula of starting material A | Structural formula of starting material B |
|---|---|---|---|
| Intermediate 1p | 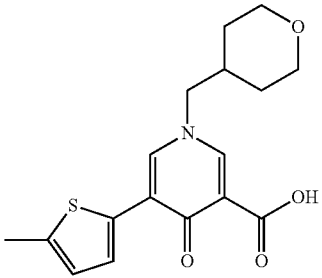 [SMILES: Cc1ccc(-c2cn(CC3CCOCC3)cc(C(=O)O)c2=O)s1]<br>¹H-NMR (CDCl₃) δ: 8.40 (1H, d, J = 2.4 Hz), 7.81 (1H, d, J = 2.4 Hz), 7.45 (1H, d, J = 3.6 Hz), 6.80-6.79 (1H, m), 4.03 (2H, dd, J = 11.8, 3.9 Hz), 3.92 (2H, d, J = 7.3 Hz), 3.38 (2H, td, J = 11.8, 1.8 Hz), 2.54 (3H, s), 2.16-2.05 (1H, m), 1.60-1.56 (2H, m), 1.48-1.38 (2H, m).<br>MS (APCI) m/z: 334 [(M + H)⁺]. | 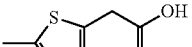 | 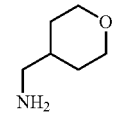 |
| Intermediate 1q | 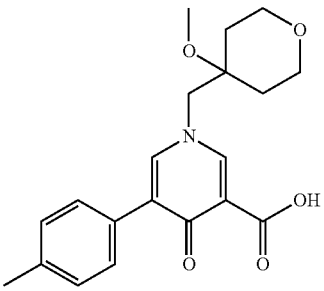 [SMILES: COC1(Cn2cc(C(=O)O)c(=O)c(-c3ccc(C)cc3)c2)CCOCC1]<br>¹H-NMR (CDCl₃) δ: 8.40-8.38 (1H, m), 7.54-7.52 (1H, m), 7.47 (2H, d, J = 7.9 Hz), 7.27 (2H, d, J = 7.9 Hz), 4.00 (2H, s), 3.82-3.77 (2H, m), 3.71-3.65 (2H, m), 3.37 (3H, s), 2.40 (3H, s), 1.70-1.57 (4H, m).<br>MS (APCI) m/z: 358 [(M + H)⁺]. | 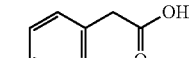 | 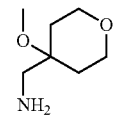 |

(Intermediate 2) 5-(4-Cyclopropyl-2-fluorophenyl)-4-oxo-1-(tetrahydro-2H-pyran-4-ylmethyl)-1,4-dihydropyridine-3-carboxylic acid

[Formula 48]

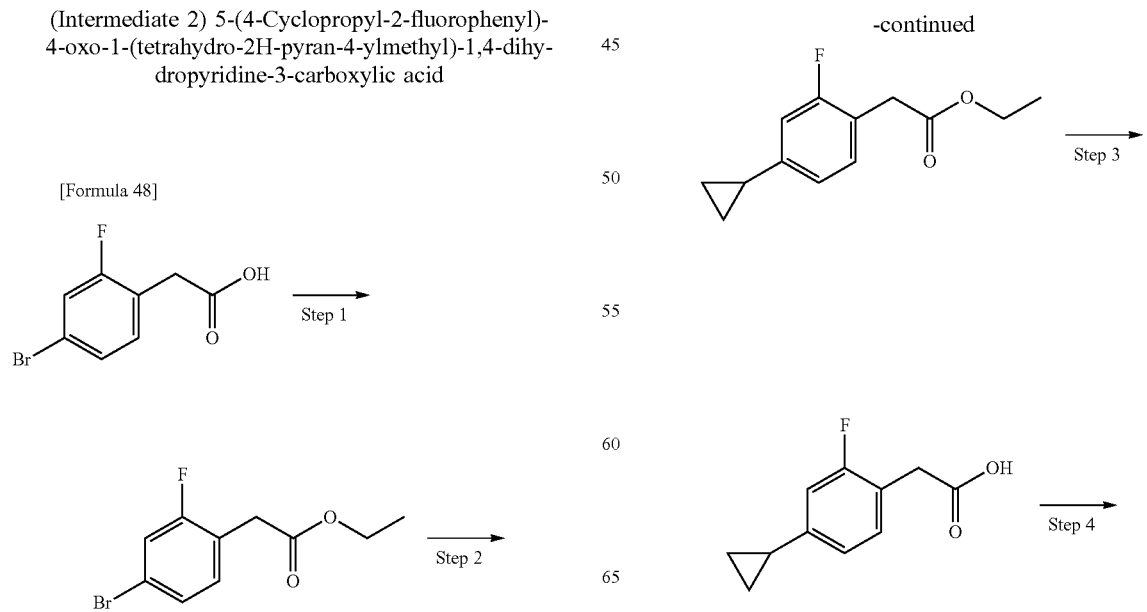

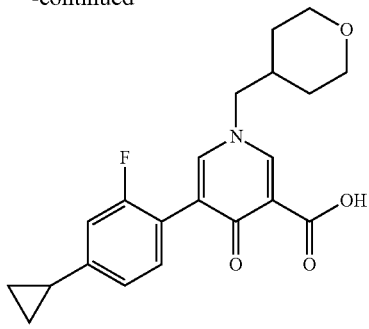

(Step 1) Ethyl (4-bromo-2-fluorophenyl)acetate

To a solution of (4-bromo-2-fluorophenyl)acetic acid (2.00 g, 8.58 mmol) in methylene chloride (40.0 mL), ethanol (0.969 mL, 0.791 g, 17.2 mmol), 4-dimethylaminopyridine (0.105 g, 0.858 mmol), and 1-(3-dimethylaminopropyl)-3-ethylcarbodiimide hydrochloride (EDAC.HCl) (1.97 g, 10.3 mmol) were added, and the mixture was stirred overnight at room temperature. To the reaction mixture, 1 N hydrochloric acid was added, followed by extraction with methylene chloride three times. The organic layer was washed with a saturated aqueous solution of sodium bicarbonate and brine in this order and then dried over anhydrous sodium sulfate. After filtration and concentration under reduced pressure, the residue obtained was purified by silica gel column chromatography (Yamazen Corp., n-hexane/ethyl acetate=(100/0→87/13) to obtain the title compound (1.96 g, yield: 87.5%) as a solid.

$^1$H-NMR (CDCl$_3$) δ: 7.27-7.24 (2H, m), 7.18-7.14 (1H, m), 4.17 (2H, q, J=7.0 Hz), 3.62 (2H, s), 1.26 (3H, t, J=7.0 Hz).

(Step 2) Ethyl (4-cyclopropyl-2-fluorophenyl)acetate

To a suspension of ethyl (4-bromo-2-fluorophenyl)acetate (1.95 g, 7.47 mmol) synthesized in step 1 in toluene (30.0 mL), cyclopropylboronic acid (0.962 g, 11.2 mmol), tricyclohexylphosphine (0.419 g, 1.49 mmol), tripotassium phosphate (5.55 g, 26.1 mmol), and water (6.00 mL) were added, and the reaction mixture was purged with nitrogen. Then, palladium(II) acetate (0.168 g, 0.747 mmol) was added, and the mixture was stirred at 100° C. for 2 hours. The reaction mixture was left to cool to room temperature, and then, water was added thereto, followed by extraction with ethyl acetate three times. The organic layer was washed with brine and then dried over anhydrous sodium sulfate. After filtration and concentration under reduced pressure, the obtained residue was purified by silica gel column chromatography (Yamazen Corp., n-hexane/ethyl acetate=100/0→87/13) and further purified by amino silica gel column chromatography (Yamazen Corp., n-hexane/ethyl acetate=100/0→87/13) to obtain the title compound (1.59 g, yield: 95.8%) as an oil.

$^1$H-NMR (CDCl$_3$) δ: 7.12 (1H, t, J=7.9 Hz), 6.84-6.82 (1H, m), 6.76-6.72 (1H, m), 4.16 (2H, q, J=7.0 Hz), 3.61 (2H, s), 1.90-1.83 (1H, m), 1.25 (3H, t, J=7.0 Hz), 1.00-0.95 (2H, m), 0.70-0.66 (2H, m).
MS (APCI) m/z: 223 [(M+H)$^+$].

(Step 3) (4-Cyclopropyl-2-fluorophenyl)acetic acid

To a solution of ethyl (4-cyclopropyl-2-fluorophenyl)acetate (1.59 g, 7.15 mmol) synthesized in step 2 in tetrahydrofuran (30.0 mL), methanol (15.0 mL) and a 1 mol/L aqueous sodium hydroxide solution (14.3 mL, 14.3 mmol) were added, and the mixture was stirred overnight at room temperature. The organic solvent was distilled off under reduced pressure, and then, water was added to the residue, followed by washing with diethyl ether. The aqueous layer was rendered acidic by the addition of 1 N hydrochloric acid, followed by extraction with ethyl acetate three times. The organic layer was washed with brine and then dried over anhydrous sodium sulfate. Filtration and concentration under reduced pressure were carried out to obtain the title compound (1.36 g, 7.00 mmol) as a solid.

$^1$H-NMR (CDCl$_3$) δ: 7.11 (1H, t, J=7.9 Hz), 6.83 (1H, dd, J=7.9, 1.8 Hz), 6.75 (1H, dd, J=11.2, 1.8 Hz), 3.65 (2H, s), 1.90-1.83 (1H, m), 1.00-0.95 (2H, m), 0.70-0.66 (2H, m).

(Step 4) 5-(4-Cyclopropyl-2-fluorophenyl)-4-oxo-1-(tetrahydro-2H-pyran-4-ylmethyl)-1,4-dihydropyridine-3-carboxylic acid The title compound was obtained as a solid by using (4-cyclopropyl-2-fluorophenyl)acetic acid instead of (4-methylphenyl)acetic acid in step 1 of intermediate 1a and carrying out the same subsequent reactions as in step 1 to step 3 of intermediate 1a.

$^1$H-NMR (DMSO-D$_6$) δ: 8.80 (1H, d, J=2.4 Hz), 8.31 (1H, d, J=2.4 Hz), 7.34 (1H, t, J=8.2 Hz), 7.03-6.99 (2H, m), 4.12 (2H, d, J=7.3 Hz), 3.85 (2H, dd, J=11.2, 3.3 Hz), 3.24 (2H, t, J=11.2 Hz), 2.12-1.97 (2H, m), 1.43 (2H, br d, J=10.9 Hz), 1.33-1.22 (2H, m), 1.04-0.99 (2H, m), 0.77-0.73 (2H, m).

MS (APCI) m/z: 372 [(M+H)$^+$].

(Intermediate 3) 5-Methyl-4'-oxo-1'-(tetrahydro-2H-pyran-4-ylmethyl)-1',4'-dihydro-2,3'-bipyridine-5'-carboxylic acid

[Formula 49]

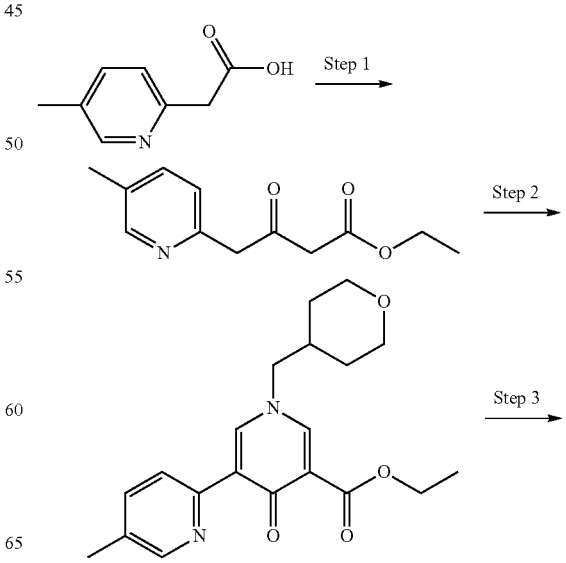

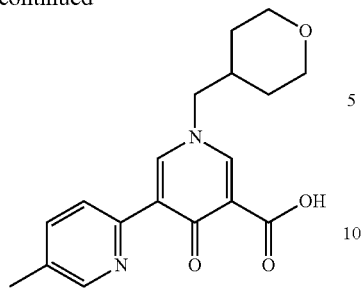

(Step 1) Ethyl
4-(5-methylpyridin-2-yl)-3-oxobutanoate

To a solution of (5-methylpyridin-2-yl)acetic acid (0.500 g, 3.31 mmol) in tetrahydrofuran (15.0 mL), 1,1'-carbonyl-bis-1H-imidazole (0.805 g, 4.96 mmol) was added, and the mixture was stirred at room temperature for 2.5 hours. In another reaction vessel, monoethyl potassium malonate (1.69 g, 9.92 mmol) and magnesium chloride (0.945 g, 9.92 mmol) were suspended in tetrahydrofuran (25.0 mL). To the suspension, triethylamine (2.38 mL, 1.74 g, 17.2 mmol) was added under ice cooling, and the mixture was stirred at room temperature for 2.5 hours and then ice-cooled again. The active ester solution prepared above was added thereto, and the mixture was stirred overnight at room temperature. To the reaction mixture, a 10% aqueous citric acid solution was added, followed by extraction with ethyl acetate five times. The organic layer was washed with a saturated aqueous solution of sodium bicarbonate and brine in this order and then dried over anhydrous sodium sulfate. After filtration and concentration under reduced pressure, the obtained residue was purified by silica gel column chromatography (Yamazen Corp., elution solvent: n-hexane/ethyl acetate=57/43→36/64) to obtain the title compound (0.634 g, yield: 86.6%) as an oil.

MS (APCI) m/z: 222 [(M+H)$^+$].

(Steps 2 and 3) 5-Methyl-4'-oxo-1'-(tetrahydro-2H-pyran-4-ylmethyl)-1',4'-dihydro-2,3'-bipyridine-5'-carboxylic acid The title compound was obtained as a solid by using ethyl 4-(5-methylpyridin-2-yl)-3-oxobutanoate instead of ethyl 4-(4-methylphenyl)-3-oxobutanoate in step 2 of intermediate 1a and carrying out the same subsequent reactions as in step 2 and step 3 of intermediate 1a.

$^1$H-NMR (DMSO-D$_6$) δ: 8.86 (1H, d, J=2.4 Hz), 8.80 (1H, d, J=2.4 Hz), 8.53 (1H, s), 8.38 (1H, d, J=8.5 Hz), 7.72 (1H, dd, J=8.5, 2.1 Hz), 4.24 (2H, d, J=7.3 Hz), 3.84 (2H, dd, J=11.2, 3.3 Hz), 3.24 (2H, t, J=11.2 Hz), 2.35 (3H, s), 2.11-2.01 (1H, m), 1.44 (2H, br d, J=10.9 Hz), 1.35-1.24 (2H, m).

MS (APCI) m/z: 329 [(M+H)$^+$].

Similarly, the intermediate of Table 2 was synthesized from the corresponding starting material.

TABLE 2

| Intermediate No. | Structural formula of intermediate Instrumental data on intermediate | Structural formula of starting material |
|---|---|---|
| Intermediate 3b | 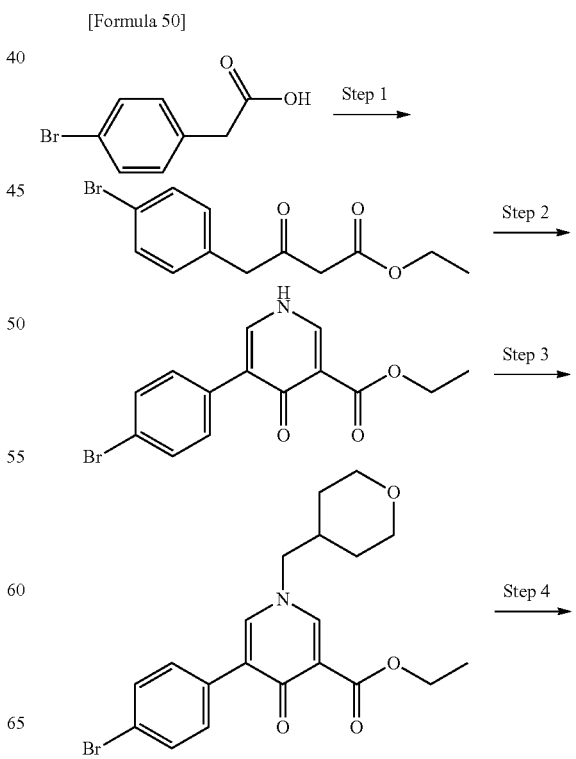 $^1$H-NMR (DMSO-D$_6$) δ: 8.83 (2H, q, J = 2.0 Hz), 8.71 (1H, d, J = 3.0 Hz), 8.54 (1H, dd, J = 8.8, 4.6 Hz), 7.86 (1H, td, J = 8.8, 3.0 Hz), 4.24 (2H, d, J = 7.3 Hz), 3.84 (2H, dd, J = 11.2, 3.3 Hz), 3.28-3.21 (2H, m), 2.10-2.02 (1H, m), 1.44 (2H, br d, J = 10.3 Hz), 1.34-1.24 (2H, m). MS (APCI) m/z: 333 [(M + H)$^+$]. | |

(Intermediate 4a) 5-(4-Bromophenyl)-4-oxo-1-(tetrahydro-2H-pyran-4-ylmethyl)-1,4-dihydropyridine-3-carboxylic acid

[Formula 50]

(Step 1) Ethyl 4-(4-bromophenyl)-3-oxobutanoate

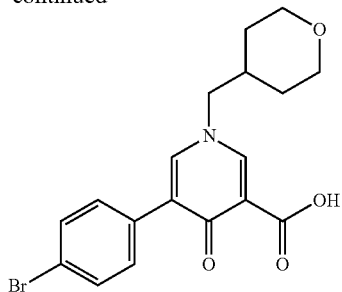

The title compound was obtained as an oil by using 2-(4-bromophenyl)acetic acid instead of (4-methylphenyl)acetic acid in step 1 of intermediate 1a and carrying out the subsequent reactions by the same operation.

$^1$H-NMR (CDCl$_3$) δ: 7.47 (2H, d, J=8.5 Hz), 7.09 (2H, d, J=8.5 Hz), 4.18 (2H, q, J=7.1 Hz), 3.81 (2H, s), 3.46 (2H, s), 1.27 (3H, t, J=7.1 Hz).

(Step 2) Ethyl 5-(4-bromophenyl)-4-oxo-1,4-dihydropyridine-3-carboxylate

To a solution of ethyl 4-(4-bromophenyl)-3-oxobutanoate (5.00 g, 17.5 mmol) synthesized in step 1 in ethanol (50.0 mL), 1,3,5-triazine (1.56 g, 19.3 mmol) and sodium ethoxide (1.43 g, 21.0 mmol) were added, and the mixture was stirred at 85° C. for 4 hours. The reaction mixture was left to cool to room temperature and then concentrated under reduced pressure. The obtained residue was rendered acidic by the addition of 1 N hydrochloric acid, and then, the deposited solid was collected by filtration, then washed with acetone, and dried to obtain a crude product of the title compound (3.73 g) as a solid.

MS (APCI) m/z: 322 [(M+H)$^+$].

(Step 3) Ethyl 5-(4-bromophenyl)-4-oxo-1-(tetrahydro-2H-pyran-4-ylmethyl)-1,4-dihydropyridine-3-carboxylate To a suspension of the crude product of ethyl 5-(4-bromophenyl)-4-oxo-1,4-dihydropyridine-3-carboxylate (0.322 g) synthesized in step 2 in N,N-dimethylformamide (45.0 mL), cesium carbonate (0.977 g, 3.00 mmol) was added, and the mixture was stirred at 80° C. for 15 minutes. Then, methanesulfonic acid tetrahydro-2H-pyran-4-ylmethyl ester (0.583 g, 3.00 mmol) was added thereto, and the mixture was stirred at 80° C. for 4 hours. The reaction mixture was left to cool to room temperature, and then, water was added thereto, followed by extraction with ethyl acetate three times. The organic layer was washed with brine and then dried over anhydrous sodium sulfate. After filtration and concentration under reduced pressure, the residue obtained was purified by silica gel column chromatography (Yamazen Corp., elution solvent: n-hexane/ethyl acetate=57/43→36/64) to obtain the title compound (0.234 g, yield in 2 steps: 36.7%) as an amorphous solid.

$^1$H-NMR (DMSO-D$_6$) δ: 8.30 (1H, d, J=2.4 Hz), 8.02 (1H, d, J=2.4 Hz), 7.59 (4H, s), 4.20 (2H, q, J=7.0 Hz), 3.92 (2H, d, J=7.3 Hz), 3.85 (2H, dd, J=10.9, 3.0 Hz), 3.25 (2H, t, J=10.9 Hz), 2.09-1.99 (1H, m), 1.43 (2H, br d, J=10.9 Hz), 1.32-1.24 (5H, m).

MS (APCI) m/z: 420 [(M+H)$^+$].

(Step 4) 5-(4-Bromophenyl)-4-oxo-1-(tetrahydro-2H-pyran-4-ylmethyl)-1,4-dihydropyridine-3-carboxylic acid The title compound was obtained as a solid by using ethyl 5-(4-bromophenyl)-4-oxo-1-(tetrahydro-2H-pyran-4-ylmethyl)-1,4-dihydropyridine-3-carboxylate instead of ethyl 5-(4-methylphenyl)-4-oxo-1-(tetrahydro-2H-pyran-4-ylmethyl)-1,4-dihydropyridine-3-carboxylate in step 3 of intermediate 1a and carrying out the subsequent reactions by the same operation.

$^1$H-NMR (DMSO-D$_6$) δ: 8.79 (1H, d, J=1.8 Hz), 8.45 (1H, d, J=1.8 Hz), 7.70-7.65 (4H, m), 4.14 (2H, d, J=7.3 Hz), 3.85 (2H, dd, J=11.2, 3.3 Hz), 3.24 (2H, t, J=11.2 Hz), 2.16-2.06 (1H, m), 1.43 (2H, br d, J=10.9 Hz), 1.34-1.24 (2H, m).

MS (APCI) m/z: 392 [(M+H)$^+$].

Similarly, the intermediates of Table 3 were synthesized from the corresponding starting materials.

TABLE 3

| Intermediate No. | Structural formula of intermediate Instrumental data on intermediate | Structural formula of starting material |
|---|---|---|
| Intermediate 4b | ![structure] $^1$H-NMR (DMSO-D$_6$) δ: 8.80 (1H, d, J = 1.8 Hz), 8.47 (1H, d, J = 1.8 Hz), 7.82 (2H, d, J = 8.5 Hz), 7.48 (2H, d, J = 8.5 Hz), 4.14 (2H, d, J = 7.3 Hz), 3.85 (2H, dd, J = 11.5, 3.0 Hz), 3.28-3.21 (2H, m), 2.17-2.07 (1H, m), 1.44 (2H, br d, J = 10.9 Hz), 1.34-1.24 (2H, m). MS (APCI) m/z: 398 [(M + H)$^+$]. | ![structure] |

TABLE 3-continued

| Intermediate No. | Structural formula of intermediate Instrumental data on intermediate | Structural formula of starting material |
|---|---|---|
| Intermediate 4c | 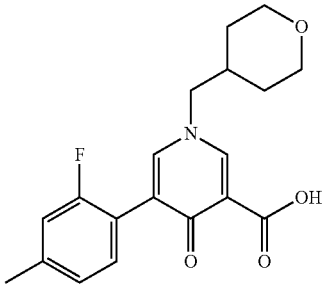 [SMILES: Cc1ccc(-c2cn(CC3CCOCC3)cc(C(=O)O)c2=O)c(F)c1]<br><br>¹H-NMR (DMSO-D₆) δ: 8.81 (1H, d, J = 1.8 Hz), 8.32 (1H, d, J = 1.8 Hz), 7.37 (1H, t, J = 7.6 Hz), 7.16-7.11 (2H, m), 4.12 (2H, d, J = 7.3 Hz), 3.85 (2H, dd, J = 11.2, 3.3 Hz), 3.25 (2H, t, J = 11.2 Hz), 2.37 (3H, s), 2.12-2.04 (1H, m), 1.43 (2H, br d, J = 10.9 Hz), 1.33-1.23 (2H, m).<br>MS (APCI) m/z: 346 [(M + H)⁺]. | 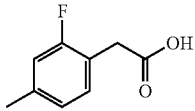 |

(Intermediate 5a) (2S)-2-{[2-Methoxy-4-(4,4,5,5-tetramethyl-1,3,2-dioxaborolan-2-yl)phenoxy]methyl}-1,4-dioxane

[Formula 51]

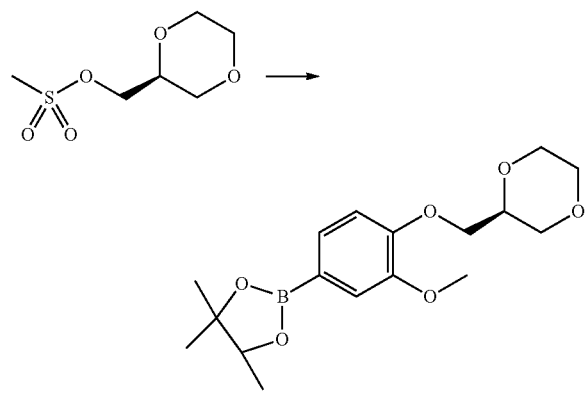

2-Methoxy-4-(4,4,5,5-tetramethyl-1,3,2-dioxaborolan-2-yl)phenol (0.500 g, 1.99 mmol) was dissolved in N,N-dimethylformamide (10.0 ml). To the solution, (2S)-1,4-dioxan-2-ylmethyl methanesulfonic acid (0.401 g, 2.04 mmol) was added, and the mixture was stirred at 90° C. for 10 hours. The reaction mixture was cooled to room temperature and separated into organic and aqueous layers by the addition of ethyl acetate and water. The organic layer was washed with brine and then dried over anhydrous magnesium sulfate. The solvent was distilled off under reduced pressure, and the residue was purified by silica gel column chromatography (Biotage Japan Ltd., elution solvent: hexane/ethyl acetate=100/0→50/50) to obtain the title compound (0.451 g, yield: 64.4%) as an oil.

¹H-NMR (CDCl₃) δ: 7.39 (1H, d, J=7.9 Hz), 7.28 (1H, s), 6.89 (1H, d, J=7.9 Hz), 4.09-4.03 (2H, m), 4.00-3.93 (2H, m), 3.89 (3H, s), 3.86-3.63 (4H, m), 3.57-3.50 (1H, m), 1.34 (12H, s).

Similarly, the intermediate of Table 4 was synthesized from the corresponding starting material.

TABLE 4

| Intermediate No. | Structural formula of intermediate Instrumental data on intermediate | Structural formula of starting material |
|---|---|---|
| Intermediate 5b | 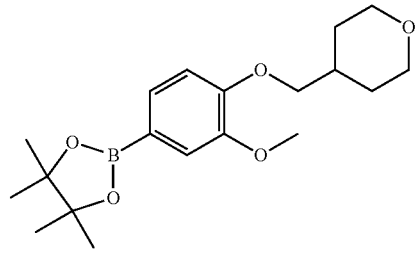 [SMILES: COc1cc(B2OC(C)(C)C(C)(C)O2)ccc1OCC1CCOCC1]<br><br>¹H-NMR (CDCl₃) δ: 7.40 (1H, dd, J = 7.9, 1.2 Hz), 7.29 (1H, s), 6.87 (1H, d, J = 7.9 Hz), 4.01 (2H, dd, J = 11.2, | 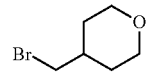 |

TABLE 4-continued

| Intermediate No. | Structural formula of intermediate Instrumental data on intermediate | Structural formula of starting material |
|---|---|---|
| | 3.9 Hz), 3.90-3.87 (5H, m), 3.44 (2H, t, J = 11.2 Hz), 2.23-2.12 (1H, m), 1.80 (2H, br d, J = 12.8 Hz), 1.49-1.38 (2H, m), 1.34 (12H, s). MS (APCI) m/z: 349 [(M + H)+]. | |

(Intermediate 6) 1-(Tetrahydro-2H-pyran-4-ylmethyl)-4-(4,4,5,5-tetramethyl-1,3,2-dioxaborolan-2-yl)-1H-pyrazole

[Formula 52]

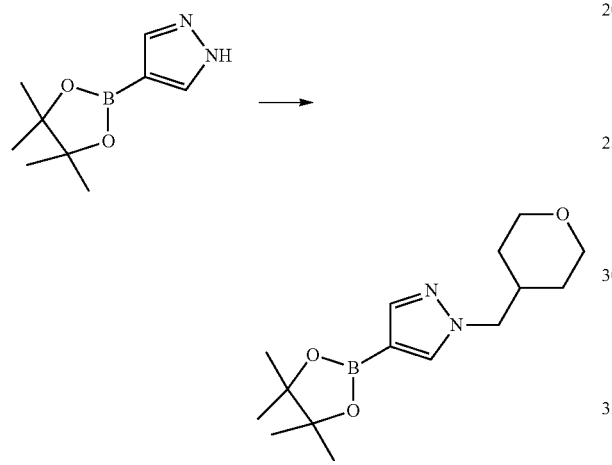

The title compound was obtained in the same way as in intermediate 5a by using 4-(4,4,5,5-tetramethyl-1,3,2-dioxaborolan-2-yl)-1H-pyrazole and 4-(bromomethyl)tetrahydropyran as starting materials.

$^1$H-NMR (CDCl$_3$) δ: 7.79 (1H, s), 7.65 (1H, s), 4.00 (2H, d, J=7.5 Hz), 3.96 (2H, dd, J=11.5, 4.5 Hz), 3.35 (2H, td, J=11.5, 2.0 Hz), 2.23-2.11 (1H, m), 1.48 (2H, d, J=11.5 Hz), 1.40-1.28 (14H, m).

MS (APCI) m/z: 293 [(M+H)+].

(Intermediate 7) (2R)-2-[({2-[($^2$H$_3$)Methoxy]-4-(4,4,5,5-tetramethyl-1,3,2-dioxaborolan-2-yl) ($^2$H$_3$) phenyl}oxy)methyl]-1,4-dioxane

[Formula 53]

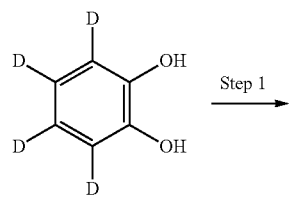

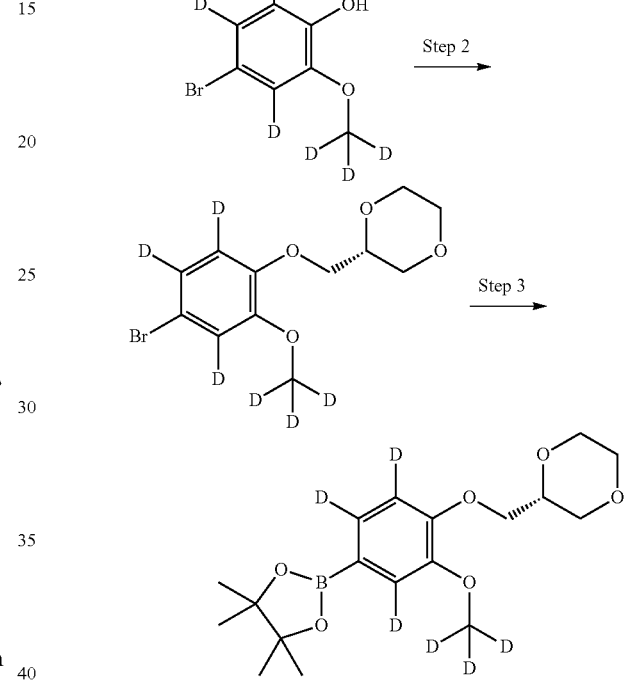

(Step 1) 4-Bromo-2,3,5-trideuterio-6-(trideuteriomethoxy)phenol 4-bromo-2-[($^2$H$_3$)methoxy] ($^2$H$_3$) phenol ($^2$H$_4$)Benzene-1,2-diol (12.0 g, 105 mmol) was suspended in dichloromethane (105 ml). To the suspension, 3,4-dihydro-2H-pyran (9.53 ml, 105 mmol) and p-toluenesulfonic acid pyridine salt (396 mg, 1.58 mmol) were added, and the mixture was stirred at room temperature for 3 hours. To the reaction mixture, a saturated aqueous solution of sodium bicarbonate was added, and the mixture was stirred for 10 minutes. The organic layer was washed with brine and dried over anhydrous sodium sulfate, and the solvent was distilled off under reduced pressure. The obtained oil was dissolved in acetone (207 ml). To the solution, potassium carbonate (45.8 g, 330 mmol) and trideuteriomethyl iodide (14.4 ml, 228 mmol) were added, and the mixture was heated with stirring at 40° C. for 24 hours under nitrogen stream. The reaction mixture was cooled to room temperature and then filtered with a Kiriyama funnel, and the filtrate was concentrated under reduced pressure. To the residue, hexane was added, and the mixture was filtered again with a Kiriyama funnel. Then, the filtrate was concentrated under reduced pressure. The obtained oil was dissolved in ethanol (181 ml).

To the solution, p-toluenesulfonic acid pyridine salt (341 mg, 1.36 mmol) was added, and the mixture was heated with stirring at 65° C. for 3 hours. The reaction mixture was cooled to room temperature and then concentrated under reduced pressure. The residue was dissolved in N,N-dimethylformamide (90.0 ml). To the solution, N-bromosuccinimide (16.1 g, 90.6 mmol) was added in small portions under ice cooling, and the mixture was stirred for 1 hour under ice cooling. To the reaction mixture, diethyl ether (500 ml) was added, and then, the reaction was terminated by the addition of an 8.85 mol/L aqueous sodium thiosulfate solution (50 ml). The organic layer was dried over anhydrous magnesium sulfate and then concentrated under reduced pressure. The residue was purified by amino silica gel column chromatography (Shoko Scientific Co., Ltd., elution solvent: hexane/ethyl acetate=90/10→55/45) to obtain the title compound (6.97 g, yield: 28.3%) as an oil.

$^1$H-NMR (CDCl$_3$) δ: 5.57 (1H, s).

MS (CI) m/z: 207 [(M−H)$^+$].

(Step 2) (2R)-2-[({4-Bromo-2-[($^2$H$_3$)methoxy]($^2$H$_3$)phenyl}oxy)methyl]-1,4-dioxane 4-Bromo-2-[($^2$H$_3$)methoxy] ($^2$H$_3$)phenol (2.00 g, 9.57 mmol) was dissolved in N,N-dimethylformamide (48.0 ml). To the solution, potassium carbonate (2.64 g, 19.1 mmol) and (2R)-1,4-dioxan-2-ylmethyl methanesulfonic acid (1.88 g, 9.57 mmol) were added, and the mixture was heated with stirring at 90° C. for 4 hours. The reaction mixture was cooled to room temperature, and ethyl acetate was added thereto. Insoluble matter was filtered off. The filtrate was concentrated under reduced pressure, and the residue was purified by silica gel column chromatography (Shoko Scientific Co., Ltd., elution solvent: hexane/ethyl acetate=100/0→70/30) to obtain the title compound (1.75 g, yield: 59.2%) as a solid.

$^1$H-NMR (CDCl$_3$) δ: 4.06-3.48 (9H, m).

MS (APCI) m/z: 309 [(M+H)$^+$].

(Step 3) (2R)-2-[({2-[($^2$H$_3$)Methoxy]-4-(4,4,5,5-tetramethyl-1,3,2-dioxaborolan-2-yl) ($^2$H$_3$) phenyl}oxy)methyl]-1,4-dioxane (2R)-2-[({4-Bromo-2-[($^2$H$_3$)methoxy] ($^2$H$_3$)phenyl}oxy)methyl]-1,4-dioxane (800 mg, 2.59 mmol) was suspended in toluene (5.20 ml). To the suspension, nickel(II) 1,3-bis(diphenylphosphino)propane]chloride (140 mg, 259 μmol), 1,3-bis(diphenylphosphino)propane (107 mg, 0.259 mmol), pinacol boron (0.744 ml, 5.17 mmol), and triethylamine (1.10 ml, 7.76 mmol) were added, and the mixture was heated with stirring at 100° C. for 16 hours under nitrogen stream. The reaction mixture was cooled to room temperature and diluted with ethyl acetate, and then, insoluble matter was filtered off through celite. The filtrate was concentrated under reduced pressure, and the residue was purified by silica gel column chromatography (Shoko Scientific Co., Ltd., elution solvent: hexane/ethyl acetate=100/0→85/15) to obtain the title compound (840 mg, 91.1%) as a solid.

$^1$H-NMR (CDCl$_3$) δ: 4.15-4.02 (2H, m), 4.00-3.93 (2H, m), 3.87-3.62 (4H, m), 3.57-3.49 (1H, m), 1.34 (12H, s).

MS (ESI) m/z: 357 [(M+H)$^+$].

(Intermediate 8) 3-(4-Aminophenyl)-5-{4-[(2S)-1,4-dioxan-2-ylmethoxy]-3-methoxyphenyl}pyridin-2-amine

[Formula 54]

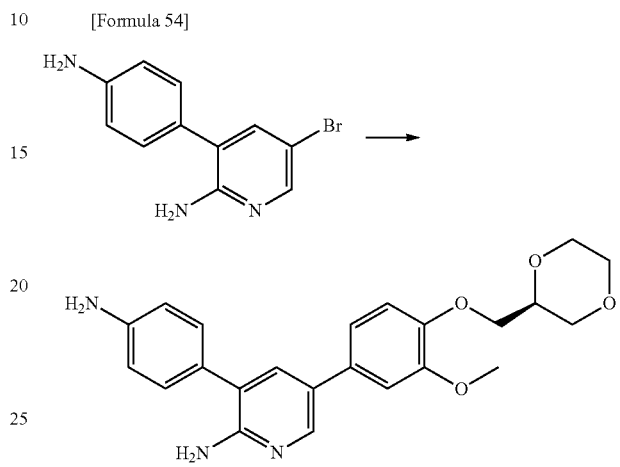

3-(4-Aminophenyl)-5-bromopyridin-2-amine (0.510 g, 1.93 mmol) synthesized by the method described in the patent (WO2013/115280 A1) was dissolved in 1,4-dioxane (5.00 ml). To the solution, water (1.00 ml), (2S)-2-{[2-methoxy-4-(4,4,5,5-tetramethyl-1,3,2-dioxaborolan-2-yl)phenoxy]methyl}-1,4-dioxane (0.451 g, 1.29 mmol), tetrakis(triphenylphosphine)palladium(0) (0.0744 g, 0.0644 mmol), and potassium carbonate (0.356 g, 2.58 mmol) were added, and the mixture was stirred at 100° C. for 5 hours under a nitrogen atmosphere. The reaction mixture was separated into organic and aqueous layers by the addition of dichloromethane and water. The organic layer was dried over anhydrous sodium sulfate, and the solvent was distilled off under reduced pressure. The residue was purified by silica gel column chromatography (Biotage Japan Ltd., elution solvent: ethyl acetate/methanol=99/1→90/10) to obtain the title compound (0.139 g, yield: 26.5%) as an oil.

$^1$H-NMR (CDCl$_3$) δ: 8.24-8.22 (1H, m), 7.53-7.51 (1H, m), 7.32-7.27 (2H, m), 7.07-6.99 (2H, m), 6.98-6.93 (1H, m), 6.81-6.76 (2H, m), 4.62-4.58 (2H, m), 4.14-4.01 (3H, m), 4.01-3.93 (3H, m), 3.92-3.63 (7H, m), 3.59-3.50 (1H, m).

MS (ESI) m/z: 408 [(M+H)$^+$]

(Intermediate 9a) 3-Bromo-5-{4-[(2S)-1,4-dioxan-2-ylmethoxy]-3-methoxyphenyl}pyridin-2-amine

[Formula 55]

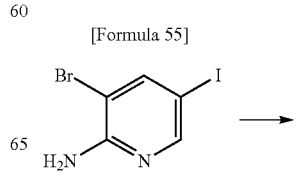

-continued

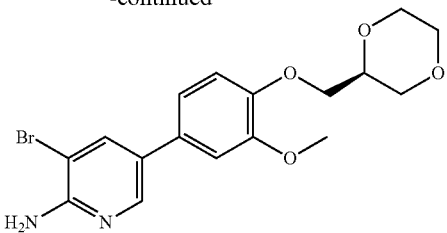

To 3-bromo-5-iodopyridin-2-amine (0.533 g, 1.79 mmol), (2S)-2-{[2-methoxy-4-(4,4,5,5-tetramethyl-1,3,2-dioxaborolan-2-yl)phenoxy]methyl}-1,4-dioxane (0.625 g, 1.79 mmol), sodium carbonate (0.378 g, 3.57 mmol), and tetrakis(triphenylphosphine)palladium(0) (0.103 g, 0.0892 mmol), 1,4-dioxane (9.00 mL) and water (1.80 mL) were added, and the mixture was stirred at 90° C. for 7 hours under a nitrogen atmosphere. The reaction mixture was left to cool to room temperature, and then, water was added thereto, followed by extraction with methylene chloride three times. The organic layer was dried over anhydrous sodium sulfate. After filtration and concentration under reduced pressure, the residue obtained was purified by silica gel column chromatography (Yamazen Corp., elution solvent: chloroform/ethyl acetate=59/41→38/62) to obtain the title compound (0.388 g, yield: 55.0%) as a solid.

$^1$H-NMR (DMSO-$D_6$) δ: 8.28 (1H, d, J=1.8 Hz), 8.05 (1H, d, J=2.4 Hz), 7.17 (1H, d, J=2.4 Hz), 7.10 (1H, dd, J=8.5, 2.4 Hz), 6.99 (1H, d, J=8.5 Hz), 6.28 (2H, s), 3.98-3.74 (8H, m), 3.69-3.60 (2H, m), 3.52-3.46 (1H, m), 3.42-3.36 (1H, m).

MS (APCI) m/z: 395 [(M+H)$^+$].

Similarly, the intermediates of Table 5 were synthesized from the corresponding starting materials.

TABLE 5

| Intermediate No. | Structural formula of intermediate<br>Instrumental data on intermediate | Structural formula of starting material |
|---|---|---|
| Intermediate 9b | ![structure]<br>$^1$H-NMR (CDCl$_3$) δ: 8.22 (1H, d, J = 2.4 Hz), 7.85 (1H, d, J = 2.4 Hz), 7.02-6.97 (2H, m), 6.92 (1H, d, J = 7.9 Hz), 4.94 (2H, s), 4.03 (2H, dd, J = 11.8, 3.3 Hz), 3.92 (3H, s), 3.89 (2H, d, J = 6.7 Hz), 3.46 (2H, td, J = 11.8, 1.8 Hz), 2.23-2.12 (1H, m), 1.82 (2H, br d, J = 12.8 Hz), 1.51-1.40 (2H, m).<br>MS (APCI) m/z: 393 [(M + H)$^+$]. | ![structure] |
| Intermediate 9c | ![structure]<br>$^1$H-NMR (CDCl$_3$) δ: 8.22 (1H, d, J = 2.4 Hz), 7.85 (1H, d, J = 2.4 Hz), 7.02-6.94 (3H, m), 4.94 (2H, s), 4.19 (2H, t, J = 6.1 Hz), 3.92 (3H, s), 3.76-3.73 (4H, m), 2.87 (2H, t, J = 6.1 Hz), 2.62-2.60 (4H, m).<br>MS (APCI) m/z: 408 [(M + H)$^+$]. | ![structure] |
| Intermediate 9d | ![structure]<br>1H-NMR (CDCl3) δ: 8.17 (1H, d, J = 2.0 Hz), 7.77 (1H, d, J = 2.0 Hz), 7.67 (1H, s), 7.62 (1H, s), 4.90 (2H, br s), 4.18-4.15 (2H, m), 4.01-3.97 (1H, m), 3.84-3.69 (4H, m), 3.60 (1H, dd, J = 11.0, 3.0 Hz), 3.31 (1H, dd, J = 11.0, 9.0 Hz), 1.24 (9H, s).<br>MS (APCI) m/z: 339 [(M + H)$^+$]. | ![structure] |

TABLE 5-continued

| Intermediate No. | Structural formula of intermediate Instrumental data on intermediate | Structural formula of starting material |
|---|---|---|
| Intermediate 9e | 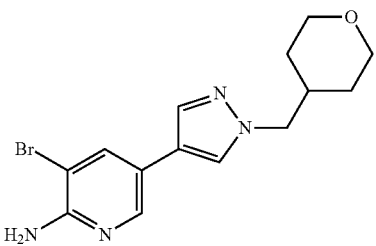 [SMILES: Nc1ncc(-c2cnn(CC3CCOCC3)c2)cc1Br]<br>¹H-NMR (CDCl₃) δ: 8.15 (1H, d, J = 2.0 Hz), 7.76 (1H, d, J = 2.0 Hz), 7.67 (1H, s), 7.52 (1H, s), 4.91 (2H, br s), 4.03-3.95 (4H, m), 3.38 (2H, td, J = 12.0, 2.0 Hz), 2.24-2.13 (1H, m), 1.53 (2H, d, J = 12.0 Hz), 1.44-1.33 (2H, m).<br>MS (APCI) m/z: 337 [(M + H)⁺]. | 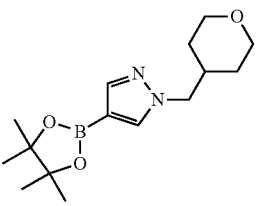 [SMILES: CC1(C)OB(c2cnn(CC3CCOCC3)c2)OC1(C)C] |
| Intermediate 9f | 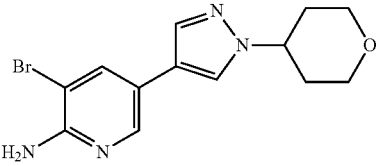 [SMILES: Nc1ncc(-c2cnn(C3CCOCC3)c2)cc1Br]<br>¹H-NMR (CDCl₃) δ: 8.16 (1H, d, J = 1.8 Hz), 7.77 (1H, d, J = 1.8 Hz), 7.68 (1H, s), 7.60 (1H, s), 4.89 (1H, br s), 4.42-4.33 (1H, m), 4.16-4.10 (2H, m), 3.56 (2H, td, J = 11.5, 3.5 Hz), 2.17-2.04 (4H, m).<br>MS (APCI) m/z: 323 [(M + H)⁺]. | 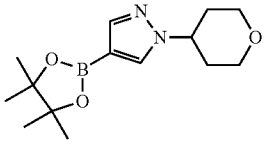 |
| Intermediate 9g | 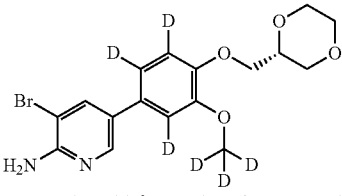<br>¹H-NMR (CDCl₃) δ: 8.22 (1H, d, J = 1.8 Hz), 7.85 (1H, d, J = 1.8 Hz), 4.95 (2H, s), 4.16-4.16 (4H, m), 3.89-3.64 (4H, m), 3.59-3.51 (1H, m).<br>MS (APCI) m/z: 401 [(M + H)⁺]. | 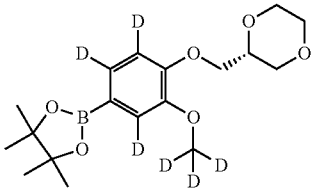 [SMILES: [2H]c1c([2H])c(B2OC(C)(C)C(C)(C)O2)c([2H])c(OC([2H])([2H])[2H])c1OC[C@H]1COCCO1] |

(Intermediate 10a) 3-(4-Amino-2-fluorophenyl)-5-{4-[(2R)-1,4-dioxan-2-ylmethoxy]-3-methoxyphenyl}pyridin-2-amine

[Formula 56]

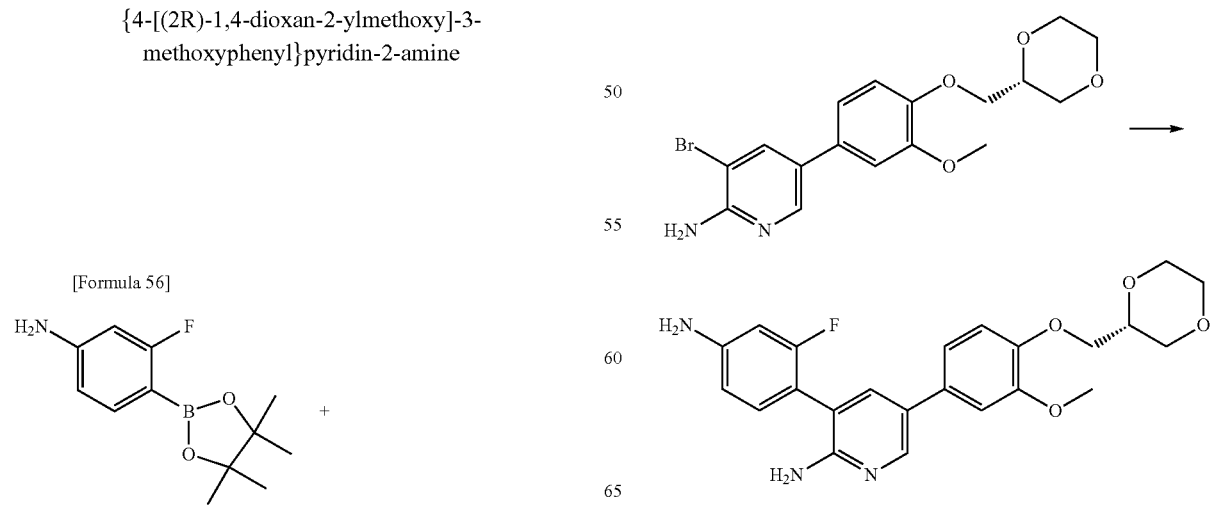

The title compound was obtained in the same way as in intermediate 8 by using 3-fluoro-4-(4,4,5,5-tetramethyl-1,3,2-dioxaborolan-2-yl)aniline and 3-bromo-5-{4-[(2R)-1,4-dioxan-2-ylmethoxy]-3-methoxyphenyl}pyridin-2-amine synthesized by the method described in the patent (WO2013/115280 A1) as starting materials, 1,4-dioxane and water as a solvent, tetrakis(triphenylphosphine)palladium(0) as a catalyst, and potassium carbonate as a base and carrying out heating with stirring at a reaction temperature of 100° C. for 5 hours.

$^1$H-NMR (CDCl$_3$) δ: 8.27 (1H, d, J=2.4 Hz), 7.54 (1H, d, J=2.4 Hz), 7.17 (1H, t, J=8.0 Hz), 7.06-7.01 (2H, m), 6.95 (1H, d, J=8.0 Hz), 6.55 (1H, dd, J=8.0, 2.4 Hz), 6.51 (1H, dd, J=11.5, 2.4 Hz), 4.52 (2H, br s), 4.13-3.52 (12H, m).

MS (APCI) m/z: 426 [(M+H)$^+$].

Similarly, the intermediates of Table 6 were synthesized from the corresponding starting materials A and B.

TABLE 6

| Intermediate No. | Structural formula of intermediate Instrumental data on intermediate | Structural formula of starting material A | Structural formula of starting material B |
|---|---|---|---|
| Intermediate 10b | [structure] <br> $^1$H-NMR (DMSO-D$_6$) δ: 8.23 (1H, d, J = 2.4 Hz), 7.50 (1H, d, J = 2.4 Hz), 7.15 (1H, d, J = 2.4 Hz), 7.09-6.97 (3H, m), 6.49-6.40 (2H, m), 5.55 (2H, s), 5.48 (2H, s), 3.97-3.75 (8H, m), 3.69-3.59 (2H, m), 3.52-3.46 (1H, m), 3.42-3.37 (1H, m). <br> MS (APCI) m/z: 426 [(M + H)$^+$]. | [structure] | [structure] |
| Intermediate 10c | [structure] <br> $^1$H-NMR (CDCl$_3$) δ: 8.27 (1H, d, J = 1.8 Hz), 7.53 (1H, d, J = 1.8 Hz), 7.16 (1H, t, J = 8.0 Hz), 6.57-6.48 (2H, m), 4.52 (2H, s), 4.16-3.49 (9H, m). <br> MS (APCI) m/z: 432 [(M + H)$^+$]. | [structure] | [structure] |
| Intermediate 10d | [structure] <br> $^1$H-NMR (CDCl$_3$) δ: 8.23 (1H, d, J = 2.4 Hz), 7.52 (1H, d, J = 2.4 Hz), 7.30 (2H, d, J = 9.0 Hz), 6.79 (2H, d, J = 9.0 Hz), 4.60 (2H, br s), 4.15-3.51 (9H, m). <br> MS (APCI) m/z: 414 [(M + H)$^+$]. | [structure] | [structure] |

(Intermediate 11a) 3-(4-Amino-3-fluorophenyl)-5-(3,4-dimethoxyphenyl)pyridin-2-amine

[Formula 57]

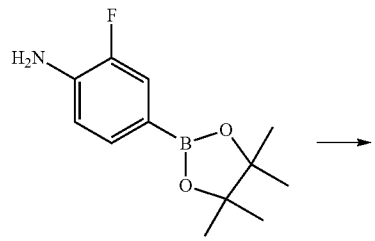

sulfate. After filtration and concentration under reduced pressure, the obtained residue was purified by silica gel column chromatography (Yamazen Corp., chloroform/ethyl acetate=50/50→0/100) and then purified by amino silica gel column chromatography (Yamazen Corp., n-hexane/ethyl acetate=25/75→0/100→ethyl acetate/methanol=100/0→90/10). After concentration under reduced pressure, the obtained solid was suspended in diethyl ether, collected by filtration, and dried to obtain the title compound (0.928 g, yield: 65.1%) as a solid.

$^1$H-NMR (DMSO-D$_6$) δ: 8.20 (1H, d, J=2.4 Hz), 7.52 (1H, d, J=2.4 Hz), 7.18-7.11 (3H, m), 7.06 (1H, dd, J=7.9, 2.4 Hz), 6.98 (1H, d, J=8.5 Hz), 6.87-6.83 (1H, m), 5.61 (2H, s), 5.30 (2H, s), 3.82 (3H, s), 3.77 (3H, s)

MS (APCI) m/z: 340 [(M+H)$^+$].

Similarly, the intermediate of Table 7 was synthesized from the corresponding starting material.

TABLE 7

| Intermediate No. | Structural formula of intermediate<br>Instrumental data on intermediate | Structural formula of starting material |
|---|---|---|
| Intermediate 11b | 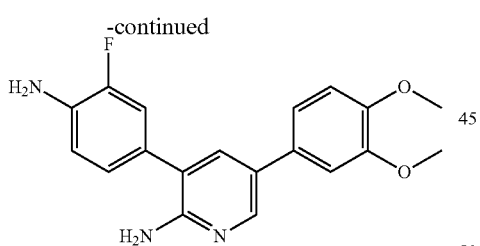<br>$^1$H-NMR (CDCl$_3$) δ: 8.25 (1H, d, J = 2.4 Hz), 7.51 (1H, d, J = 2.4 Hz), 7.41 (1H, d, J = 1.8 Hz), 7.23 (1H, dd, J = 7.9, 1.8 Hz), 7.08 (1H, dd, J = 8.5, 1.8 Hz), 7.02 (1H, d, J = 2.4 Hz), 6.94 (1H, d, J = 8.5 Hz), 6.87 (1H, d, J = 7.9 Hz), 4.60-4.55 (2H, m), 4.20-4.16 (2H, m), 3.94 (3H, s), 3.92 (3H, s).<br>MS (ESI) m/z: 356 [(M + H)$^+$]. | |

-continued

To 3-bromo-5-(3,4-dimethoxyphenyl)pyridin-2-amine (1.30 g, 4.20 mmol) synthesized by the method described in the patent (WO2013/115280 A1), 2-fluoro-4-(4,4,5,5-tetramethyl-1,3,2-dioxaborolan-2-yl)aniline (1.20 g, 5.06 mmol), [1,1'-bis(diphenylphosphino)ferrocene]palladium (II) dichloride-dichloromethane complex (1:1) (0.340 g, 0.416 mmol), and cesium carbonate (4.10 g, 12.6 mmol), 1,4-dioxane (25.0 mL) and water (5.00 mL) were added, and the mixture was stirred at 80° C. for 5 hours. The reaction mixture was left to cool to room temperature, and then, water and methylene chloride were added thereto. Insoluble matter was filtered off through celite, and the filtrate was subjected to extraction with methylene chloride three times. Then, the organic layer was dried over anhydrous sodium (Intermediate 12a) 3-(4-Amino-3-fluorophenyl)-4-methoxypyridin-2-amine

[Formula 58]

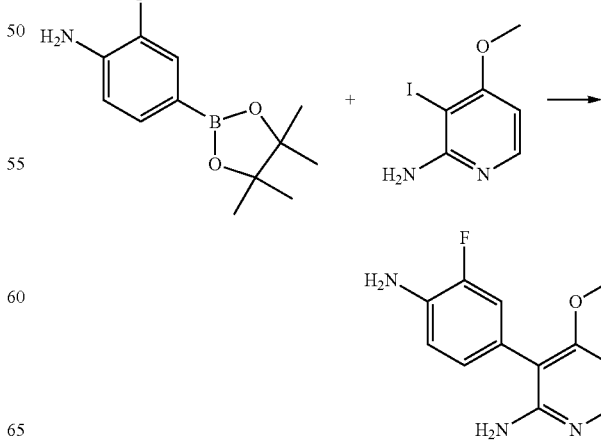

To 3-iodo-4-methoxypyridin-2-amine (0.500 g, 2.00 mmol), 2-fluoro-4-(4,4,5,5-tetramethyl-1,3,2-dioxaborolan-2-yl)aniline (0.498 g, 2.10 mmol), tetrakis(triphenylphosphine)palladium(0) (0.231 g, 0.200 mmol), and sodium carbonate (0.636 g, 6.00 mmol), 1,4-dioxane (10.0 mL) and water (2.00 mL) were added, and the mixture was stirred at 80° C. for 12 hours under a nitrogen atmosphere. The reaction mixture was left to cool to room temperature, and then, water was added thereto, followed by extraction with ethyl acetate three times. The organic layer was washed with brine and then dried over anhydrous sodium sulfate. After filtration and concentration under reduced pressure, the residue obtained was purified by silica gel column chromatography (Yamazen Corp., ethyl acetate/methanol=100/0→90/10) and then purified by amino silica gel column chromatography (Yamazen Corp., ethyl acetate/methanol=100/0→90/10) to obtain the title compound (0.177 g, yield: 38.0%) as a solid.

$^1$H-NMR (DMSO-D$_6$) δ: 7.83 (1H, d, J=5.5 Hz), 7.65-7.53 (1H, m), 6.83-6.72 (3H, m), 6.39 (1H, d, J=6.1 Hz), 5.18 (2H, s), 5.10 (2H, s), 3.65 (3H, s).

MS (APCI) m/z: 234 [(M+H)$^+$].

Similarly, the intermediates of Table 8 were synthesized from the corresponding starting materials A and B.

TABLE 8

| Intermediate No. | Structural formula of intermediate Instrumental data on intermediate | Structural formula of starting material A | Structural formula of starting material B |
|---|---|---|---|
| Intermediate 12b | [structure: 4-aminophenyl-3-yl-4-methyl-2-aminopyridine]<br>$^1$H-NMR (DMSO-D$_6$) δ: 7.74 (1H, d, J = 4.9 Hz), 6.84 (2H, d, J = 8.5 Hz), 6.65 (2H, d, J = 8.5 Hz), 6.48 (1H, d, J = 5.5 Hz), 5.18 (2H, s), 4.95 (2H, s), 1.91 (3H, s).<br>MS (APCI) m/z: 200 [(M + H)$^+$]. | [4-aminophenyl boronic acid pinacol ester] | [3-iodo-4-methylpyridin-2-amine] |
| Intermediate 12c | [structure: 4-aminophenyl-3-yl-4-chloro-2-aminopyridine]<br>$^1$H-NMR (CDCl$_3$) δ: 7.90 (1H, d, J = 5.5 Hz), 7.12-7.08 (2H, m), 6.81-6.75 (3H, m), 4.49 (2H, br s), 3.81 (2H, br s).<br>MS (ESI) m/z: 220 [(M + H)$^+$] | [4-aminophenyl boronic acid pinacol ester] | [4-chloro-3-iodopyridin-2-amine] |
| Intermediate 12d | [structure: 4-amino-3-fluorophenyl-3-yl-4-chloro-2-aminopyridine]<br>$^1$H-NMR (CDCl$_3$) δ: 7.95 (1H, d, J = 5.5 Hz), 7.04 (1H, t, J = 8.2 Hz), 6.79 (1H, d, J = 6.1 Hz), 6.59-6.48 (2H, m), 4.50 (2H, br s), 3.94 (2H, br s).<br>MS (ESI) m/z: 238 [(M + H)$^+$] | [4-amino-3-fluorophenyl boronic acid pinacol ester] | [4-chloro-3-iodopyridin-2-amine] |
| Intermediate 12e | [structure: 4-amino-3-fluorophenyl-3-yl-4-chloro-2-aminopyridine isomer] | [4-amino-2-fluorophenyl boronic acid pinacol ester] | [4-chloro-3-iodopyridin-2-amine] |

TABLE 8-continued

| Intermediate No. | Structural formula of intermediate Instrumental data on intermediate | Structural formula of starting material A | Structural formula of starting material B |
|---|---|---|---|
| | $^1$H-NMR (CDCl$_3$) δ: 7.92 (1H, d, J = 5.5 Hz), 6.99-6.95 (1H, m), 6.92-6.85 (2H, m), 6.77 (1H, d, J = 5.5 Hz), 4.49 (2H, br s), 3.88 (2H, br s). MS (ESI) m/z: 238 [(M + H)$^+$] | | |

(Intermediate 13) 3-(4-Aminophenyl)-5-(3,4-dimethoxyphenyl) pyrazin-2-amine

[Formula 59]

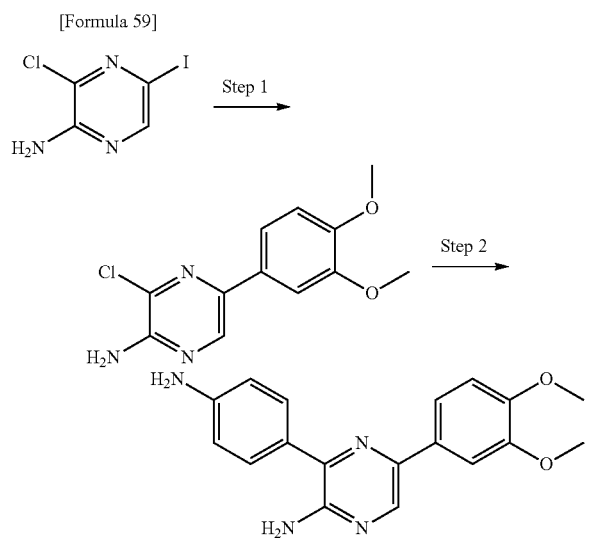

(Step 1)
3-Chloro-5-(3,4-dimethoxyphenyl)pyrazin-2-amine

To 3-chloro-5-iodopyrazin-2-amine (0.510 g, 2.00 mmol) synthesized according to the method described in the patent (WO2011/110545 A1), (3,4-dimethoxyphenyl)boronic acid (0.363 g, 2.00 mmol), [1,1'-bis(diphenylphosphino)ferrocene]palladium(II) dichloride-dichloromethane complex (1:1) (0.163 g, 0.200 mmol), and cesium carbonate (1.30 g, 4.00 mmol), 1,4-dioxane (7.50 mL) and water (2.50 mL) were added, and the mixture was stirred at 80° C. for 4 hours. The reaction mixture was left to cool to room temperature, and then, water was added thereto, followed by extraction with methylene chloride three times. The organic layer was dried over anhydrous sodium sulfate. After filtration and concentration under reduced pressure, the residue obtained was purified by silica gel column chromatography (Yamazen Corp., chloroform/ethyl acetate=100/0→90/10) and further purified by amino silica gel column chromatography (Yamazen Corp., n-hexane/ethyl acetate=25/75→0/100) to obtain the title compound (0.412 g, yield: 77.7%) as a solid.

$^1$H-NMR (DMSO-D$_6$) δ: 8.57 (1H, s), 7.47-7.45 (2H, m), 7.01 (1H, d, J=7.9 Hz), 6.85 (2H, s), 3.83 (3H, s), 3.79 (3H, s).

MS (APCI) m/z: 266 [(M+H)$^+$].

(Step 2) 3-(4-Aminophenyl)-5-(3,4-dimethoxyphenyl)pyrazin-2-amine

To 3-chloro-5-(3,4-dimethoxyphenyl)pyrazin-2-amine (0.0800 g, 0.301 mmol) synthesized in step 1,4-(4,4,5,5-tetramethyl-1,3,2-dioxaborolan-2-yl)aniline (0.0990 g, 0.452 mmol), [1,1'-bis(diphenylphosphino)ferrocene]palladium(II) dichloride-dichloromethane complex (1:1) (0.0246 g, 0.030 mmol), and cesium carbonate (0.294 g, 0.903 mmol), 1,4-dioxane (2.00 mL) and water (0.200 mL) were added, and the mixture was stirred at 100° C. for 4 hours. The reaction mixture was left to cool to room temperature, and then, water was added thereto, followed by extraction with methylene chloride three times. The organic layer was dried over anhydrous sodium sulfate. After filtration and concentration under reduced pressure, the residue obtained was purified by silica gel column chromatography (Yamazen Corp., ethyl acetate alone) to obtain the title compound (0.0940 g, yield: 96.8%) as an amorphous solid.

$^1$H-NMR (DMSO-D$_6$) δ: 8.39 (1H, s), 7.54-7.50 (4H, m), 7.01 (1H, d, J=8.5 Hz), 6.67 (2H, d, J=8.5 Hz), 6.00 (2H, s), 5.44 (2H, s), 3.83 (3H, s), 3.79 (3H, s)

MS (APCI) m/z: 323 [(M+H)$^+$].

(Intermediate 14a) N-(6-Chloropyridazin-3-yl)-5-(4-methylphenyl)-4-oxo-1-(tetrahydro-2H-pyran-4-ylmethyl)-1,4-dihydropyridine-3-carboxamide

[Formula 60]

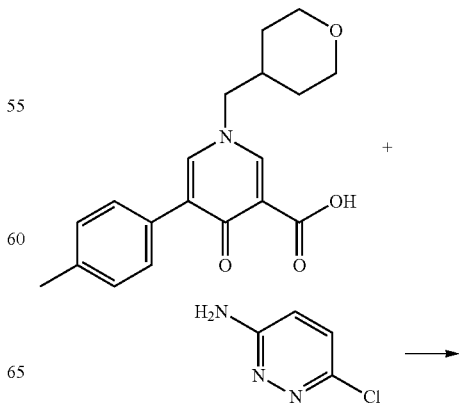

-continued

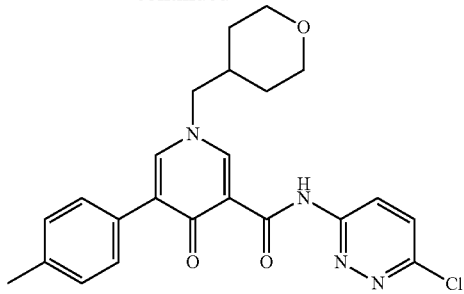

5-(4-Methylphenyl)-4-oxo-1-(tetrahydro-2H-pyran-4-yl-methyl)-1,4-dihydropyridine-3-carboxylic acid (3.00 g, 9.16 mmol) was dissolved in N,N-dimethylformamide (30.0 ml). To the solution, N-[1-(cyano-2-ethoxy-2-oxoethylideneaminooxy)dimethylamino(morpholino)]uronium hexafluorophosphate (COMU) (4.32 g, 10.1 mmol) was added, and the mixture was stirred at room temperature for 1 hour. Then, 3-amino-6-chloropyridazine (1.31 g, 10.1 mmol) was added thereto, and the mixture was stirred at room temperature for 3 days. The reaction mixture was diluted with ethyl acetate, and then, 1 N hydrochloric acid was added thereto. The organic layer was washed with a saturated aqueous solution of sodium bicarbonate and brine in this order. The organic layer was dried over anhydrous sodium sulfate. The solvent was concentrated under reduced pressure, and the residue was purified by silica gel column chromatography (Shoko Scientific Co., Ltd., ethyl acetate/methanol=100/0→96/4) to obtain an amorphous solid. This solid was washed with methanol by the slurry method to obtain the title compound (2.10 g, yield: 52.2%) as a solid.

$^1$H-NMR (CDCl$_3$) δ: 13.68 (1H, s), 8.59 (1H, d, J=9.0 Hz), 8.48 (1H, d, J=2.0 Hz), 7.51-7.46 (4H, m), 7.26 (2H, d, J=8.0 Hz), 4.03 (2H, dd, J=11.5, 4.0 Hz), 3.87 (2H, d, J=7.5 Hz), 3.39 (2H, t, J=11.5 Hz), 2.40 (3H, s), 2.16-2.06 (1H, m), 1.64-1.55 (2H, m), 1.50-1.38 (2H, m).

MS (APCI) m/z: 439 [(M+H)$^+$].

Similarly, the intermediates of Table 9 were synthesized from the corresponding starting materials A and B.

TABLE 9

| Intermediate No. | Structural formula of intermediate<br>Instrumental data on intermediate | Structural formula of starting material A | Structural formula of starting material B |
|---|---|---|---|
| Intermediate 14b | [structure]<br>$^1$H-NMR (CDCl$_3$) δ: 12.98 (1H, s), 8.68 (1H, s), 8.52 (1H, s), 7.96 (1H, d, J = 8.5 Hz), 7.66 (1H, d, J = 8.5 Hz), 7.49-7.40 (3H, m), 7.30-7.25 (2H, m), 4.03 (2H, d, J = 11.6 Hz), 3.87 (2H, d, J = 7.3 Hz), 3.38 (2H, t, J = 11.6 Hz), 2.40 (3H, s), 2.16-2.02 (1H, m) 1.65-1.36 (4H, m).<br>MS (ESI) m/z: 530 [(M + H)$^+$]. | [structure] | [structure] |
| Intermediate 14c | [structure]<br>$^1$H-NMR (CDCl$_3$) δ: 12.87 (1H, s), 8.68 (1H, d, J = 2.4 Hz), 8.54 (1H, d, J = 2.4 Hz), 7.95 (1H, dd, J = 8.5, 2.4 Hz), 7.67 (1H, d, J = 8.5 Hz), 7.56-7.51 (2H, m), 7.48 (1H, d, J = 2.4 Hz), 7.20-7.14 (2H, m), 4.03 (2H, dd, J = 11.6, 3.1 Hz), 3.88 (2H, d, J = 7.3 Hz), 3.39 (2H, td, J = 11.7, 2.0 Hz), 2.18-2.04 (1H, m), 1.63-1.53 (2H, m), 1.50-1.38 (2H, m).<br>MS (ESI) m/z: 534 [(M + H)$^+$]. | [structure] | [structure] |

TABLE 9-continued

| Intermediate No. | Structural formula of intermediate Instrumental data on intermediate | Structural formula of starting material A | Structural formula of starting material B |
|---|---|---|---|
| Intermediate 14d | 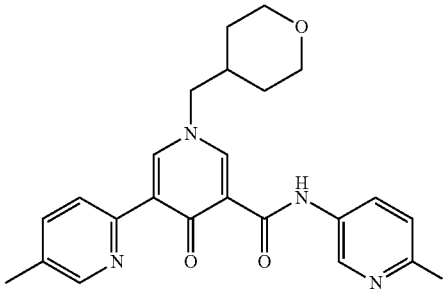 | 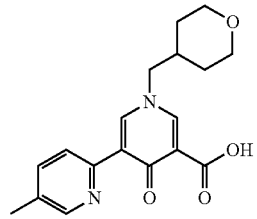 [SMILES: Cc1ccc(-c2cn(CC3CCOCC3)cc(C(=O)O)c2=O)nc1] | 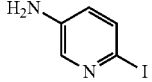 |
| | $^1$H-NMR (CDCl$_3$) δ: 12.92 (1H, br s), 8.69 (1H, d, J = 2.4 Hz), 8.54 (1H, s), 8.49-8.42 (3H, m), 8.00 (1H, dd, J = 8.5, 3.1 Hz), 7.69 (2H, d, J = 8.5 Hz), 4.01 (2H, dd, J = 11.9, 3.4 Hz), 3.95 (2H, d, J = 6.7 Hz), 3.42-3.33 (2H, m), 2.41 (3H, s), 2.22-2.09 (1H, m), 1.62-1.38 (4H, m). MS (ESI) m/z: 531 [(M + H)$^+$]. | | |
| Intermediate 14e | 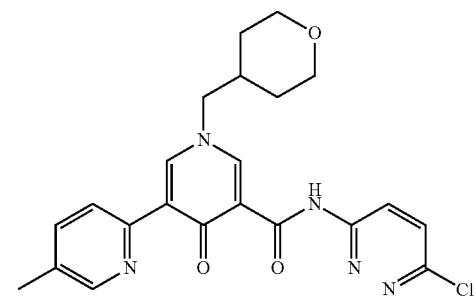 | 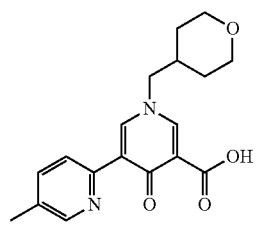 [SMILES: Cc1ccc(-c2cn(CC3CCOCC3)cc(C(=O)O)c2=O)nc1] | 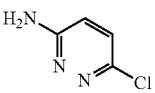 |
| | $^1$H-NMR (CDCl$_3$) δ: 13.79 (1H, s), 8.61 (2H, d, J = 9.1 Hz), 8.48 (2H, dd, J = 8.5, 2.4 Hz), 8.44 (1H, s), 7.61 (1H, dd, J = 8.5, 1.8 Hz), 7.50 (1H, d, J = 9.7 Hz), 4.02 (2H, dd, J = 11.5, 3.6 Hz), 3.93 (2H, d, J = 7.3 Hz), 3.39 (2H, td, J = 11.5, 1.8 Hz), 2.39 (3H, s), 2.21-2.10 (1H, m), 1.62-1.59 (2H, m), 1.51-1.40 (2H, m). MS (APCI) m/z: 440 [(M + H)$^+$]. | | |

TABLE 9-continued

| Intermediate No. | Structural formula of intermediate Instrumental data on intermediate | Structural formula of starting material A | Structural formula of starting material B |
|---|---|---|---|
| Intermediate 14f | 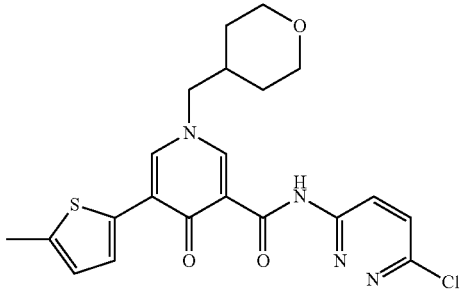 [SMILES: Cc1ccc(-c2cn(CC3CCOCC3)cc(C(=O)NC(=N)/C=C\C(=N)Cl)c2=O)s1] <br> $^1$H-NMR (DMSO-D$_6$) δ: 13.77 (1H, s), 8.72 (1H, d, J = 2.4 Hz), 8.69 (1H, d, J = 2.4 Hz), 8.58 (1H, d, J = 9.7 Hz), 7.95 (1H, d, J = 9.1 Hz), 7.58 (1H, d, J = 3.6 Hz), 6.86 (1H, d, J = 3.0 Hz), 4.14 (2H, d, J = 7.3 Hz), 3.86 (2H, dd, J = 10.9, 3.0 Hz), 3.26 (2H, t, J = 10.9 Hz), 2.49 (3H, s), 2.18-2.08 (1H, m), 1.44 (2H, br d, J = 10.9 Hz), 1.37-1.26 (2H, m). <br> MS (APCI) m/z: 445 [(M + H)$^+$]. | 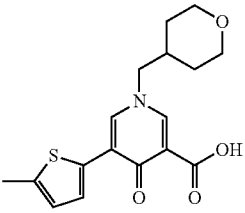 [SMILES: Cc1ccc(-c2cn(CC3CCOCC3)cc(C(=O)O)c2=O)s1] | 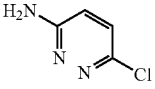 |
| Intermediate 14g | 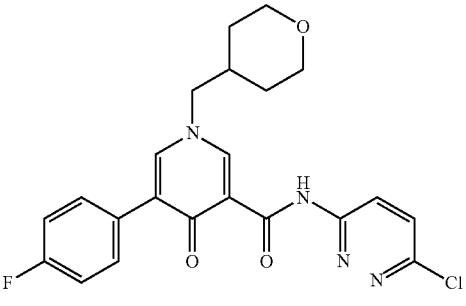 [SMILES: N=C(Cl)/C=C\C(=N)NC(=O)c1cn(CC2CCOCC2)cc(-c2ccc(F)cc2)c1=O] <br> $^1$H-NMR (DMSO-D$_6$) δ: 13.87 (1H, s), 8.74 (1H, d, J = 2.4 Hz), 8.55 (1H, d, J = 9.1 Hz), 8.23 (1H, d, J = 2.4 Hz), 7.91 (1H, d, J = 9.1 Hz), 7.73-7.69 (2H, m), 7.27 (2H, t, J = 9.1 Hz), 4.08 (2H, d, J = 7.3 Hz), 3.83 (2H, dd, J = 11.5, 3.0 Hz), 3.22 (2H, t, J = 11.5 Hz), 2.11-2.05 (1H, m), 1.43-1.40 (2H, m), 1.44-1.22 (2H, m). <br> MS (APCI) m/z: 443 [(M + H)$^+$]. | 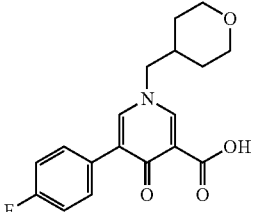 | 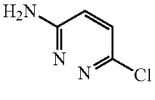 |

(Intermediate 16a) N-(5-Iodopyridin-2-yl)-5-(4-methylphenyl)-4-oxo-1-(tetrahydro-2H-pyran-4-ylmethyl)-1,4-dihydropyridine-3-carboxamide

[Formula 61]

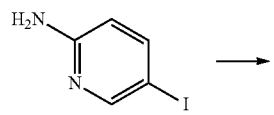

To a solution of 5-(4-methylphenyl)-4-oxo-1-(tetrahydro-2H-pyran-4-ylmethyl)-1,4-dihydropyridine-3-carboxylic acid (300 mg, 0.916 mmol) in dimethylacetamide (1 ml), thionyl chloride (0.087 ml, 1.19 mmol) was added in an ice water bath. After stirring for 0.5 hours, 5-iodopyridin-2-amine (201 mg, 0.916 mmol) and diisopropylethylamine (0.23 ml, 1.37 mmol) were added thereto in an ice water bath, and the temperature of the reaction mixture was gradually raised to room temperature. The reaction mixture was stirred at room temperature for 5 hours, and then, water was added thereto. Insoluble matter was collected by filtration. The product obtained was washed with hexane and then dried at 50° C. for 1 hour under reduced pressure. The residue was purified by silica gel column chromatography (chloroform/methanol=99/1→95/5) to obtain the title compound (302 mg, yield: 62.3%) as a solid.

$^1$H-NMR (CDCl$_3$) δ: 13.19 (1H, s), 8.53 (1H, d, J=2.4 Hz), 8.49 (1H, d, J=2.4 Hz), 8.15 (1H, d, J=8.5 Hz), 7.95 (1H, dd, J=8.5, 2.4 Hz), 7.51 (2H, d, J=7.9 Hz), 7.46 (1H, d, J=2.4 Hz), 7.28-7.23 (2H, m), 4.03 (2H, dd, J=11.0, 3.7 Hz), 3.85 (2H, d, J=7.3 Hz), 3.42-3.34 (2H, m), 2.40 (3H, s), 2.15-2.03 (1H, m), 1.63-1.51 (2H, m), 1.49-1.37 (2H, m).

MS (ESI/APCI) m/z: 530 [(M+H)$^+$].

Similarly, the intermediate of Table 10 was synthesized from the corresponding starting material.

TABLE 10

| Intermediate No. | Structural formula of intermediate Instrumental data on intermediate | Structural formula of starting material |
|---|---|---|
| Intermediate 16b | 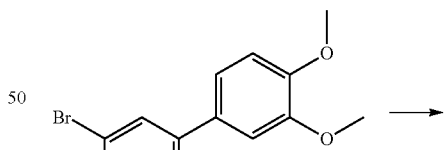<br>$^1$H-NMR (CDCl$_3$) δ: 13.37 (1H, s), 9.42 (1H, s), 8.52 (1H, d, J = 2.4 Hz), 8.39 (1H, d, J = 2.4 Hz), 7.50-7.48 (3H, m), 7.27-7.25 (2H, m), 4.03 (2H, dd, J = 11.5, 3.6 Hz), 3.86 (2H, d, J = 7.3 Hz), 3.38 (2H, t, J = 11.5 Hz), 2.40 (3H, s), 2.15-2.05 (1H, m), 1.62-1.56 (2H, m), 1.49-1.38 (2H, m).<br>MS (APCI) m/z: 483 [(M + H)$^+$]. | |

(Intermediate 17a) 5-(3,4-Dimethoxyphenyl)-3-(4,4,5,5-tetramethyl-1,3,2-dioxaborolan-2-yl)pyridin-2-amine

[Formula 62]

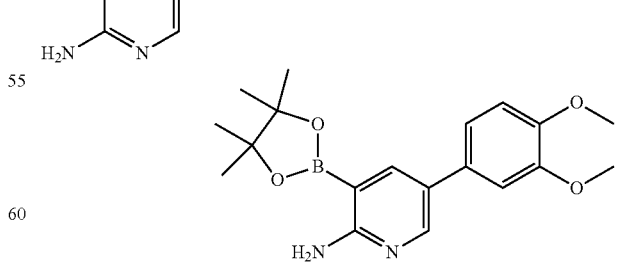

To 3-bromo-5-(3,4-dimethoxyphenyl)pyridin-2-amine (2.48 g, 8.02 mmol) synthesized by the method described in the patent (WO2013/115280 A1), bis(pinacolato)diboron (3.05 g, 12.0 mmol), tris(dibenzylideneacetone)palladium (0) (0.441 g, 0.481 mmol), tricyclohexylphosphine (0.315 g, 1.12 mmol), and potassium acetate (1.18 g, 12.0 mmol), 1,4-dioxane (40.0 mL) was added, and the mixture was stirred at 80° C. for 6.5 hours under a nitrogen atmosphere. The reaction mixture was left to cool to room temperature, and then, water was added thereto, followed by extraction with ethyl acetate three times. The organic layer was washed with brine. After filtration and concentration under reduced pressure, the obtained solid was suspended in diethyl ether, collected by filtration, and dried to obtain the title compound (2.20 g, yield: 77.0%) as a yellow solid.

$^1$H-NMR (DMSO-D$_6$) δ: 8.36 (1H, d, J=3.0 Hz), 7.86 (1H, d, J=3.0 Hz), 7.09-6.97 (3H, m), 6.18 (2H, s), 3.83 (3H, s), 3.77 (3H, s), 1.32 (12H, s).

Similarly, the intermediates of Table 11 were synthesized from the corresponding starting materials.

TABLE 11

| Intermediate No. | Structural formula of intermediate Instrumental data on intermediate | Structural formula of starting material |
|---|---|---|
| Intermediate 17b | 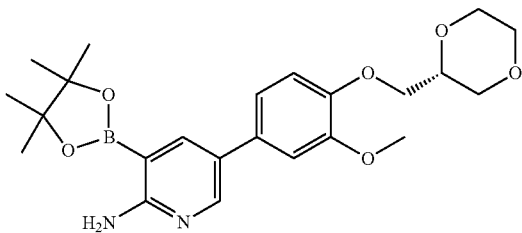 [SMILES: COc1cc(-c2cnc(N)c(B3OC(C)(C)C(C)(C)O3)c2)ccc1OC[C@H]1COCCO1] $^1$H-NMR (CDCl$_3$) δ: 8.35 (1H, d, J = 2.4 Hz), 8.06 (1H, d, J = 2.4 Hz), 7.07-6.96 (3H, m), 5.54 (2H, s), 4.12-3.54 (12H, m), 1.39 (12H, s). | 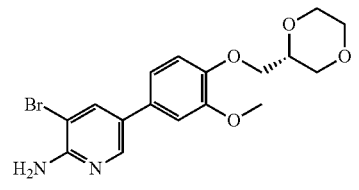 |
| Intermediate 17c | 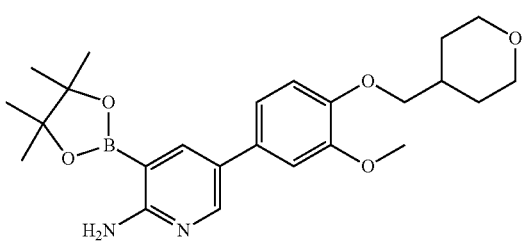 [SMILES: COc1cc(-c2cnc(N)c(B3OC(C)(C)C(C)(C)O3)c2)ccc1OCC1CCOCC1] $^1$H-NMR (CDCl$_3$) δ: 8.33 (1H, d, J = 2.4 Hz), 8.03 (1H, d, J = 2.4 Hz), 7.05-7.01 (2H, m), 6.91 (1H, d, J = 7.9 Hz), 5.50 (2H, s), 4.02 (2H, dd, J = 11.5, 3.6 Hz), 3.92 (3H, s), 3.88 (2H, d, J = 6.7 Hz), 3.45 (2H, td, J = 11.5, 1.6 Hz), 2.23-2.12 (1H, m), 1.82 (2H, br d, J = 13.1 Hz), 1.51-1.40 (2H, m), 1.36 (12H, s). | 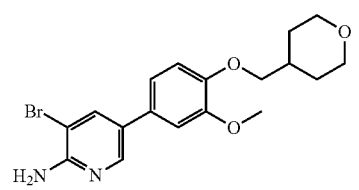 [SMILES: COc1cc(-c2cnc(N)c(Br)c2)ccc1OCC1CCOCC1] |
| Intermediate 17d | 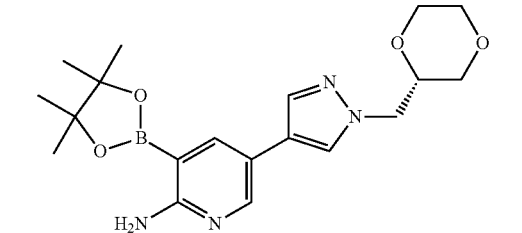 [SMILES: CC1(C)OB(c2cc(-c3cnn(C[C@H]4COCCO4)c3)cnc2N)OC1(C)C] $^1$H-NMR (CDCl$_3$) δ: 8.28 (1H, d, J = 2.4 Hz), 7.95 (1H, d, J = 2.4 Hz), 7.71 (1H, s), 7.64 (1H, s), 5.47 (2H, br s), 4.16 (2H, d, J = 5.5 Hz), 4.01-3.94 (1H, m), 3.85-3.54 (5H, m), 3.31 (1H, dd, J = 11.5, 10.5 Hz), 1.36 (12H, s). MS (ESI) m/z: 387 [(M + H)$^+$]. | 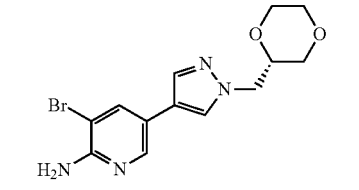 [SMILES: Nc1ncc(-c2cnn(C[C@H]3COCCO3)c2)cc1Br] |
| Intermediate 17e | 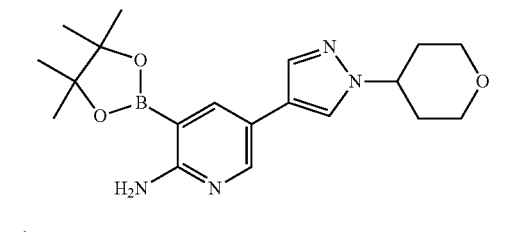 $^1$H-NMR (CDCl$_3$) δ: 8.27 (1H, d, J = 2.4 Hz), 7.94 (1H, d, J = 2.4 Hz), 7.72 (1H, s), 7.62 (1H, s), 5.49 (2H, s), 4.41-4.31 (1H, | 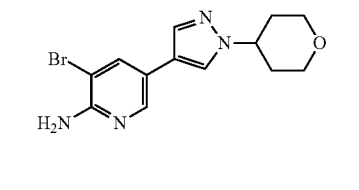 [SMILES: Nc1ncc(-c2cnn(C3CCOCC3)c2)cc1Br] |

TABLE 11-continued

| Intermediate No. | Structural formula of intermediate  Instrumental data on intermediate | Structural formula of starting material |
|---|---|---|
| Intermediate 17f | (structure shown)  ¹H-NMR (CDCl₃) δ: 8.23 (1H, d, J = 2.4 Hz), 7.95 (1H, d, J = 2.4 Hz), 7.71 (1H, s), 7.55 (1H, s), 5.71 (2H, br s), 4.02-3.95 (4H, m), 3.38 (2H, td, J = 12.0, 2.0 Hz), 2.25-2.13 (1H, m), 1.52 (2H, d, J = 12.0 Hz), 1.44-1.31 (2H, m), 1.24 (12H, s).  MS (ESI) m/z: 385 [(M + H)⁺]. | (structure shown) |

Continued from previous entry: m), 4.13 (2H, d, J = 11.5 Hz), 3.56 (2H, td, J = 11.5, 2.5 Hz), 2.17-2.07 (4H, m), 1.36 (12H, s). MS (ESI) m/z: 371 [(M + H)⁺].

(Intermediate 18) 5'-(3,4-Dimethoxyphenyl)-3-fluoro-2,3'-bipyridine-2',5-diamine

[Formula 63]

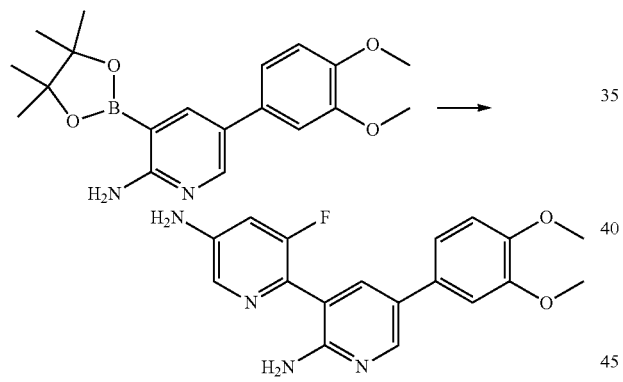

To 6-chloro-5-fluoropyridin-3-amine (0.0300 g, 0.205 mmol), 5-(3,4-dimethoxyphenyl)-3-(4,4,5,5-tetramethyl-1,3,2-dioxaborolan-2-yl)pyridin-2-amine (0.109 g, 0.307 mmol), [1,1'-bis(diphenylphosphino)ferrocene]palladium (II) dichloride-dichloromethane complex (1:1) (0.0167 g, 0.0205 mmol), and cesium carbonate (0.200 g, 0.614 mmol), 1,4-dioxane (2.00 mL) and water (0.200 mL) were added, and the mixture was stirred at 100° C. for 3 hours. The reaction mixture was left to cool to room temperature, and then, water was added thereto, followed by extraction with methylene chloride three times. The organic layer was dried over anhydrous sodium sulfate. After filtration and concentration under reduced pressure, the residue obtained was purified by silica gel column chromatography (Shoko Scientific Co., Ltd., ethyl acetate/methanol=100/0→85/15) to obtain the title compound (0.0690 g, yield: 99.0%) as an oil.

¹H-NMR (CDCl₃) δ: 8.27 (1H, d, J=2.4 Hz), 7.98-7.95 (2H, m), 7.10-7.04 (2H, m), 6.94 (1H, d, J=7.9 Hz), 6.85 (1H, dd, J=12.1, 2.4 Hz), 5.99 (2H, s), 3.99-3.92 (8H, m). MS (APCI) m/z: 341 [(M+H)⁺].

(Intermediate 19) 5-Bromo-4-oxo-1-(tetrahydro-2H-pyran-4-ylmethyl)-1,4-dihydropyridine-3-carboxylic acid

[Formula 64]

(Step 1) Methyl 5-bromo-4-oxo-1-(tetrahydro-2H-pyran-4-ylmethyl)-1,4-dihydropyridine-3-carboxylate To methyl 5-bromo-4-hydroxypyridine-3-carboxylate (2.36 g, 10.2 mmol) synthesized according to the method described in the literature (J. Med. Chem. 2008, 51, 5330-5341), cesium carbonate (9.94 g, 30.5 mmol) and N,N-dimethylformamide (30.0 mL) were added, and the mixture was stirred at 80° C. for 15 minutes. Then, 4-(bromomethyl) tetrahydro-2H-pyran (5.46 g, 30.5 mmol) was added thereto, and the mixture was stirred at 80° C. for 11 hours and then left overnight at room temperature. To the reaction mixture, water and brine were added, followed by extraction with ethyl acetate three times and then extraction with methylene chloride five times. The organic layers were combined and dried over anhydrous sodium sulfate. After filtration and concentration under reduced pressure, the residue obtained was purified by amino silica gel column chromatography (Yamazen Corp., elution solvent: ethyl acetate/methanol=100/0→85/15) to obtain a crude product of the title compound (2.83 g) as an oil.

MS (APCI) m/z: 330 [(M+H)$^+$].

(Step 2) 5-Bromo-4-oxo-1-(tetrahydro-2H-pyran-4-ylmethyl)-1,4-dihydropyridine-3-carboxylic acid To a solution of the crude product of methyl 5-bromo-4-oxo-1-(tetrahydro-2H-pyran-4-ylmethyl)-1,4-dihydropyridine-3-carboxylate (2.83 g) synthesized in step 1 in tetrahydrofuran (50.0 mL), methanol (25.0 mL) and a 1 N aqueous sodium hydroxide solution (25.7 mL, 25.7 mmol) were added, and the mixture was stirred overnight at room temperature. The organic solvent was distilled off under reduced pressure, and then, water was added to the residue, followed by washing with ethyl acetate twice. The aqueous layer was rendered acidic by the addition of 1 N hydrochloric acid, and then, ethyl acetate was added thereto. The deposited solid was collected by filtration, and then, the filtrate was subjected to extraction with ethyl acetate three times. The organic layer was washed with brine and then dried over anhydrous sodium sulfate. After filtration and concentration under reduced pressure, the obtained solid was suspended in diethyl ether and collected by filtration. This solid was combined with the preliminarily obtained solid and dried to obtain the title compound (1.93 g, yield in 2 steps: 60.0%) as a solid.

$^1$H-NMR (DMSO-D$_6$) δ: 8.79 (1H, d, J=1.8 Hz), 8.75 (1H, d, J=1.8 Hz), 4.08 (2H, d, J=7.9 Hz), 3.84 (2H, dd, J=11.6, 3.4 Hz), 3.23 (2H, t, J=11.6 Hz), 2.10-2.00 (1H, m), 1.40 (2H, br d, J=10.4 Hz), 1.30-1.20 (2H, m).

MS (APCI) m/z: 316 [(M+H)$^+$].

(Intermediate 20) N-{4-[2-Amino-5-(3,4-dimethoxyphenyl)pyridin-3-yl]phenyl}-5-bromo-4-oxo-1-(tetrahydro-2H-pyran-4-ylmethyl)-1,4-dihydropyridine-3-carboxamide

[Formula 65]

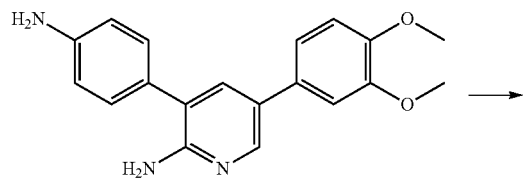

→

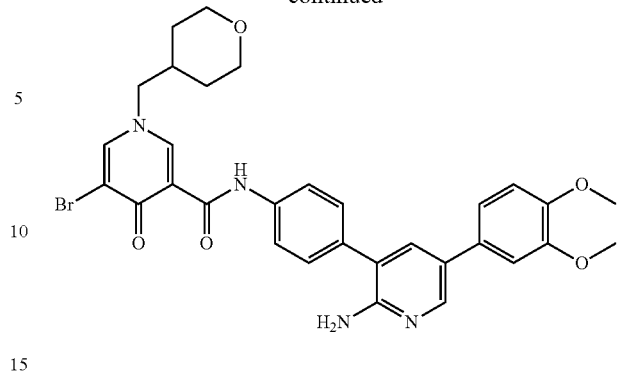

To 5-bromo-4-oxo-1-(tetrahydro-2H-pyran-4-ylmethyl)-1,4-dihydropyridine-3-carboxylic acid (0.754 g, 2.39 mmol), 3-(4-aminophenyl)-5-(3,4-dimethoxyphenyl)pyridin-2-amine (0.730 g, 2.27 mmol) synthesized by the method described in the patent (WO2013/115280 A1), and N-[1-(cyano-2-ethoxy-2-oxoethylideneaminooxy)dimethylamino(morpholino)]uronium hexafluorophosphate (COMU) (1.27 g, 2.95 mmol), N,N-dimethylformamide (12.0 mL) was added, then N,N-diisopropylethylamine (0.593 mL, 0.440 g, 3.41 mmol) was added, and the mixture was stirred overnight at room temperature. The reaction mixture was concentrated under reduced pressure, and then, a saturated aqueous solution of sodium bicarbonate was added to the residue, followed by extraction with ethyl acetate three times. The organic layer was washed with brine and then dried over anhydrous sodium sulfate. After filtration and concentration under reduced pressure, the residue obtained was purified by silica gel column chromatography (Yamazen Corp., elution solvent: ethyl acetate/methanol=100/0→85/15). After concentration under reduced pressure, the residue was solidified by the addition of diethyl ether, and the solid was collected by filtration and dried to obtain the title compound (0.724 g, yield: 51.5%) as a solid.

$^1$H-NMR (DMSO-D$_6$) δ: 12.61 (1H, s), 8.74 (1H, d, J=2.4 Hz), 8.63 (1H, d, J=2.4 Hz), 8.26 (1H, d, J=2.4 Hz), 7.82 (2H, d, J=8.5 Hz), 7.64 (1H, d, J=2.4 Hz), 7.55 (2H, d, J=8.5 Hz), 7.20-7.14 (2H, m), 6.99 (1H, d, J=8.5 Hz), 5.77 (2H, s), 4.07 (2H, d, J=7.3 Hz), 3.87-3.83 (5H, m), 3.77 (3H, s), 3.26 (2H, t, J=10.7 Hz), 2.11-2.02 (1H, m), 1.42 (2H, br d, J=10.9 Hz), 1.33-1.23 (2H, m).

MS (APCI) m/z: 619 [(M+H)$^+$].

Similarly, the intermediate of Table 12 was synthesized from the corresponding starting material.

TABLE 12

| Intermediate No. | Structural formula of intermediate Instrumental data on intermediate | Structural formula of starting material |
|---|---|---|
| Intermediate 20b | | |

| Intermediate No. | Structural formula of intermediate Instrumental data on intermediate | Structural formula of starting material |
|---|---|---|
| | $^1$H-NMR (DMSO-D$_6$) δ: 12.61 (1H, s), 8.75 (1H, d, J = 2.4 Hz), 8.63 (1H, d, J = 2.4 Hz), 8.26 (1H, d, J = 2.4 Hz), 7.81 (2H, d, J = 8.5 Hz), 7.61 (1H, d, J = 2.4 Hz), 7.54 (2H, d, J = 8.5 Hz), 7.20 (1H, d, J = 2.4 Hz), 7.13 (1H, dd, J = 8.5, 2.4 Hz), 6.99 (1H, d, J = 8.5 Hz), 5.70 (2H, s), 4.07 (2H, d, J = 7.3 Hz), 3.98-3.75 (10H, m), 3.69-3.60 (2H, m), 3.53-3.46 (1H, m), 3.42-3.37 (1H, m), 3.26 (2H, t, J = 10.9 Hz), 2.12-2.02 (1H, m), 1.42 (2H, br d, J = 10.9 Hz), 1.33-1.24 (2H, m). MS (APCI) m/z: 705 [(M + H)$^+$]. | |

(Intermediate 21) N-[4-(2-Amino-5-{4-[(2R)-1,4-dioxan-2-ylmethoxy]-3-methoxyphenyl}pyridin-3-yl)-3-fluorophenyl]-5-bromo-1'-[(4-cyanotetrahydro-2H-pyran-4-yl)methyl]-4'-oxo-1',4'-dihydro-2,3'-bipyridine-5'-carboxamide

[Formula 66]

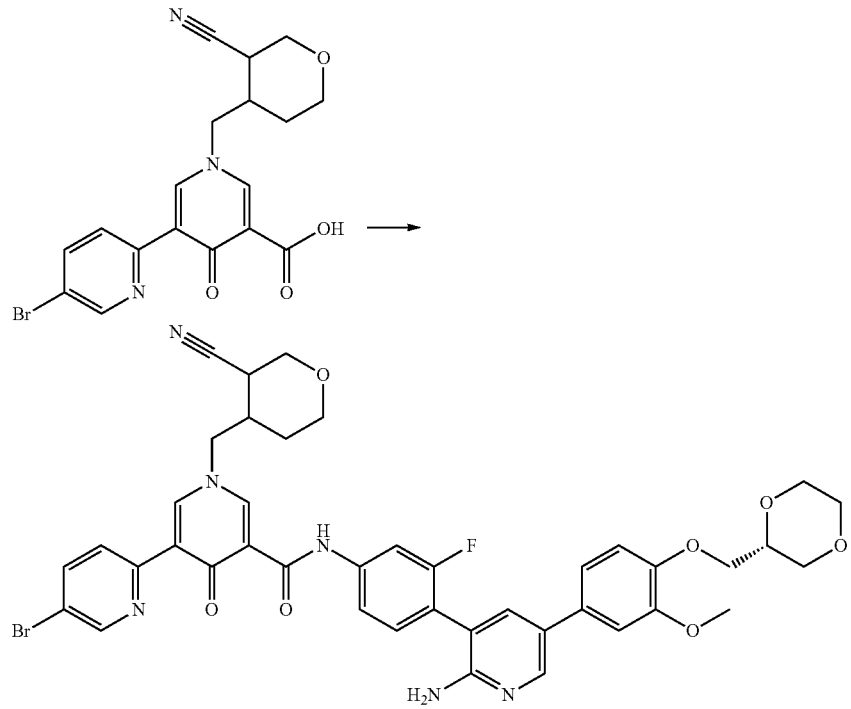

To a suspension of 5-bromo-1'-[(4-cyanotetrahydro-2H-pyran-4-yl)methyl]-4'-oxo-1',4'-dihydro-2,3'-bipyridine-5'-carboxylic acid (0.168 g, 0.401 mmol) in N,N-dimethylformamide (5.00 mL), N-[1-(cyano-2-ethoxy-2-oxoethylideneaminooxy)dimethylamino(morpholino)]uronium hexafluorophosphate (COMU) (0.172 g, 0.401 mmol) and N,N-diisopropylethylamine (0.0825 mL, 0.0612 g, 0.474 mmol) were added, and the mixture was stirred at room temperature for 1 hour. In this operation, the reaction mixture became homogeneous. 3-(4-Amino-2-fluorophenyl)-5-{4-[(2R)-1,4-dioxan-2-ylmethoxy]-3-methoxyphenyl}pyridin-2-amine (0.155 g, 0.364 mmol) was added thereto, and the mixture was stirred overnight at room temperature. The reaction mixture was concentrated under reduced pressure, and then, a saturated aqueous solution of sodium bicarbonate was added to the residue, followed by extraction with ethyl acetate three times. The organic layer was washed with brine and then dried over anhydrous sodium sulfate. After filtration and concentration under reduced pressure, the residue obtained was purified by silica gel column chromatography (Yamazen Corp., ethyl acetate/methanol=99/1→85/15) and then purified by amino silica gel column chromatography (Yamazen Corp., ethyl acetate/methanol=99/1→93/7) to obtain the title compound (0.238 g, yield: 79.1%) as an amorphous solid.

$^1$H-NMR (DMSO-D$_6$) δ: 12.95 (1H, s), 8.89-8.80 (3H, m), 8.59 (1H, d, J=8.5 Hz), 8.31 (1H, d, J=2.4 Hz), 8.18 (1H, dd, J=8.5, 2.4 Hz), 7.96-7.92 (1H, m), 7.63 (1H, d, J=2.4 Hz), 7.51-7.42 (2H, m), 7.19 (1H, d, J=2.4 Hz), 7.11 (1H, dd, J=8.5, 2.4 Hz), 6.99 (1H, d, J=8.5 Hz), 5.71 (2H, s), 4.71 (2H, s), 3.97-3.75 (10H, m), 3.69-3.59 (2H, m), 3.53-3.30 (4H, m), 1.88-1.78 (4H, m).

MS (APCI) m/z: 825 [(M+H)$^+$].

Example 1

N-[4-(2-Amino-5-{4-[(2R)-1,4-dioxan-2-yl-methoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide

[Formula 67]

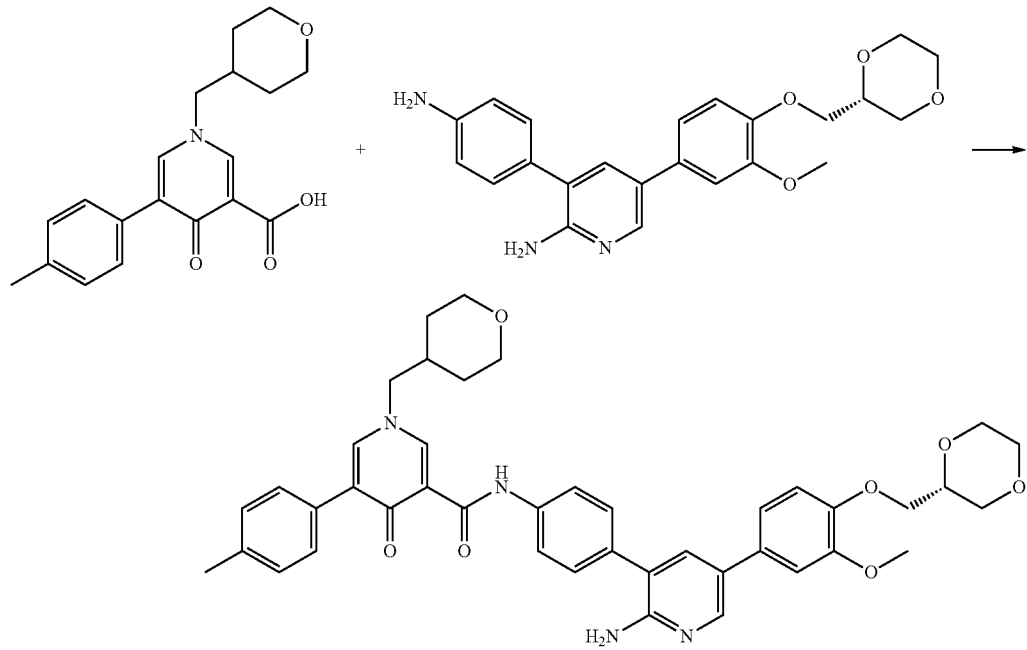

5-(4-Methylphenyl)-4-oxo-1-(tetrahydro-2H-pyran-4-yl-methyl)-1,4-dihydropyridine-3-carboxylic acid (0.121 g, 0.367 mmol) was dissolved in N,N-dimethylformamide (3.00 ml). To the solution, N-[1-(cyano-2-ethoxy-2-oxoeth-ylideneaminooxy)dimethylamino(morpholino)]uronium hexafluorophosphate (COMU) (0.236 g, 0.367 mmol) was added, and the mixture was stirred at room temperature for 30 minutes. Then, 3-(4-aminophenyl)-5-{4-[(2R)-1,4-dioxan-2-ylmethoxy]-3-methoxyphenyl}pyridin-2-amine (0.149 g, 0.367 mmol) synthesized by the method described in the patent (WO2013/115280 A1) was added thereto, and the mixture was stirred at room temperature for 4 hours. To the reaction mixture, water was added, and the deposited solid was collected by filtration. This solid was purified by silica gel column chromatography (Biotage Japan Ltd., elution solvent: dichloromethane/methanol=99/1→95/5) to obtain the title compound (0.18 g, yield: 69.8%) as a foam.

$^1$H-NMR (CDCl$_3$) δ: 12.85 (1H, s), 8.57 (1H, d, J=2.4 Hz), 8.25 (1H, d, J=1.8 Hz), 7.87 (2H, d, J=8.5 Hz), 7.57 (1H, d, J=1.8 Hz), 7.47 (5H, dd, J=8.2, 5.8 Hz), 7.29 (2H, d, J=8.5 Hz), 7.08-7.02 (2H, m), 6.98-6.94 (1H, m), 4.71 (2H, s), 4.11-3.94 (6H, m), 3.93-3.79 (8H, m), 3.79-3.63 (1H, m), 3.59-3.51 (1H, m), 3.44-3.35 (2H, m), 2.41 (3H, s), 2.18-2.04 (1H, m), 1.64-1.58 (2H, m), 1.51-1.35 (2H, m).

MS (ESI) m/z: 717 [(M+H)$^+$]

Similarly, the final compounds of Table 13 were synthesized from the corresponding starting materials A and B.

TABLE 13

| Example No. | Structural formula for Example Instrumental data on Example | Structural formula of starting material A | Structural formula of starting material B |
|---|---|---|---|
| Example 2 | | | |

TABLE 13-continued

| Example No. | Structural formula for Example Instrumental data on Example | Structural formula of starting material A | Structural formula of starting material B |
|---|---|---|---|
| | ¹H-NMR (CDCl₃) δ: 12.85 (1H, s), 8.57 (1H, d, J = 2.4 Hz), 8.27 (1H, d, J = 2.4 Hz), 7.87 (2H, d, J = 8.5 Hz), 7.57 (1H, d, J = 1.8 Hz), 7.51-7.44 (5H, m), 7.29 (2H, d, J = 7.9 Hz), 7.09 (1H, dd, J = 8.2, 2.1 Hz), 7.04 (1H, d, J = 1.8 Hz), 6.94 (1H, d, J = 8.5 Hz), 4.64 (2H, s), 4.03 (2H, dd, J = 11.5, 4.3 Hz), 3.94 (3H, s), 3.92 (3H, s), 3.88 (2H, d, J = 7.3 Hz), 3.39 (2H, t, J = 11.2 Hz), 2.41 (3H, s), 2.19-2.07 (1H, m), 1.65-1.55 (2H, m), 1.51-1.38 (2H, m). MS (ESI) m/z: 631 [(M + H)⁺]. | | |
| Example 3 | 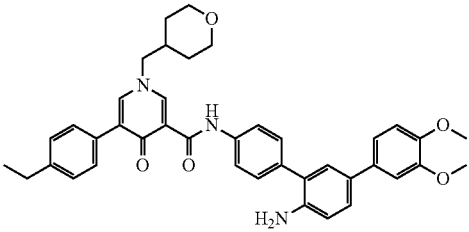 [SMILES: CCc1ccc(-c2cn(CC3CCOCC3)cc(C(=O)Nc3ccc(-c4cc(-c5ccc(OC)c(OC)c5)ccc4N)cc3)c2=O)cc1] | 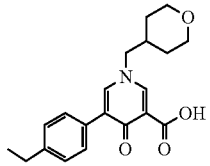 [SMILES: CCc1ccc(-c2cn(CC3CCOCC3)cc(C(=O)O)c2=O)cc1] | 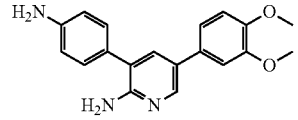 [SMILES: COc1ccc(-c2cnc(N)c(-c3ccc(N)cc3)c2)cc1OC] |
| | ¹H-NMR (CDCl₃) δ: 12.85 (1H, s), 8.57 (1H, d, J = 2.4 Hz), 8.27 (1H, d, J = 2.4 Hz), 7.87 (2H, d, J = 8.5 Hz), 7.57 (1H, d, J = 2.4 Hz), 7.49 (5H, dd, J = 8.5, 2.4 Hz), 7.31 (2H, d, J = 8.5 Hz), 7.26 (2H, s), 7.09 (1H, dd, J = 8.5, 2.4 Hz), 7.04 (1H, d, J = 2.4 Hz), 6.94 (1H, d, J = 8.5 Hz), 4.63 (2H, d, J = 8.5 Hz), 4.03 (2H, dd, J = 11.5, 4.0 Hz), 3.94 (3H, s), 3.92 (3H, s), 3.87 (2H, d, J = 7.5 Hz), 3.39 (2H, t, J = 11.5 Hz), 2.71 (2H, q, J = 7.5 Hz), 2.18-2.06 (1H, m), 1.50-1.38 (2H, m), 1.27 (3H, t, J = 7.5 Hz). MS (APCI) m/z: 645 [(M + H)⁺]. | | |
| Example 4 | 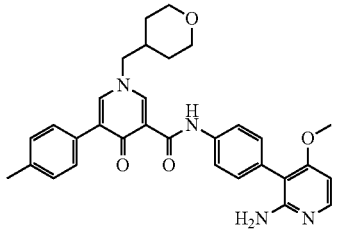 | 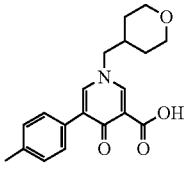 | 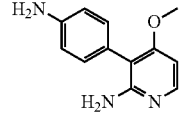 [SMILES: COc1ccnc(N)c1-c1ccc(N)cc1] |
| | ¹H-NMR (CDCl₃) δ: 12.78 (1H, s), 8.56 (1H, d, J = 2.4 Hz), 7.99 (1H, d, J = 6.1 Hz), 7.84 (2H, d, J = 6.7 Hz), 7.49-7.43 (3H, m), 7.34-7.23 (4H, m), 6.39 (1H, d, J = 6.1 Hz), 4.37 (2H, s), 4.07-4.00 (2H, m), 3.86 (2H, d, J = 7.3 Hz), 3.75 (3H, s), 3.44-3.35 (2H, m), 2.41 (3H, s), 2.16-2.07 (1H, m), 1.65-1.56 (3H, m), 1.50-1.38 (1H, m). MS (ESI) m/z: 525 [(M + H)⁺]. | | |
| Example 5 | 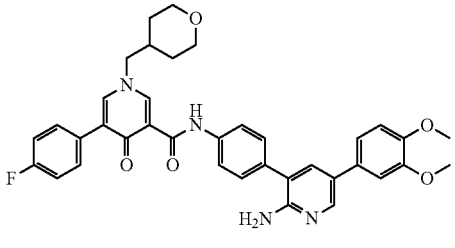 [SMILES: COc1ccc(-c2cnc(N)c(-c3ccc(NC(=O)c4cn(CC5CCOCC5)cc(-c5ccc(F)cc5)c4=O)cc3)c2)cc1OC] | 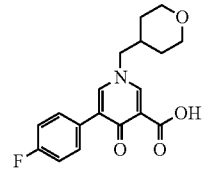 [SMILES: O=C(O)c1cn(CC2CCOCC2)cc(-c2ccc(F)cc2)c1=O] | 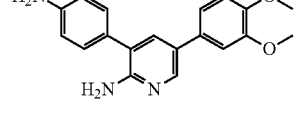 |
| | ¹H-NMR (CDCl₃) δ: 12.76 (1H, s), 8.59 (1H, d, J = 2.4 Hz), 8.27 (1H, d, J = 2.4 Hz), 7.87 (2H, d, J = 7.9 Hz), 7.60-7.53 (3H, m), 7.52-7.46 (3H, m), 7.21-7.14 (2H, m), 7.11-7.07 (1H, m), 7.05-7.02 (1H, m), 6.94 (1H, d, J = 8.5 Hz), 4.65 (2H, s), 4.04 (2H, dd, J = 11.5, 3.6 Hz), 3.94 (3H, s), 3.92 (3H, s), 3.89 (2H, d, J = 7.3 Hz), 3.44-3.35 | | |

TABLE 13-continued

| Example No. | Structural formula for Example Instrumental data on Example | Structural formula of starting material A | Structural formula of starting material B |
|---|---|---|---|
| | (2H, m), 2.19-2.05 (1H, m), 1.66-1.55 (2H, m), 1.53-1.38 (2H, m).<br>MS (ESI) m/z: 635 [(M + H)⁺]. | | |
| Example 6 | 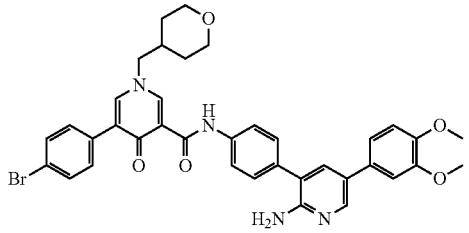<br>¹H-NMR (DMSO-D₆) δ: 13.00 (1H, s), 8.74 (1H, d, J = 2.4 Hz), 8.26-8.25 (2H, m), 7.82 (2H, d, J = 8.5 Hz), 7.67 (4H, s), 7.61 (1H, d, J = 2.4 Hz), 7.53 (2H, d, J = 8.5 Hz), 7.19 (1H, d, J = 2.4 Hz), 7.15 (1H, dd, J = 8.5, 2.4 Hz), 6.99 (1H, d, J = 8.5 Hz), 5.68 (2H, s), 4.11 (2H, d, J = 7.3 Hz), 3.88-3.83 (5H, m), 3.77 (3H, s), 3.30-3.24 (2H, m), 2.16-2.06 (1H, m), 1.46 (2H, br d, J = 11.5 Hz), 1.36-1.26 (2H, m).<br>MS (APCI) m/z: 695 [(M + H)⁺]. | 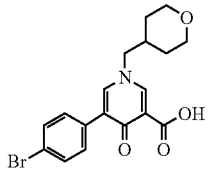 [SMILES: O=C(O)c1cn(CC2CCOCC2)cc(-c2ccc(Br)cc2)c1=O] | 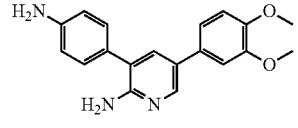 |
| Example 7 | 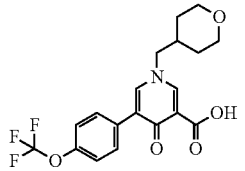 [SMILES: O=C(O)c1cn(CC2CCOCC2)cc(-c2ccc(OC(F)(F)F)cc2)c1=O]<br>¹H-NMR (DMSO-D₆) δ: 13.00 (1H, s), 8.75 (1H, d, J = 2.4 Hz), 8.27 (2H, dd, J = 11.8, 2.4 Hz), 7.82 (4H, d, J = 8.5 Hz), 7.61 (1H, d, J = 2.4 Hz), 7.53 (2H, d, J = 8.5 Hz), 7.47 (2H, d, J = 8.5 Hz), 7.19-7.13 (2H, m), 6.98 (1H, d, J = 8.5 Hz), 5.68 (2H, s), 4.11 (2H, d, J = 7.3 Hz), 3.89-3.82 (5H, m), 3.77 (3H, s), 3.30-3.24 (2H, m), 2.17-2.07 (1H, m), 1.47 (2H, br d, J = 11.5 Hz), 1.37-1.27 (2H, m).<br>MS (APCI) m/z: 701 [(M + H)⁺]. | 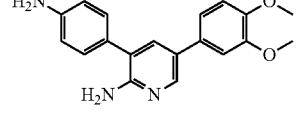 | |
| Example 8 | 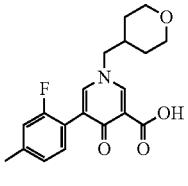<br>¹H-NMR (DMSO-D₆) δ: 12.95 (1H, s), 8.76 (1H, d, J = 2.4 Hz), 8.25 (1H, d, J = 2.4 Hz), 8.13 (1H, d, J = 1.8 Hz), 7.80 (2H, d, J = 8.5 Hz), 7.61 (1H, d, J = 2.4 Hz), 7.52 (2H, d, J = 8.5 Hz), 7.35 (1H, t, J = 7.6 Hz), 7.19-7.09 (4H, m), 6.98 (1H, d, J = 8.5 Hz), 5.67 (2H, s), 4.10 (2H, d, J = 7.3 Hz), 3.89-3.82 (5H, m), 3.77 (3H, s), 3.31-3.24 (2H, m), 2.38 (3H, s), 2.14-2.02 (1H, m), 1.47 (2H, br d, J = 11.5 Hz), 1.36-1.25 (2H, m).<br>MS (APCI) m/z: 649 [(M + H)⁺]. | 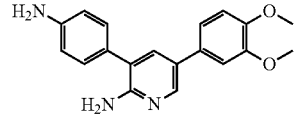 | |

TABLE 13-continued

| Example No. | Structural formula for Example Instrumental data on Example | Structural formula of starting material A | Structural formula of starting material B |
|---|---|---|---|
| Example 9 | 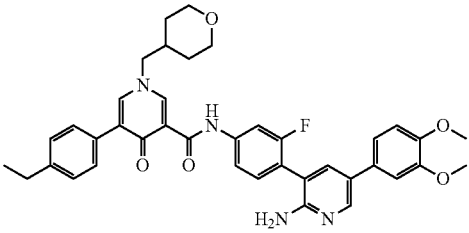 [SMILES: CCc1ccc(-c2cn(CC3CCOCC3)cc(C(=O)Nc3ccc(-c4cc(-c5ccc(OC)c(OC)c5)cnc4N)c(F)c3)c2=O)cc1] <sup>1</sup>H-NMR (CDCl<sub>3</sub>) δ: 12.99 (1H, s), 8.56 (1H, d, J = 3.0 Hz), 8.31 (1H, d, J = 2.4 Hz), 7.92 (1H, dd, J = 12.1, 1.8 Hz), 7.59 (1H, d, J = 2.4 Hz), 7.51-7.44 (4H, m), 7.40-7.29 (3H, m), 7.11-7.06 (1H, m), 7.05-7.02 (1H, m), 6.93 (1H, d, J = 8.5 Hz), 4.56 (2H, s), 4.07-4.00 (2H, m), 3.94 (3H, s), 3.92 (3H, s), 3.88 (2H, d, J = 7.3 Hz), 3.39 (2H, t, J = 11.2 Hz), 2.71 (2H, q, J = 7.5 Hz), 2.18-2.07 (1H, m), 1.66-1.58 (1H, m), 1.51-1.38 (2H, m), 1.31-1.24 (4H, m). MS (ESI) m/z: 663 [(M + H)<sup>+</sup>] | 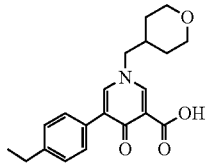 [SMILES: CCc1ccc(-c2cn(CC3CCOCC3)cc(C(=O)O)c2=O)cc1] | 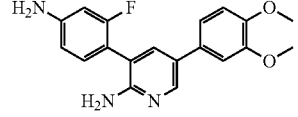 |
| Example 10 | 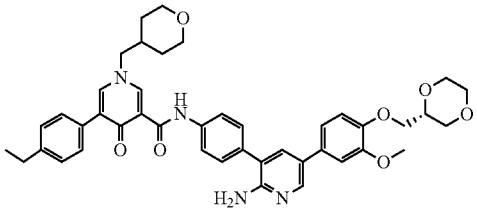 [SMILES: CCc1ccc(-c2cn(CC3CCOCC3)cc(C(=O)Nc3ccc(-c4cc(-c5ccc(OC[C@H]6COCCO6)c(OC)c5)cnc4N)cc3)c2=O)cc1] $^1$H-NMR (CDCl$_3$) δ: 12.86 (1H, s), 8.58 (1H, d, J = 2.4 Hz), 8.25 (1H, d, J = 2.4 Hz), 7.87 (2H, d, J = 7.9 Hz), 7.57 (1H, d, J = 1.8 Hz), 7.51-7.46 (5H, m), 7.32 (2H, d, J = 7.9 Hz), 7.08-7.02 (2H, m), 6.96 (1H, d, J = 8.5 Hz), 4.66 (2H, s), 4.10-3.94 (7H, m), 3.91 (3H, s), 3.90-3.80 (4H, m), 3.79-3.64 (2H, m), 3.59-3.51 (1H, m), 3.44-3.35 (2H, m), 2.71 (2H, q, J = 7.7 Hz), 2.18-2.05 (1H, m), 1.69-1.58 (1H, m), 1.51-1.39 (2H, m), 1.27 (3H, t, J = 7.6 Hz). MS (ESI) m/z: 731 [(M + H)$^+$] | 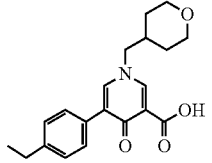 | 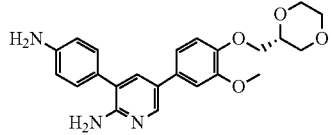 |
| Example 11 | 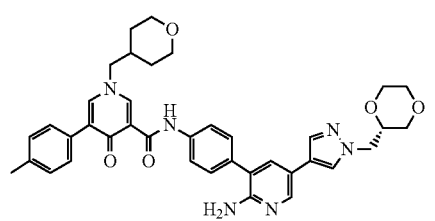 [SMILES: Cc1ccc(-c2cn(CC3CCOCC3)cc(C(=O)Nc3ccc(-c4cc(-c5cnn(C[C@H]6COCCO6)c5)cnc4N)cc3)c2=O)cc1] $^1$H-NMR (CDCl$_3$) δ: 12.85 (1H, s), 8.57 (1H, d, J = 2.4 Hz), 8.20 (1H, d, J = 2.4 Hz), 7.86 (2H, d, J = 8.5 Hz), 7.71 (1H, s), 7.65 (1H, s), 7.50-7.43 (6H, m), 7.29 (2H, d, J = 8.5 Hz), 4.61 (2H, s), 4.17 (2H, d, J = 5.5 Hz), 4.07-3.95 (3H, m), 3.88 (2H, d, J = 7.3 Hz), 3.84-3.78 (2H, m), 3.77-3.67 (2H, m), 3.62-3.54 (1H, m), 3.44-3.27 (3H, m), 2.41 (3H, s), 2.18-2.04 (1H, m), 1.69-1.56 (2H, m), 1.51-1.38 (2H, m). MS (ESI) m/z: 661 [(M + H)$^+$] | 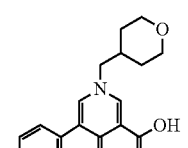 | 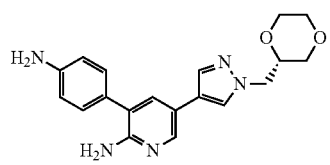 [SMILES: Nc1ccc(-c2cc(-c3cnn(C[C@H]4COCCO4)c3)cnc2N)cc1] |
| Example 12 | 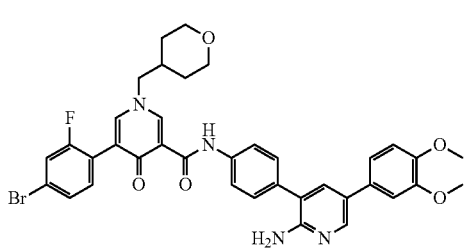 [SMILES: COc1ccc(-c2cnc(N)c(-c3ccc(NC(=O)c4cn(CC5CCOCC5)cc(-c5ccc(Br)cc5F)c4=O)cc3)c2)cc1OC] | 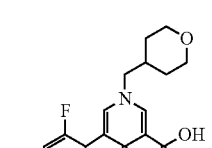 | 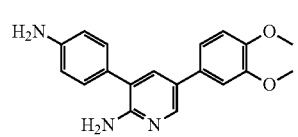 [SMILES: COc1ccc(-c2cnc(N)c(-c3ccc(N)cc3)c2)cc1OC] |

TABLE 13-continued

| Example No. | Structural formula for Example Instrumental data on Example | Structural formula of starting material A | Structural formula of starting material B |
| --- | --- | --- | --- |
| | ¹H-NMR (DMSO-D₆) δ: 12.85 (1H, s), 8.78 (1H, d, J = 2.4 Hz), 8.25 (1H, d, J = 2.4 Hz), 8.21 (1H, d, J = 1.8 Hz), 7.80 (2H, d, J = 8.5 Hz), 7.67 (1H, dd, J = 9.1, 1.8 Hz), 7.60 (1H, d, J = 2.4 Hz), 7.55-7.52 (3H, m), 7.48-7.44 (1H, m), 7.19-7.13 (2H, m), 6.98 (1H, d, J = 8.5 Hz), 5.67 (2H, s), 4.10 (2H, d, J = 7.3 Hz), 3.89-3.82 (5H, m), 3.77 (3H, s), 3.27 (2H, t, J = 10.9 Hz), 2.13-2.04 (1H, m), 1.47 (2H, br d, J = 10.9 Hz), 1.35-1.25 (2H, m). MS (APCI) m/z: 713 [(M + H)⁺]. | | |
| Example 13 | ¹H-NMR (CDCl₃) δ: 12.78 (1H, s), 8.57 (1H, d, J = 2.4 Hz), 7.98 (1H, d, J = 6.1 Hz), 7.87-7.81 (2H, m), 7.51-7.45 (3H, m), 7.31 (4H, d, J = 8.5 Hz), 6.39 (1H, d, J = 6.1 Hz), 4.38 (2H, s), 4.06-4.00 (2H, m), 3.86 (2H, d, J = 7.3 Hz), 3.75 (3H, s), 3.39 (2H, t, J = 10.9 Hz), 2.70 (2H, q, J = 7.7 Hz), 2.17-2.06 (1H, m), 1.49-1.40 (4H, m), 1.30-1.23 (3H, m). MS (ESI) m/z: 539 [(M + H)⁺] | | |
| Example 14 | ¹H-NMR (CDCl₃) δ: 12.88 (1H, s), 8.57 (1H, d, J = 2.4 Hz), 8.50 (1H, d, J = 5.5 Hz), 8.37 (1H, d, J = 2.4 Hz), 7.88 (2H, d, J = 8.5 Hz), 7.65 (1H, d, J = 1.8 Hz), 7.50-7.43 (5H, m), 7.34 (1H, s), 7.32-7.27 (3H, m), 4.81 (2H, s), 4.04 (2H, dd, J = 11.5, 3.6 Hz), 3.88 (2H, d, J = 7.3 Hz), 3.39 (2H, t, J = 11.5 Hz), 2.61 (3H, s), 2.41 (3H, s), 2.18-2.04 (1H, m), 1.68-1.57 (2H, m), 1.51-1.39 (2H, m). MS (ESI) m/z: 586 [(M + H)⁺] | | |
| Example 15 | ¹H-NMR (CDCl₃) δ: 12.99 (1H, s), 8.56 (1H, d, J = 2.4 Hz), 8.30 (1H, d, J = 1.8 Hz), 7.92 (1H, dd, J = 12.1, 1.8 Hz), 7.58 (1H, d, J = 2.4 Hz), 7.51-7.43 (4H, m), 7.39-7.35 (1H, m), 7.35-7.29 (2H, m), 7.07-7.01 (2H, m), 6.96 (1H, d, J = 7.9 Hz), 4.57 (2H, s), 4.10-3.94 (6H, m), 3.92-3.86 (5H, m), 3.86-3.80 (2H, m), 3.79-3.63 (2H, m), 3.59-3.51 (1H, m), 3.44-3.35 (2H, m), 2.71 (2H, q, J = 7.5 Hz), 2.18-2.04 (1H, m), 1.70-1.57 (2H, m), 1.53-1.38 (2H, m), 1.27 (3H, t, J = 7.5 Hz). MS (ESI) m/z: 749 [(M + H)⁺] | | |

TABLE 13-continued

| Example No. | Structural formula for Example Instrumental data on Example | Structural formula of starting material A | Structural formula of starting material B |
|---|---|---|---|
| Example 16 | 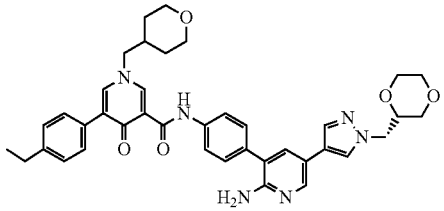<br>¹H-NMR (CDCl₃) δ: 12.86 (1H, s), 8.57 (1H, d, J = 3.0 Hz), 8.21 (1H, d, J = 2.4 Hz), 7.86 (2H, d, J = 8.5 Hz), 7.72 (1H, s), 7.65 (1H, s), 7.53-7.44 (6H, m), 7.32 (2H, d, J = 7.9 Hz), 4.61 (2H, s), 4.17 (2H, d, J = 5.5 Hz), 4.08-3.94 (3H, m), 3.88 (2H, d, J = 7.3 Hz), 3.84-3.78 (2H, m), 3.77-3.67 (2H, m), 3.63-3.54 (1H, m), 3.44-3.27 (3H, m), 2.71 (2H, q, J = 7.6 Hz), 2.18-2.04 (1H, m), 1.71-1.55 (2H, m), 1.51-1.38 (2H, m), 1.27 (3H, t, J = 7.6 Hz).<br>MS (ESI) m/z: 675 [(M + H)⁺] | 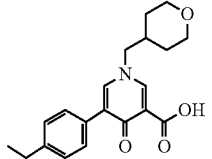 [SMILES: CCc1ccc(-c2cn(CC3CCOCC3)cc(C(=O)O)c2=O)cc1] | 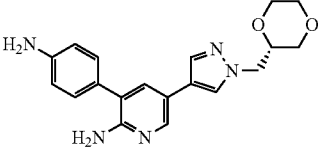 [SMILES: Nc1ccc(-c2cc(-c3cnn(C[C@H]4COCCO4)c3)cnc2N)cc1] |
| Example 17 | 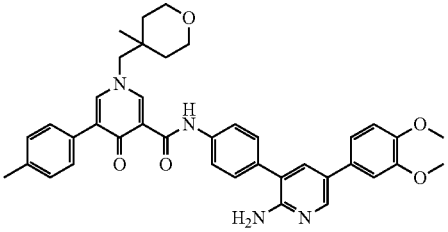<br>¹H-NMR (CDCl₃) δ: 12.83 (1H, s), 8.53 (1H, d, J = 2.0 Hz), 8.27 (1H, d, J = 2.0 Hz), 7.87 (2H, d, J = 8.0 Hz), 7.57 (1H, d, J = 2.0 Hz), 7.50-7.42 (5H, m), 7.29 (2H, d, J = 8.0 Hz), 7.09 (1H, d, J = 8.0 Hz), 7.03 (1H, s), 6.94 (1H, d, J = 8.0 Hz), 4.62 (2H, br s), 3.94 (3H, s), 3.92 (3H, s), 3.89-3.80 (4H, m), 3.64 (2H, t, J = 11.5 Hz), 2.41 (3H, s), 1.73-1.63 (2H, m), 1.37 (2H, d, J = 12.5 Hz), 1.17 (3H, s).<br>MS (APCI) m/z: 645 [(M + H)⁺]. | 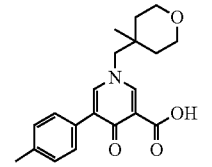 [SMILES: Cc1ccc(-c2cn(CC3(C)CCOCC3)cc(C(=O)O)c2=O)cc1] | 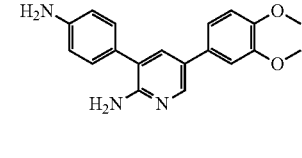 [SMILES: COc1ccc(-c2cnc(N)c(-c3ccc(N)cc3)c2)cc1OC] |
| Example 18 | 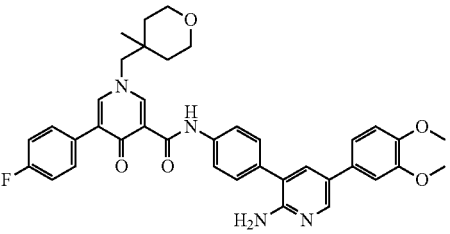 [SMILES: COc1ccc(-c2cnc(N)c(-c3ccc(NC(=O)c4cn(CC5(C)CCOCC5)cc(-c5ccc(F)cc5)c4=O)cc3)c2)cc1OC]<br>¹H-NMR (CDCl₃) δ: 12.74 (1H, s), 8.55 (1H, d, J = 2.0 Hz), 8.27 (1H, d, J = 2.0 Hz), 7.87 (2H, d, J = 8.0 Hz), 7.59-7.53 (3H, m), 7.49 (2H, d, J = 8.0 Hz), 7.44 (1H, d, J = 2.0 Hz), 7.17 (2H, t, J = 8.0 Hz), 7.09 (1H, d, J = 8.0 Hz), 7.04 (1H, s), 6.94 (1H, d, J = 8.0 Hz), 4.63 (1H, br s), 3.94 (3H, s), 3.92 (3H, s), 3.89-3.82 (4H, m), 3.64 (2H, t, J = 11.0 Hz), 1.74-1.65 (2H, m), 1.38 (2H, d, J = 13.0 Hz), 1.18 (3H, s).<br>MS (APCI) m/z: 649 [(M + H)⁺]. | 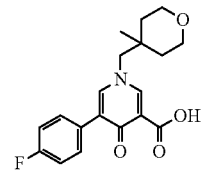 [SMILES: CC1(Cn2cc(C(=O)O)c(=O)c(-c3ccc(F)cc3)c2)CCOCC1] |  |
| Example 19 | 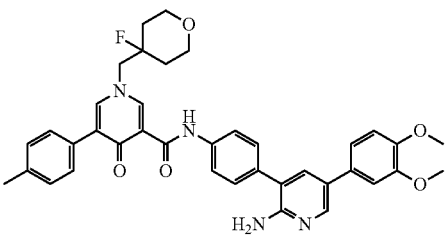<br>¹H-NMR (CDCl₃) δ: 12.75 (1H, s), 8.52 (1H, d, J = 2.5 Hz), 8.22 (1H, t, J = 2.5 Hz), 7.83 (2H, d, J = 8.5 Hz), 7.55-7.51 | 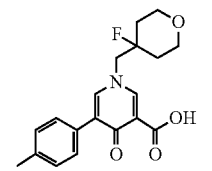 [SMILES: Cc1ccc(-c2cn(CC3(F)CCOCC3)cc(C(=O)O)c2=O)cc1] | 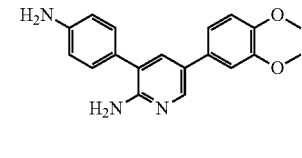 [SMILES: COc1ccc(-c2cnc(N)c(-c3ccc(N)cc3)c2)cc1OC] |

TABLE 13-continued

| Example No. | Structural formula for Example Instrumental data on Example | Structural formula of starting material A | Structural formula of starting material B |
| --- | --- | --- | --- |
| | (2H, m), 7.47-7.42 (4H, m), 7.25 (2H, d, J = 8.5 Hz), 7.05 (1H, dd, J = 8.5, 2.0 Hz), 7.00 (1H, d, J = 2.0 Hz), 6.90 (1H, d, J = 8.5 Hz), 4.62 (2H, s), 4.07 (2H, d, J = 20.5 Hz), 3.90 (3H, s), 3.90-3.85 (5H, m), 3.72-3.64 (2H, m), 2.37 (3H, s), 1.89-1.68 (4H, m).<br>MS (APCI) m/z: 649 [(M + H)$^+$]. | | |
| Example 20 | $^1$H-NMR (CDCl$_3$) δ: 12.84 (1H, s), 8.53 (1H, d, J = 2.4 Hz), 8.26 (1H, d, J = 2.4 Hz), 7.87 (2H, d, J = 8.0 Hz), 7.56 (1H, d, J = 2.4 Hz), 7.50-7.43 (5H, m), 7.29 (2H, d, J = 8.5 Hz), 7.07-7.02 (2H, m), 6.96 (1H, d, J = 8.5 Hz), 4.67-4.61 (2H, m), 4.17-3.48 (18H, m), 2.41 (3H, s), 1.74-1.64 (2H, m), 1.38 (2H, d, J = 12.5 Hz), 1.17 (3H, s).<br>MS (APCI) m/z: 731 [(M + H)$^+$]. | | |
| Example 21 | $^1$H-NMR (CDCl$_3$) δ: 12.74 (1H, s), 8.55 (1H, d, J = 2.4 Hz), 8.26 (1H, d, J = 2.4 Hz), 7.87 (2H, d, J = 8.5 Hz), 7.58-7.44 (6H, m), 7.18 (2H, t, J = 8.5 Hz), 7.07-7.02 (2H, m), 6.96 (1H, d, J = 8.5 Hz), 4.65-4.61 (2H, m), 4.15-3.51 (18H, m), 1.74-1.65 (2H, m), 1.38 (2H, d, J = 13.5 Hz), 1.18 (3H, s).<br>MS (APCI) m/z: 735 [(M + H)$^+$]. | | |
| Example 22 | $^1$H-NMR (CDCl$_3$) δ: 12.87 (1H, s), 8.54 (1H, d, J = 2.0 Hz), 8.32 (1H, d, J = 2.0 Hz), 7.92 (1H, dd, J = 11.8, 2.0 Hz), 7.59 (1H, d, J = 2.0 Hz), 7.57-7.52 (2H, m), 7.48-7.44 (2H, m), 7.38 (1H, t, J = 8.5 Hz), 7.18 (2H, t, J = 8.5 Hz), 7.09 (1H, dd, J = 8.5, 2.0 Hz), 7.04 (1H, d, J = 2.0 Hz), 6.94 (1H, d, J = 8.5 Hz), 4.56-4.52 (2H, m), 3.95 (3H, s), 3.92 (3H, s), 3.91-3.84 (4H, m), 3.69-3.61 (2H, m), 1.74-1.66 (2H, m), 1.39 (2H, d, J = 13.0 Hz), 1.18 (3H, s).<br>MS (APCI) m/z: 667 [(M + H)$^+$]. | | |

TABLE 13-continued

| Example No. | Structural formula for Example Instrumental data on Example | Structural formula of starting material A | Structural formula of starting material B |
|---|---|---|---|
| Example 23 | 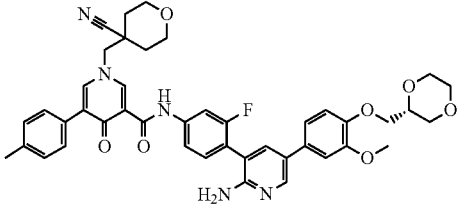 [SMILES: COc1cc(-c2cnc(N)c(-c3ccc(NC(=O)c4cn(CC5(C#N)CCOCC5)cc(-c5ccc(C)cc5)c4=O)cc3F)c2)ccc1OC[C@H]1COCCO1] <br> ¹H-NMR (CDCl₃) δ: 12.83 (1H, s), 8.57 (1H, d, J = 2.4 Hz), 8.30 (1H, d, J = 2.4 Hz), 7.91 (1H, dd, J = 12.2, 1.8 Hz), 7.72 (1H, d, J = 2.4 Hz), 7.58 (1H, d, J = 1.8 Hz), 7.49 (2H, d, J = 7.9 Hz), 7.44 (1H, dd, J = 8.5, 1.8 Hz), 7.40-7.33 (1H, m), 7.32-7.24 (2H, m), 7.08-7.01 (2H, m), 6.96 (1H, d, J = 7.9 Hz), 4.57 (1H, br s), 4.16-4.02 (6H, m), 4.02-3.93 (2H, m), 3.92-3.80 (5H, m), 3.78-3.64 (5H, m), 3.62-3.51 (1H, m), 2.41 (3H, s), 1.94-1.87 (2H, m), 1.86-1.75 (2H, m). <br> MS (ESI) m/z: 760 [(M + H)⁺] | 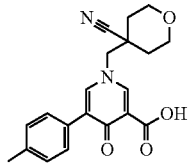 [SMILES: Cc1ccc(-c2cn(CC3(C#N)CCOCC3)cc(C(=O)O)c2=O)cc1] | 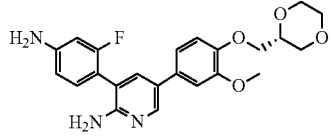 [SMILES: COc1cc(-c2cnc(N)c(-c3ccc(N)cc3F)c2)ccc1OC[C@H]1COCCO1] |
| Example 24 | 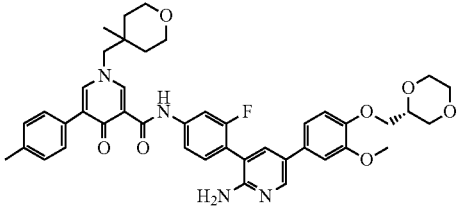 [SMILES: COc1cc(-c2cnc(N)c(-c3ccc(NC(=O)c4cn(CC5(C)CCOCC5)cc(-c5ccc(C)cc5)c4=O)cc3F)c2)ccc1OC[C@H]1COCCO1] <br> ¹H-NMR (CDCl₃) δ: 12.97 (1H, s), 8.52 (1H, d, J = 2.4 Hz), 8.30 (1H, d, J = 1.8 Hz), 7.92 (1H, dd, J = 12.2, 1.8 Hz), 7.58 (1H, d, J = 1.8 Hz), 7.49-7.42 (4H, m), 7.36 (1H, t, J = 8.2 Hz), 7.29 (2H, d, J = 7.9 Hz), 7.07-7.01 (2H, m), 6.96 (1H, d, J = 8.5 Hz), 4.59-4.54 (1H, m), 4.10-4.03 (2H, m), 4.01-3.95 (2H, m), 3.91 (3H, s), 3.89-3.80 (6H, m), 3.79-3.51 (5H, m), 2.41 (3H, s), 1.74-1.61 (2H, m), 1.54-1.42 (1H, m), 1.41-1.34 (2H, m), 1.17 (3H, s). <br> MS (ESI) m/z: 749 [(M + H)⁺] | 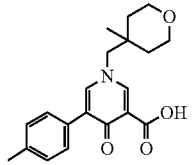 [SMILES: Cc1ccc(-c2cn(CC3(C)CCOCC3)cc(C(=O)O)c2=O)cc1] | 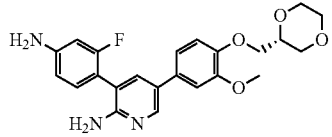 |
| Example 25 | 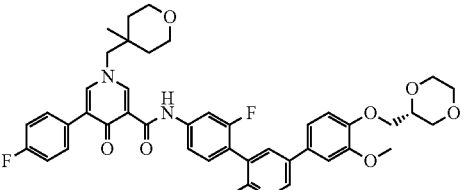 <br> ¹H-NMR (CDCl₃) δ: 12.87 (1H, s), 8.54 (1H, d, J = 2.4 Hz), 8.30 (1H, d, J = 1.8 Hz), 7.92 (1H, dd, J = 12.2, 1.8 Hz), 7.61-7.51 (3H, m), 7.48-7.43 (2H, m), 7.36 (1H, t, J = 8.2 Hz), 7.18 (2H, t, J = 8.9 Hz), 7.06-7.00 (2H, m), 6.98-6.94 (1H, m), 4.59 (1H, s), 4.11-4.03 (2H, m), 4.02-3.94 (2H, m), 3.91 (3H, s), 3.90-3.82 (6H, m), 3.79-3.60 (5H, m), 3.59-3.51 (1H, m), 1.74-1.61 (1H, m), 1.55-1.34 (3H, m), 1.18 (3H, s). <br> MS (ESI) m/z: 753 [(M + H)⁺] | 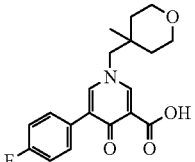 | 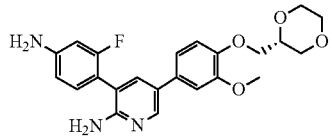 |
| Example 26 | 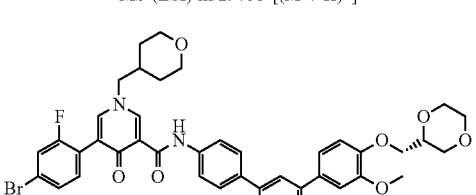 <br> ¹H-NMR (CDCl₃) δ: 12.61 (1H, s), 8.60 (1H, d, J = 2.4 Hz), 8.26 (1H, d, J = 2.4 Hz), 7.85 (2H, d, J = 8.5 Hz), 7.56-7.38 | 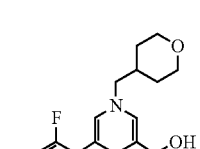 | 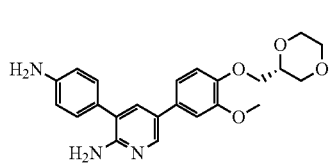 |

TABLE 13-continued

| Example No. | Structural formula for Example Instrumental data on Example | Structural formula of starting material A | Structural formula of starting material B |
| --- | --- | --- | --- |
| | (7H, m), 7.07-6.95 (3H, m), 4.65-4.62 (2H, m), 4.10-3.95 (6H, m), 3.90-3.64 (9H, m), 3.58-3.52 (1H, m), 3.40 (2H, t, J = 10.9 Hz), 2.15-2.09 (1H, m), 1.63-1.60 (2H, m), 1.50-1.41 (2H, m).<br>MS (APCI) m/z: 799 [(M + H)+]. | | |
| Example 27 | <br>¹H-NMR (DMSO-D₆) δ: 12.99 (1H, s), 8.80 (1H, d, J = 2.4 Hz), 8.30 (1H, d, J = 2.4 Hz), 8.23 (1H, d, J = 2.4 Hz), 7.91-7.88 (1H, m), 7.69-7.41 (6H, m), 7.18 (1H, d, J = 2.4 Hz), 7.11 (1H, dd, J = 8.5, 2.4 Hz), 6.98 (1H, d, J = 8.5 Hz), 5.70 (2H, s), 4.10 (2H, d, J = 7.3 Hz), 3.98-3.74 (10H, m), 3.68-3.59 (2H, m), 3.52-3.47 (1H, m), 3.42-3.37 (1H, m), 3.27 (2H, t, J = 10.9 Hz), 2.09 (1H, s), 1.47 (2H, br d, J = 10.3 Hz), 1.35-1.25 (2H, m).<br>MS (APCI) m/z: 817 [(M + H)+]. | | |
| Example 28 | <br>¹H-NMR (CDCl₃) δ: 12.72 (1H, s), 8.59 (1H, s), 8.26 (1H, s), 7.86 (2H, d, J = 8.5 Hz), 7.62-7.46 (8H, m), 7.06-6.95 (3H, m), 4.65 (2H, s), 4.13-3.65 (15H, m), 3.58-3.52 (1H, m), 3.39 (2H, t, J = 11.8 Hz), 2.17-2.07 (1H, m), 1.65-1.60 (2H, m), 1.50-1.39 (2H, m).<br>MS (APCI) m/z: 781 [(M + H)+]. | | |
| Example 29 | <br>¹H-NMR (DMSO-D₆) δ: 13.10 (1H, s), 8.77 (1H, d, J = 2.4 Hz), 8.30 (1H, d, J = 2.4 Hz), 8.15 (1H, d, J = 2.4 Hz), 7.91-7.88 (1H, m), 7.62-7.61 (1H, m), 7.42-7.33 (3H, m), 7.18-7.09 (4H, m), 6.98 (1H, d, J = 8.5 Hz), 5.70 (2H, s), 4.10 (2H, d, J = 7.3 Hz), 3.98-3.73 (10H, m), 3.69-3.59 (2H, m), 3.52-3.46 (1H, m), 3.42-3.37 (1H, m), 3.27 (2H, t, J = 10.9 Hz), 2.38 (3H, s), 2.12-2.03 (1H, m), 1.46 (2H, br d, J = 10.9 Hz), 1.35-1.25 (2H, m).<br>MS (APCI) m/z: 753 [(M + H)+]. | | |
| Example 30 | | | |

TABLE 13-continued

| Example No. | Structural formula for Example Instrumental data on Example | Structural formula of starting material A | Structural formula of starting material B |
| --- | --- | --- | --- |
| | ¹H-NMR (DMSO-D₆) δ: 12.95 (1H, s), 8.76 (1H, d, J = 2.4 Hz), 8.25 (1H, d, J = 2.4 Hz), 8.14 (1H, d, J = 2.4 Hz), 7.80 (2H, d, J = 8.5 Hz), 7.61 (1H, d, J = 2.4 Hz), 7.52 (2H, d, J = 8.5 Hz), 7.35 (1H, t, J = 7.6 Hz), 7.20 (1H, d, J = 2.4 Hz), 7.15-7.09 (3H, m), 6.99 (1H, d, J = 8.5 Hz), 5.70 (2H, s), 4.10 (2H, d, J = 6.7 Hz), 3.98-3.75 (10H, m), 3.69-3.59 (2H, m), 3.53-3.47 (1H, m), 3.42-3.37 (1H, m), 3.27 (2H, t, J = 11.8 Hz), 2.38 (3H, s), 2.12-2.03 (1H, m), 1.47 (2H, br d, J = 10.9 Hz), 1.35-1.25 (2H, m). MS (APCI) m/z: 735 [(M + H)⁺]. | | |
| Example 31 | ¹H-NMR (CDCl₃) δ: 12.73 (1H, s), 8.58 (1H, d, J = 2.4 Hz), 8.31 (1H, d, J = 2.4 Hz), 7.90 (1H, dd, J = 11.5, 1.8 Hz), 7.75 (1H, d, J = 2.4 Hz), 7.63-7.56 (3H, m), 7.44 (1H, dd, J = 8.2, 2.1 Hz), 7.37 (1H, t, J = 8.2 Hz), 7.21-7.14 (2H, m), 7.07-7.00 (2H, m), 6.96 (1H, d, J = 8.5 Hz), 4.58-4.53 (1H, m), 4.14 (3H, s), 4.12-4.02 (3H, m), 4.01-3.94 (2H, m), 3.92-3.79 (5H, m), 3.78-3.64 (5H, m), 3.59-3.51 (1H, m), 1.94-1.87 (2H, m), 1.86-1.77 (2H, m). MS (ESI) m/z: 764 [(M + H)⁺] | | |
| Example 32 | ¹H-NMR (CDCl₃) δ: 12.73 (1H, s), 8.58 (1H, d, J = 2.4 Hz), 8.31 (1H, d, J = 2.4 Hz), 7.90 (1H, dd, J = 12.1, 1.8 Hz), 7.74 (1H, d, J = 2.4 Hz), 7.63-7.55 (3H, m), 7.47-7.42 (1H, m), 7.37 (1H, t, J = 8.2 Hz), 7.17 (2H, t, J = 8.8 Hz), 7.08 (1H, dd, J = 8.5, 1.8 Hz), 7.03 (1H, d, J = 1.8 Hz), 6.93 (1H, d, J = 8.5 Hz), 4.56 (1H, s), 4.14 (2H, s), 4.12-4.05 (2H, m), 3.94 (3H, s), 3.91 (3H, s), 3.78-3.68 (2H, m), 1.94-1.87 (2H, m), 1.86-1.77 (2H, m), 1.53-1.41 (1H, m). MS (ESI) m/z: 678 [(M + H)⁺] | | |
| Example 33 | ¹H-NMR (CDCl₃) δ: 12.83 (1H, s), 8.57 (1H, d, J = 2.4 Hz), 8.31 (1H, d, J = 1.8 Hz), 7.94-7.88 (1H, m), 7.72 (1H, d, J = 2.4 Hz), 7.59 (1H, d, J = 1.8 Hz), 7.52-7.41 (3H, m), 7.37 (1H, t, J = 8.2 Hz), 7.29 (2H, d, J = 7.9 Hz), 7.11-7.05 (1H, m), 7.05-7.01 (1H, m), 6.93 (1H, d, J = 8.5 Hz), 4.58 (1H, s), 4.13 (2H, s), 4.11-4.04 (2H, m), 3.94 (3H, s), 3.92 (3H, s), 3.73 (2H, t, J = 11.5 Hz), 2.41 (3H, s), 1.94-1.87 (2H, m), 1.86-1.75 (2H, m), 1.53-1.41 (1H, m). MS (ESI) m/z: 674 [(M + H)⁺] | | |

TABLE 13-continued

| Example No. | Structural formula for Example Instrumental data on Example | Structural formula of starting material A | Structural formula of starting material B |
|---|---|---|---|
| Example 34 | 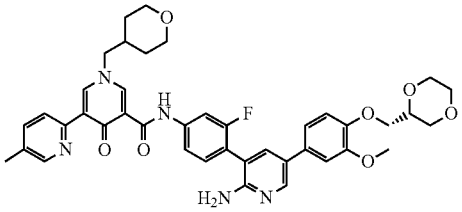<br>¹H-NMR (CDCl₃) δ: 13.02 (1H, s), 8.56 (1H, d, J = 2.4 Hz), 8.48-8.46 (2H, m), 8.41 (1H, d, J = 2.4 Hz), 8.31 (1H, d, J = 2.4 Hz), 7.93 (1H, dd, J = 11.8, 2.4 Hz), 7.64-7.59 (2H, m), 7.50 (1H, dd, J = 8.5, 2.4 Hz), 7.38 (1H, t, J = 8.2 Hz), 7.07-7.03 (2H, m), 6.96 (1H, d, J = 8.5 Hz), 4.56 (2H, s), 4.15-3.64 (15H, m), 3.59-3.52 (1H, m), 3.42-3.35 (2H, m), 2.40 (3H, s), 2.22-2.10 (1H, m), 1.62 (2H, d, J = 18.8 Hz), 1.51-1.41 (2H, m).<br>MS (APCI) m/z: 736 [(M + H)⁺]. | 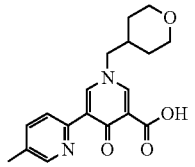 [SMILES: Cc1ccc(-c2cn(CC3CCOCC3)cc(C(=O)O)c2=O)nc1] | 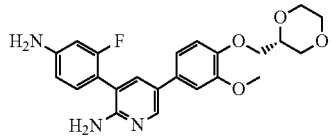 [SMILES: COc1cc(-c2cnc(N)c(-c3ccc(N)cc3F)c2)ccc1OC[C@H]1COCCO1] |
| Example 35 | 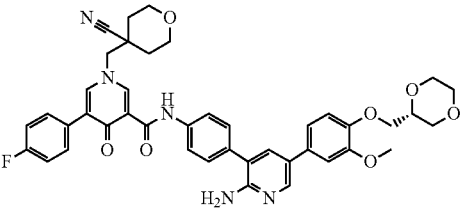<br>¹H-NMR (CDCl₃) δ: 12.61 (1H, s), 8.58 (1H, d, J = 2.4 Hz), 8.26 (1H, d, J = 1.8 Hz), 7.85 (2H, d, J = 8.5 Hz), 7.74 (1H, d, J = 2.4 Hz), 7.64-7.55 (3H, m), 7.49 (2H, d, J = 8.5 Hz), 7.21-7.15 (2H, m), 7.08-7.01 (2H, m), 6.96 (1H, d, J = 8.5 Hz), 4.68-4.63 (1H, m), 4.15-4.02 (6H, m), 4.01-3.95 (2H, m), 3.90 (3H, s), 3.86-3.80 (2H, m), 3.79-3.64 (5H, m), 3.59-3.52 (1H, m), 1.95-1.88 (2H, m), 1.86-1.76 (2H, m).<br>MS (ESI) m/z: 746 [(M + H)⁺] | 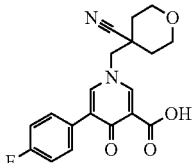 | 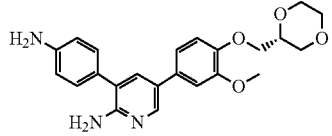 [SMILES: COc1cc(-c2cnc(N)c(-c3ccc(N)cc3)c2)ccc1OC[C@H]1COCCO1] |
| Example 36 | 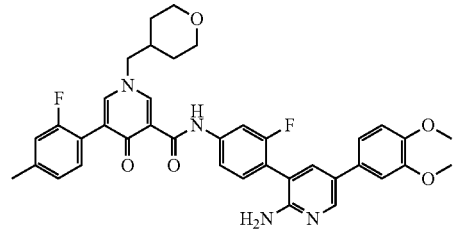<br>¹H-NMR (DMSO-D₆) δ: 13.10 (1H, s), 8.77 (1H, d, J = 2.4 Hz), 8.29 (1H, d, J = 2.4 Hz), 8.15 (1H, d, J = 2.4 Hz), 7.91-7.88 (1H, m), 7.61 (1H, d, J = 2.4 Hz), 7.43-7.33 (3H, m), 7.17-7.09 (4H, m), 6.98 (1H, d, J = 8.5 Hz), 5.69 (2H, s), 4.10 (2H, d, J = 7.3 Hz), 3.88-3.82 (5H, m), 3.76 (3H, s), 3.27 (2H, t, J = 10.9 Hz), 2.38 (3H, s), 2.13-2.02 (1H, m), 1.47 (2H, br d, J = 10.3 Hz), 1.35-1.25 (2H, m).<br>MS (APCI) m/z: 667 [(M + H)⁺]. |  | 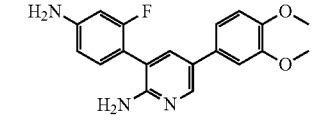 [SMILES: COc1ccc(-c2cnc(N)c(-c3ccc(N)cc3F)c2)cc1OC] |
| Example 37 | 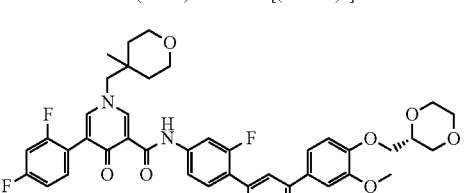<br>¹H-NMR (CDCl₃) δ: 12.75 (1H, s), 8.55 (1H, d, J = 2.4 Hz), 8.30 (1H, d, J = 2.4 Hz), 7.94-7.87 (1H, m), 7.61-7.50 (3H, m), 7.46-7.42 (1H, m), 7.36 (1H, t, J = 8.2 Hz), 7.07-6.92 (5H, m), 4.57-4.51 (1H, m), 4.10-4.03 (2H, m), 4.01-3.94 | 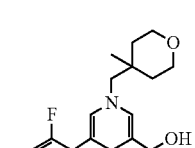 | 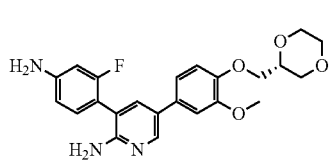 [SMILES: COc1cc(-c2cnc(N)c(-c3ccc(N)cc3F)c2)ccc1OC[C@H]1COCCO1] |

TABLE 13-continued

| Example No. | Structural formula for Example Instrumental data on Example | Structural formula of starting material A | Structural formula of starting material B |
|---|---|---|---|
| | (2H, m), 3.90 (3H, s), 3.89-3.82 (5H, m), 3.82-3.59 (6H, m), 3.59-3.51 (1H, m), 1.73-1.64 (2H, m), 1.42-1.35 (2H, m), 1.18 (3H, s).<br>MS (ESI) m/z: 771 [(M + H)+] | | |
| Example 38 | [structure]<br><sup>1</sup>H-NMR (CDCl$_3$) δ: 12.63 (1H, s), 8.58-8.55 (1H, m), 8.27-8.24 (1H, m), 7.86 (2H, d, J = 8.5 Hz), 7.62-7.54 (2H, m), 7.50 (3H, t, J = 9.4 Hz), 7.08-6.92 (5H, m), 4.68-4.62 (1H, m), 4.12-4.02 (2H, m), 4.01-3.94 (2H, m), 3.91 (3H, s), 3.89-3.82 (6H, m), 3.81-3.62 (5H, m), 3.59-3.51 (1H, m), 1.74-1.56 (2H, m), 1.42-1.35 (2H, m), 1.17 (3H, s).<br>MS (ESI) m/z: 753 [(M + H)+] | [structure] | [structure] |
| Example 39 | [structure]<br><sup>1</sup>H-NMR (CDCl$_3$) δ: 12.47 (1H, s), 8.63 (1H, d, J = 2.4 Hz), 8.26 (1H, d, J = 1.8 Hz), 7.84 (2H, d, J = 8.5 Hz), 7.74 (1H, d, J = 2.4 Hz), 7.58-7.45 (4H, m), 7.08-6.93 (5H, m), 4.68-4.62 (1H, m), 4.14 (2H, s), 4.12-4.02 (4H, m), 4.01-3.94 (2H, m), 3.91 (3H, s), 3.88-3.80 (2H, m), 3.79-3.64 (5H, m), 3.59-3.51 (1H, m), 1.95-1.88 (2H, m), 1.86-1.77 (2H, m).<br>MS (ESI) m/z: 764 [(M + H)+] | [structure] | [structure] |
| Example 40 | [structure]<br><sup>1</sup>H-NMR (DMSO-D$_6$) δ: 13.10 (1H, s), 8.77 (1H, d, J = 2.4 Hz), 8.30 (1H, d, J = 2.4 Hz), 8.14 (1H, d, J = 2.4 Hz), 7.89 (1H, d, J = 12.8 Hz), 7.61 (1H, d, J = 2.4 Hz), 7.42-7.41 (2H, m), 7.33 (1H, t, J = 7.9 Hz), 7.18 (1H, d, J = 2.4 Hz), 7.11 (1H, dd, J = 8.5, 2.4 Hz), 7.03-6.97 (3H, m), 5.70 (2H, s), 4.09 (2H, d, J = 7.3 Hz), 3.98-3.81 (9H, m), 3.78-3.74 (1H, m), 3.69-3.59 (2H, m), 3.53-3.46 (1H, m), 3.42-3.36 (1H, m), 3.27 (2H, t, J = 10.9 Hz), 2.12-1.97 (2H, m), 1.46 (2H, br d, J = 10.9 Hz), 1.35-1.26 (2H, m), 1.04-1.00 (2H, m), 0.78-0.73 (2H, m).<br>MS (APCI) m/z: 779 [(M + H)+]. | [structure] | [structure] |
| Example 41 | [structure] | [structure] | [structure] |

| Example No. | Structural formula for Example Instrumental data on Example | Structural formula of starting material A | Structural formula of starting material B |
|---|---|---|---|
| | ¹H-NMR (CDCl₃) δ: 12.85 (1H, s), 8.57 (1H, d, J = 2.4 Hz), 8.26 (1H, d, J = 2.4 Hz), 7.87 (2H, d, J = 8.5 Hz), 7.57 (1H, d, J = 2.4 Hz), 7.51-7.44 (5H, m), 7.29 (2H, d, J = 8.5 Hz), 7.08-7.02 (2H, m), 6.96 (1H, d, J = 8.5 Hz), 4.68-4.62 (2H, m), 4.10-3.94 (6H, m), 3.91 (3H, s), 3.89-3.81 (4H, m), 3.79-3.64 (2H, m), 3.59-3.52 (1H, m), 3.43-3.35 (2H, m), 2.41 (3H, s), 2.19-2.04 (1H, m), 1.65-1.57 (2H, m), 1.51-1.38 (2H, m). <br> MS (ESI) m/z: 717 [(M + H)⁺] | | |
| Example 42 | 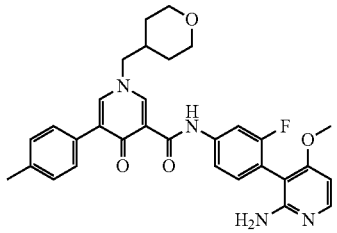 <br> ¹H-NMR (DMSO-D₆) δ: 13.20 (1H, s), 8.72 (1H, d, J = 2.4 Hz), 8.17 (1H, d, J = 2.4 Hz), 7.92 (1H, d, J = 6.1 Hz), 7.85 (1H, dd, J = 12.1, 2.4 Hz), 7.58 (2H, d, J = 7.9 Hz), 7.36 (1H, dd, J = 8.2, 2.4 Hz), 7.27-7.18 (3H, m), 6.43 (1H, d, J = 6.1 Hz), 5.28 (2H, s), 4.11 (2H, d, J = 7.3 Hz), 3.86 (2H, dd, J = 10.9, 3.3 Hz), 3.68 (3H, s), 3.27 (2H, t, J = 10.9 Hz), 2.36 (3H, s), 2.14-2.06 (1H, m), 1.46 (2H, br d, J = 10.3 Hz), 1.36-1.26 (2H, m), 1.09 (0H, t, J = 7.0 Hz). <br> MS (APCI) m/z: 543 [(M + H)⁺]. | 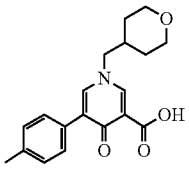 |  |
| Example 43 | 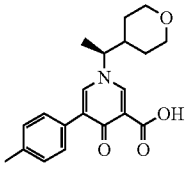 <br> ¹H-NMR (CDCl₃) δ: 12.91 (1H, s), 8.62 (1H, d, J = 2.4 Hz), 8.27 (1H, d, J = 2.4 Hz), 7.88 (2H, d, J = 8.5 Hz), 7.58 (1H, d, J = 2.4 Hz), 7.52-7.44 (5H, m), 7.30 (2H, d, J = 8.5 Hz), 7.11-7.07 (1H, m), 7.05-7.02 (1H, m), 6.94 (1H, d, J = 8.5 Hz), 4.68-4.62 (1H, m), 4.11-4.04 (1H, m), 4.01-3.89 (7H, m), 3.82-3.72 (1H, m), 3.45-3.36 (1H, m), 3.36-3.28 (1H, m), 2.42 (3H, s), 2.00-1.87 (1H, m), 1.80-1.59 (4H, m), 1.55-1.26 (4H, m). <br> MS (APCI) m/z: 645 [(M + H)⁺] | 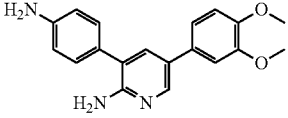 [SMILES: COc1ccc(-c2cnc(N)c(-c3ccc(N)cc3)c2)cc1OC] | 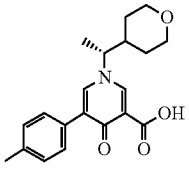 [SMILES: Cc1ccc(-c2cn([C@H](C)C3CCOCC3)cc(C(=O)O)c2=O)cc1] |
| Example 44 | 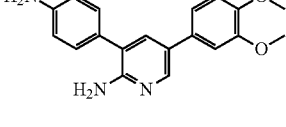 <br> ¹H-NMR (CDCl₃) δ: 12.92 (1H, s), 8.62 (1H, d, J = 2.4 Hz), 8.26 (1H, d, J = 2.4 Hz), 7.88 (2H, d, J = 8.5 Hz), 7.60 (1H, d, J = 2.4 Hz), 7.53-7.45 (5H, m), 7.30 (2H, d, J = 8.5 Hz), 7.11-7.06 (1H, m), 7.05-7.02 (1H, m), 6.94 (1H, d, J = 8.5 Hz), 4.83-4.76 (1H, m), 4.10-4.04 (1H, m), 4.01-3.90 (7H, m), 3.82-3.73 (1H, m), 3.45-3.36 (1H, m), 3.36-3.27 (1H, m), 2.42 (3H, s), 2.11-1.87 (2H, m), 1.79-1.72 (1H, m), | | |

TABLE 13-continued

| Example No. | Structural formula for Example Instrumental data on Example | Structural formula of starting material A | Structural formula of starting material B |
|---|---|---|---|
| | 1.62 (3H, d, J = 6.7 Hz), 1.48-1.29 (3H, m). MS (APCI) m/z: 645 [(M + H)+] | | |
| Example 45 | ¹H-NMR (DMSO-D₆) δ: 13.34 (1H, d, J = 1.8 Hz), 8.74 (1H, d, J = 2.4 Hz), 8.61 (1H, t, J = 8.5 Hz), 8.27 (1H, d, J = 2.4 Hz), 8.18 (1H, d, J = 2.4 Hz), 7.65 (1H, d, J = 2.4 Hz), 7.58 (2H, d, J = 7.9 Hz), 7.49 (1H, dd, J = 11.8, 1.5 Hz), 7.40-7.38 (1H, m), 7.27 (2H, d, J = 7.9 Hz), 7.20-7.14 (2H, m), 6.99 (1H, d, J = 8.5 Hz), 5.81 (2H, s), 4.12 (2H, d, J = 7.3 Hz), 3.88-3.83 (5H, m), 3.77 (3H, s), 3.27 (2H, t, J = 10.9 Hz), 2.36 (3H, s), 2.17-2.05 (1H, m), 1.46 (2H, br d, J = 10.9 Hz), 1.36-1.26 (2H, m). MS (APCI) m/z: 649 [(M + H)+]. | | |
| Example 46 | ¹H-NMR (DMSO-D₆) δ: 13.27 (1H, d, J = 2.4 Hz), 8.73 (1H, d, J = 2.4 Hz), 8.53 (1H, t, J = 8.5 Hz), 8.17 (1H, d, J = 2.4 Hz), 7.89 (1H, d, J = 6.1 Hz), 7.57 (2H, d, J = 8.5 Hz), 7.27 (2H, d, J = 8.5 Hz), 7.16-7.06 (2H, m), 6.43 (1H, d, J = 6.1 Hz), 5.29 (2H, s), 4.11 (2H, d, J = 7.3 Hz), 3.86 (2H, dd, J = 11.2, 3.0 Hz), 3.68 (3H, s), 3.27 (2H, t, J = 11.2 Hz), 2.36 (3H, s), 2.15-2.06 (1H, m), 1.46 (2H, br d, J = 10.9 Hz), 1.36-1.26 (2H, m). MS (APCI) m/z: 543 [(M + H)+]. | | |
| Example 47 | ¹H-NMR (CDCl₃) δ: 12.86-12.84 (1H, m), 8.57 (1H, d, J = 2.4 Hz), 8.20 (1H, d, J = 2.4 Hz), 7.88-7.84 (2H, m), 7.70-7.69 (1H, m), 7.56-7.55 (1H, m), 7.48-7.45 (6H, m), 7.31-7.27 (2H, m), 4.60-4.55 (2H, m), 4.06-4.00 (2H, m), 3.94 (3H, s), 3.87 (2H, d, J = 7.3 Hz), 3.43-3.35 (2H, m), 2.41 (3H, s), 2.16-2.06 (1H, m), 1.65-1.57 (2H, m), 1.50-1.38 (2H, m). MS (ES + APCI) m/z: 575 [(M + H)+]. | | |

TABLE 13-continued

| Example No. | Structural formula for Example Instrumental data on Example | Structural formula of starting material A | Structural formula of starting material B |
|---|---|---|---|
| Example 48 | 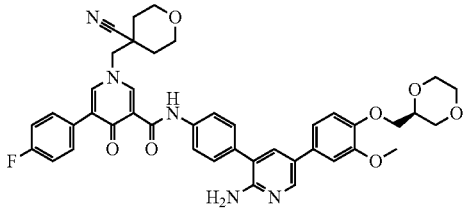 <br> ¹H-NMR (CDCl₃) δ: 12.61 (1H, s), 8.59 (1H, d, J = 2.4 Hz), 8.26 (1H, d, J = 2.4 Hz), 7.85 (2H, d, J = 8.5 Hz), 7.74 (1H, d, J = 2.4 Hz), 7.64-7.55 (3H, m), 7.49 (2H, d, J = 8.5 Hz), 7.21-7.14 (2H, m), 7.08-7.01 (2H, m), 6.96 (1H, d, J = 7.9 Hz), 4.68-4.62 (2H, m), 4.17-4.03 (6H, m), 4.01-3.94 (2H, m), 3.91 (3H, s), 3.89-3.80 (2H, m), 3.79-3.64 (4H, m), 3.60-3.51 (1H, m), 1.95-1.88 (2H, m), 1.87-1.76 (2H, m). <br> MS (APCI) m/z: 746 [(M + H)⁺] | 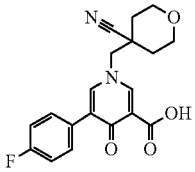 [SMILES: N#CC1(Cn2cc(C(=O)O)c(=O)c(-c3ccc(F)cc3)c2)CCOCC1] | 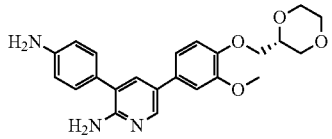 |
| Example 49 | 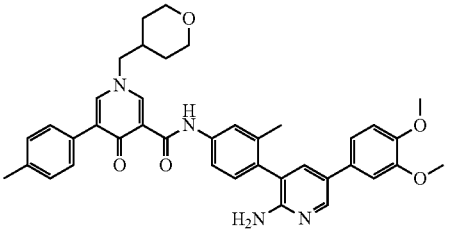 <br> ¹H-NMR (CDCl₃) δ: 12.80 (1H, s), 8.57 (1H, d, J = 2.4 Hz), 8.31 (1H, d, J = 2.4 Hz), 7.74-7.69 (2H, m), 7.51-7.45 (4H, m), 7.29 (2H, d, J = 7.9 Hz), 7.23 (1H, d, J = 8.5 Hz), 7.09 (1H, dd, J = 8.2, 2.1 Hz), 7.04 (1H, d, J = 2.4 Hz), 6.93 (1H, d, J = 7.9 Hz), 4.42-4.35 (2H, m), 4.03 (2H, dd, J = 11.6, 3.7 Hz), 3.94 (3H, s), 3.92 (3H, s), 3.88 (2H, d, J = 7.3 Hz), 3.39 (2H, t, J = 11.3 Hz), 2.41 (3H, s), 2.22 (3H, s), 2.16-2.07 (1H, m), 1.66-1.57 (2H, m), 1.51-1.39 (2H, m). <br> MS (APCI) m/z: 645 [(M + H)⁺]. | 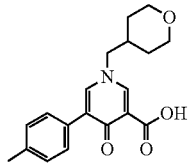 [SMILES: Cc1ccc(-c2cn(CC3CCOCC3)cc(C(=O)O)c2=O)cc1] | 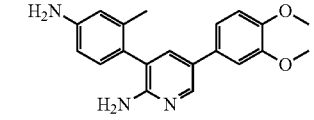 [SMILES: COc1ccc(-c2cnc(N)c(-c3ccc(N)cc3C)c2)cc1OC] |
| Example 50 | 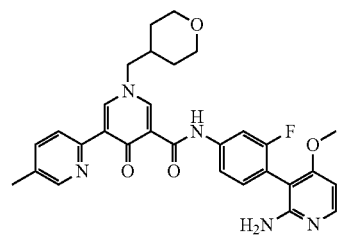 <br> ¹H-NMR (DMSO-D₆) δ: 13.16 (1H, s), 8.76 (1H, d, J = 2.4 Hz), 8.69 (1H, d, J = 2.4 Hz), 8.52-8.46 (2H, m), 7.93-7.85 (2H, m), 7.71 (1H, dd, J = 8.5, 2.4 Hz), 7.40 (1H, dd, J = 8.5, 2.4 Hz), 7.22 (1H, t, J = 8.5 Hz), 6.43 (1H, d, J = 5.5 Hz), 5.29 (2H, s), 4.20 (2H, d, J = 7.3 Hz), 3.86 (2H, dd, J = 11.2, 3.3 Hz), 3.69 (3H, s), 3.27 (2H, t, J = 11.2 Hz), 2.36 (3H, s), 2.11-2.01 (1H, m), 1.47 (2H, br d, J = 10.3 Hz), 1.37-1.26 (2H, m). <br> MS (APCI) m/z: 544 [(M + H)⁺]. | 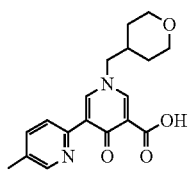 [SMILES: Cc1ccc(-c2cn(CC3CCOCC3)cc(C(=O)O)c2=O)nc1] | 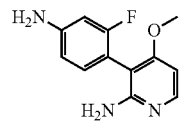 |
| Example 51 | 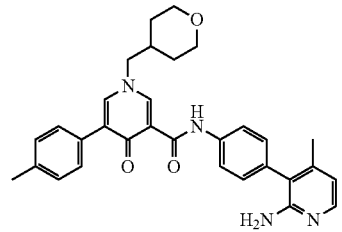 [SMILES: Cc1ccc(-c2cn(CC3CCOCC3)cc(C(=O)Nc3ccc(-c4c(C)ccnc4N)cc3)c2=O)cc1] | 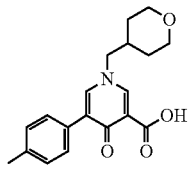 | 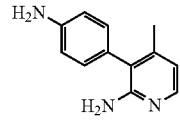 |

TABLE 13-continued

| Example No. | Structural formula for Example Instrumental data on Example | Structural formula of starting material A | Structural formula of starting material B |
|---|---|---|---|
| | ¹H-NMR (DMSO-D₆) δ: 13.09 (1H, s), 8.71 (1H, d, J = 2.4 Hz), 8.17 (1H, d, J = 2.4 Hz), 7.82-7.80 (3H, m), 7.59 (2H, d, J = 8.5 Hz), 7.26 (2H, d, J = 8.5 Hz), 7.20 (2H, d, J = 8.5 Hz), 6.53 (1H, d, J = 4.9 Hz), 5.09 (2H, s), 4.11 (2H, d, J = 7.3 Hz), 3.86 (2H, dd, J = 10.9, 3.0 Hz), 3.27 (2H, t, J = 10.9 Hz), 2.36 (3H, s), 2.14-2.05 (1H, m), 1.92 (3H, s), 1.46 (2H, br d, J = 10.9 Hz), 1.37-1.26 (2H, m). MS (APCI) m/z: 509 [(M + H)⁺]. | | |
| Example 52 | 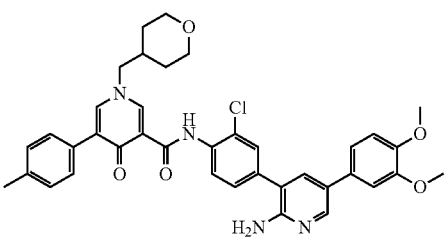 ¹H-NMR (CDCl₃) δ: 13.10 (1H, s), 8.66 (1H, d, J = 8.5 Hz), 8.56 (1H, d, J = 2.4 Hz), 8.29 (1H, d, J = 2.4 Hz), 7.58-7.55 (2H, m), 7.51 (2H, d, J = 7.9 Hz), 7.47-7.43 (2H, m), 7.29-7.25 (2H, m), 7.09 (1H, dd, J = 7.9, 2.4 Hz), 7.03 (1H, d, J = 2.4 Hz), 6.94 (1H, d, J = 7.9 Hz), 4.67-4.62 (2H, m), 4.03 (2H, dd, J = 11.6, 4.3 Hz), 3.95 (3H, s), 3.92 (3H, s), 3.87 (2H, d, J = 7.3 Hz), 3.43-3.35 (2H, m), 2.40 (3H, s), 2.18-2.05 (1H, m), 1.64-1.57 (2H, m), 1.50-1.38 (2H, m). MS (APCI) m/z: 665 [(M + H)⁺]. | 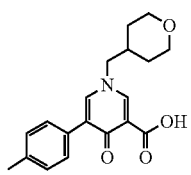 [SMILES: Cc1ccc(-c2cn(CC3CCOCC3)cc(C(=O)O)c2=O)cc1] | 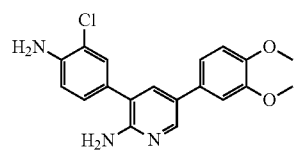 [SMILES: COc1ccc(-c2cnc(N)c(-c3ccc(N)c(Cl)c3)c2)cc1OC] |
| Example 53 | 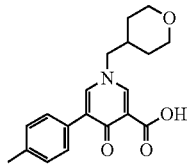 ¹H-NMR (CDCl₃) δ: 12.98 (1H, s), 8.56 (1H, d, J = 2.4 Hz), 8.24 (1H, d, J = 2.4 Hz), 7.91 (1H, dd, J = 12.0, 2.0 Hz), 7.69 (1H, s), 7.55 (1H, s), 7.49-7.42 (5H, m), 7.36-7.26 (3H, m), 4.51-4.46 (2H, m), 4.04 (2H, dd, J = 11.5, 3.0 Hz), 3.94 (3H, s), 3.88 (2H, d, J = 7.5 Hz), 3.39 (2H, td, J = 12.0, 2.0 Hz), 2.41 (3H, s), 2.18-2.05 (1H, m), 1.51-1.39 (2H, m). MS (APCI) m/z: 593 [(M + H)⁺]. | |  |
| Example 54 | 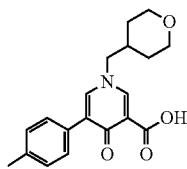 ¹H-NMR (CDCl₃) δ: 12.86 (1H, s), 8.56 (1H, d, J = 2.4 Hz), 7.95-7.86 (3H, m), 7.49-7.44 (3H, m), 7.32-7.27 (4H, m), 6.79 (1H, d, J = 5.5 Hz), 4.56-4.51 (2H, m), 4.07-4.00 (2H, m), 3.87 (2H, d, J = 7.3 Hz), 3.43-3.35 (2H, m), 2.41 (3H, s), 2.18-2.04 (1H, m), 1.65-1.57 (2H, m), 1.51-1.38 (2H, m). MS (APCI) m/z: 529 [(M + H)⁺] | | 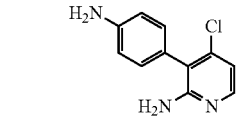 |

TABLE 13-continued

| Example No. | Structural formula for Example Instrumental data on Example | Structural formula of starting material A | Structural formula of starting material B |
|---|---|---|---|
| Example 55 | 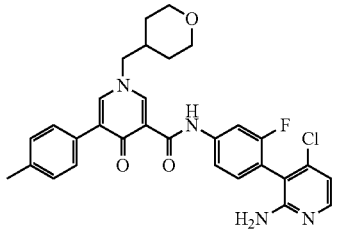 [SMILES: Cc1ccc(-c2cn(CC3CCOCC3)cc(C(=O)Nc3ccc(-c4c(Cl)ccnc4N)c(F)c3)c2=O)cc1]<br><sup>1</sup>H-NMR (CDCl<sub>3</sub>) δ: 13.00 (1H, s), 8.55 (1H, d, J = 3.0 Hz), 7.97 (1H, d, J = 6.1 Hz), 7.93 (1H, dd, J = 11.5, 1.8 Hz), 7.49-7.44 (4H, m), 7.32-7.21 (3H, m), 6.82 (1H, d, J = 5.5 Hz), 4.58-4.52 (2H, m), 4.07-4.00 (2H, m), 3.88 (2H, d, J = 7.3 Hz), 3.44-3.35 (2H, m), 2.41 (3H, s), 2.18-2.05 (1H, m), 1.65-1.58 (2H, m), 1.51-1.41 (2H, m).<br>MS (APCI) m/z: 547 [(M + H)<sup>+</sup>] | 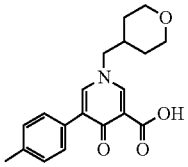 | 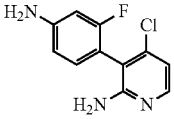 [SMILES: Nc1ccc(-c2c(Cl)ccnc2N)c(F)c1] |
| Example 56 | 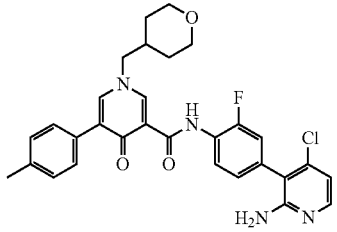<br><sup>1</sup>H-NMR (CDCl<sub>3</sub>) δ: 13.06 (1H, s), 8.63 (1H, t, J = 8.2 Hz), 8.55 (1H, d, J = 2.4 Hz), 7.94 (1H, d, J = 6.1 Hz), 7.52-7.45 (3H, m), 7.31-7.25 (2H, m), 7.15-7.09 (2H, m), 6.80 (1H, d, J = 5.5 Hz), 4.57-4.50 (2H, m), 4.07-4.00 (2H, m), 3.87 (2H, d, J = 7.3 Hz), 3.44-3.35 (2H, m), 2.40 (3H, s), 2.16-2.06 (1H, m), 1.65-1.58 (2H, m), 1.51-1.39 (2H, m).<br>MS (APCI) m/z: 547 [(M + H)<sup>+</sup>] | 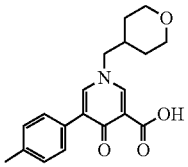 | 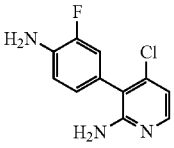 [SMILES: Nc1ccc(-c2c(Cl)ccnc2N)cc1F] |
| Example 57 | 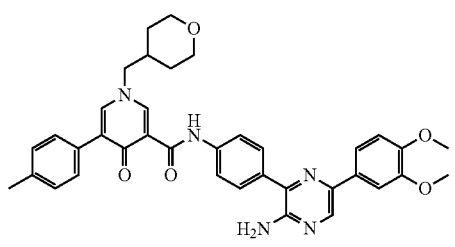<br><sup>1</sup>H-NMR (DMSO-D<sub>6</sub>) δ: 13.18 (1H, s), 8.72 (1H, d, J = 2.4 Hz), 8.51 (1H, s), 8.18 (1H, d, J = 2.4 Hz), 7.87-7.81 (4H, m), 7.60-7.53 (4H, m), 7.27 (2H, d, J = 8.5 Hz), 7.02 (1H, d, J = 8.5 Hz), 6.23 (2H, s), 4.11 (2H, d, J = 7.3 Hz), 3.88-3.83 (5H, m), 3.79 (3H, s), 3.27 (2H, t, J = 10.9 Hz), 2.36 (3H, s), 2.16-2.05 (1H, m), 1.46 (2H, br d, J = 10.9 Hz), 1.37-1.26 (2H, m).<br>MS (APCI) m/z: 632 [(M + H)<sup>+</sup>]. | 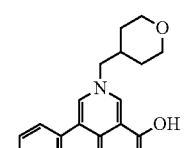 | 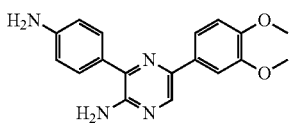 |
| Example 58 | 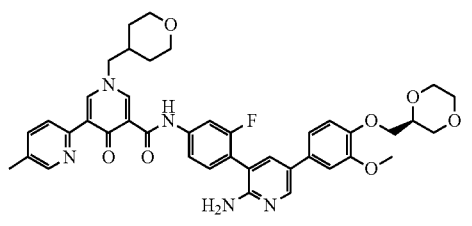 [SMILES: COc1cc(-c2cnc(N)c(-c3ccc(NC(=O)c4cn(CC5CCOCC5)cc(-c5ccc(C)cn5)c4=O)cc3F)c2)ccc1OC[C@@H]1COCCO1] | 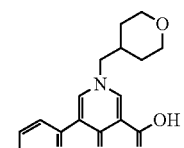 | 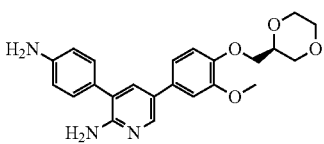 [SMILES: COc1cc(-c2cnc(N)c(-c3ccc(N)cc3)c2)ccc1OC[C@@H]1COCCO1] |

TABLE 13-continued

| Example No. | Structural formula for Example Instrumental data on Example | Structural formula of starting material A | Structural formula of starting material B |
| --- | --- | --- | --- |
| | ¹H-NMR (DMSO-D₆) δ: 13.22 (1H, s), 8.77 (1H, d, J = 2.4 Hz), 8.69 (1H, d, J = 2.4 Hz), 8.52-8.46 (2H, m), 8.31 (1H, d, J = 2.4 Hz), 7.93 (1H, dd, J = 12.1, 2.4 Hz), 7.71 (1H, dd, J = 8.5, 2.4 Hz), 7.63 (1H, d, J = 2.4 Hz), 7.49-7.41 (2H, m), 7.18 (1H, d, J = 2.4 Hz), 7.11 (1H, dd, J = 8.5, 2.4 Hz), 6.99 (1H, d, J = 8.5 Hz), 5.71 (2H, s), 4.21 (2H, d, J = 7.3 Hz), 3.98-3.75 (10H, m), 3.68-3.59 (2H, m), 3.53-3.46 (1H, m), 3.42-3.36 (1H, m), 3.27 (2H, t, J = 10.9 Hz), 2.36 (3H, s), 2.11-2.02 (1H, m), 1.46 (2H, br d, J = 10.9 Hz), 1.37-1.26 (2H, m). MS (APCI) m/z: 736 [(M + H)⁺]. | | |
| Example 59 | ¹H-NMR (CDCl₃) δ: 12.72 (1H, s), 8.95 (2H, s), 8.62 (1H, d, J = 2.4 Hz), 8.29-8.25 (2H, m), 7.89 (2H, d, J = 8.5 Hz), 7.60 (1H, d, J = 2.4 Hz), 7.50 (2H, d, J = 8.5 Hz), 7.11-7.07 (1H, m), 7.05-7.01 (1H, m), 6.94 (1H, d, J = 8.5 Hz), 4.79-4.72 (2H, m), 4.07-4.00 (2H, m), 3.96-3.90 (8H, m), 3.40 (2H, t, J = 10.9 Hz), 2.21-2.09 (1H, m), 1.66-1.58 (2H, m), 1.53-1.41 (2H, m). MS (APCI) m/z: 697 [(M + H)⁺] | | |
| Example 60 | ¹H-NMR (CDCl₃) δ: 12.84 (1H, s), 8.95 (2H, s), 8.61 (1H, d, J = 2.4 Hz), 8.30 (2H, dd, J = 10.6, 2.1 Hz), 7.93 (1H, dd, J = 12.1, 1.8 Hz), 7.60 (1H, d, J = 2.4 Hz), 7.47 (1H, dd, J = 8.5, 1.8 Hz), 7.38 (1H, t, J = 8.2 Hz), 7.09 (1H, dd, J = 8.2, 2.1 Hz), 7.03 (1H, d, J = 1.8 Hz), 6.94 (1H, d, J = 7.9 Hz), 4.65-4.55 (2H, m), 4.08-4.00 (2H, m), 3.98-3.90 (8H, m), 3.44-3.35 (2H, m), 2.22-2.09 (1H, m), 1.66-1.58 (2H, m), 1.53-1.40 (2H, m). MS (APCI) m/z: 715 [(M + H)⁺] | | |
| Example 61 | ¹H-NMR (DMSO-D₆) δ: 13.01 (1H, s), 8.78 (1H, d, J = 2.4 Hz), 8.69-8.62 (3H, m), 8.26 (1H, d, J = 2.4 Hz), 7.87-7.82 (3H, m), 7.62-7.54 (3H, m), 7.20-7.14 (2H, m), 6.99 (1H, d, J = 8.5 Hz), 5.70 (2H, s), 4.21 (2H, d, J = 7.3 Hz), 3.88-3.77 (8H, m), 3.27 (2H, t, J = 10.9 Hz), 2.12-2.02 (1H, m), 1.47 (2H, br d, J = 10.9 Hz), 1.37-1.27 (2H, m). MS (APCI) m/z: 636 [(M + H)⁺]. | | |

TABLE 13-continued

| Example No. | Structural formula for Example Instrumental data on Example | Structural formula of starting material A | Structural formula of starting material B |
|---|---|---|---|
| Example 62 | 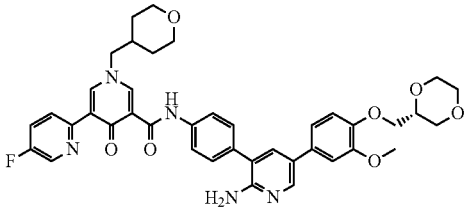 [SMILES: COc1cc(-c2cnc(N)c(-c3ccc(NC(=O)c4cn(CC5CCOCC5)cc(-c5ccc(F)cn5)c4=O)cc3)c2)ccc1OC[C@H]1COCCO1]<br>¹H-NMR (DMSO-D₆) δ: 13.01 (1H, s), 8.78 (1H, d, J = 2.4 Hz), 8.69-8.62 (3H, m), 8.26 (1H, d, J = 2.4 Hz), 7.87-7.82 (3H, m), 7.62-7.54 (3H, m), 7.21-7.12 (2H, m), 7.00 (1H, d, J = 8.5 Hz), 5.71 (2H, s), 4.21 (2H, d, J = 7.3 Hz), 3.98-3.75 (10H, m), 3.69-3.60 (2H, m), 3.53-3.46 (1H, m), 3.42-3.37 (1H, m), 3.30-3.24 (2H, m), 2.12-2.02 (1H, m), 1.47 (2H, br d, J = 10.9 Hz), 1.37-1.26 (2H, m).<br>MS (APCI) m/z: 722 [(M + H)⁺]. | 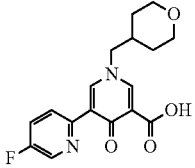 [SMILES: O=C(O)c1cn(CC2CCOCC2)cc(-c2ccc(F)cn2)c1=O] | 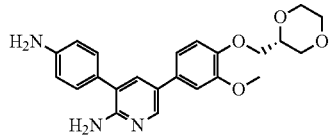 [SMILES: COc1cc(-c2cnc(N)c(-c3ccc(N)cc3)c2)ccc1OC[C@H]1COCCO1] |
| Example 63 | 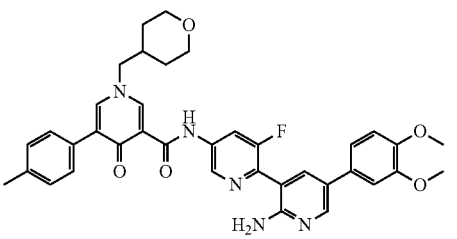<br>¹H-NMR (DMSO-D₆) δ: 13.46 (1H, s), 8.77-8.75 (2H, m), 8.43-8.35 (2H, m), 8.21 (1H, d, J = 2.4 Hz), 7.95 (1H, t, J = 2.4 Hz), 7.60 (2H, d, J = 8.5 Hz), 7.27 (2H, d, J = 8.5 Hz), 7.18-7.12 (2H, m), 7.00 (1H, d, J = 8.5 Hz), 6.51 (2H, s), 4.12 (2H, d, J = 7.3 Hz), 3.88-3.83 (5H, m), 3.77 (3H, s), 3.27 (2H, t, J = 10.9 Hz), 2.36 (3H, s), 2.16-2.06 (1H, m), 1.46 (2H, br d, J = 10.9 Hz), 1.36-1.26 (2H, m).<br>MS (APCI) m/z: 650 [(M + H)⁺]. | 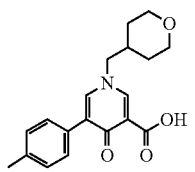 [SMILES: Cc1ccc(-c2cn(CC3CCOCC3)cc(C(=O)O)c2=O)cc1] | 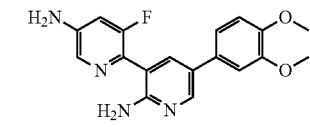 [SMILES: COc1ccc(-c2cnc(N)c(-c3ncc(N)cc3F)c2)cc1OC] |
| Example 64 | 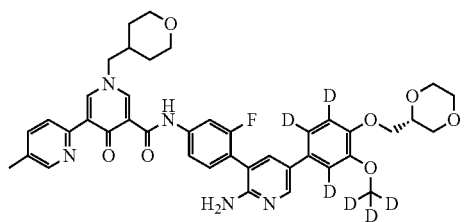 [SMILES: [2H]c1c([2H])c(-c2cnc(N)c(-c3ccc(NC(=O)c4cn(CC5CCOCC5)cc(-c5ccc(C)cn5)c4=O)cc3F)c2)c([2H])c(OC([2H])([2H])[2H])c1OC[C@H]1COCCO1]<br>¹H-NMR (CDCl₃) δ: 13.02 (1H, s), 8.56 (1H, d, J = 2.0 Hz), 8.49-8.45 (2H, m), 8.41 (1H, d, J = 3.0 Hz), 8.31 (1H, d, J = 2.0 Hz), 7.93 (1H, dd, J = 12.0, 2.0 Hz), 7.63 (1H, dd, J = 8.0, 2.0 Hz), 7.59 (1H, d, J = 2.0 Hz), 7.50 (1H, dd, J = 8.0, 2.0 Hz), 7.38 (1H, t, J = 8.0 Hz), 4.56 (1H, br s), 4.11-3.34 (15H, m), 2.40 (3H, s), 2.22-2.10 (1H, m), 1.61 (2H, d, J = 12.0 Hz), 1.52-1.40 (2H, m).<br>MS (APCI) m/z: 742 [(M + H)⁺]. | 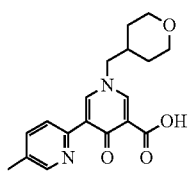 [SMILES: Cc1ccc(-c2cn(CC3CCOCC3)cc(C(=O)O)c2=O)nc1] | 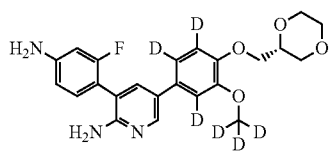 [SMILES: [2H]c1c([2H])c(-c2cnc(N)c(-c3ccc(N)cc3F)c2)c([2H])c(OC([2H])([2H])[2H])c1OC[C@H]1COCCO1] |
| Example 65 | 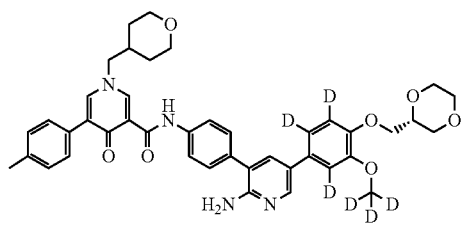 [SMILES: [2H]c1c([2H])c(-c2cnc(N)c(-c3ccc(NC(=O)c4cn(CC5CCOCC5)cc(-c5ccc(C)cc5)c4=O)cc3)c2)c([2H])c(OC([2H])([2H])[2H])c1OC[C@H]1COCCO1]<br>¹H-NMR (CDCl₃) δ: 12.85 (1H, s), 8.57 (1H, d, J = 2.4 Hz), 8.26 (1H, d, J = 2.4 Hz), 7.87 (2H, d, J = 8.5 Hz), 7.56 (1H, d, J = 2.4 Hz), 7.50-7.45 (5H, m), 7.29 (2H, d, J = 8.5 Hz), 4.62 (2H, br s), 4.15-3.33 (15H, m), 2.41 (3H, s), 2.17-2.06 | 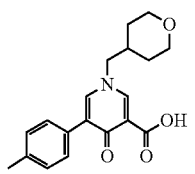 [SMILES: Cc1ccc(-c2cn(CC3CCOCC3)cc(C(=O)O)c2=O)cc1] | 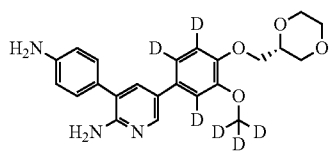 [SMILES: [2H]c1c([2H])c(-c2cnc(N)c(-c3ccc(N)cc3)c2)c([2H])c(OC([2H])([2H])[2H])c1OC[C@H]1COCCO1] |

TABLE 13-continued

| Example No. | Structural formula for Example Instrumental data on Example | Structural formula of starting material A | Structural formula of starting material B |
|---|---|---|---|
| | (1H, m), 1.46 (2H, td, J = 12.4, 4.3 Hz). MS (APCI) m/z: 723 [(M + H)+]. | | |
| Example 66 | ¹H-NMR (CDCl₃) δ: 12.83 (1H, s), 8.50 (1H, d, J = 2.4 Hz), 8.27 (1H, d, J = 2.4 Hz), 7.87 (2H, d, J = 8.5 Hz), 7.57 (1H, d, J = 2.4 Hz), 7.49-7.44 (5H, m), 7.29 (2H, d, J = 8.5 Hz), 7.09 (1H, dd, J = 8.5, 2.4 Hz), 7.04 (1H, d, J = 2.4 Hz), 6.94 (1H, d, J = 8.5 Hz), 4.63-4.61 (2H, m), 3.96-3.94 (5H, m), 3.92 (3H, s), 3.83-3.78 (2H, m), 3.72-3.66 (2H, m), 3.39 (3H, s), 2.41 (3H, s), 1.73-1.59 (4H, m). MS (APCI) m/z: 661 [(M + H)+]. | | |
| Example 67 | ¹H-NMR (CDCl₃) δ: 12.83 (1H, s), 8.50 (1H, d, J = 2.4 Hz), 8.26 (1H, d, J = 2.4 Hz), 7.86 (2H, d, J = 8.5 Hz), 7.56 (1H, d, J = 2.4 Hz), 7.49-7.44 (5H, m), 7.29 (2H, d, J = 7.9 Hz), 7.07-7.03 (2H, m), 6.96 (1H, d, J = 7.9 Hz), 4.64-4.61 (2H, m), 4.10-4.03 (2H, m), 4.01-3.94 (4H, m), 3.91-3.64 (11H, m), 3.58-3.52 (1H, m), 3.39 (3H, s), 2.41 (3H, s), 1.73-1.59 (4H, m). LC-MS (APCI): 747 (M + H)+. | | |

Example 68

N-{4-[2-Amino-5-(3,4-dimethoxyphenyl)pyridin-3-yl]-3-fluorophenyl}-5-(4-methylphenyl)-4-oxo-1-(tetrahydro-2H-pyran-4-ylmethyl)-1,4-dihydropyridine-3-carboxamide methanesulfonate

[Formula 68]

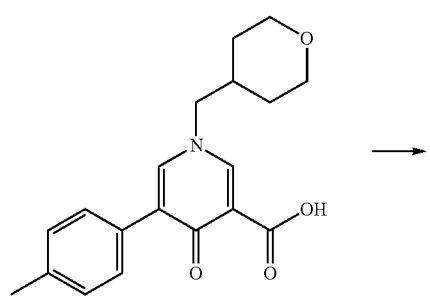

→

-continued

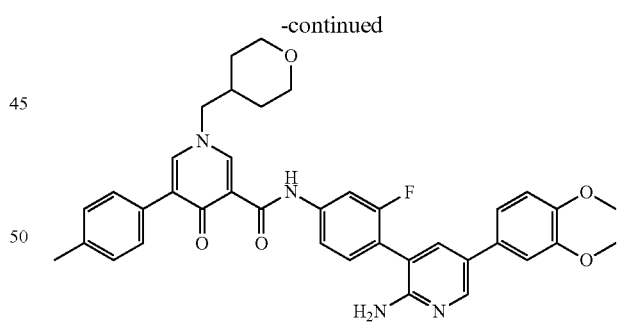

5-(4-Methylphenyl)-4-oxo-1-(tetrahydro-2H-pyran-4-ylmethyl)-1,4-dihydropyridine-3-carboxylic acid (0.127 g, 0.389 mmol) was dissolved in N-methyl-2-pyrrolidone (3.00 ml). To the solution, thionyl chloride (0.0277 ml, 0.382 mmol) was added, and the mixture was stirred at room temperature for 30 minutes. Then, 3-(4-amino-2-fluorophenyl)-5-(3,4-dimethoxyphenyl)pyridin-2-amine (0.121 g, 0.354 mmol) was added thereto under ice cooling, and the mixture was stirred at room temperature for 5 hours. The reaction mixture was ice-cooled again and neutralized with saturated sodium bicarbonate, followed by extraction with ethyl acetate. The organic layer was washed with brine and then dried over anhydrous magnesium sulfate, and the solvent was distilled off under reduced pressure. The residue was purified by silica gel column chromatography (Biotage Japan Ltd., elution solvent: dichloromethane/methanol=99/1→96/4) to obtain the title compound (0.106 g, yield: 46.2%) as a foam.

$^1$H-NMR (CDCl$_3$) δ: 12.98 (1H, s), 8.56 (1H, d, J=2.4 Hz), 8.31 (1H, d, J=2.4 Hz), 7.92 (1H, dd, J=12.1, 1.8 Hz), 7.59 (1H, d, J=2.4 Hz), 7.49-7.43 (4H, m), 7.36 (1H, t, J=8.2 Hz), 7.29 (2H, d, J=7.9 Hz), 7.08 (1H, dd, J=8.2, 2.1 Hz), 7.03 (1H, d, J=1.8 Hz), 6.93 (1H, d, J=7.9 Hz), 4.57-4.52 (2H, m), 4.07-4.00 (2H, m), 3.94 (3H, s), 3.92 (3H, s), 3.88 (2H, d, J=7.3 Hz), 3.44-3.35 (2H, m), 2.41 (3H, s), 2.19-2.04 (1H, m), 1.65-1.57 (2H, m), 1.51-1.38 (2H, m).

MS (ESI) m/z: 649 [(M+H)$^+$]

Similarly, the final compounds of Table 14 were synthesized from the corresponding starting materials.

TABLE 14

| Example No. | Structural formula for Example Instrumental data on Example | Structural formula of starting material |
|---|---|---|
| Example 69 | <chemical structure> $^1$H-NMR (DMSO-D$_6$) δ: 13.15 (1H, s), 8.77 (1H, d, J = 2.4 Hz), 8.30 (2H, t, J = 2.4 Hz), 7.91 (1H, d, J = 11.6 Hz), 7.81 (2H, d, J = 8.5 Hz), 7.61 (1H, d, J = 2.4 Hz), 7.48-7.40 (4H, m), 7.17-7.12 (2H, m), 6.98 (1H, d, J = 8.5 Hz), 5.68 (2H, s), 4.12 (2H, d, J = 6.7 Hz), 3.89-3.82 (5H, m), 3.76 (3H, s), 3.27 (2H, t, J = 11.3 Hz), 2.17-2.07 (1H, m), 1.47 (2H, br d, J = 11.6 Hz), 1.37-1.26 (2H, m). MS (APCI) m/z: 719 [(M + H)$^+$]. | <chemical structure> |
| Example 70 | <chemical structure> $^1$H-NMR (DMSO-D$_6$) δ: 12.99 (1H, s), 8.79 (1H, d, J = 2.4 Hz), 8.29 (1H, d, J = 2.4 Hz), 8.23 (1H, d, J = 2.4 Hz), 7.91-7.87 (1H, m), 7.67 (1H, dd, J = 9.8, 1.8 Hz), 7.61 (1H, d, J = 2.4 Hz), 7.53 (1H, dd, J = 8.5, 1.8 Hz), 7.48-7.39 (3H, m), 7.17-7.11 (2H, m), 6.98 (1H, d, J = 8.5 Hz), 5.67 (2H, s), 4.10 (2H, d, J = 7.3 Hz), 3.89-3.82 (2H, m), 3.82 (3H, s), 3.76 (3H, s), 3.27 (2H, t, J = 12.2 Hz), 2.13-2.04 (1H, m), 1.47 (2H, br d, J = 11.0 Hz), 1.35-1.25 (2H, m). MS (APCI) m/z: 732 [(M + H)$^+$]. | <chemical structure> |

(Example 71) N-[4-(2-Amino-5-{4-[(4-methylpiperazin-1-yl)methyl] phenyl}pyridin-3-yl)phenyl]-5-(4-methylphenyl)-4-oxo 1-(tetrahydro-2H-pyran-4-ylmethyl)-1,4-dihydropyridine-3-carboxamide methanesulfonate
[Formula 69]
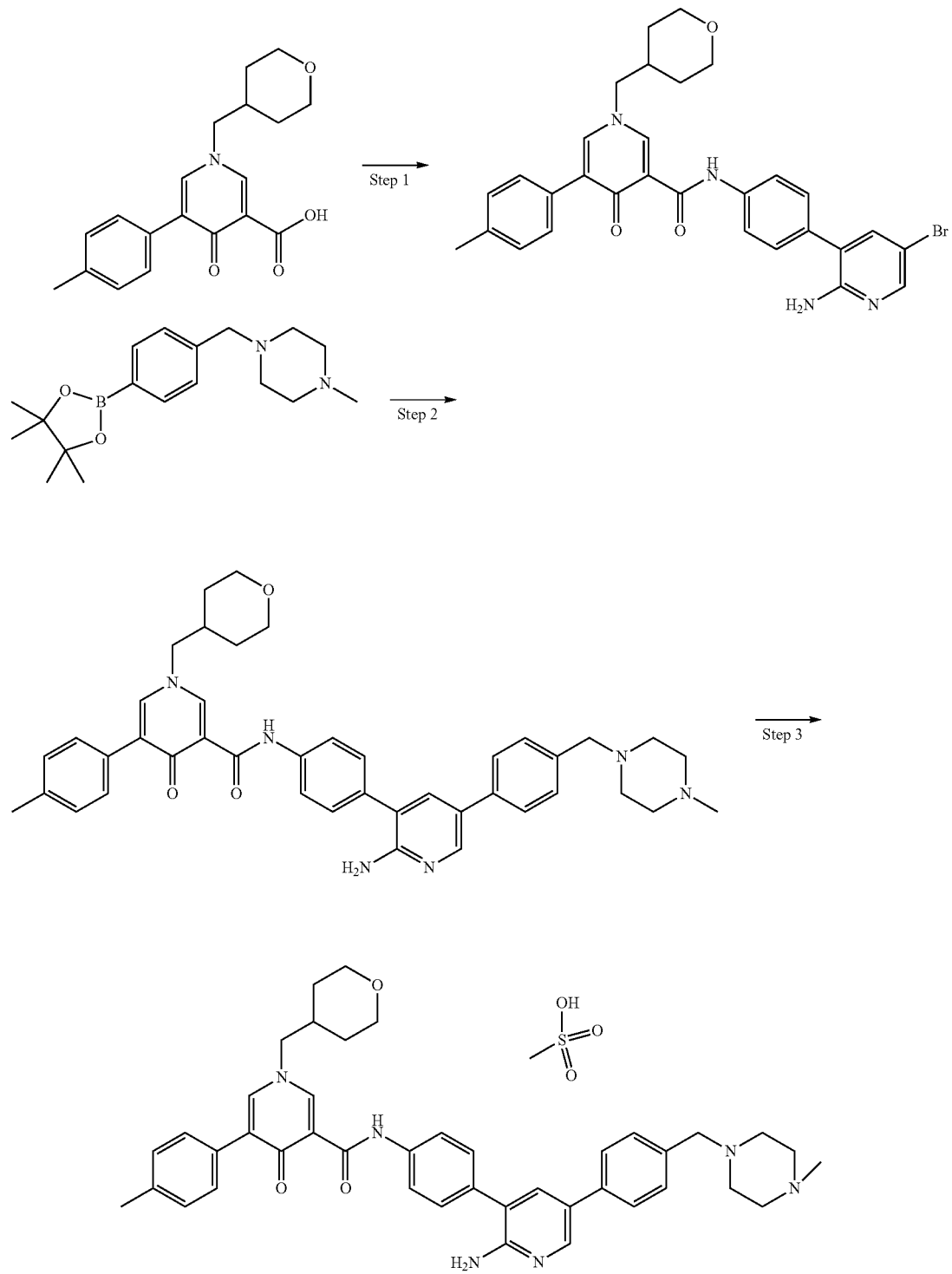

159

(Step 2) N-[4-(2-Amino-5-{4-[(4-methylpiperazin-1-yl)methyl]phenyl}pyridin-3-yl)phenyl]-5-(4-methylphenyl)-4-oxo-1-(tetrahydro-2H-pyran-4-ylmethyl)-1,4-dihydropyridine-3-carboxamide The title compound was obtained in the same way as in intermediate 8 by using N-[4-(2-amino-5-bromopyridin-3-yl)phenyl]-5-(4-methylphenyl)-4-oxo-1-(tetrahydro-2H-pyran-4-ylmethyl)-1,4-dihydropyridine-3-carboxamide and 1-methyl-4-[[4-(4,4,5,5-tetramethyl-1,3,2-dioxaborolan-2-yl)phenyl]methyl]piperazine as starting materials, 1,4-dioxane and water as a solvent, tetrakis(triphenylphosphine)palladium(0) as a catalyst, and potassium carbonate as a base and carrying out heating with stirring at a reaction temperature of 100° C. for 2 hours.

$^1$H-NMR (CDCl$_3$) δ: 12.87-12.85 (1H, m), 8.57 (1H, d, J=2.4 Hz), 8.31 (1H, d, J=2.4 Hz), 7.87 (2H, d, J=7.9 Hz), 7.61 (1H, d, J=2.4 Hz), 7.52-7.45 (7H, m), 7.37 (2H, d, J=7.9 Hz), 7.29 (2H, d, J=7.9 Hz), 4.69-4.64 (2H, m), 4.06-4.00 (2H, m), 3.87 (2H, d, J=7.3 Hz), 3.54 (2H, s), 3.43-3.35 (2H, m), 2.63-2.34 (8H, m), 2.41 (3H, s), 2.29 (3H, s), 2.15-2.07 (1H, m), 1.64-1.57 (2H, m), 1.50-1.38 (2H, m).

MS (ES+APCI) m/z: 683 [(M+H)$^+$].

160

(Step 3) N-[4-(2-Amino-5-{4-[(4-methylpiperazin-1-yl)methyl]phenyl}pyridin-3-yl)phenyl]-5-(4-methylphenyl)-4-oxo-1-(tetrahydro-2H-pyran-4-ylmethyl)-1,4-dihydropyridine-3-carboxamide methanesulfonate N-[4-(2-Amino-5-{4-[(4-methylpiperazin-1-yl)methyl]phenyl}pyridin-3-yl)phenyl]-5-(4-methylphenyl)-4-oxo-1-(tetrahydro-2H-pyran-4-ylmethyl)-1,4-dihydropyridine-3-carboxamide (34.0 mg, 49.8 µmol) was dissolved in chloroform (3.00 mL). To the solution, a 1 mol/L solution of methanesulfonic acid in ethanol (49.8 µL, 49.8 µmol) was added at room temperature, and then, the solvent was distilled off under reduced pressure. To the residue obtained, diisopropyl ether was added, and the deposited solid was collected by filtration to obtain the title compound (25.7 mg, yield: 66.3%).

$^1$H-NMR (CDCl$_3$) δ: 12.92-12.90 (1H, m), 8.57 (1H, d, J=2.4 Hz), 8.20 (1H, d, J=2.4 Hz), 7.91-7.87 (2H, m), 7.69 (1H, d, J=2.4 Hz), 7.52-7.44 (7H, m), 7.39-7.35 (2H, m), 7.31-7.27 (2H, m), 4.07-4.00 (2H, m), 3.88 (2H, d, J=7.3 Hz), 3.69-3.63 (2H, m), 3.44-3.35 (2H, m), 3.08-2.61 (8H, m), 2.86 (3H, s), 2.41 (3H, s), 2.18 (3H, s), 2.16-2.06 (1H, m), 1.65-1.58 (2H, m), 1.51-1.39 (2H, m).

MS (ES+APCI) m/z: 683 [(M+H)$^+$].

Similarly, the final compounds of Table 15 were synthesized from the corresponding starting materials.

TABLE 15

| Example No. | Structural formula for Example Instrumental data on Example | Structural formula of starting material |
|---|---|---|
| Example 72 | 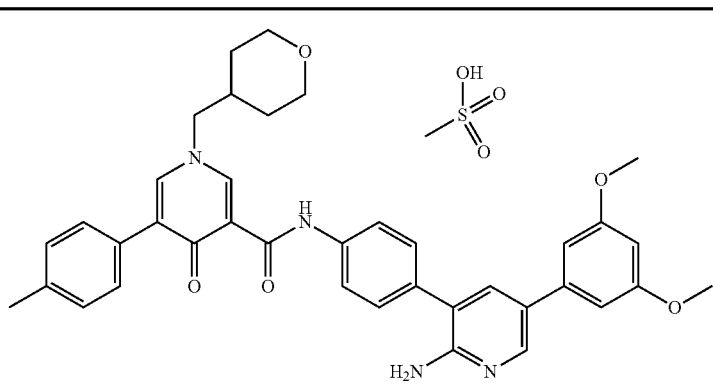 $^1$H-NMR (CDCl$_3$) δ: 13.04-13.01 (1H, m), 8.56 (1H, d, J = 2.4 Hz), 7.97-7.93 (3H, m), 7.90-7.89 (1H, m), 7.50-7.40 (5H, m), 7.31-7.27 (2H, m), 6.58 (2H, d, J = 2.4 Hz), 6.51-6.49 (1H, m), 4.07-4.00 (2H, m), 3.89 (2H, d, J = 7.3 Hz), 3.83 (6H, s), 3.43-3.35 (2H, m), 2.92 (3H, s), 2.41 (3H, s), 2.17-2.06 (1H, m), 1.65-1.58 (2H, m), 1.51-1.39 (2H, m). MS (ES + APCI) m/z: 631 [(M + H)$^+$]. | 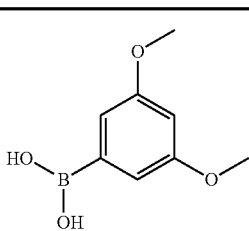 |

TABLE 15-continued
| Example No. | Structural formula for Example Instrumental data on Example | Structural formula of starting material |
|---|---|---|
| Example 73 | 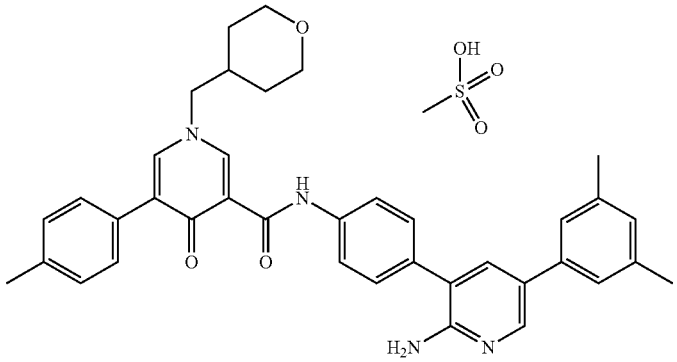 ¹H-NMR (CDCl₃) δ: 13.02-13.00 (1H, m), 8.56 (1H, d, J = 2.4 Hz), 7.96-7.90 (4H, m), 7.50-7.40 (5H, m), 7.31-7.27 (2H, m), 7.10-7.08 (2H, m), 7.06-7.04 (1H, m), 4.07-4.00 (2H, m), 3.89 (2H, d, J = 7.3 Hz), 3.43-3.35 (2H, m), 2.92 (3H, s), 2.41 (3H, s), 2.37 (6H, s), 2.16-2.06 (1H, m), 1.65-1.57 (2H, m), 1.51-1.39 (2H, m). MS (ES + APCI) m/z: 599 [(M + H)⁺]. | 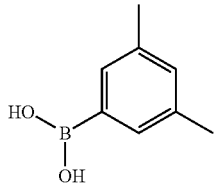 |
| Example 74 | 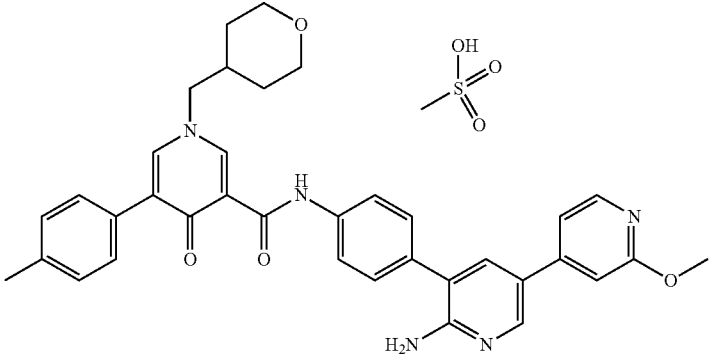 ¹H-NMR (CDCl₃) δ: 13.07-13.04 (1H, m), 8.58-8.54 (1H, m), 8.26 (1H, d, J = 5.5 Hz), 8.01-7.90 (4H, m), 7.52-7.34 (5H, m), 7.31-7.27 (2H, m), 7.01-6.96 (1H, m), 6.87-6.82 (1H, m), 4.06-4.00 (2H, m), 3.98 (3H, s), 3.93-3.88 (2H, m), 3.44-3.34 (2H, m), 2.92 (3H, s), 2.41 (3H, s), 2.18-2.05 (1H, m), 1.68-1.56 (2H, m), 1.51-1.41 (2H, m) MS (ES + APCI) m/z: 602 [(M + H)⁺]. | 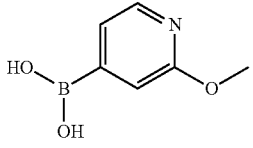 |

TABLE 15-continued

| Example No. | Structural formula for Example Instrumental data on Example | Structural formula of starting material |
|---|---|---|
| Example 75 | 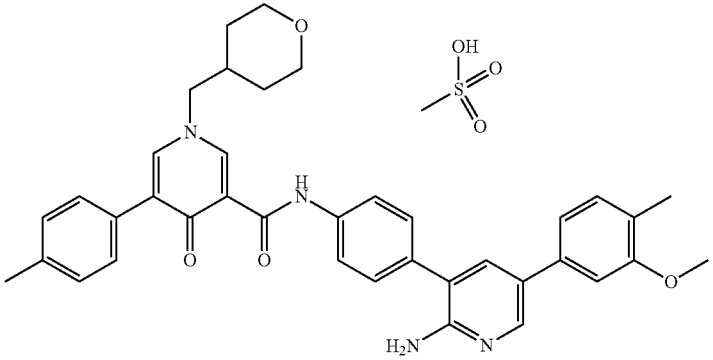<br>¹H-NMR (CDCl₃) δ: 13.01-12.94 (1H, m), 8.69-8.61 (1H, m), 7.99-7.89 (4H, m), 7.54-7.51 (1H, m), 7.49-7.40 (4H, m), 7.32-7.28 (2H, m), 7.22 (1H, d, J = 7.9 Hz), 6.97 (1H, dd, J = 7.9, 2.4 Hz), 6.86 (1H, d, J = 2.4 Hz), 4.07-4.00 (2H, m), 3.94 (2H, d, J = 6.7 Hz), 3.89 (3H, s), 3.44-3.35 (2H, m), 2.93 (3H, s), 2.42 (3H, s), 2.25 (3H, s), 2.20-2.07 (1H, m), 1.73-1.56 (2H, m), 1.52-1.39 (2H, m).<br>MS (ES + APCI) m/z: 615 [(M + H)⁺]. | 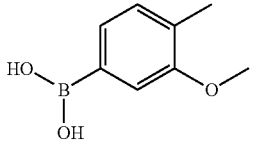 |
| Example 76 | 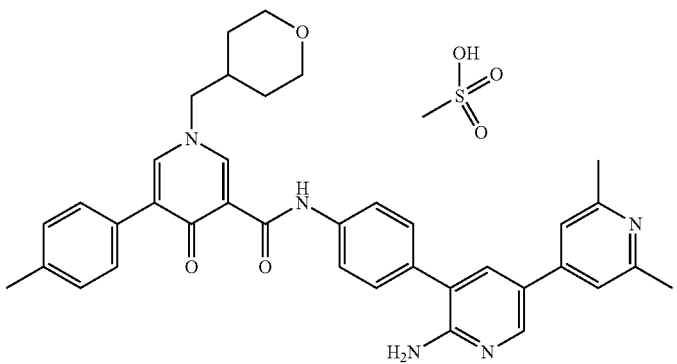<br>¹H-NMR (DMSO-D₆) δ: 13.17-13.15 (1H, m), 8.74-8.71 (2H, m), 8.18 (1H, d, J = 2.4 Hz), 8.16-8.14 (2H, m), 8.08-8.05 (1H, m), 7.86 (2H, d, J = 7.9 Hz), 7.58 (2H, d, J = 7.9 Hz), 7.53 (2H, d, J = 7.9 Hz), 7.27 (2H, d, J = 7.9 Hz), 7.01-6.79 (2H, m), 4.11 (2H, d, J = 6.1 Hz), 3.90-3.84 (2H, m), 3.31-3.23 (2H, m), 2.65 (6H, s), 2.36 (3H, s), 2.30 (3H, s), 2.16-2.05 (1H, m), 1.49-1.42 (2H, m), 1.37-1.25 (2H, m).<br>MS (ES + APCI) m/z: 600 [(M + H)⁺]. | 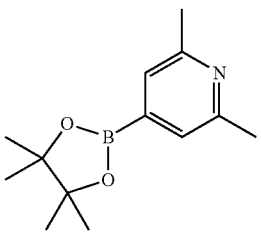 |

| Example No. | Structural formula for Example Instrumental data on Example | Structural formula of starting material |
|---|---|---|
| Example 77 | 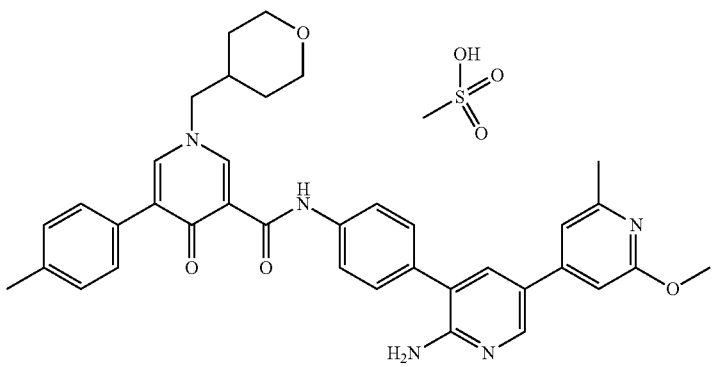<br>¹H-NMR (CDCl₃) δ: 13.07-13.03 (1H, m), 8.58-8.54 (1H, m), 8.00-7.89 (4H, m), 7.52-7.37 (5H, m), 7.32-7.26 (2H, m), 6.85-6.82 (1H, m), 6.65-6.62 (1H, m), 4.07-3.99 (2H, m), 3.96 (3H, s), 3.92-3.88 (2H, m), 3.44-3.34 (2H, m), 2.93 (3H, s), 2.51 (3H, s), 2.41 (3H, s), 2.17-2.05 (1H, m), 1.69-1.56 (2H, m), 1.52-1.38 (2H, m).<br>MS (ES + APCI) m/z: 616 [(M + H)⁺]. | 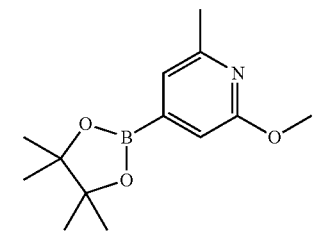 |
| Example 78 | 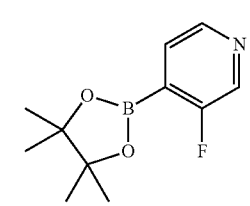<br>¹H-NMR (DMSO-D₆) δ: 13.23-13.21 (1H, m), 8.73-8.70 (2H, m), 8.53 (1H, d, J = 4.9 Hz), 8.39-8.37 (1H, m), 8.19 (1H, d, J = 2.4 Hz), 8.12-8.10 (1H, m), 7.90 (2H, d, J = 7.9 Hz), 7.84 (1H, dd, J = 7.9, 4.9 Hz), 7.83-7.71 (2H, m), 7.60-7.54 (4H, m), 7.27 (2H, d, J = 7.9 Hz), 4.11 (2H, d, J = 7.3 Hz), 3.90-3.84 (2H, m), 3.31-3.23 (2H, m), 2.36 (3H, s), 2.32 (3H, s), 2.16-2.05 (1H, m), 1.50-1.42 (2H, m), 1.38-1.25 (2H, m).<br>MS (ES + APCI) m/z: 590 [(M + H)⁺]. | |

TABLE 15-continued

| Example No. | Structural formula for Example Instrumental data on Example | Structural formula of starting material |
|---|---|---|
| Example 79 | 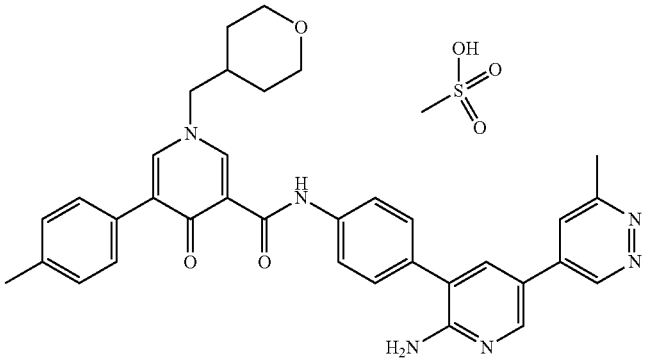 <br> ¹H-NMR (DMSO-D₆) δ: 13.21-13.18 (1H, m), 9.70-9.67 (1H, m), 8.74-8.71 (2H, m), 8.34-8.30 (1H, m), 8.27-8.22 (1H, m), 8.18 (1H, d, J = 2.4 Hz), 7.88 (2H, d, J = 7.9 Hz), 7.60-7.54 (4H, m), 7.47-7.32 (2H, m), 7.27 (2H, d, J = 7.9 Hz), 4.12 (2H, d, J = 7.3 Hz), 3.90-3.84 (2H, m), 3.31-3.23 (2H, m), 2.69 (3H, s), 2.36 (3H, s), 2.31 (3H, s), 2.17-2.05 (1H, m), 1.49-1.42 (2H, m), 1.38-1.25 (2H, m). <br> MS (ES + APCI) m/z: 587 [(M + H)⁺]. | 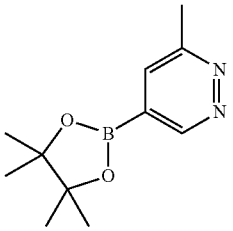 [SMILES: Cc1cc(B2OC(C)(C)C(C)(C)O2)cnn1] |
| Example 80 | 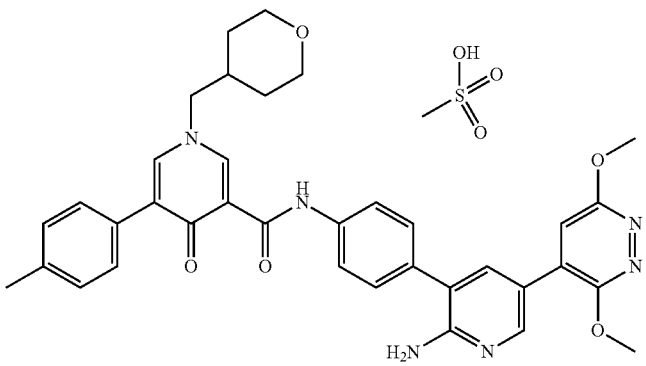 <br> ¹H-NMR (DMSO-D₆) δ: 13.22-13.19 (1H, m), 8.72 (1H, d, J = 2.4 Hz), 8.39 (1H, d, J = 2.4 Hz), 8.18 (1H, d, J = 2.4 Hz), 8.11-8.10 (1H, m), 7.90-7.86 (2H, m), 7.76-7.61 (2H, m), 7.60-7.51 (5H, m), 7.26 (2H, d, J = 7.9 Hz), 4.11 (2H, d, J = 7.3 Hz), 4.02 (3H, s), 3.98 (3H, s), 3.90-3.84 (2H, m), 3.31-3.23 (2H, m), 2.36 (3H, s), 2.32 (3H, s), 2.15-2.06 (1H, m), 1.49-1.42 (2H, m), 1.37-1.25 (2H, m). <br> MS (ES + APCI) m/z: 633 [(M + H)⁺]. | 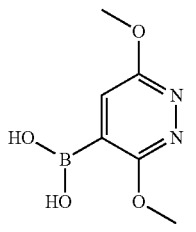 |

TABLE 15-continued

| Example No. | Structural formula for Example Instrumental data on Example | Structural formula of starting material |
|---|---|---|
| Example 81 | [Structure: 1-(tetrahydropyran-4-ylmethyl)-5-(4-methylphenyl)-4-oxo-1,4-dihydropyridine-3-carboxamide linked to N-phenyl-(2-amino-5-(4-ethoxy-3-methoxyphenyl)pyridin-3-yl), methanesulfonic acid salt]<br><br>¹H-NMR (DMSO-D₆) δ: 13.23-13.21 (1H, m), 8.72 (1H, d, J = 2.4 Hz), 8.27 (1H, d, J = 2.4 Hz), 8.21-8.18 (2H, m), 7.90 (2H, d, J = 7.9 Hz), 7.60-7.55 (4H, m), 7.54-7.45 (2H, m), 7.30 (1H, d, J = 2.4 Hz), 7.29-7.24 (3H, m), 7.03 (1H, d, J = 7.9 Hz), 4.11 (2H, d, J = 7.3 Hz), 4.05 (2H, q, J = 7.3 Hz), 3.90-3.83 (2H, m), 3.84 (3H, s), 3.31-3.22 (2H, m), 2.36 (3H, s), 2.31 (3H, s), 2.16-2.04 (1H, m), 1.49-1.42 (2H, m), 1.37-1.26 (2H, m), 1.34 (3H, t, J = 7.3 Hz).<br>MS (ES + APCI) m/z: 645 [(M + H)⁺]. | [Structure: 4-ethoxy-3-methoxyphenyl pinacol boronate] |
| Example 82 | [Structure: 1-(tetrahydropyran-4-ylmethyl)-5-(4-methylphenyl)-4-oxo-1,4-dihydropyridine-3-carboxamide linked to N-phenyl-(2-amino-5-(3-ethoxy-4-methoxyphenyl)pyridin-3-yl), methanesulfonic acid salt]<br><br>¹H-NMR (DMSO-D₆) δ: 13.23-13.21 (1H, m), 8.72 (1H, d, J = 2.4 Hz), 8.26 (1H, d, J = 2.4 Hz), 8.20-8.16 (2H, m), 7.89 (2H, d, J = 7.9 Hz), 7.60-7.55 (4H, m), 7.49-7.37 (2H, m), 7.30-7.25 (4H, m), 7.04 (1H, d, J = 7.9 Hz), 4.14-4.07 (4H, m), 3.90-3.83 (2H, m), 3.80 (3H, s), 3.32-3.23 (2H, m), 2.36 (3H, s), 2.32 (3H, s), 2.16-2.05 (1H, m), 1.49-1.42 (2H, m), 1.37-1.25 (2H, m), 1.34 (3H, t, J = 7.3 Hz).<br>MS (ES + APCI) m/z: 645 [(M + H)⁺]. | [Structure: 3-ethoxy-4-methoxyphenyl pinacol boronate] |

(Example 83) N-(4-{2-Amino-5-[3-fluoro-4-(morpholin-4-ylmethyl)phenyl]pyridin-3-yl}phenyl)-5-(4-methylphenyl)-4-oxo-1-(tetrahydro-2H-pyran-4-ylmethyl)-1,4-dihydropyridine-3-carboxamide methanesulfonate

[Formula 70]

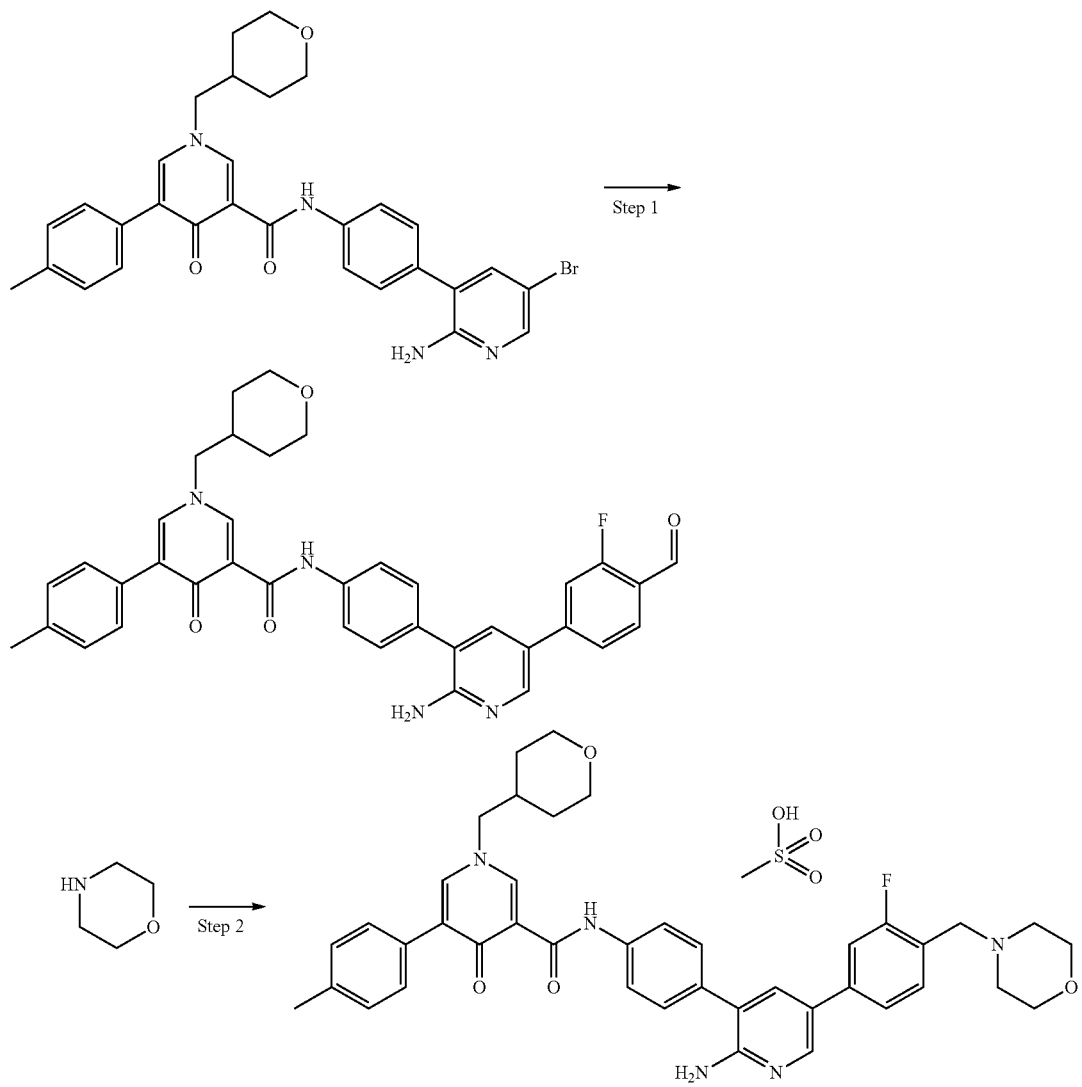

(Step 1) N-{4-[2-Amino-5-(3-fluoro-4-formylphenyl)pyridin-3-yl]phenyl}-5-(4-methylphenyl)-4-oxo-1-(tetrahydro-2H-pyran-4-ylmethyl)-1,4-dihydropyridine-3-carboxamide The title compound was obtained in the same way as in intermediate 8 by using N-[4-(2-amino-5-bromopyridin-3-yl)phenyl]-5-(4-methylphenyl)-4-oxo-1-(tetrahydro-2H-pyran-4-ylmethyl)-1,4-dihydropyridine-3-carboxamide and 3-fluoro-4-formylphenylboric acid, 1,4-dioxane and water (ratio: 10:1) as a solvent, tetrakis(triphenylphosphine)palladium(0) as a catalyst, and potassium carbonate as a base and carrying out heating with stirring at a reaction temperature of 100° C. for 7 hours.

$^1$H-NMR (CDCl$_3$) δ: 12.89 (1H, s), 10.37-10.35 (1H, m), 8.58-8.57 (1H, m), 8.37 (1H, d, J=2.4 Hz), 7.94-7.87 (3H, m), 7.64 (1H, d, J=2.4 Hz), 7.49-7.45 (6H, m), 7.36 (1H, dd, J=12.1, 1.8 Hz), 7.31-7.28 (2H, m), 4.86-4.81 (2H, m), 4.07-4.01 (2H, m), 3.88 (2H, d, J=7.3 Hz), 3.43-3.35 (2H, m), 2.41 (3H, s), 2.17-2.07 (1H, m), 1.64-1.53 (2H, m), 1.51-1.39 (2H, m).

MS (ES+APCI) m/z: 617 [(M+H)$^+$].

(Step 2) N-(4-{2-Amino-5-[3-fluoro-4-(morpholin-4-ylmethyl)phenyl]pyridin-3-yl}phenyl)-5-(4-methylphenyl)-4-oxo-1-(tetrahydro-2H-pyran-4-ylmethyl)-1,4-dihydropyridine-3-carboxamide methanesulfonate N-{4-[2-Amino-5-(3-fluoro-4-formylphenyl)pyridin-3-yl]phenyl}-5-(4-methylphenyl)-4-oxo-1-(tetrahydro-2H-pyran-4-ylmethyl)-1,4-dihydropyridine-3-carboxamide (70.0 mg, 0.114 mmol) was suspended in dichloroethane (2.27 ml). To the suspension, morpholine (19.8 μl, 0.227 mmol) was added, and the mixture was stirred at room temperature for 5 minutes. To the reaction mixture, sodium triacetoxyborohydride (48.1 mg, 0.227 mmol) was added, and the mixture was stirred at room temperature for 3 hours. To the reaction mixture, water and sodium bicarbonate were added, followed by extraction with chloroform. The extracts were dried over anhydrous sodium sulfate. The solvent was distilled off under reduced pressure, and the residue obtained was purified by silica gel column chromatography (Biotage Japan Ltd., dichloromethane/ethanol=100/1→50/1) to obtain a solid. This solid was dissolved in chloroform (8.00 ml). To the solution, a 1 M solution of methanesulfonic acid in ethanol (91.2 μl, 91.2 μmol) was added, and the mixture was concentrated under reduced pressure. To the residue, diethyl ether was added, and the deposited solid was collected by filtration to obtain the title compound (30.5 mg, 34.7%) as a solid.

$^1$H-NMR (DMSO-D$_6$) δ: 13.21-13.18 (1H, m), 10.01-9.83 (1H, m), 8.72 (1H, d, J=2.4 Hz), 8.42 (1H, d, J=2.4 Hz), 8.19 (1H, d, J=2.4 Hz), 8.10-8.03 (1H, m), 7.91-7.81 (3H, m), 7.78-7.73 (1H, m), 7.69-7.63 (1H, m), 7.61-7.55 (4H, m), 7.27 (2H, d, J=7.9 Hz), 4.49-4.36 (2H, m), 4.12 (2H, d, J=7.3 Hz), 4.03-3.92 (2H, m), 3.90-3.84 (2H, m), 3.72-3.59 (2H, m), 3.47-3.10 (8H, m), 2.36 (3H, s), 2.32 (3H, s), 2.17-2.05 (1H, m), 1.50-1.42 (2H, m), 1.38-1.25 (2H, m).

MS (ES+APCI) m/z: 688 [(M+H)$^+$].

Similarly, the final compound of Table 16 was synthesized from the corresponding starting material.

(Example 85) N-(4-{2-Amino-5-[1-(tetrahydro-2H-pyran-4-yl)-1H-pyrazol-4-yl]pyridin-3-yl}-3-fluorophenyl)-5-(4-methylphenyl)-4-oxo-1-(tetrahydro-2H-pyran-4-ylmethyl)-1,4-dihydropyridine-3-carboxamide methanesulfonate

[Formula 71]

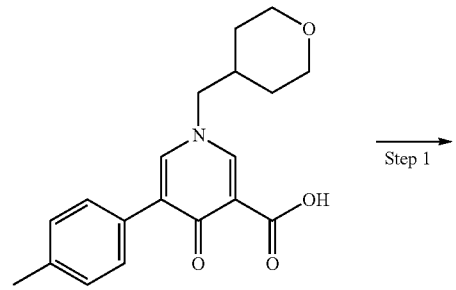

Step 1

TABLE 16

| Example No. | Structural formula for Example Instrumental data on Example | Structural formula of starting material |
|---|---|---|
| Example 84 | (structure shown) $^1$H-NMR (DMSO-D$_6$) δ: 13.16-13.13 (1H, m), 9.32-9.23 (1H, m), 8.72 (1H, d, J = 2.4 Hz), 8.35 (1H, d, J = 2.4 Hz), 8.18 (1H, d, J = 2.4 Hz), 7.88-7.79 (3H, m), 7.63-7.52 (6H, m), 7.47-7.41 (1H, m), 7.27 (2H, d, J = 7.9 Hz), 6.50-6.12 (2H, m), 4.11 (2H, d, J = 7.3 Hz), 3.90-3.83 (2H, m), 3.64 (2H, s), 3.44-3.22 (6H, m), 3.08-2.91 (4H, m), 2.78 (3H, s), 2.36 (3H, s), 2.30 (3H, s), 2.16-2.05 (1H, m), 1.50-1.42 (2H, m), 1.37-1.25 (2H, m). MS (ES + APCI) m/z: 701 [(M + H)$^+$]. | (structure shown) |

(Step 1) N-[4-(2-Amino-5-bromopyridin-3-yl)-3-fluorophenyl]-5-(4-methylphenyl)-4-oxo-1-(tetrahydro-2H-pyran-4-ylmethyl)-1,4-dihydropyridine-3-carboxamide The title compound was obtained in the same way as in Example 1 by using 3-(4-amino-2-fluorophenyl)-5-bromopyridin-2-amine synthesized by the method described in the patent (WO2013/115280 A1) as a starting material.

$^1$H-NMR (CDCl$_3$) δ: 13.01-12.98 (1H, m), 8.55 (1H, d, J=2.4 Hz), 8.13 (1H, d, J=2.4 Hz), 7.91 (1H, dd, J=12.1, 2.4 Hz), 7.51-7.41 (5H, m), 7.32-7.25 (3H, m), 4.54-4.50 (2H, m), 4.07-4.01 (2H, m), 3.88 (2H, d, J=7.3 Hz), 3.43-3.35 (2H, m), 2.41 (3H, s), 2.16-2.05 (1H, m), 1.64-1.54 (2H, m), 1.51-1.38 (2H, m).

MS (ES+APCI) m/z: 591 [(M+H)$^+$].

(Step 2) N-(4-{2-Amino-5-[1-(tetrahydro-2H-pyran-4-yl)-1H-pyrazol-4-yl]pyridin-3-yl}-3-fluorophenyl)-5-(4-methylphenyl)-4-oxo-1-(tetrahydro-2H-pyran-4-ylmethyl)-1,4-dihydropyridine-3-carboxamide methanesulfonate

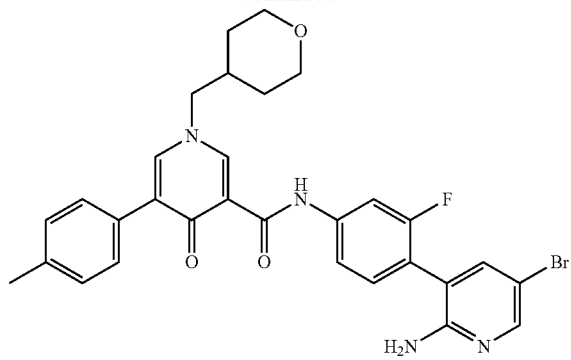

N-(4-{2-Amino-5-[1-(tetrahydro-2H-pyran-4-yl)-1H-pyrazol-4-yl]pyridin-3-yl}-3-fluorophenyl)-5-(4-methylphenyl)-4-oxo-1-(tetrahydro-2H-pyran-4-ylmethyl)-1,4-dihydropyridine-3-carboxamide was obtained in the same way as in intermediate 8 by using N-[4-(2-amino-5-bromopyridin-3-yl)-3-fluorophenyl]-5-(4-methylphenyl)-4-oxo-1-(tetrahydro-2H-pyran-4-ylmethyl)-1,4-dihydropyridine-3-carboxamide obtained in step 1 and 1-(tetrahydro-2H-pyran-4-yl)-4-(4,4,5,5-tetramethyl-1,3,2-dioxaborolan-2-yl)-1H-pyrazole as starting materials, 1,4-dioxane and water (ratio: 10:1) as a solvent, tetrakis(triphenylphosphine)palladium(0) as a catalyst, and potassium carbonate as a base and carrying out heating with stirring at reaction temperature of 100° C. for 7 hours. The title compound was obtained by the same operation as in step 3 of Example 71 by using this compound.

$^1$H-NMR (DMSO-D$_6$) δ: 13.38-13.36 (1H, m), 8.73 (1H, d, J=2.4 Hz), 8.42-8.40 (1H, m), 8.26-8.19 (3H, m), 8.03-7.98 (2H, m), 7.61-7.44 (6H, m), 7.27 (2H, d, J=7.9 Hz), 4.44-4.35 (1H, m), 4.12 (2H, d, J=6.7 Hz), 3.99-3.93 (2H, m), 3.90-3.84 (2H, m), 3.52-3.43 (2H, m), 3.31-3.23 (2H, m), 2.36 (3H, s), 2.31 (3H, s), 2.17-2.06 (1H, m), 2.05-1.98 (2H, m), 1.97-1.84 (2H, m), 1.49-1.42 (2H, m), 1.37-1.25 (2H, m).

MS (ES+APCI) m/z: 663 [(M+H)$^+$].

Similarly, the final compounds of Table 17 were synthesized from the corresponding starting materials.

TABLE 17

| Example No. | Structural formula for Examle Instrumental data on Example | Structural formula of starting material |
|---|---|---|
| Example 86 | ¹H-NMR (DMSO-D₆) δ: 13.39-13.36 (1H, m), 8.73 (1H, d, J = 2.4 Hz), 8.32-8.30 (1H, m), 8.25-8.23 (1H, m), 8.21-8.19 (2H, m), 8.03-7.96 (2H, m), 7.62-7.44 (6H, m), 7.27 (2H, d, J = 7.9 Hz), 4.17-4.09 (4H, m), 3.90-3.84 (2H, m), 3.31-3.22 (2H, m), 2.36 (3H, s), 2.31 (3H, s), 2.16-2.05 (1H, m), 1.49-1.42 (2H, m), 1.39 (3H, t, J = 7.3 Hz), 1.38-1.25 (2H, m). MS (ES + APCI) m/z: 607 [(M + H)⁺]. | |
| Example 87 | ¹H-NMR (DMSO-D₆) δ: 13.36-13.33 (1H, m), 8.73 (1H, d, J = 2.4 Hz), 8.44 (1H, d, J = 2.4 Hz), 8.19 (1H, d, J = 2.4 Hz), 8.14-8.11 (1H, m), 8.00-7.95 (1H, m), 7.62-7.54 (2H, m), 7.60-7.56 (2H, m), 7.52-7.44 (3H, m), 7.27 (2H, d, J = 7.9 Hz), 4.11 (2H, d, J = 7.3 Hz), 4.01 (3H, s), 3.98 (3H, s), 3.90-3.83 (2H, m), 3.31-3.23 (2H, m), 2.36 (3H, s), 2.31 (3H, s), 2.16-2.05 (1H, m), 1.49-1.42 (2H, m), 1.37-1.25 (2H, m). MS (ES + APCI) m/z: 651 [(M + H)⁺]. | |

(Example 88) N-[2'-Amino-5'-(3,4-dimethoxyphenyl)-2,3'-bipyridin-5-yl]-5-(4-methylphenyl)-4-oxo-1-(tetrahydro-2H-pyran-4-ylmethyl)-1,4-dihydropyridine-3-carboxamide methanesulfonate

[Formula 72]

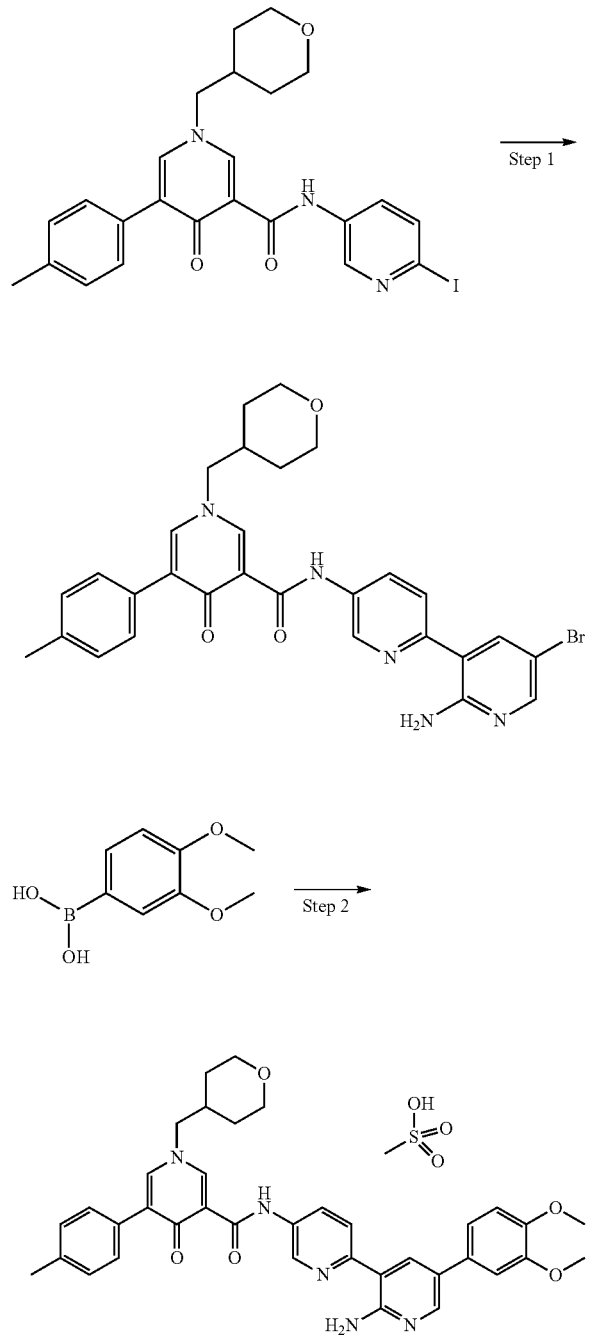

(Step 1) N-(2'-Amino-5'-bromo-2,3'-bipyridin-5-yl)-5-(4-methylphenyl)-4-oxo-1-(tetrahydro-2H-pyran-4-ylmethyl)-1,4-dihydropyridine-3-carboxamide To a solution of 5-bromo-3-(4,4,5,5-tetramethyl-1,3,2-dioxaborolan-2-yl)pyridin-2-amine (200 mg, 0.669 mmol) in dioxane (10.0 ml) and water (1.00 ml), N-(6-iodopyridin-3-yl)-5-(4-methylphenyl)-4-oxo-1-(tetrahydro-2H-pyran-4-ylmethyl)-1,4-dihydropyridine-3-carboxamide (354 mg, 0.669 mmol), potassium carbonate (277 mg, 2.01 mmol), and tetrakis(triphenylphosphine)palladium(0) (38.0 mg, 0.0344 mmol) were added, and the mixture was stirred at 90° C. for 3 hours under a nitrogen atmosphere. 5-Bromo-3-(4,4,5,5-tetramethyl-1,3,2-dioxaborolan-2-yl)pyridin-2-amine (200 mg, 0.669 mmol) was further added thereto, and the mixture was stirred at 90° C. for 5 hours. The reaction mixture was left to cool and then separated into organic and aqueous layers by the addition of water, methylene chloride, and methanol. The organic layer was dried over anhydrous sodium sulfate and then filtered, and the filtrate was concentrated. The residue was converted into slurry with ethyl acetate to obtain the title compound (352 mg, 91.6%) as a solid.

$^1$H-NMR (CDCl$_3$) δ: 13.05 (1H, s), 8.94 (1H, d, J=2.4 Hz), 8.56 (1H, d, J=2.4 Hz), 8.32 (1H, dd, J=8.5, 2.4 Hz), 8.10 (1H, d, J=1.8 Hz), 7.92 (1H, d, J=2.4 Hz), 7.68 (1H, d, J=9.2 Hz), 7.50-7.44 (3H, m), 7.29 (2H, d, J=7.9 Hz), 6.76 (2H, br s), 4.04 (2H, dd, J=11.9, 3.4 Hz), 3.89 (2H, d, J=7.3 Hz), 3.39 (2H, t, J=11.0 Hz), 2.42 (3H, s), 2.16-2.06 (1H, m), 1.65-1.57 (2H, m), 1.51-1.38 (2H, m).

MS (APCI) m/z: 574 [(M+H)$^+$].

(Step 2) N-[2'-Amino-5'-(3,4-dimethoxyphenyl)-2,3'-bipyridin-5-yl]-5-(4-methylphenyl)-4-oxo-1-(tetrahydro-2H-pyran-4-ylmethyl)-1,4-dihydropyridine-3-carboxamide methanesulfonate To a suspension of N-(2'-amino-5'-bromo-2,3'-bipyridin-5-yl)-5-(4-methylphenyl)-4-oxo-1-(tetrahydro-2H-pyran-4-ylmethyl)-1,4-dihydropyridine-3-carboxamide (130 mg, 0.226 mmol) and 3,4-dimethoxyphenylboronic acid (50 mg, 0.272 mmol) in dioxane (10 ml) and water (1 ml), potassium carbonate (94 mg, 0.679 mmol) and tetrakis(triphenylphosphine)palladium(0) (13 mg, 0.0113 mmol) were added, and the mixture was stirred at 100° C. for 2 hours under a nitrogen atmosphere. The reaction mixture was diluted with methylene chloride and then washed with water. The organic layer was dried over anhydrous sodium sulfate and filtered, and then, the solvent was distilled off. The residue was purified by silica gel column chromatography (methylene chloride/methanol=19/1; an amino silica gel column was used as a precolumn) to obtain N-[2'-amino-5'-(3,4-dimethoxyphenyl)-2,3'-bipyridin-5-yl]-5-(4-methylphenyl)-4-oxo-1-(tetrahydro-2H-pyran-4-ylmethyl)-1,4-dihydropyridine-3-carboxamide (69.0 mg, 48.3%) as a solid. To a solution of this compound in methylene chloride (1.00 ml) and ethanol (1.00 ml), methanesulfonic acid (10.5 mg, 0.192 mmol) was added, and the solvent was distilled off. The residue was suspended in methylene chloride/ethyl acetate/isopropyl ether, and insoluble matter was collected by filtration to obtain the title compound (65.0 mg, 81.8%) as a solid.

$^1$H-NMR (CDCl$_3$) δ: 14.93 (1H, s), 13.27 (1H, s), 9.03 (1H, d, J=2.4 Hz), 8.57 (1H, s), 8.41-8.36 (2H, m), 7.91-7.85 (2H, m), 7.52 (1H, d, J=2.4 Hz), 7.46 (2H, d, J=8.5 Hz), 7.30 (2H, d, J=7.9 Hz), 7.05 (1H, dd, J=8.2, 2.1 Hz), 7.00-6.94 (2H, m), 4.04 (2H, dd, J=11.6, 3.7 Hz), 3.96 (3H, s), 3.95 (3H, s), 3.91 (2H, d, J=7.3 Hz), 3.40 (2H, t, J=11.0 Hz), 2.95 (3H, s), 2.42 (3H, s), 2.18-2.07 (1H, m), 1.65-1.55 (2H, m), 1.52-1.39 (2H, m).

MS (ESI) m/z: 632 [(M+H)$^+$].

Similarly, the final compounds of Table 18 were synthesized from the corresponding starting materials A and B.

TABLE 18
| Ex. No. | Structural formula for Example Instrumental data on Example | Structural formula of starting material A | Structural formula of starting material B |
|---|---|---|---|
| Ex. 89 | 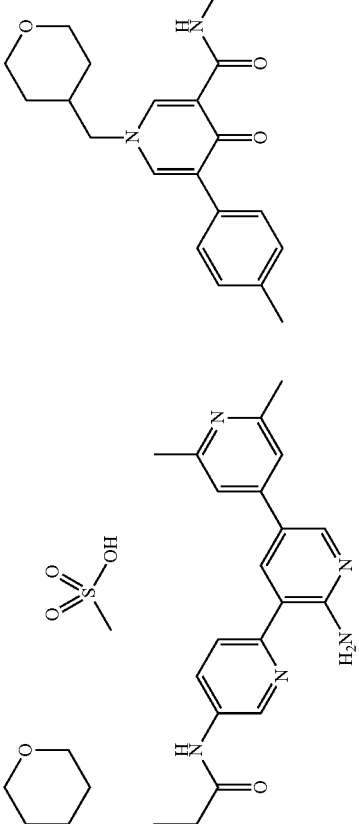 ¹H-NMR (DMSO-D₆) δ: 13.30 (1H, s), 9.04 (1H, d, J = 1.8 Hz), 8.74-8.70 (2H, m), 8.58 (1H, s), 8.34-8.30 (1H, m), 8.20 (1H, d, J = 9.2 Hz), 8.12-8.02 (5H, m), 7.54 (2H, d, J = 7.9 Hz), 7.25 (2H, d, J = 7.9 Hz), 4.10 (2H, d, J = 6.7 Hz), 3.93 (2H, d, J = 11.0 Hz), 3.38-3.28 (2H, m), 2.73 (6H, s), 2.54-2.52 (3H, m), 2.40 (3H, s), 2.20-2.07 (1H, m), 1.59-1.51 (2H, m), 1.48-1.35 (2H, m). MS (ES + APCI) m/z: 601 [(M + H)⁺]. | 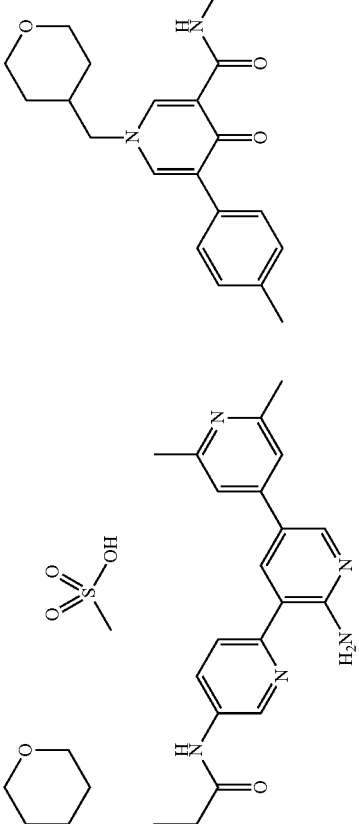 | 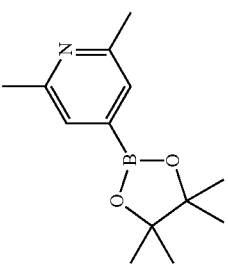 |

TABLE 18-continued
| Ex. No. | Structural formula for Example Instrumental data on Example | Structural formula of starting material A | Structural formula of starting material B |
|---|---|---|---|
| Ex. 90 | 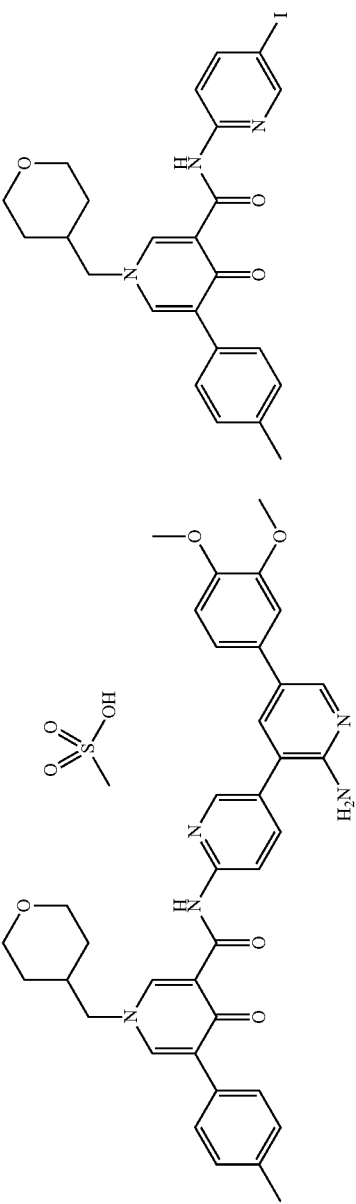<br>$^1$H-NMR (CDCl$_3$) δ: 8.72 (1H, br s), 8.54 (1H, s), 8.44 (1H, d, J = 6.7 Hz), 7.93-7.83 (3H, m), 7.59-7.51 (3H, m), 7.17 (2H, d, J = 7.9 Hz), 7.03 (1H, dd, J = 8.5, 1.8 Hz), 6.98-6.93 (2H, m), 4.06-3.92 (12H, m), 3.38 (2H, t, J = 11.3 Hz), 2.82 (3H, s), 2.30 (3H, s), 2.16-2.04 (1H, m), 1.65-1.56 (2H, m), 1.50-1.36 (2H, m).<br>MS (ES/ APCI) m/z: 632 [(M + H)$^+$]. | 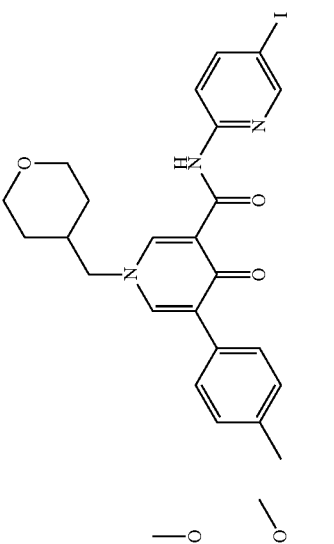 | 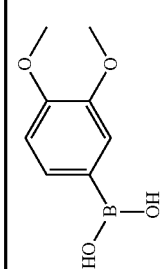 |

TABLE 18-continued

| Ex. No. | Structural formula for Example Instrumental data on Example | Structural formula of starting material A | Structural formula of starting material B |
|---|---|---|---|
| Ex. 91 | 1H-NMR (CDCl3) δ: 13.26 (1H, s), 9.02 (1H, s), 8.56 (1H, s), 8.40-8.32 (2H, m), 7.91-7.85 (2H, m), 7.53-7.43 (3H, m), 7.33-7.23 (2H, m), 7.05-6.92 (3H, m), 4.12-3.51 (16H, m), 3.39 (2H, t, J = 11.9 Hz), 2.95 (3H, s), 2.42 (3H, s), 2.20-2.06 (1H, m), 1.68-1.38 (4H, m) MS (ES/APCI) m/z: 718 [(M + H)$^+$]. | | |

TABLE 18-continued
| Ex. No. | Structural formula for Example Instrumental data on Example | Structural formula of starting material A | Structural formula of starting material B |
|---|---|---|---|
| Ex. 92 | 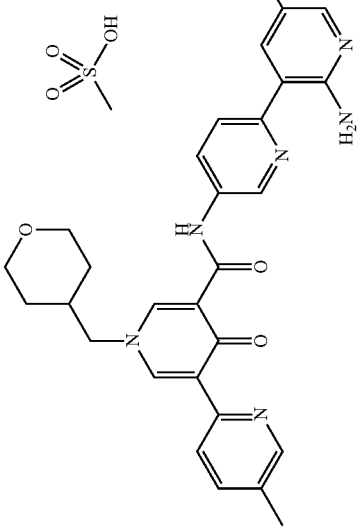<br>¹H-NMR (DMSO-D₆) δ: 13.26 (1H, s), 9.11 (1H, s), 9.07-8.70 (4H, m), 8.54 (1H, s), 8.47 (1H, d, J = 8.5 Hz), 8.43-8.37 (3H, m), 7.79 (1H, d, J = 8.5 Hz), 7.38-7.34 (2H, m), 7.08 (1H, d, J = 7.9 Hz), 4.22 (2H, d, J = 7.3 Hz), 3.91-3.83 (5H, m), 3.82 (3H, s), 3.27 (2H, t, J = 11.5 Hz), 2.38 (3H, s), 2.35 (3H, s), 2.15-1.99 (1H, m), 1.51-1.43 (2H, m), 1.39-1.26 (2H, m).<br>MS (ES/APCI) m/z: 633 [(M + H)⁺]. | 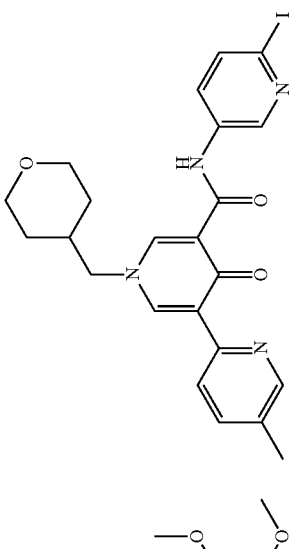 | 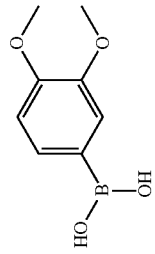 |

TABLE 18-continued
| Ex. No. | Structural formula for Example Instrumental data on Example | Structural formula of starting material A | Structural formula of starting material B |
|---|---|---|---|
| Ex. 93 | <br><br>¹H-NMR (DMSO-D₆) δ: 13.33-13.31 (1H, m), 9.11-9.09 (1H, m), 8.84-8.71 (4H, m), 8.41-8.37 (3H, m), 8.27 (1H, d, J = 2.4 Hz), 7.77-7.71 (2H, m), 7.37-7.28 (4H, m), 7.08 (1H, d, J = 7.9 Hz), 4.13 (2H, d, J = 7.3 Hz), 3.88 (3H, s), 3.87-3.84 (2H, m), 3.81 (3H, s), 3.31-3.23 (2H, m), 2.31 (3H, s), 2.16-2.07 (1H, m), 1.49-1.43 (2H, m), 1.38-1.26 (2H, m).<br><br>MS (ES + APCI) m/z: 636 [(M + H)⁺]. | 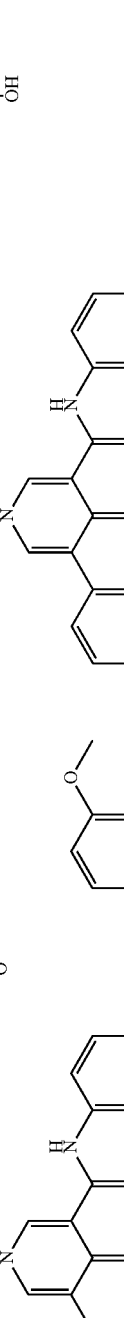 |  |

TABLE 18-continued
| Ex. No. | Structural formula for Example Instrumental data on Example | Structural formula of starting material A | Structural formula of starting material B |
|---|---|---|---|
| Ex. 94 | 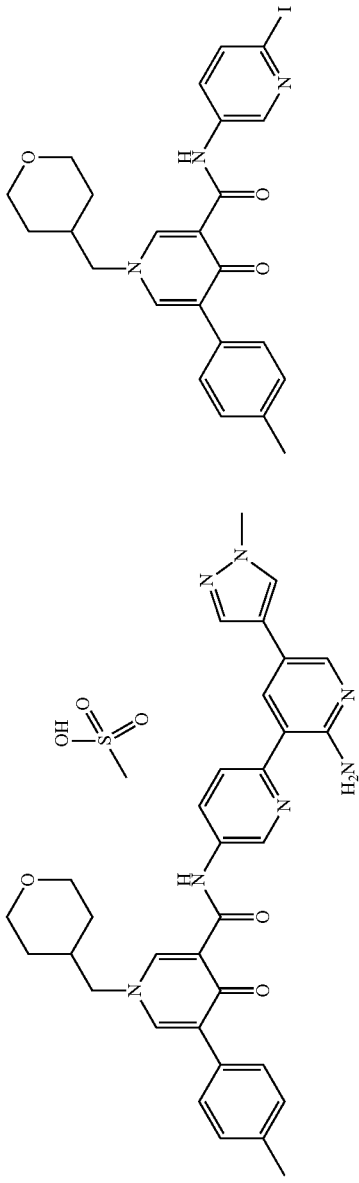 ¹H-NMR (DMSO-D₆) δ: 13.40-13.38 (1H, m), 9.12 (1H, d, J = 2.4 Hz), 8.91-8.70 (4H, m), 8.42-8.32 (3H, m), 8.30 (1H, d, J = 2.4 Hz), 8.21 (1H, d, J = 2.4 Hz), 8.05-8.04 (1H, m), 7.60 (2H, d, J = 7.9 Hz), 7.27 (2H, d, J = 7.9 Hz), 4.12 (2H, d, J = 6.7 Hz), 3.91-3.83 (2H, m), 3.90 (3H, s), 3.31-3.23 (2H, m), 2.36 (3H, s), 2.31 (3H, s), 2.17-2.05 (1H, m), 1.49-1.42 (2H, m), 1.38-1.25 (2H, m). MS (APCI) m/z: 576 [(M + H)⁺]. | 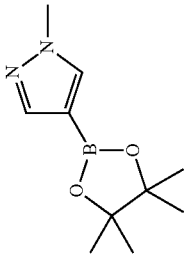 | 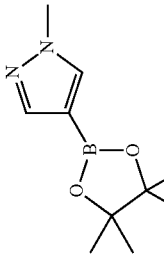 |

TABLE 18-continued
| Ex. No. | Structural formula for Example Instrumental data on Example | Structural formula of starting material A | Structural formula of starting material B |
|---|---|---|---|
| Ex. 95 | 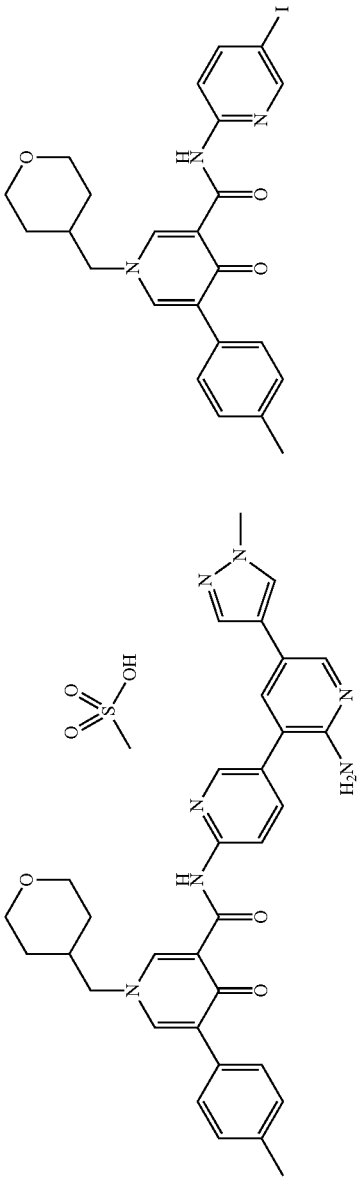 <br> $^1$H-NMR (CDCl$_3$) δ: 13.38 (1H, s), 8.54-8.35 (3H, m), 7.86-7.75 (3H, m), 7.68-7.41 (5H, m), 7.34-7.19 (3H, m), 4.07-3.85 (7H, m), 3.38 (2H, t, J = 11.5 Hz), 2.93 (3H, s), 2.38 (3H, s), 2.15-2.04 (1H, m), 1.66-1.35 (4H, m). <br> MS (ESI/APCI) m/z: 576 [(M + H)$^+$]. | 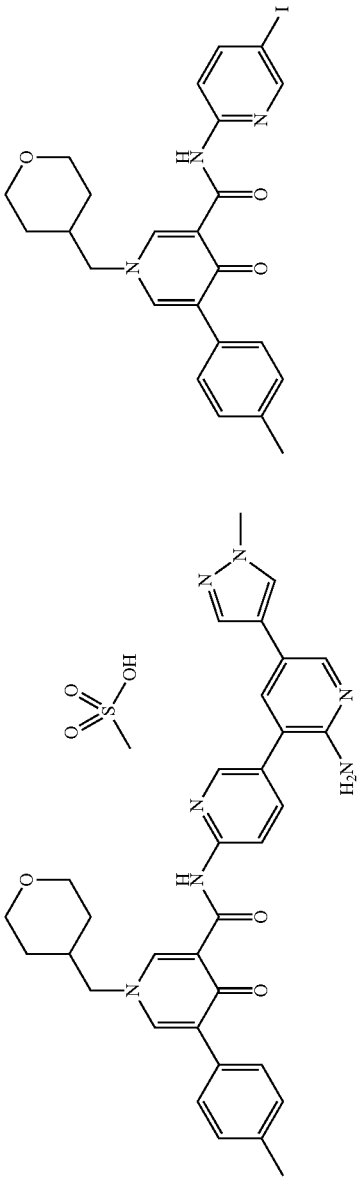 | 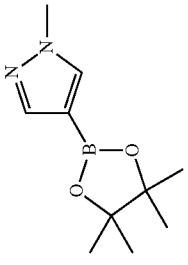 |

TABLE 18-continued
| Ex. No. | Structural formula for Example Instrumental data on Example | Structural formula of starting material A | Structural formula of starting material B |
|---|---|---|---|
| Ex. 96 | 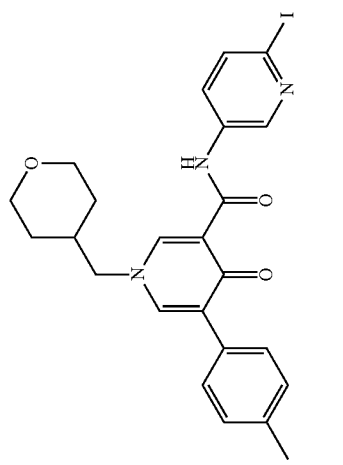<br>¹H-NMR (DMSO-D₆) δ: 13.37-13.35 (1H, m), 9.08 (1H, d, J = 2.4 Hz), 8.75 (1H, d, J = 2.4 Hz), 8.70-8.67 (1H, m), 8.49 (1H, d, J = 2.4 Hz), 8.37 (1H, dd, J = 8.5, 2.4 Hz), 8.28-8.24 (1H, m), 8.20 (1H, d, J = 2.4 Hz), 7.61-7.56 (3H, m), 7.27 (2H, d, J = 7.9 Hz), 4.12 (2H, d, J = 7.3 Hz), 4.04 (3H, s), 4.01 (3H, s), 3.90-3.84 (2H, m), 3.31-3.23 (2H, m), 2.36 (3H, s), 2.31 (3H, s), 2.16-2.06 (1H, m), 1.49-1.42 (2H, m), 1.38-1.25 (2H, M).<br>MS (ESI/APCI) m/z: 634 [(M + H)⁺]. | 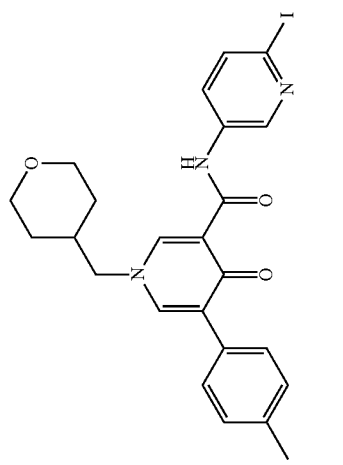 | 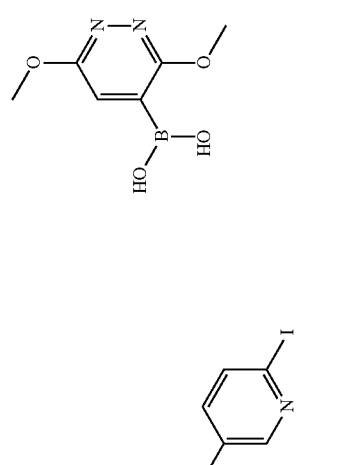 |

TABLE 18-continued
| Ex. No. | Structural formula for Example Instrumental data on Example | Structural formula of starting material A | Structural formula of starting material B |
|---|---|---|---|
| Ex. 97 | 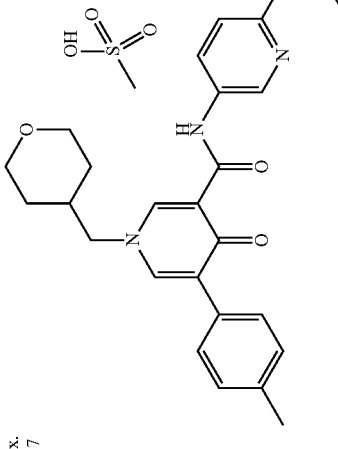<br>¹H-NMR (DMSO-D₆) δ: 13.41-13.39 (1H, m), 9.12 (1H, d, J = 2.4 Hz), 8.95-8.72 (4H, m), 8.51-8.50 (1H, m), 8.44-8.35 (2H, m), 8.32 (1H, d, J = 2.4 Hz), 8.21 (1H, d, J = 2.4 Hz), 8.09-8.07 (1H, m), 7.60 (2H, d, J = 7.9 Hz), 7.27 (2H, d, J = 7.9 Hz), 4.49-4.39 (1H, m), 4.13 (2H, d, J = 7.3 Hz), 4.02-3.96 (2H, m), 3.90-3.84 (2H, m), 3.55-3.46 (2H, m), 3.31-3.22 (2H, m), 2.36 (3H, s), 2.31 (3H, s), 2.17-2.02 (3H, m), 2.01-1.89 (2H, m), 1.49-1.42 (2H, m), 1.37-1.25 (2H, m).<br>MS (ESI + APCI) m/z: 646 [(M + H)⁺]. | 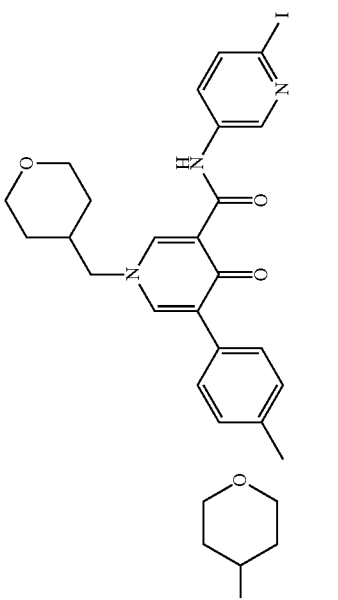 | 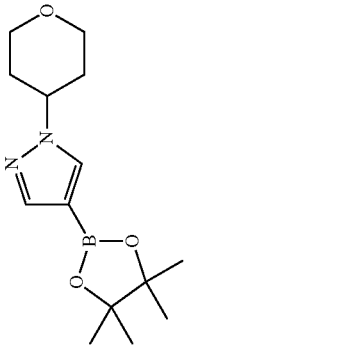 |

TABLE 18-continued
| Ex. No. | Structural formula for Example Instrumental data on Example | Structural formula of starting material A | Structural formula of starting material B |
|---|---|---|---|
| Ex. 98 | 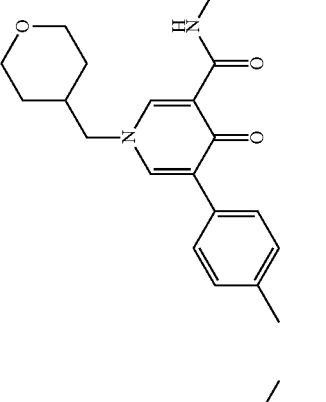<br>$^1$H-NMR (CDCl$_3$) δ: 14.65 (1H, br s), 13.42 (1H, s), 8.76 (2H, dd, J = 8.5, 2.4 Hz), 8.47 (1H, d, J = 1.8 Hz), 8.41 (1H, d, J = 8.5 Hz), 8.18 (1H, d, J = 1.8 Hz), 8.13 (2H, br s), 8.08 (1H, d, J = 2.4 Hz), 7.99 (1H, dd, J = 8.5, 2.4 Hz), 7.60 (2H, d, J = 7.9 Hz), 7.27 (2H, d, J = 7.9 Hz), 6.86 (2H, br s), 4.12 (2H, d, J = 7.3 Hz), 3.90-3.83 (2H, m), 3.33-3.20 (2H, m), 2.64 (6H, s), 2.36 (3H, s), 2.30 (3H, s), 2.17-2.06 (1H, m), 1.51-1.42 (2H, m), 1.38-1.25 (2H, m).<br>MS (ESI/APCI) m/z: 601 [(M + H)$^+$]. | 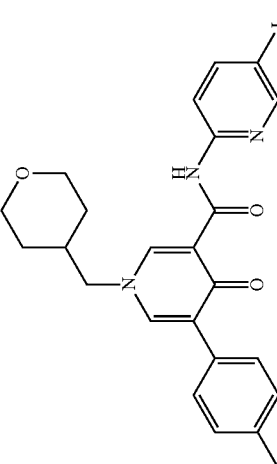 | 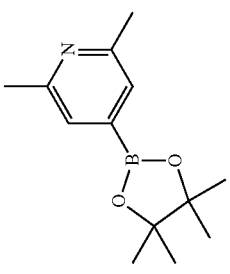 |

TABLE 18-continued
| Ex. No. | Structural formula for Example Instrumental data on Example | Structural formula of starting material A | Structural formula of starting material B |
|---|---|---|---|
| Ex. 99 | 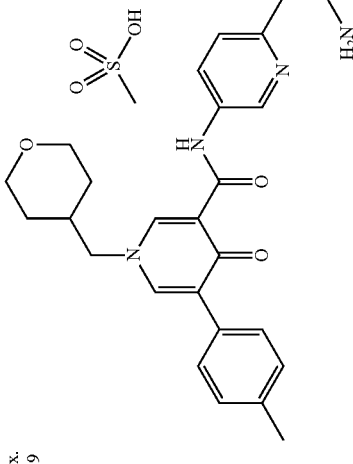<br>¹H-NMR (DMSO-D₆) δ: 13.41 (1H, s), 9.13-9.12 (1H, m), 8.98 (2H, br s), 8.81 (1H, d, J = 2.4 Hz), 8.76 (1H, d, J = 2.4 Hz), 8.41-8.39 (3H, m), 8.34 (1H, d, J = 2.4 Hz), 8.21 (1H, d, J = 2.4 Hz), 8.10 (1H, s), 7.60 (2H, d, J = 8.5 Hz), 7.27 (2H, d, J = 8.5 Hz), 4.25-4.12 (2H, m), 3.93-3.85 (3H, m), 3.79-3.74 (2H, m), 3.65 (1H, br d, J = 11.2 Hz), 3.56 (1H, td, J = 11.2, 2.6 Hz), 3.45 (1H, td, J = 11.2, 2.6 Hz), 3.30-3.24 (3H, m), 2.37 (3H, s), 2.36 (3H, s), 2.16-2.06 (1H, m), 1.46 (2H, br d, J = 10.9 Hz), 1.37-1.26 (2H, m).<br>MS (APCI) m/z: 662 [(M + H)⁺]. | 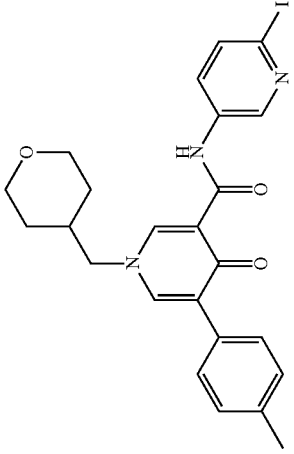 | 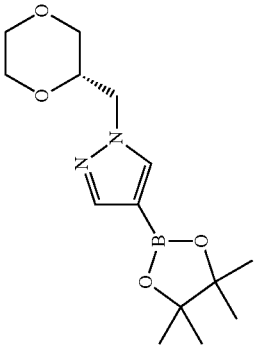 |

(Example 100) N-{6-[2-Amino-5-(3,4-dimethoxyphenyl)pyridin-3-yl]pyridazin-3-yl}-5-(4-methylphenyl)-4-oxo-1-(tetrahydro-2H-pyran-4-ylmethyl)-1,4-dihydropyridine-3-carboxamide

[Formula 73]

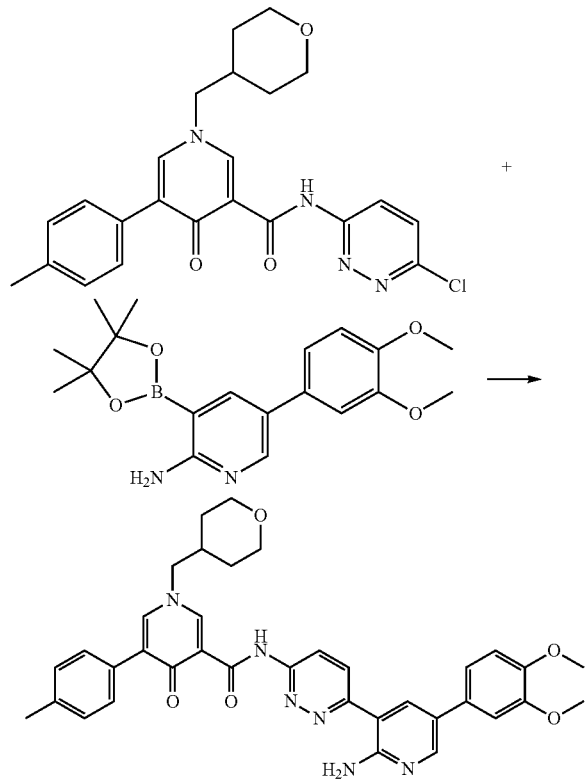

To 5-(3,4-dimethoxyphenyl)-3-(4,4,5,5-tetramethyl-1,3,2-dioxaborolan-2-yl)pyridin-2-amine (0.0800 g, 0.182 mmol), N-(6-chloropyridazin-3-yl)-5-(4-methylphenyl)-4-oxo-1-(tetrahydro-2H-pyran-4-ylmethyl)-1,4-dihydropyridine-3-carboxamide (0.0974 g, 0.273 mmol), tris(dibenzylideneacetone)palladium(0) (0.0167 g, 0.0182 mmol), 2-dicyclohexylphosphino-2',4',6'-triisopropylbiphenyl (XPhos) (0.0348 g, 0.0729 mmol), and sodium carbonate (0.0229 g, 0.547 mmol), 1,4-dioxane (2.00 mL) and water (0.200 mL) were added, and the mixture was stirred at 100° C. for 4 hours. The reaction mixture was left to cool to room temperature, and then, water was added thereto, followed by extraction with methylene chloride three times. The organic layer was dried over anhydrous sodium sulfate. After filtration and concentration under reduced pressure, the residue obtained was purified by silica gel column chromatography (Yamazen Corp., ethyl acetate/methanol=100/0→80/20). After concentration under reduced pressure, the solid obtained was suspended in ethanol, collected by filtration, and dried to obtain the title compound (0.067 g, yield: 58.1%) as a solid.

$^1$H-NMR (DMSO-$D_6$) δ: 13.94 (1H, s), 8.78 (1H, d, J=2.4 Hz), 8.64 (1H, d, J=9.7 Hz), 8.52 (1H, d, J=9.7 Hz), 8.42 (1H, d, J=2.4 Hz), 8.25-8.21 (2H, m), 7.61 (2H, d, J=7.9 Hz), 7.48 (2H, s), 7.28-7.23 (4H, m), 7.02 (1H, d, J=8.5 Hz), 4.12 (2H, d, J=7.3 Hz), 3.91-3.83 (5H, m), 3.79 (3H, s), 3.27 (2H, t, J=10.9 Hz), 2.37 (3H, s), 2.16-2.07 (1H, m), 1.47 (2H, br d, J=10.9 Hz), 1.37-1.26 (2H, m).

MS (APCI) m/z: 633 [(M+H)$^+$].

Similarly, the final compounds of Table 19 were synthesized from the corresponding starting materials A and B.

TABLE 19
| Ex. No. | Structural formula for Example Instrumental data on Example |
|---|---|
| Ex. 101 | 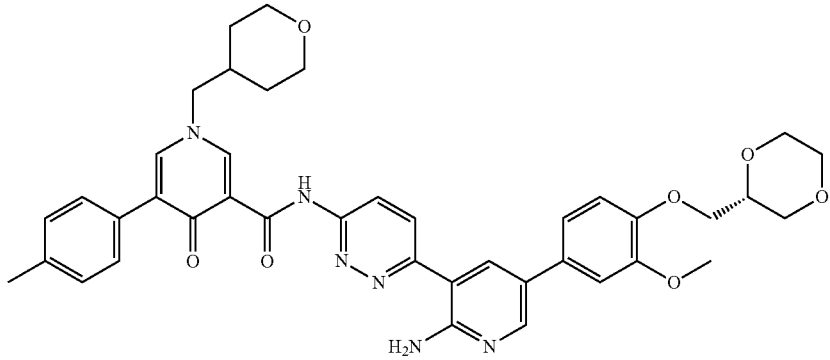 ¹H-NMR (DMSO-D₆) δ: 13.94 (1H, s), 8.78 (1H, d, J = 2.4 Hz), 8.64 (1H, d, J = 9.7 Hz), 8.52 (1H, d, J = 9.7 Hz), 8.42 (1H, d, J = 2.4 Hz), 8.25-8.21 (2H, m), 7.61 (2H, d, J = 8.5 Hz), 7.49 (2H, s), 7.29-7.21 (4H, m), 7.03 (1H, d, J = 8.5 Hz), 4.12 (2H, d, J = 7.3 Hz), 4.01-3.76 (10H, m), 3.70-3.61 (2H, m), 3.54-3.38 (2H, m), 3.27 (2H, t, J = 11.2 Hz), 2.37 (3H, s), 2.18-2.05 (1H, m), 1.47 (2H, br d, J = 10.9 Hz), 1.37-1.26 (2H, m). MS (ESI/APCI) m/z: 719 [(M + H)⁺]. |
| Ex. 102 | 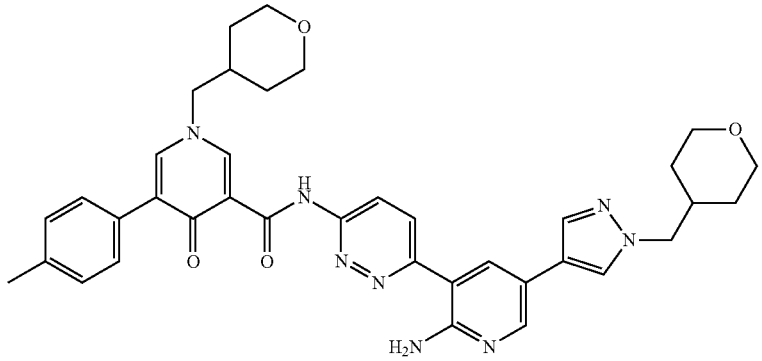 ¹H-NMR (CDCl₃) δ: 13.78 (1H, s), 8.67 (1H, d, J = 10.0 Hz), 8.51 (1H, d, J = 2.0 Hz), 8.29 (1H, d, J = 2.0 Hz), 7.93 (1H, d, J = 10.0 Hz), 7.86 (1H, d, J = 2.0 Hz), 7.75 (1H, s), 7.58 (1H, s), 7.53 (2H, d, J = 8.0 Hz), 7.49 (1H, d, J = 2.0 Hz), 7.27 (2H, d, J = 8.0 Hz), 6.84-6.77 (2H, m), 4.07-3.96 (6H, m), 3.88 (2H, d, J = 7.5 Hz), 3.39 (4H, t, J = 12.0 Hz), 2.41 (3H, s), 2.27-2.05 (2H, m), 1.65-1.35 (8H, m). MS (ESI/APCI) m/z: 661 [(M + H)⁺]. |

| Ex. 103 | 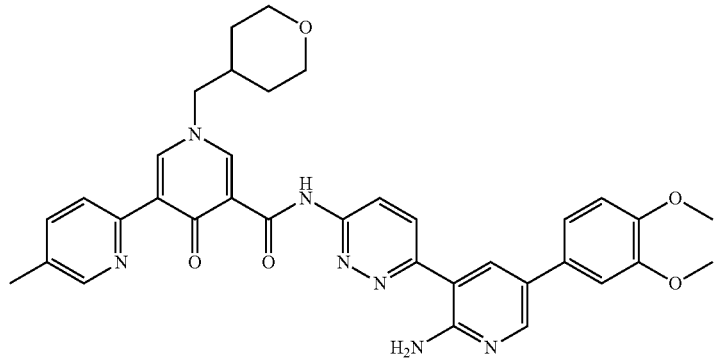 |
|---|---|
¹H-NMR (DMSO-D₆) δ: 13.91 (1H, s), 8.82 (1H, d, J = 2.4 Hz), 8.72 (1H, d, J = 2.4 Hz), 8.64 (1H, d, J = 9.7 Hz), 8.54-8.48 (3H, m), 8.42 (1H, d, J = 2.4 Hz), 8.25 (1H, d, J = 2.4 Hz), 7.73 (1H, dd, J = 8.5, 1.8 Hz), 7.50 (2H, s), 7.29-7.23 (2H, m), 7.02 (1H, d, J = 8.5 Hz), 4.22 (2H, d, J = 7.3 Hz), 3.87-3.84 (5H, m), 3.79 (3H, s), 3.27 (2H, t, J = 10.9 Hz), 2.36 (3H, s), 2.13-2.02 (1H, m), 1.48 (2H, br d, J = 10.9 Hz), 1.38-1.27 (2H, m).
MS (APCI) m/z: 634 [(M + H)⁺].
| Ex. 104 | 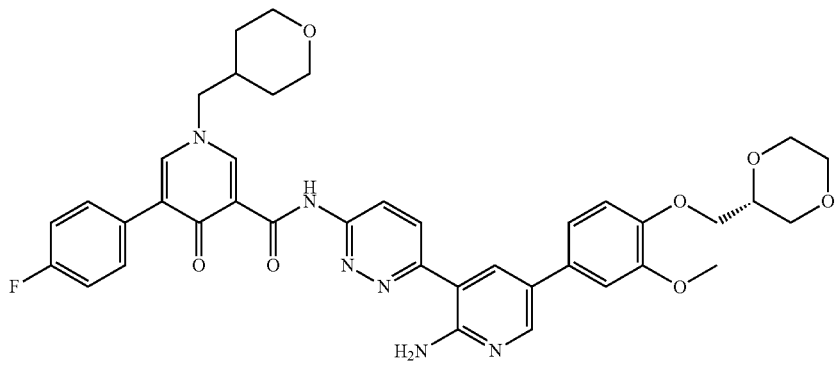 |
|---|---|
¹H-NMR (CDCl₃) δ: 13.68 (1H, s), 8.66 (1H, d, J = 9.1 Hz), 8.52 (1H, d, J = 2.4 Hz), 8.35 (1H, d, J = 2.4 Hz), 7.97-7.94 (2H, m), 7.63-7.60 (2H, m), 7.49 (1H, d, J = 2.4 Hz), 7.18-7.12 (2H, m), 7.07-7.04 (2H, m), 6.99 (1H, d, J = 7.9 Hz), 6.89-6.86 (2H, m), 4.11-3.65 (15H, m), 3.60-3.53 (1H, m), 3.40 (2H, t, J = 11.5 Hz), 2.16-2.07 (1H, m), 1.62 (2H, br d, J = 10.9 Hz), 1.50-1.40 (2H, m).
MS (APCI) m/z: 723 [(M + H)⁺].

TABLE 19-continued
Ex. 105
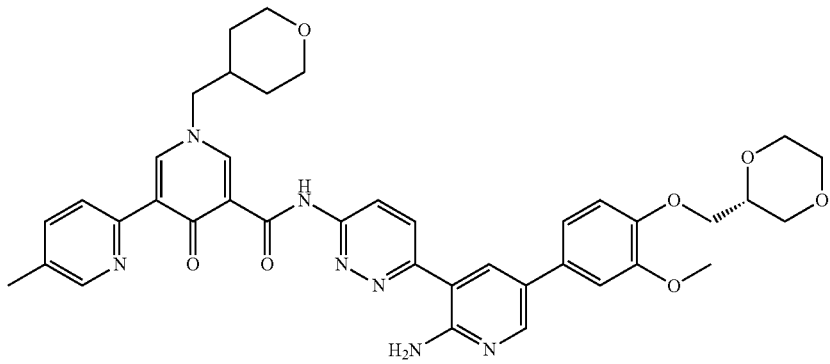
¹H-NMR (CDCl₃) δ: 13.92 (1H, s), 8.71-8.65 (2H, m), 8.51 (2H, dd, J = 9.7, 2.4 Hz), 8.45 (1H, s), 8.36 (1H, d, J = 2.4 Hz), 7.99-7.96 (2H, m), 7.61 (1H, dd, J = 8.2, 2.4 Hz), 7.08-7.04 (2H, m), 7.00-6.89 (3H, m), 4.13-3.65 (15H, m), 3.60-3.53 (1H, m), 3.39 (2H, t, J = 10.9 Hz), 2.39 (3H, s), 2.21-2.11 (1H, m), 1.61 (2H, br d, J = 12.8 Hz), 1.51-1.41 (2H, m).
MS (APCI) m/z: 720 [(M + H)⁺].
Ex. 106
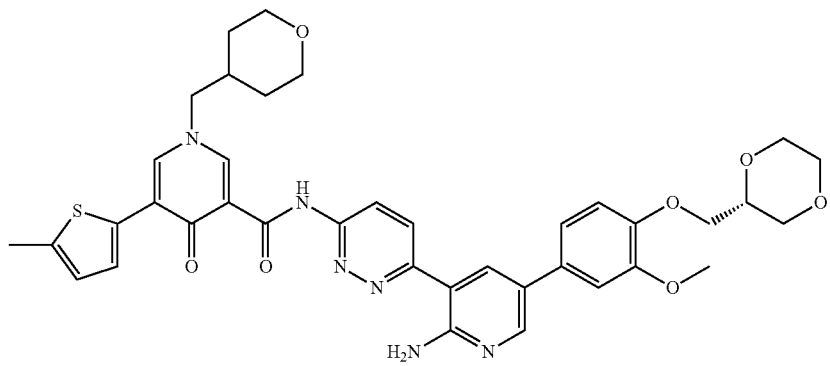
¹H-NMR (CDCl₃) δ: 13.65 (1H, s), 8.67 (1H, d, J = 9.1 Hz), 8.44 (1H, d, J = 2.4 Hz), 8.35 (1H, d, J = 2.4 Hz), 7.97-7.94 (2H, m), 7.76 (1H, d, J = 2.4 Hz), 7.43 (1H, d, J = 3.6 Hz), 7.07-7.04 (2H, m), 7.00-6.89 (3H, m), 6.78 (1H, d, J = 3.6 Hz), 4.12-3.65 (15H, m), 3.60-3.53 (1H, m), 3.42-3.36 (2H, m), 2.54 (3H, s), 2.17-2.06 (1H, m), 1.60 (2H, br d, J = 12.8 Hz), 1.50-1.40 (2H, m).
MS (APCI) m/z: 725 [(M + H)⁺].

| Ex. 107 | 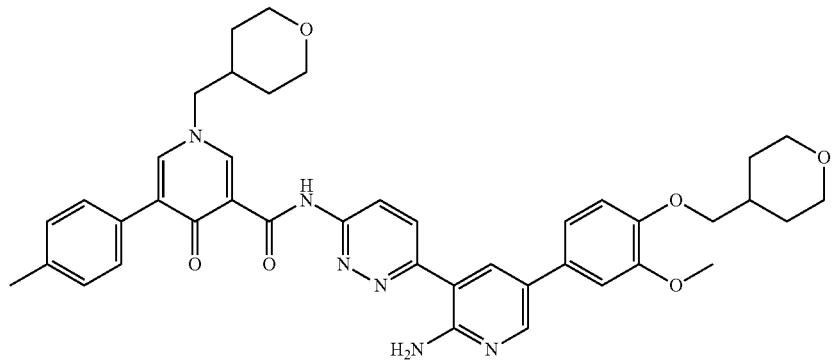<br>¹H-NMR (CDCl₃) δ: 13.77 (1H, s), 8.67 (1H, d, J = 9.7 Hz), 8.50 (1H, d, J = 2.4 Hz), 8.35 (1H, d, J = 2.4 Hz), 7.96-7.93 (2H, m), 7.53-7.48 (3H, m), 7.27-7.25 (2H, m), 7.08-7.05 (2H, m), 6.96-6.85 (3H, m), 4.05-4.01 (4H, m), 3.94 (3H, s), 3.91-3.86 (4H, m), 3.49-3.36 (4H, m), 2.40 (3H, s), 2.24-2.08 (2H, m), 1.83 (2H, br d, J = 13.1 Hz), 1.61 (2H, br d, J = 10.9 Hz), 1.52-1.39 (4H, m).<br>MS (APCI) m/z: 717 [(M + H)⁺]. |
|---|---|
| Ex. 108 | 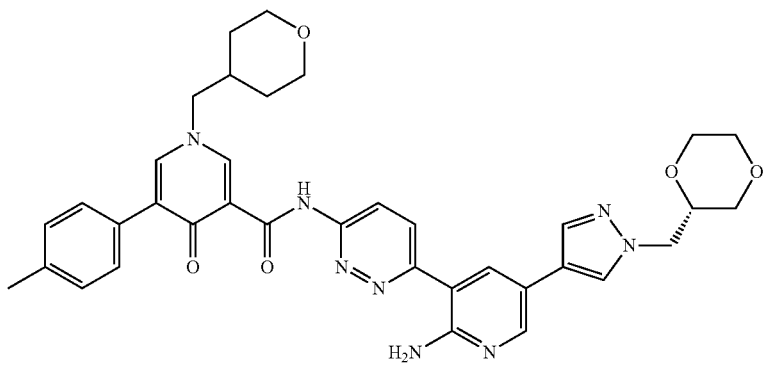<br>¹H-NMR (CDCl₃) δ: 13.77 (1H, s), 8.68 (1H, d, J = 9.8 Hz), 8.51 (1H, d, J = 2.4 Hz), 8.30 (1H, d, J = 2.4 Hz), 7.94 (1H, d, J = 9.8 Hz), 7.87 (1H, d, J = 2.4 Hz), 7.74 (1H, s), 7.68 (1H, s), 7.53 (2H, d, J = 8.0 Hz), 7.49 (1H, d, J = 2.4 Hz), 7.27 (2H, d, J = 8.0 Hz), 6.84-6.77 (2H, br m), 4.19 (2H, d, J = 5.6 Hz), 4.07-3.97 (3H, m), 3.89-3.69 (6H, m), 3.64-3.56 (1H, m), 3.43-3.30 (3H, m), 2.41 (3H, s), 2.17-2.05 (1H, m), 1.65-1.56 (2H, m), 1.51-1.39 (2H, m).<br>MS (APCI) m/z: 663 [(M + H)⁺]. |

TABLE 19-continued
| Ex. 109 | |
|---|---|
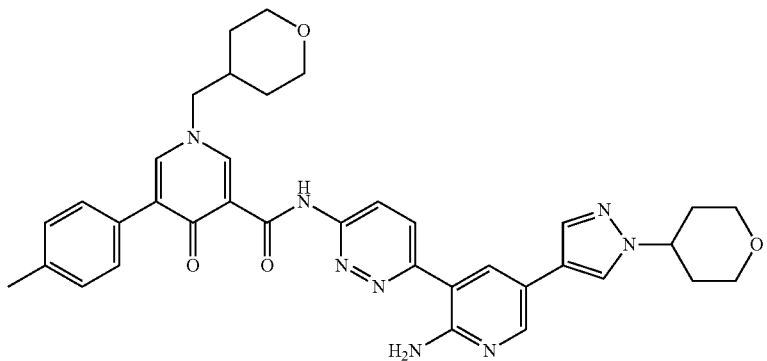
¹H-NMR (DMSO-D₆) δ: 13.93 (1H, s), 8.78 (1H, d, J = 2.4 Hz), 8.64 (1H, d, J = 9.0 Hz), 8.47 (1H, d, J = 9.0 Hz), 8.38 (1H, d, J = 2.4 Hz), 8.29 (1H, s), 8.22 (2H, dd, J = 9.0, 2.0 Hz), 7.94 (1H, s), 7.62 (2H, d, J = 8.0 Hz), 7.40 (2H, s), 7.28 (2H, d, J = 8.0 Hz), 4.45-4.36 (1H, m), 4.12 (2H, d, J = 7.5 Hz), 4.02-3.95 (2H, m), 3.87 (2H, dd, J = 11.0, 3.0 Hz), 3.50 (2H, td, J = 12.0, 3.0 Hz), 3.32-3.23 (2H, m), 2.37 (3H, s), 2.18-1.89 (5H, m), 1.47 (2H, d, J = 12.0 Hz), 1.38-1.26 (2H, m).
MS (APCI) m/z: 647 [(M + H)⁺].
| Ex. No. | Structural formula of starting material A | Structural formula of starting material B |
|---|---|---|
| Ex. 101 | | |
| Ex. 102 | | |
| Ex. 103 | | |
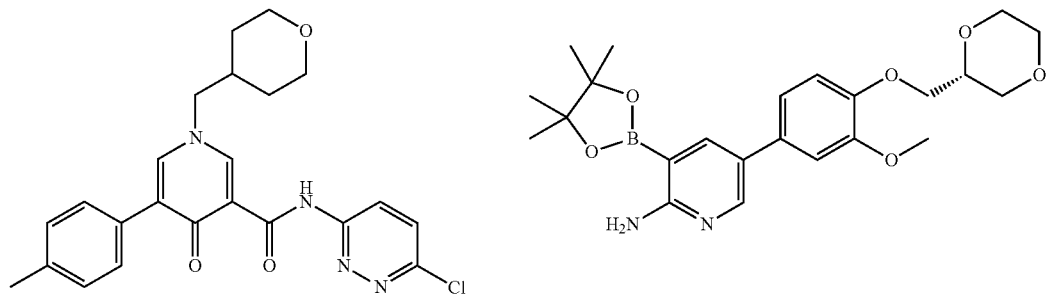
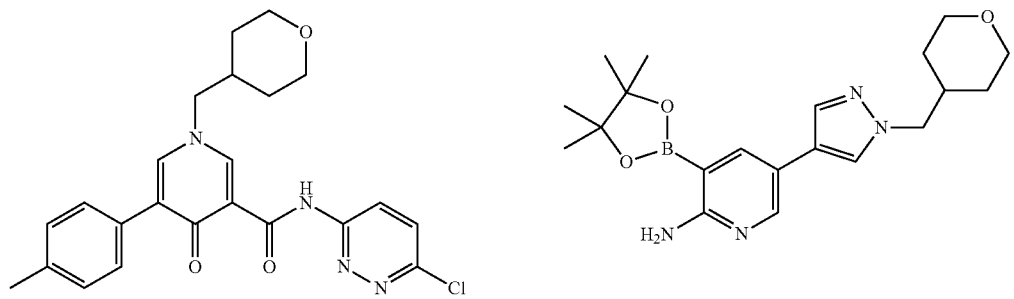
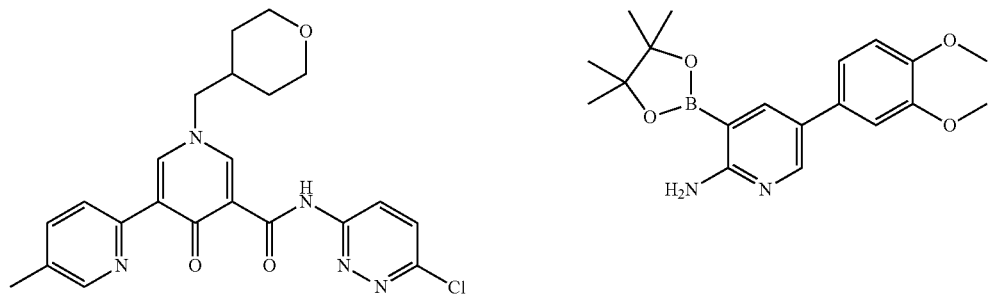

TABLE 19-continued
| Ex. 104 | 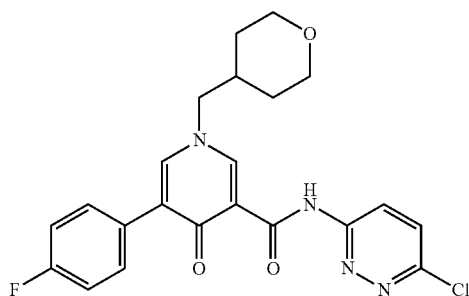 [SMILES: O=C(Nc1ccc(Cl)nn1)c1cn(CC2CCOCC2)cc(-c2ccc(F)cc2)c1=O] | 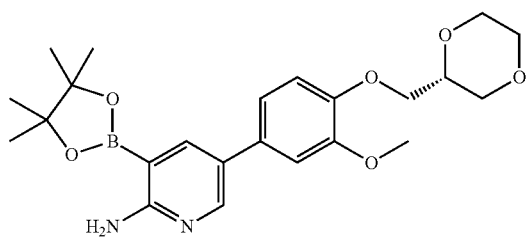 [SMILES: COc1cc(-c2cnc(N)c(B3OC(C)(C)C(C)(C)O3)c2)ccc1OC[C@H]1COCCO1] |
| Ex. 105 | 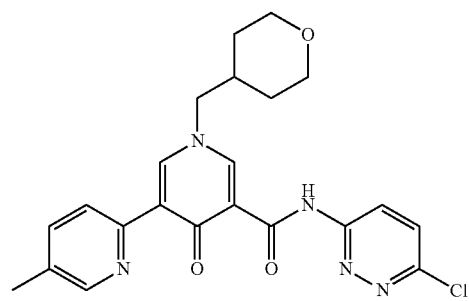 [SMILES: Cc1ccc(-c2cn(CC3CCOCC3)cc(C(=O)Nc3ccc(Cl)nn3)c2=O)nc1] | 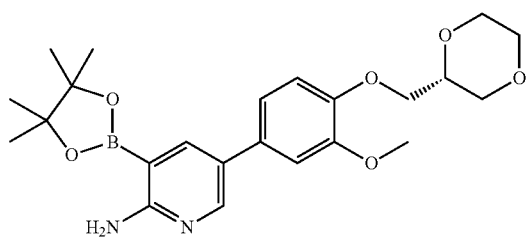 [SMILES: COc1cc(-c2cnc(N)c(B3OC(C)(C)C(C)(C)O3)c2)ccc1OC[C@H]1COCCO1] |
| Ex. 106 | 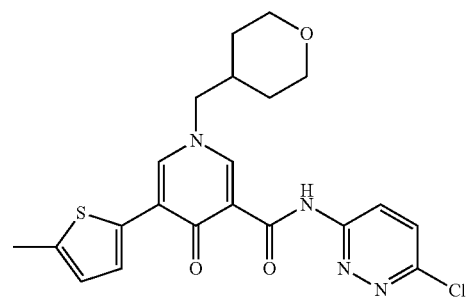 [SMILES: Cc1ccc(-c2cn(CC3CCOCC3)cc(C(=O)Nc3ccc(Cl)nn3)c2=O)s1] | 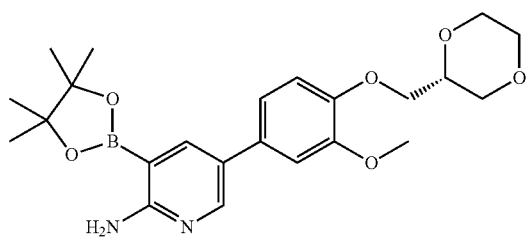 |
| Ex. 107 | 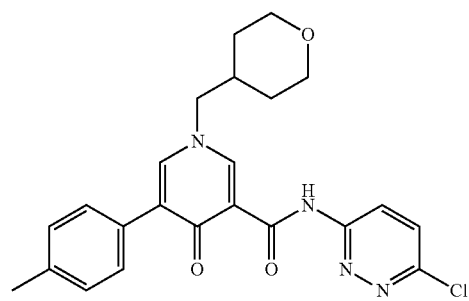 [SMILES: Cc1ccc(-c2cn(CC3CCOCC3)cc(C(=O)Nc3ccc(Cl)nn3)c2=O)cc1] | 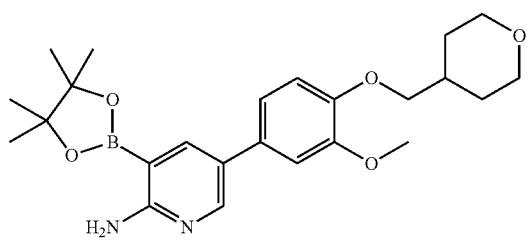 [SMILES: COc1cc(-c2cnc(N)c(B3OC(C)(C)C(C)(C)O3)c2)ccc1OCC1CCOCC1] |
| Ex. 108 | 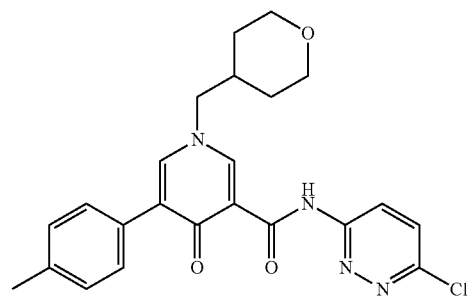 [SMILES: Cc1ccc(-c2cn(CC3CCOCC3)cc(C(=O)Nc3ccc(Cl)nn3)c2=O)cc1] | 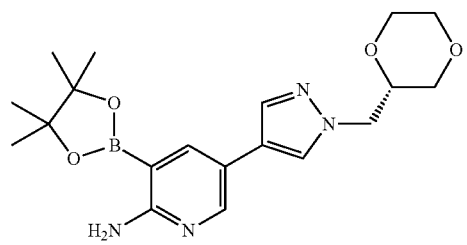 [SMILES: CC1(C)OB(c2cc(-c3cnn(C[C@H]4COCCO4)c3)cnc2N)OC1(C)C] |

TABLE 19-continued

Ex. 109

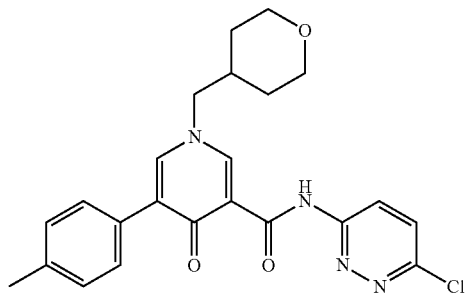 [SMILES: Cc1ccc(-c2cn(CC3CCOCC3)cc(C(=O)Nc3ccc(Cl)nn3)c2=O)cc1]

(Example 110) N-[6-(2-Amino-5-{3-methoxy-4-[2-(morpholin-4-yl)ethoxy]phenyl}pyridin-3-yl)pyridazin-3-yl]-5-(4-methylphenyl)-4-oxo-1-(tetrahydro-2H-pyran-4-ylmethyl)-1,4-dihydropyridine-3-carboxamide

[Formula 74]

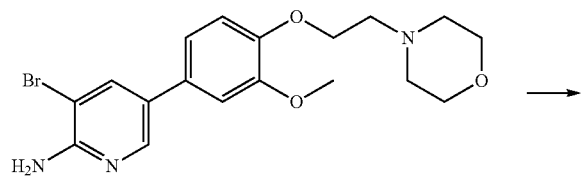

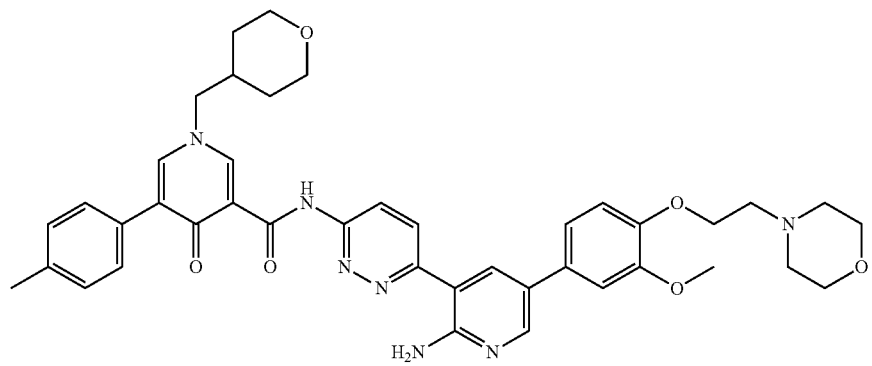

To 3-bromo-5-{3-methoxy-4-[2-(morpholin-4-yl)ethoxy]phenyl}pyridin-2-amine (0.245 g, 0.600 mmol), bis(pinacolato)diboron (0.229 g, 0.900 mmol), tris(dibenzylideneacetone)dipalladium(0) (0.0330 g, 0.0360 mmol), tricyclohexylphosphine (0.0236 g, 0.0840 mmol), and potassium acetate (0.0883 g, 0.900 mmol), 1,4-dioxane (3.00 mL) was added, and the mixture was stirred at 80° C. for 6 hours under a nitrogen atmosphere. The reaction mixture was left to cool to room temperature and then filtered, and the filtrate was concentrated under reduced pressure. To the residue obtained, N-(6-chloropyridazin-3-yl)-5-(4-methylphenyl)-4-oxo-1-(tetrahydro-2H-pyran-4-ylmethyl)-1,4-dihydropyridine-3-carboxamide (0.175 g, 0.399 mmol), [1,1'-bis(diphenylphosphino)ferrocene]palladium(II) dichloride-methylene chloride complex (1:1) (0.0326 g, 0.0399 mmol), cesium carbonate (0.390 g, 1.20 mmol), 1,4-dioxane (4.00 mL), and water (0.400 mL) were added, and the mixture was stirred at 100° C. for 4 hours under a nitrogen atmosphere. The reaction mixture was left to cool to room temperature, and then, a saturated aqueous solution of sodium bicarbonate was added thereto, followed by extraction with methylene chloride three times. The organic layer was dried over anhydrous sodium sulfate. After filtration and concentration under reduced pressure, the residue obtained was purified by amino silica gel column chromatography (Yamazen Corp., ethyl acetate/methanol=100/0→80/20). After concentration under reduced pressure, the obtained solid was suspended in ethyl acetate, collected by filtration, and dried to obtain the title compound (0.153 g, yield: 52.4%) as a solid.

$^1$H-NMR (CDCl$_3$) δ: 13.77 (1H, s), 8.67 (1H, d, J=9.7 Hz), 8.51 (1H, d, J=2.4 Hz), 8.35 (1H, d, J=2.4 Hz), 7.96-7.94 (2H, m), 7.53-7.48 (3H, m), 7.27 (2H, d, J=7.9 Hz), 7.08-7.05 (2H, m), 6.98 (1H, d, J=7.9 Hz), 6.89 (2H, s), 4.21 (2H, t, J=6.1 Hz), 4.03 (2H, dd, J=11.2, 3.3 Hz), 3.94 (3H, s), 3.87 (2H, d, J=7.3 Hz), 3.76 (4H, t, J=4.9 Hz), 3.39 (2H, t, J=11.2 Hz), 2.88 (2H, t, J=6.1 Hz), 2.63-2.61 (4H, m), 2.41 (3H, s), 2.15-2.07 (1H, m), 1.62-1.60 (2H, br d, J=11.2 Hz), 1.49-1.39 (2H, m).

MS (APCI) m/z: 732 [(M+H)$^+$].

Similarly, the final compound of Table 20 was synthesized from the corresponding starting material.

TABLE 20

| Example No. | Structural formula for Example Instrumental data on Example |
|---|---|
| Example 111 | 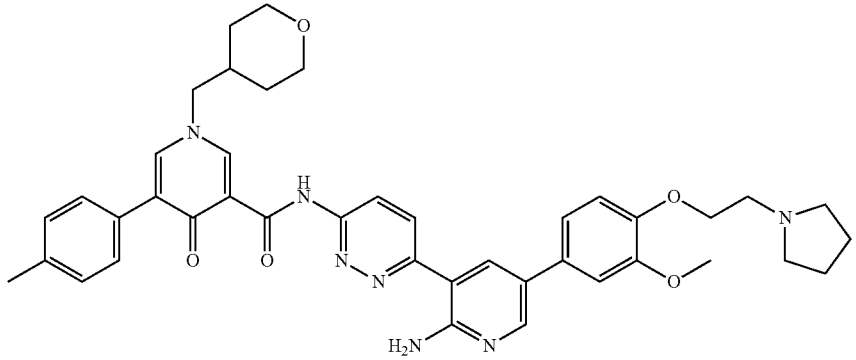 |

¹H-NMR (CDCl₃) δ: 13.77 (1H, s), 8.66 (1H, d, J = 9.1 Hz), 8.50 (1H, d, J = 2.4 Hz), 8.35 (1H, d, J = 2.4 Hz), 7.96-7.94 (2H, m), 7.53-7.48 (3H, m), 7.26 (2H, d, J = 7.9 Hz), 7.08-7.04 (2H, m), 6.99 (1H, d, J = 7.9 Hz), 6.88 (2H, s), 4.21 (2H, t, J = 6.4 Hz), 4.03 (2H, dd, J = 11.5, 3.6 Hz), 3.94 (3H, s), 3.87 (2H, d, J = 7.3 Hz), 3.39 (2H, t, J = 11.5 Hz), 2.98 (2H, t, J = 6.4 Hz), 2.67-2.63 (4H, m), 2.40 (3H, s), 2.16-2.05 (1H, m), 1.84-1.80 (4H, m), 1.62-1.59 (2H, br d, J = 12.1 Hz), 1.49-1.39 (2H, m).
MS (APCI) m/z: 716 [(M + H)⁺].

| Example No. | Structural formula of starting material |
|---|---|
| Example 11 | 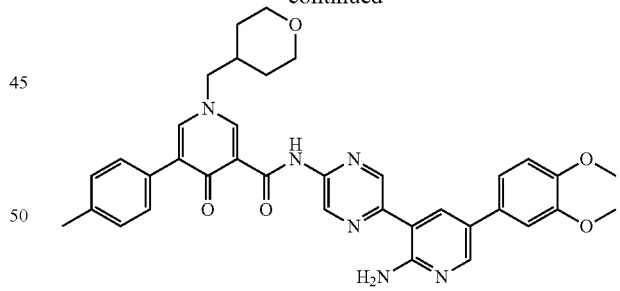 |

(Example 112) N-{5-[2-Amino-5-(3,4-dimethoxyphenyl)pyridin-3-yl]pyrazin-2-yl}-5-(4-methylphenyl)-4-oxo-1-(tetrahydro-2H-pyran-4-ylmethyl)-1,4-dihydropyridine-3-carboxamide

[Formula 75]

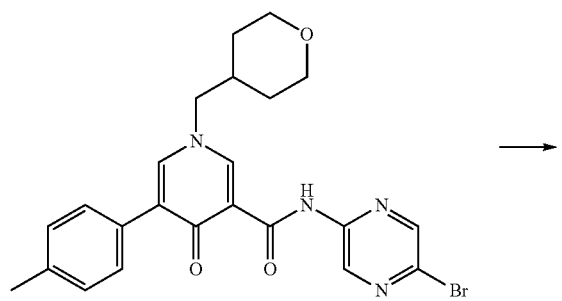

To 5-(3,4-dimethoxyphenyl)-3-(4,4,5,5-tetramethyl-1,3,2-dioxaborolan-2-yl)pyridin-2-amine (0.111 g, 0.310 mmol), N-(5-bromopyrazin-2-yl)-5-(4-methylphenyl)-4-oxo-1-(tetrahydro-2H-pyran-4-ylmethyl)-1,4-dihydropyridine-3-carboxamide (0.100 g, 0.207 mmol), [1,1'-bis(diphenylphosphino)ferrocene]palladium(II) dichloride-methylene chloride complex (1:1) (0.0169 g, 0.0207 mmol), and cesium carbonate (0.202 g, 0.621 mmol), 1,4-dioxane (2.00 mL) and water (0.400 mL) were added, and the mixture was stirred at 80° C. for 1 hour. The reaction mixture was left to cool to room temperature, and then, water was added thereto, followed by extraction with ethyl acetate three times. The organic layer was washed with brine and then dried over anhydrous sodium sulfate. After filtration and concentration under reduced pressure, the residue obtained was purified by amino silica gel column chromatography (Yamazen Corp., ethyl acetate/methanol=100/0→90/10). After concentration under reduced pressure, the residue was solidified using ethyl acetate and diethyl ether, and the solid was collected by filtration and dried to obtain the title compound (0.111 g, yield: 84.8%) as a solid.

1H-NMR (DMSO-D6) δ: 13.61 (1H, s), 9.58 (1H, d, J=1.2 Hz), 9.17 (1H, d, J=2.4 Hz), 8.79 (1H, d, J=2.4 Hz), 8.39 (1H, d, J=2.4 Hz), 8.32 (1H, d, J=2.4 Hz), 8.20 (1H, d, J=2.4 Hz), 7.59 (2H, d, J=8.5 Hz), 7.29-7.23 (6H, m), 7.02 (1H, d, J=8.5 Hz), 4.13 (2H, d, J=6.7 Hz), 3.89-3.85 (5H, m), 3.79 (3H, s), 3.27 (2H, t, J=10.9 Hz), 2.36 (3H, s), 2.16-2.07 (1H, m), 1.49-1.44 (2H, m), 1.37-1.27 (2H, m)

MS (APCI) m/z: 633 [(M+H)$^+$].

(Example 113) N-{4-[2-Amino-5-(3,4-dimethoxyphenyl)pyridin-3-yl]phenyl}-5-(4-cyclopropylphenyl)-4-oxo-1-(tetrahydro-2H-pyran-4-ylmethyl)-1,4-dihydropyridine-3-carboxamide Then, palladium(II) acetate (0.0113 g, 0.0503 mmol) was added thereto, and the mixture was heated to 100° C. Then, 1,4-dioxane (2.00 mL) was added thereto, and the mixture was stirred at the same temperature as above for 4 hours. The reaction mixture was left to cool to room temperature, and then, water was added thereto, followed by extraction with methylene chloride three times. The organic layer was washed with brine and then dried over anhydrous sodium sulfate. After filtration and concentration under reduced pressure, the residue obtained was purified by silica gel column chromatography (Yamazen Corp., ethyl acetate/methanol=100/0→85/15) and further purified by high-performance liquid chromatography (NOMURA Develosil Combi, acetonitrile/water/0.1% formic acid). The organic solvent was distilled off under reduced pressure, and then, a saturated aqueous solution of sodium bicarbonate was added to the residue. The deposited solid was collected by filtration, and dried to obtain the title compound (0.200 g, yield: 60.5%) as a solid.

$^1$H-NMR (DMSO-D$_6$) δ: 13.11 (1H, s), 8.71 (1H, d, J=2.4 Hz), 8.25 (1H, d, J=2.4 Hz), 8.16 (1H, d, J=2.4 Hz), 7.82

[Formula 76]

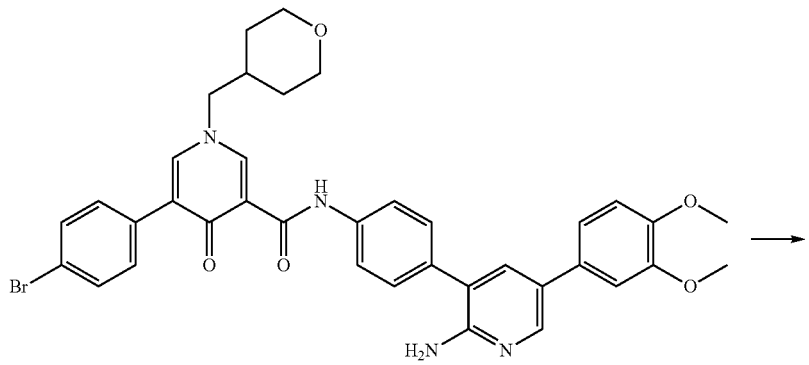

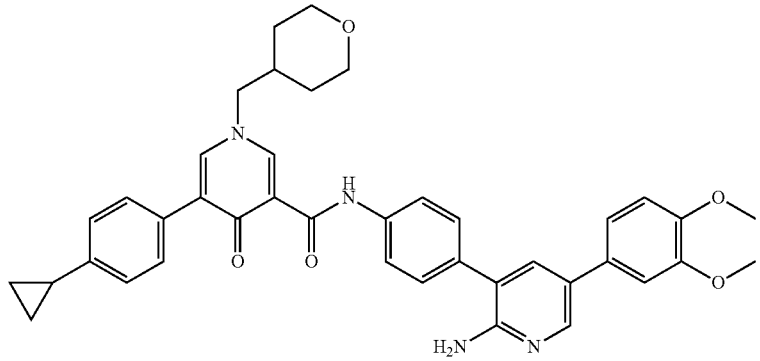

To a suspension of N-{4-[2-amino-5-(3,4-dimethoxyphenyl)pyridin-3-yl]phenyl}-5-(4-bromophenyl)-4-oxo-1-(tetrahydro-2H-pyran-4-ylmethyl)-1,4-dihydropyridine-3-carboxamide (0.350 g, 0.503 mmol) in toluene (5.00 mL), cyclopropylboronic acid (0.0648 g, 0.755 mmol), tricyclohexylphosphine (0.0282 g, 0.101 mmol), tripotassium phosphate (0.374 g, 1.76 mmol), and water (1.00 mL) were added, and the reaction mixture was purged with nitrogen.

(2H, d, J=8.5 Hz), 7.63 (1H, d, J=2.4 Hz), 7.58-7.52 (4H, m), 7.20-7.14 (4H, m), 6.99 (1H, d, J=8.5 Hz), 5.76 (2H, s), 4.10 (2H, d, J=7.3 Hz), 3.88-3.83 (5H, m), 3.77 (3H, s), 3.27 (2H, t, J=10.9 Hz), 2.16-2.04 (1H, m), 2.00-1.93 (1H, m), 1.46 (2H, br d, J=10.9 Hz), 1.35-1.26 (2H, m), 1.02-0.97 (2H, m), 0.73-0.69 (2H, m).

MS (APCI) m/z: 657 [(M+H)$^+$].

(Example 114) N-{4-[2-Amino-5-(3,4-dimethoxyphenyl)pyridin-3-yl]phenyl}-5-methyl-4'-oxo-1'-(tetrahydro-2H-pyran-4-ylmethyl)-1',4'-dihydro-2,3'-bipyridine-5'-carboxamide

[Formula 77]

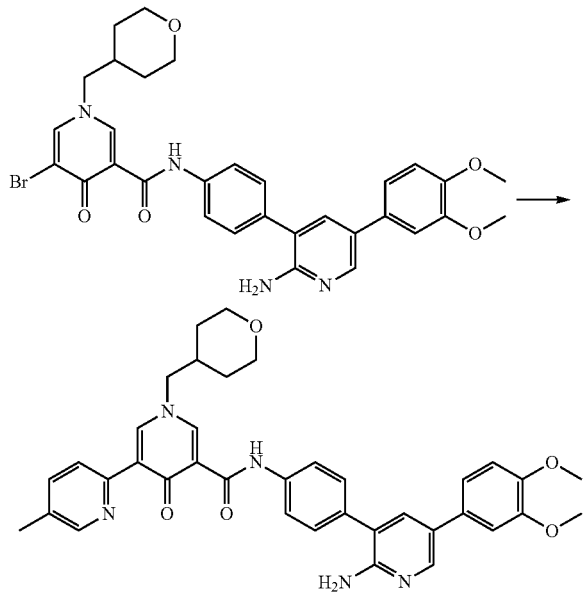

To N-{4-[2-amino-5-(3,4-dimethoxyphenyl)pyridin-3-yl]phenyl}-5-bromo-4-oxo-1-(tetrahydro-2H-pyran-4-ylmethyl)-1,4-dihydropyridine-3-carboxamide (0.620 g, 1.00 mmol), 5-methylpyridine-2-boronic acid N-phenyldiethanolamine ester (0.480 g, 1.70 mmol), and copper(I) iodide (0.0762 g, 0.400 mmol), toluene (6.00 mL), methanol (1.85 mL), and a solution of potassium carbonate (1.84 g, 13.3 mmol) in water (1.20 mL) were added, and the reaction mixture was purged with nitrogen. Then, tetrakis(triphenylphosphine)palladium(0) (0.116 g, 0.100 mmol) was added thereto, and the mixture was stirred at 100° C. for 4 hours. The reaction mixture was left to cool to room temperature, and then, ethyl acetate and water were added thereto. Insoluble matter was filtered off. The filtrate was subjected to extraction with ethyl acetate three times. The organic layer was washed with brine and then dried over anhydrous sodium sulfate. After filtration and concentration under reduced pressure, the residue obtained was purified by silica gel column chromatography (Yamazen Corp., ethyl acetate/methanol=99/1→85/15). After concentration under reduced pressure, the residue was solidified by the addition of ethyl acetate, and the solid was collected by filtration and dried to obtain the title compound (0.229 g, yield: 36.2%) as a solid.

$^1$H-NMR (DMSO-D$_6$) δ: 12.98 (1H, s), 8.75 (1H, d, J=2.4 Hz), 8.71 (1H, d, J=2.4 Hz), 8.30 (1H, d, J=2.4 Hz), 8.25 (1H, d, J=2.4 Hz), 8.02 (1H, dd, J=8.5, 2.4 Hz), 7.82 (2H, d, J=8.5 Hz), 7.61 (1H, d, J=2.4 Hz), 7.53 (2H, d, J=8.5 Hz), 7.34 (1H, d, J=8.5 Hz), 7.19-7.13 (2H, m), 6.98 (1H, d, J=8.5 Hz), 5.69 (2H, s), 4.12 (2H, d, J=7.3 Hz), 3.88-3.83 (5H, m), 3.77 (3H, s), 3.27 (2H, t, J=11.0 Hz), 2.52 (3H, s), 2.17-2.07 (1H, m), 1.47 (2H, br d, J=11.0 Hz), 1.37-1.26 (2H, m).

MS (APCI) m/z: 632 [(M+H)$^+$].

Similarly, the final compound of Table 21 was synthesized from the corresponding starting material.

TABLE 21
| Example No. | Structural formula for Example Instrumental data on Example | Structural formula of starting material |
|---|---|---|
| Example 115 | 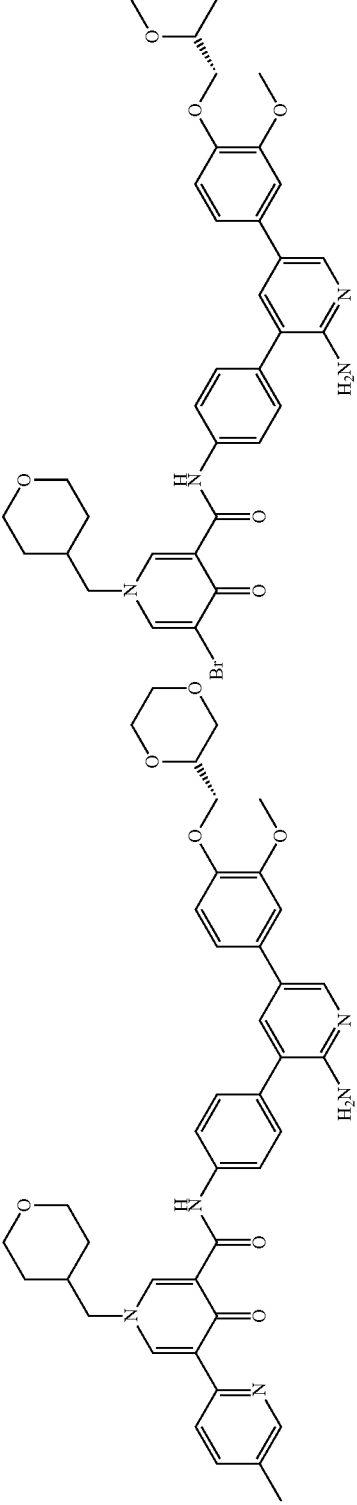<br>¹H-NMR (DMSO-D₆) δ: 13.07 (1H, s), 8.76-8.68 (2H, m), 8.51-8.47 (2H, m), 8.26 (1H, s), 7.84 (2H, d, J = 8.5 Hz), 7.72-7.70 (1H, m), 7.62 (1H, d, J = 1.8 Hz), 7.55 (2H, d, J = 8.5 Hz), 7.21 (1H, d, J = 1.8 Hz), 7.13 (1H, dd, J = 8.5, 1.8 Hz), 7.00 (1H, d, J = 8.5 Hz), 5.70 (2H, s), 4.20 (2H, d, J = 6.7 Hz), 3.98-3.75 (10H, m), 3.69-3.60 (2H, m), 3.53-3.46 (1H, m), 3.42-3.37 (1H, m), 3.27 (2H, t, J = 11.0 Hz), 2.36 (3H, s), 2.12-2.02 (1H, m), 1.47 (2H, br d, J = 11.0 Hz), 1.37-1.26 (2H, m).<br>MS (APCI) m/z: 718 [(M + H)⁺]. | 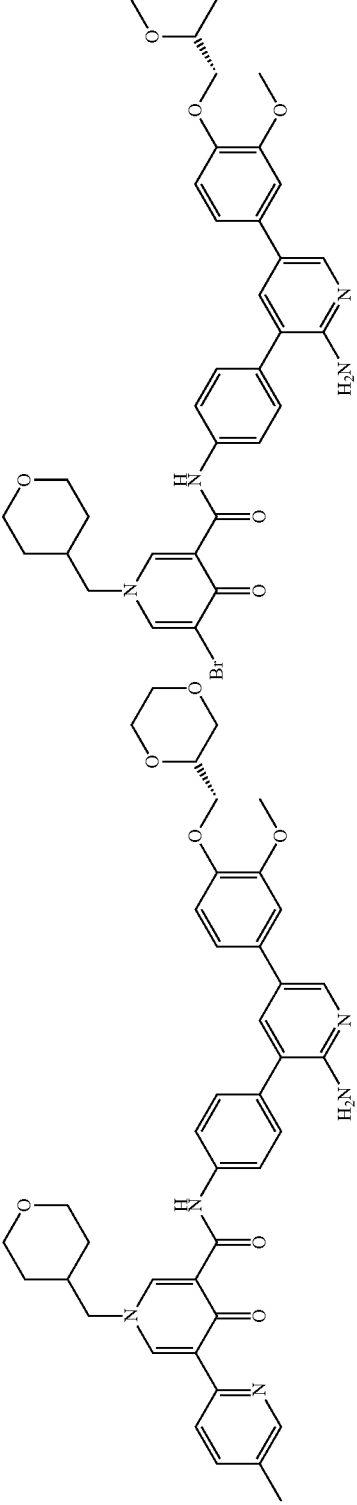 |

(Example 116) N-{4-[2-Amino-5-(3,4-dimethoxyphenyl)pyridin-3-yl]phenyl}-6'-methyl-4-oxo-1-(tetrahydro-2H-pyran-4-ylmethyl)-1,4-dihydro-3,3'-bipyridine-5-carboxamide

[Formula 78]

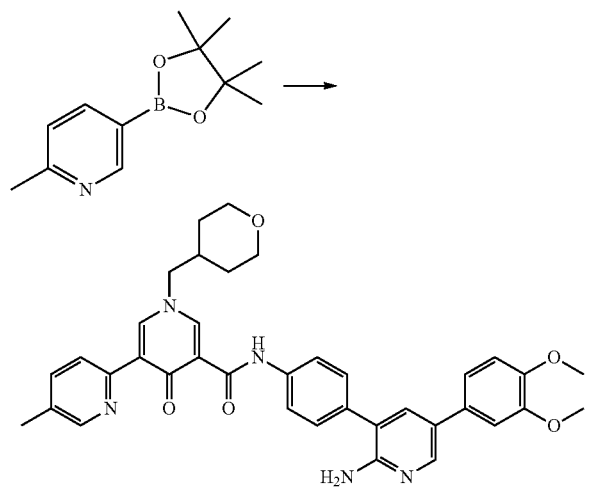

To N-{4-[2-amino-5-(3,4-dimethoxyphenyl)pyridin-3-yl]phenyl}-5-bromo-4-oxo-1-(tetrahydro-2H-pyran-4-ylmethyl)-1,4-dihydropyridine-3-carboxamide (0.400 g, 0.646 mmol), 2-methyl-5-(4,4,5,5-tetramethyl-1,3,2-dioxaborolan-2-yl)pyridine (0.212 g, 0.969 mmol), cesium carbonate (0.631 g, 1.94 mmol), and [1,1'-bis(diphenylphosphino)ferrocene]palladium(II) dichloride-methylene chloride complex (1:1) (0.0527 g, 0.0646 mmol), 1,4-dioxane (5.00 mL) and water (1.00 mL) were added under a nitrogen atmosphere, and the mixture was stirred at 80° C. for 4 hours. The reaction mixture was left to cool to room temperature, and then, water and ethyl acetate were added thereto. Insoluble matter was filtered off. The filtrate was subjected to extraction with ethyl acetate three times. The organic layer was washed with brine and then dried over anhydrous sodium sulfate. After filtration and concentration under reduced pressure, the residue obtained was purified by amino silica gel column chromatography (Yamazen Corp., ethyl acetate/methanol=99/1→90/10) and further purified by silica gel column chromatography (Yamazen Corp., ethyl acetate/methanol=99/1→5/95). After concentration under reduced pressure, the residue was purified by high-performance liquid chromatography (NOMURA Develosil Combi, acetonitrile/water/0.1% formic acid). The organic solvent was distilled off under reduced pressure, and then, a saturated aqueous solution of sodium bicarbonate was added to the residue, followed by extraction with ethyl acetate three times. The organic layer was washed with brine and then dried over anhydrous sodium sulfate. Filtration and concentration under reduced pressure were carried out to obtain the title compound (0.129 g, yield: 31.6%) as an amorphous solid.

$^1$H-NMR (DMSO-D$_6$) δ: 13.08 (1H, s), 8.76 (1H, d, J=2.4 Hz), 8.69 (1H, d, J=2.4 Hz), 8.51-8.47 (2H, m), 8.26 (1H, d, J=2.4 Hz), 7.84 (2H, d, J=8.5 Hz), 7.71 (1H, dd, J=8.5, 2.4 Hz), 7.62 (1H, d, J=2.4 Hz), 7.55 (2H, d, J=8.5 Hz), 7.20-7.14 (2H, m), 6.99 (1H, d, J=8.5 Hz), 5.69 (2H, s), 4.20 (2H, d, J=7.3 Hz), 3.88-3.83 (5H, m), 3.77 (3H, s), 3.27 (2H, t, J=11.3 Hz), 2.36 (3H, s), 2.11-2.03 (1H, m), 1.47 (2H, br d, J=11.0 Hz), 1.37-1.26 (2H, m).

MS (APCI) m/z: 632 [(M+H)$^+$].

Similarly, the final compounds of Table 22 were synthesized from the corresponding starting materials.

TABLE 22

| Example No. | Structural formula for Example Instrumental data on Example | Structural formula of starting material |
| --- | --- | --- |
| Example 117 | (structure shown) $^1$H-NMR (DMSO-D$_6$) δ: 12.92 (1H, s), 8.77 (1H, d, J = 2.4 Hz), 8.36 (1H, d, J = 2.4 Hz), 8.25 (1H, d, J = 2.4 Hz), 7.96-7.91 (4H, m), 7.82 (2H, d, J = 8.5 Hz), 7.61-7.52 (3H, m), 7.19-7.13 (2H, m), 6.99 (1H, d, J = 8.5 Hz), 5.68 (2H, s), 4.12 (2H, d, J = 7.3 Hz), 3.89-3.83 (5H, m), 3.77 (3H, s), 3.27 (2H, t, J = 11.2 Hz), 2.17-2.06 (1H, m), 1.47 (2H, br d, J = 10.9 Hz), 1.37-1.27 (2H, m). MS (APCI) m/z: 642 [(M + H)$^+$]. | (structure shown) |

TABLE 22-continued

| Example No. | Structural formula for Example Instrumental data on Example | Structural formula of starting material |
|---|---|---|
| Example 118 | 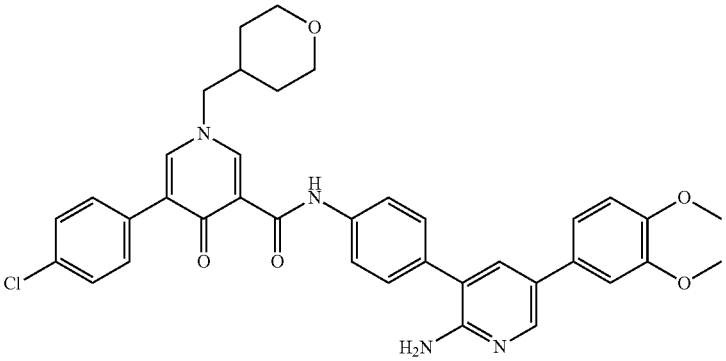<br>$^1$H-NMR (DMSO-D$_6$) δ: 13.01 (1H, s), 8.75 (1H, d, J = 2.4 Hz), 8.27-8.25 (2H, m), 7.82 (2H, d, J = 8.5 Hz), 7.74 (2H, d, J = 8.5 Hz), 7.61 (1H, d, J = 2.4 Hz), 7.54-7.52 (4H, m), 7.19-7.13 (2H, m), 6.99 (1H, d, J = 8.5 Hz), 5.69 (2H, s), 4.11 (2H, d, J = 7.3 Hz), 3.88-3.83 (5H, m), 3.77 (3H, s), 3.27 (2H, t, J = 11.2 Hz), 2.17-2.05 (1H, m), 1.46 (2H, br d, J = 11.5 Hz), 1.36-1.26 (2H, m).<br>MS (APCI) m/z: 651 [(M + H)$^+$]. | 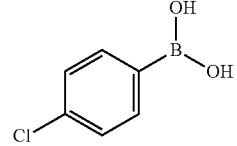 |

(Example 119) N-{4-[2-Amino-5-(3,4-dimethoxyphenyl)pyridin-3-yl]phenyl}-5-(5-methylthiophen-2-yl)-4-oxo-1-(tetrahydro-2H-pyran-4-ylmethyl)-1,4-dihydropyridine-3-carboxamide

[Formula 79]

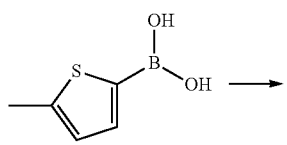 →

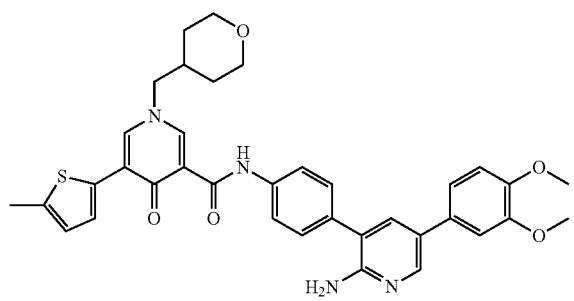

To N-{4-[2-amino-5-(3,4-dimethoxyphenyl)pyridin-3-yl]phenyl}-5-bromo-4-oxo-1-(tetrahydro-2H-pyran-4-ylmethyl)-1,4-dihydropyridine-3-carboxamide (0.200 g, 0.323 mmol), (5-methyl-2-thienyl)boronic acid (0.055 g, 0.387 mmol), potassium carbonate (0.134 g, 0.969 mmol), and tetrakis(triphenylphosphine)palladium(0) (0.0373 g, 0.0323 mmol), 1,2-dimethoxyethane (5.00 mL) and water (0.500 mL) were added, and the mixture was stirred at 90° C. for 12 hours and then left to cool. To the reaction mixture, water was added, followed by extraction with methylene chloride three times. The organic layer was dried over anhydrous sodium sulfate. After filtration and concentration under reduced pressure, the residue obtained was purified by silica gel column chromatography (Yamazen Corp., ethyl acetate/methanol=99/1→80/20) and purified by amino silica gel column chromatography (Yamazen Corp., ethyl acetate/methanol=99/1→93/7). The resulting compound was further purified by high-performance liquid chromatography (NOMURA Develosil Combi, acetonitrile/water/0.1% formic acid) to obtain the title compound (0.0860 g, yield: 41.8%) as a solid.

$^1$H-NMR (DMSO-D$_6$) δ: 12.90 (1H, s), 8.69-8.66 (2H, m), 8.26 (1H, d, J=2.4 Hz), 7.84 (2H, d, J=8.5 Hz), 7.62 (1H, d, J=2.4 Hz), 7.57-7.54 (3H, m), 7.20-7.14 (2H, m), 6.99 (1H, d, J=8.5 Hz), 6.87-6.85 (1H, m), 5.70 (2H, s), 4.14 (2H, d, J=7.3 Hz), 3.88-3.83 (5H, m), 3.77 (3H, s), 3.27 (2H, t, J=10.9 Hz), 2.49 (3H, s), 2.16-2.10 (1H, m), 1.45 (2H, br d, J=10.9 Hz), 1.38-1.27 (2H, m).

MS (APCI) m/z: 637 [(M+H)$^+$].

Similarly, the final compound of Table 23 was synthesized from the corresponding starting material.

TABLE 23

| Example No. | Structural formula for Example Instrumental data on Example | Structural formula of starting material |
|---|---|---|
| Example 120 | 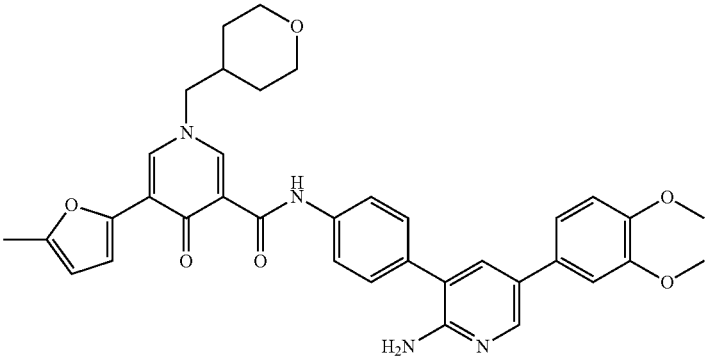<br>$^1$H-NMR (DMSO-D$_6$) δ: 12.97 (1H, s), 8.68 (1H, d, J = 2.4 Hz), 8.36 (1H, d, J = 2.4 Hz), 8.26 (1H, d, J = 2.4 Hz), 7.84 (2H, d, J = 8.5 Hz), 7.62-7.53 (3H, m), 7.35 (1H, d, J = 2.4 Hz), 7.20-7.14 (2H, m), 6.99 (1H, d, J = 8.5 Hz), 6.26-6.25 (1H, m), 5.70 (2H, s), 4.19 (2H, d, J = 7.3 Hz), 3.88-3.83 (5H, m), 3.77 (3H, s), 3.27 (2H, t, J = 10.9 Hz), 2.38 (3H, s), 2.13-2.04 (1H, m), 1.44 (2H, br d, J = 10.3 Hz), 1.37-1.27 (2H, m).<br>MS (APCI) m/z: 621 [(M + H)$^+$]. | 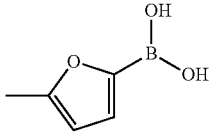 |

(Example 121) N-[4-(2-Amino-5-{4-[(2R)-1,4-dioxan-2-ylmethoxy]-3-methoxyphenyl}pyridin-3-yl)-3-fluorophenyl]-1'-[(4-cyanotetrahydro-2H-pyran-4-yl)methyl]-5-methyl-4'-oxo-1',4'-dihydro-2,3'-bipyridine-5'-carboxamide

[Formula 80]

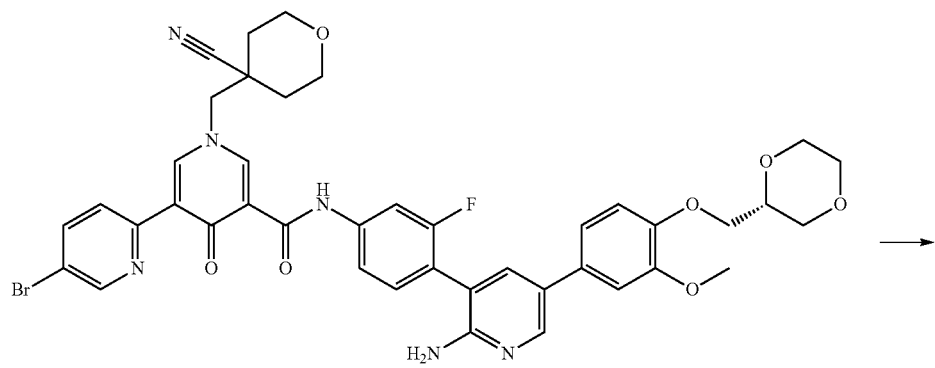

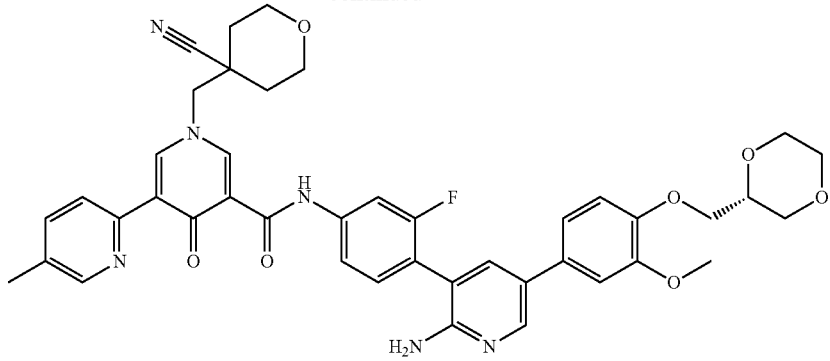

-continued

To N-[4-(2-amino-5-{4-[(2R)-1,4-dioxan-2-ylmethoxy]-3-methoxyphenyl}pyridin-3-yl)-3-fluorophenyl]-5-bromo-1'-[(4-cyanotetrahydro-2H-pyran-4-yl)methyl]-4'-oxo-1',4'-dihydro-2,3'-bipyridine-5'-carboxamide (0.230 g, 0.279 mmol), [1,1'-bis(diphenylphosphino)ferrocene]palladium (II) dichloride-methylene chloride complex (1:1) (0.0228 g, 0.0279 mmol), and cesium carbonate (0.272 g, 0.836 mmol), 1,4-dioxane (5.00 mL), water (0.500 mL), and a 50% solution of trimethylboroxine in tetrahydrofuran (3.5 mol/L, 0.0960 mL, 0.334 mmol) were added under a nitrogen atmosphere, and the mixture was stirred at 100° C. for 3.5 hours. The reaction mixture was left to cool to room temperature, and then, a saturated aqueous solution of sodium bicarbonate and ethyl acetate were added thereto. Insoluble matter was filtered off. The filtrate was subjected to extraction with ethyl acetate three times. The organic layer was washed with brine and then dried over anhydrous sodium sulfate. After filtration and concentration under reduced pressure, the residue obtained was purified by silica gel column chromatography (Yamazen Corp., ethyl acetate/methanol=99/1→80/20) and then further purified by amino silica gel column chromatography (Yamazen Corp., ethyl acetate/methanol=99/1→93/7) to obtain the title compound (0.145 g, yield: 68.4%) as an amorphous solid.

$^1$H-NMR (DMSO-D$_6$) δ: 13.07 (1H, s), 8.86 (1H, d, J=2.4 Hz), 8.80 (1H, d, J=2.4 Hz), 8.52-8.48 (2H, m), 8.31 (1H, d, J=2.4 Hz), 7.94 (1H, dd, J=12.1, 2.4 Hz), 7.72 (1H, dd, J=8.2, 2.4 Hz), 7.63 (1H, d, J=2.4 Hz), 7.50-7.42 (2H, m), 7.18 (1H, d, J=2.4 Hz), 7.11 (1H, dd, J=8.5, 2.4 Hz), 6.99 (1H, d, J=8.5 Hz), 5.71 (2H, s), 4.70 (2H, s), 3.97-3.74 (10H, m), 3.69-3.60 (2H, m), 3.52-3.32 (4H, m), 2.36 (3H, s), 1.88-1.77 (4H, m).

MS (APCI) m/z: 761 [(M+H)$^+$].

Similarly, the final compounds of Table 24 were synthesized from the corresponding starting materials.

TABLE 24

| Example No. | Structural formula for Example<br>Instrumental data on Example |
|---|---|
| Example 122 | ![structure]<br>$^1$H-NMR (CDCl$_3$) δ: 12.84 (1H, s), 8.74 (2H, s), 8.61 (1H, d, J = 2.4 Hz), 8.27 (1H, d, J = 2.4 Hz), 8.21 (1H, d, J = 2.4 Hz), 7.89 (2H, d, J = 8.5 Hz), 7.59 (1H, d, J = 2.4 Hz), 7.49 (2H, d, J = 8.5 Hz), 7.09 (1H, dd, J = 8.2, 2.1 Hz), 7.04 (1H, d, J = 1.8 Hz), 6.94 (1H, d, J = 8.5 Hz), 4.72-4.64 (2H, m), 4.07-3.99 (2H, m), 3.97-3.89 (10H, m), 3.39 (2H, t, J = 11.8 Hz), 2.39 (3H, s), 2.21-2.09 (1H, m), 1.69-1.58 (2H, m), 1.53-1.39 (2H, m).<br>MS (APCI) m/z: 633 [(M + H)$^+$]. |

TABLE 24-continued
| Example 123 | 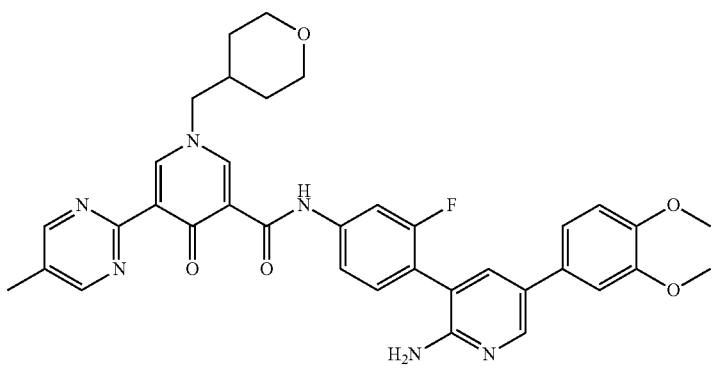 |
¹H-NMR (CDCl₃) δ: 12.96 (1H, s), 8.74 (2H, s), 8.60 (1H, d, J = 2.4 Hz), 8.32 (1H, d, J = 2.4 Hz), 8.21 (1H, d, J = 2.4 Hz), 7.93 (1H, dd, J = 12.1, 1.8 Hz), 7.59 (1H, d, J = 1.8 Hz), 7.47 (1H, dd, J = 8.5, 1.8 Hz), 7.37 (1H, t, J = 8.2 Hz), 7.09 (1H, dd, J = 8.2, 2.1 Hz), 7.03 (1H, d, J = 2.4 Hz), 6.93 (1H, d, J = 7.9 Hz), 4.59-4.52 (2H, m), 4.07-4.00 (2H, m), 3.97-3.89 (8H, m), 3.44-3.35 (2H, m), 2.39 (3H, s), 2.21-2.08 (1H, m), 1.66-1.54 (2H, m), 1.52-1.39 (2H, m).
MS (APCI) m/z: 651 [(M + H)⁺].
| Example No. | Structural formula of starting material |
|---|---|
| Example 122 | 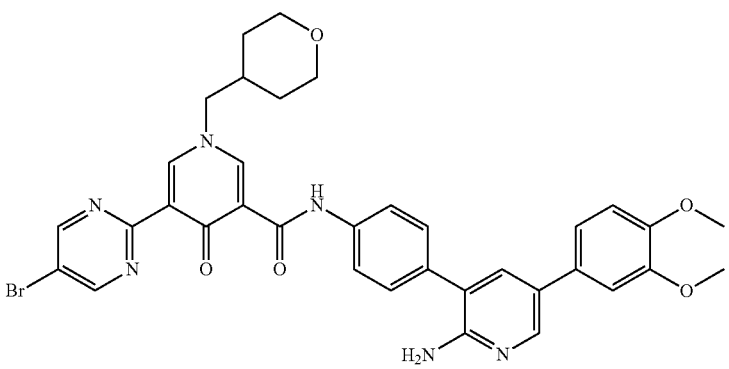 [SMILES: COc1ccc(-c2cnc(N)c(-c3ccc(NC(=O)c4cn(CC5CCOCC5)cc(-c5ncc(Br)cn5)c4=O)cc3)c2)cc1OC] |
| Example 123 | 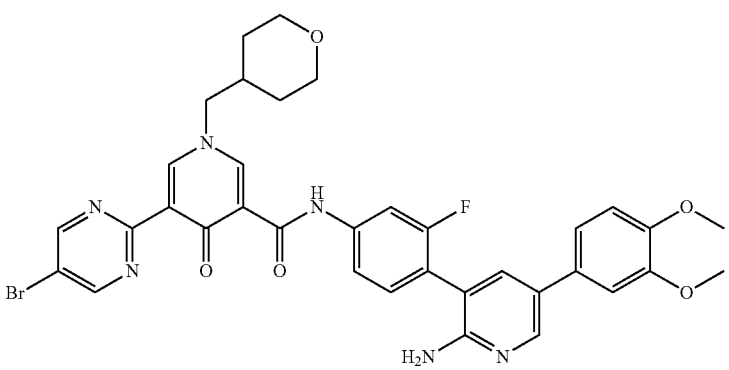 [SMILES: COc1ccc(-c2cnc(N)c(-c3ccc(NC(=O)c4cn(CC5CCOCC5)cc(-c5ncc(Br)cn5)c4=O)cc3F)c2)cc1OC] |

(Example 124) N-[4-(2-Amino-5-{4-[(2R)-1,4-di-oxan-2-ylmethoxy]-3-methoxyphenyl}pyridin-3-yl)-3-fluorophenyl]-5-methyl-4-oxo-1'-(tetrahydro-2H-pyran-4-ylmethyl)-1',4-dihydro-2,3'-bipyridine-5'-carboxamide methanesulfonate (amorphous solid)

[Formula 81]

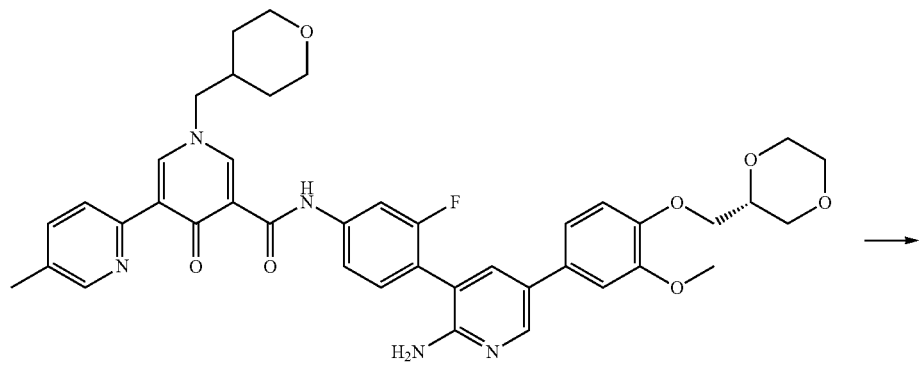

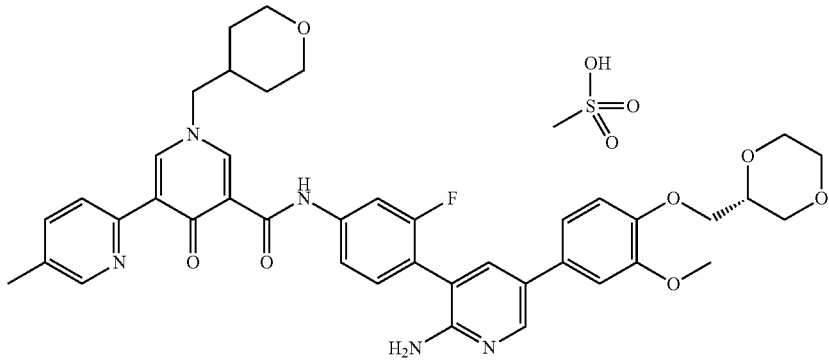

To a solution of N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide (23.9 g, 32.5 mmol) in methylene chloride (110 mL), a solution of methanesulfonic acid (2.11 mL, 3.12 g, 32.5 mmol) in ethanol (36.0 mL) was added, and the mixture was stirred at room temperature for 15 minutes. The reaction mixture was concentrated under reduced pressure. Then, the amorphous solid obtained was suspended in ethyl acetate, collected by filtration, and dried to obtain the title compound (25.7 g, yield: 95.1%) as an amorphous solid.

1H-NMR (DMSO-D6) δ: 13.27 (1H, s), 8.79 (1H, d, J=2.4 Hz), 8.72 (1H, d, J=2.4 Hz), 8.54 (1H, d, J=2.4 Hz), 8.46 (1H, d, J=8.5 Hz), 8.34 (1H, d, J=2.4 Hz), 8.29 (1H, d, J=2.4 Hz), 8.03-7.99 (1H, m), 7.78 (1H, d, J=8.5 Hz), 7.59-7.51 (4H, m), 7.31 (1H, d, J=2.4 Hz), 7.25 (1H, dd, J=8.5, 2.4 Hz), 7.06 (1H, d, J=8.5 Hz), 4.21 (2H, d, J=7.3 Hz), 4.01-3.93 (2H, m), 3.90-3.74 (8H, m), 3.69-3.24 (6H, m), 2.37 (3H, s), 2.34 (3H, s), 2.13-2.02 (1H, m), 1.47 (2H, br d, J=10.9 Hz), 1.37-1.28 (2H, m).

MS (APCI) m/z: 736 [(M+H)$^+$].

Elemental analysis values for $C_{41}H_{42}FN_5O_7 \cdot 1.0CH_3SO_3H \cdot 1.0H_2O$ Calcd: C, 59.35; H, 5.69; N, 8.24; F, 2.24; S, 3.77.
Found: C, 59.38; H, 5.80; N, 8.10; F, 2.23; S, 3.71.

Similarly, each mesylate of Table 25 was obtained as an amorphous solid from the corresponding starting materials.

TABLE 25

| Example No. | Structural formula for Example<br>Instrumental data on Example |
|---|---|
| Example 125 | (amorphous solid)<br>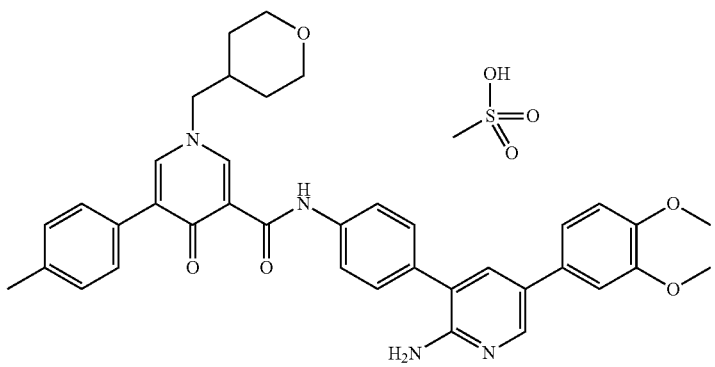<br>$^1$H-NMR (DMSO-D$_6$ δ: 13.70 (1H, br s), 13.23 (1H, s), 8.73 (1H, d, J = 1.8 Hz), 8.29 (1H, d, J = 1.8 Hz), 8.24 (1H, d, J = 1.8 Hz), 8.19 (1H, d, J = 1.8 Hz), 7.90 (2H, d, J = 8.5 Hz), 7.65-7.56 (6H, m), 7.32-7.26 (4H, m), 7.05 (1H, d, J = 8.5 Hz), 4.12 (2H, d, J = 7.5 Hz), 3.90-3.84 (5H, m), 3.80 (3H, s), 3.27 (2H, t, J = 11.0 Hz), 2.36 (3H, s), 2.35 (3H, s), 2.17-2.04 (1H, m), 1.46 (2H, d, J = 11.0 Hz), 1.38-1.25 (2H, m).<br>MS (APCI) m/z: 631[(M + H)$^+$].<br>Elemental analysis values for C$_{38}$H$_{38}$N$_4$O$_5$•1.0CH$_3$SO$_3$H•2.1H$_2$O<br>Calcd: C, 61.26; H, 6.09; N, 7.33; S, 4.19.<br>Found: C, 60.99; H, 5.96; N, 7.13; S; 4.48. |
| Example 126 | (amorphous solid)<br>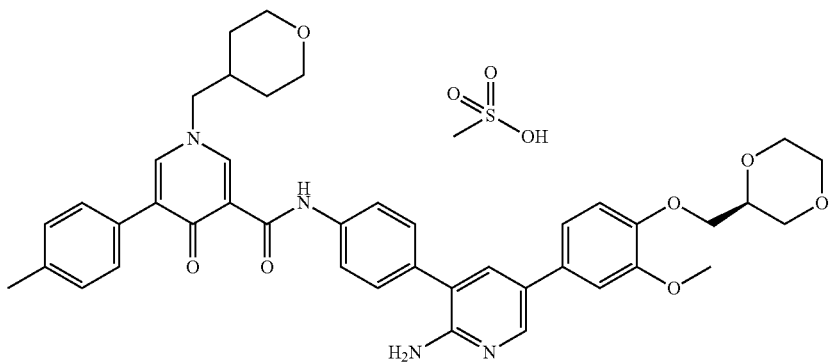<br>$^1$H-NMR (CDCl$_3$) δ: 12.97 (1H, s), 8.65 (1H, br s), 7.95 (2H, d, J = 8.5 Hz), 7.91-7.85 (2H, m), 7.53 (1H, d, J = 2.4 Hz), 7.44 (4H, dd, J = 18.5, 8.2 Hz), 7.30 (2H, d, J = 7.9 Hz), 7.02-6.95 (2H, m), 6.93 (1H, d, J = 1.8 Hz), 4.11-3.92 (9H, m), 3.90 (3H, s), 3.88-3.63 (5H, m), 3.59-3.51 (1H, m), 3.44-3.34 (2H, m), 2.91 (3H, s), 2.41 (3H, s), 2.20-2.06 (1H, m), 1.65-1.57 (2H, m), 1.52-1.38 (2H, m)<br>MS (ESI) m/z: 717 [(M + H)$^+$]. |

| Example 127 | 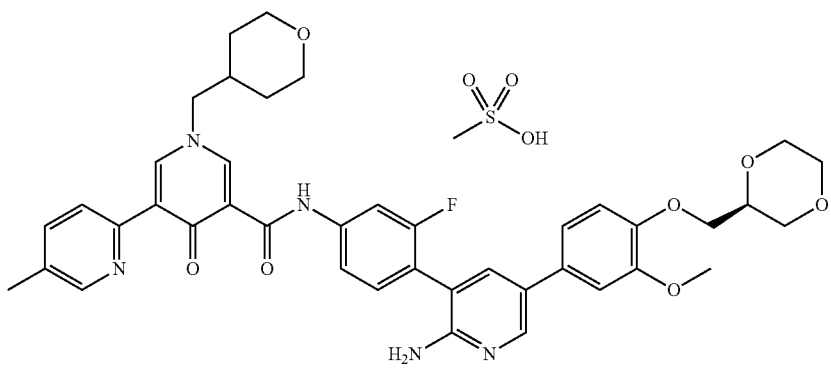 (amorphous solid) |
|---|---|
¹H-NMR (DMSO-D₆) δ: 13.22 (1H, s), 8.80 (1H, d, J = 2.4 Hz), 8.75 (1H, d, J = 2.4 Hz), 8.56 (1H, s), 8.45 (1H, d, J = 8.5 Hz), 8.35-8.32 (2H, m), 8.03-8.00 (1H, m), 7.84-7.83 (1H, m), 7.69 (2H, s), 7.56-7.52 (2H, m), 7.32-7.24 (2H, m), 7.06 (1H, d, J = 8.5 Hz), 4.22 (2H, d, J = 7.3 Hz), 4.05-3.60 (12H, m), 3.52-3.37 (2H, m), 3.27 (2H, t, J = 10.9 Hz), 2.39 (3H, s), 2.34 (3H, s), 2.14-2.03 (1H, m), 1.47 (2H, br d, J = 10.9 Hz), 1.37-1.27 (2H, m).
MS (APCI) m/z: 736 [(M + H)⁺].
| Example 128 | 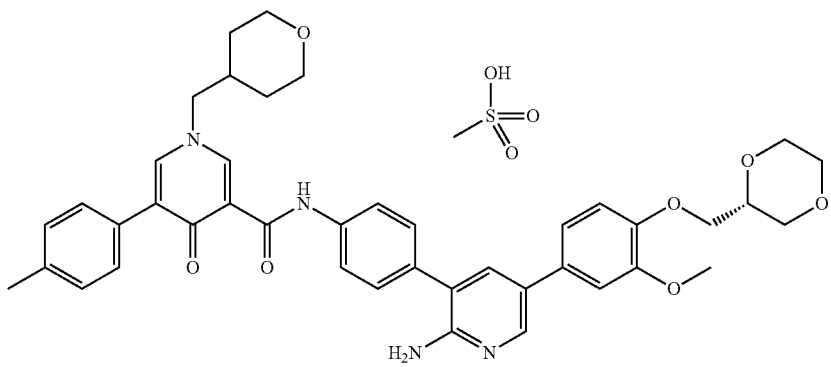 (amorphous solid) |
|---|---|
¹H-NMR (DMSO-D₆) δ: 13.74 (1H, br s), 13.23 (1H, s), 8.73 (1H, d, J = 2.4 Hz), 8.30 (1H, d, J = 2.4 Hz), 8.23 (1H, d, J = 2.4 Hz), 8.19 (1H, d, J = 2.4 Hz), 7.90 (2H, d, J = 8.5 Hz), 7.71-7.55 (6H, m), 7.35-7.25 (4H, m), 7.06 (1H, d, J = 8.5 Hz), 4.12 (2H, d, J = 7.5 Hz), 4.04-3.24 (16H, m), 2.38 (3H, s), 2.36 (3H, s), 2.17-2.04 (1H, m), 1.46 (2H, d, J = 11.0 Hz), 1.38-1.25 (2H, m).
MS (APCI) m/z: 717 [(M + H)⁺].
Elemental analysis values for C₄₂H₄₄N₄O₇•1.0CH₃SO₃H•1.0H₂O
Calcd: C, 62.15; H, 6.06; N, 6.74; S, 3.86.
Found: C, 62.13; H, 6.21; N, 6.64; S; 3.86.

TABLE 25-continued
| Example 129 | (amorphous solid) |
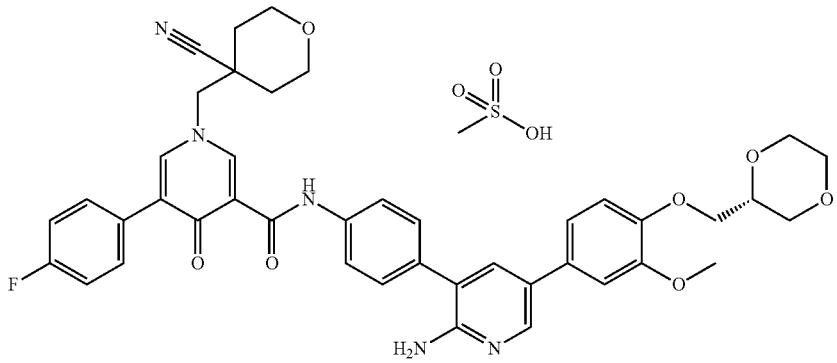
¹H-NMR (CDCl₃) δ: 12.79 (1H, br s), 8.64 (1H, br s), 7.88-7.80 (2H, m), 7.80-7.73 (2H, m), 7.62 (2H, dd, J = 8.5, 5.5 Hz), 7.37 (2H, d, J = 8.5 Hz), 7.16 (2H, t, J = 8.5 Hz), 7.02-6.94 (2H, m), 6.94-6.90 (1H, m), 4.41 (2H, s), 4.09-3.91 (8H, m), 3.91-3.62 (10H, m), 3.59-3.51 (1H, m), 2.94 (3H, s), 2.08-1.94 (2H, m), 1.92-1.82 (2H, m).
MS (APCI) m/z: 746 [(M + H)⁺].
Elemental analysis values for $C_{42}H_{40}FN_5O_7$•2.0CH₃SO₃H•1.0H₂O
Calcd: C, 58.83; H, 5.51; N, 7.98; F, 2.16; S, 3.65.
Found: C, 59.02; H, 5.65; N, 7.69; F, 2.13; S; 3.88.
| Example No. | Structural formula of starting material |
|---|---|
| Example 125 | 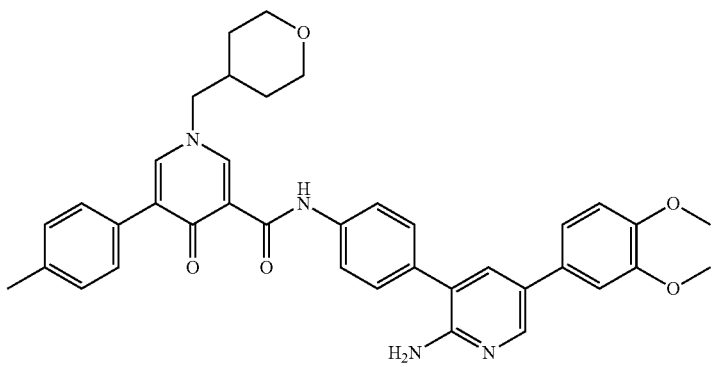 |
| Example 126 | 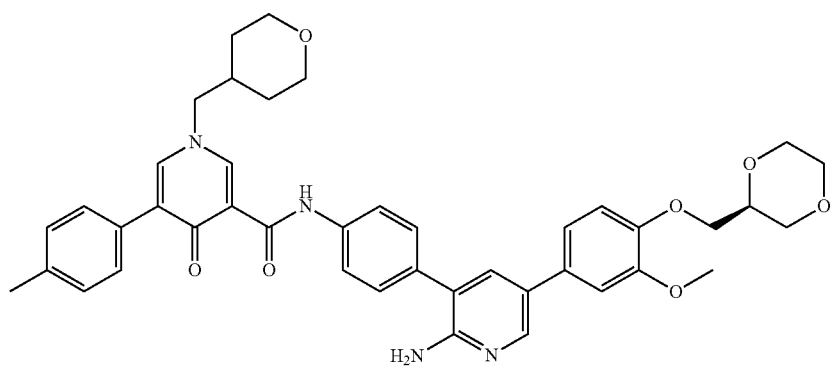 [SMILES: COc1cc(-c2cnc(N)c(-c3ccc(NC(=O)c4cn(CC5CCOCC5)cc(-c5ccc(C)cc5)c4=O)cc3)c2)ccc1OC[C@@H]1COCCO1] |

TABLE 25-continued

Example 127

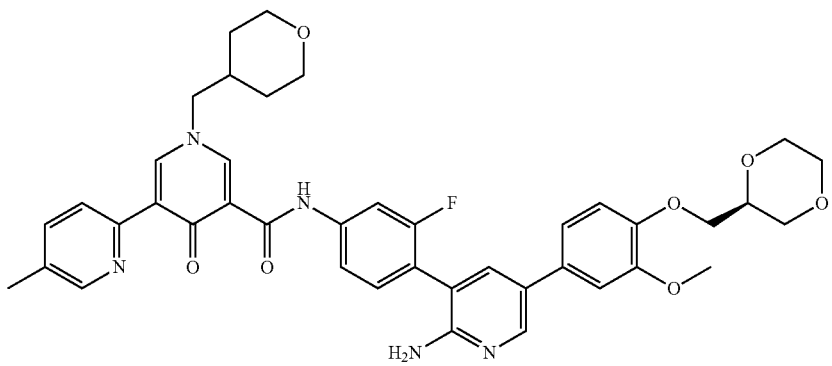 [SMILES: COc1cc(-c2cnc(N)c(-c3ccc(NC(=O)c4cn(CC5CCOCC5)cc(-c5ccc(C)cn5)c4=O)cc3F)c2)ccc1OC[C@@H]1COCCO1]

Example 128

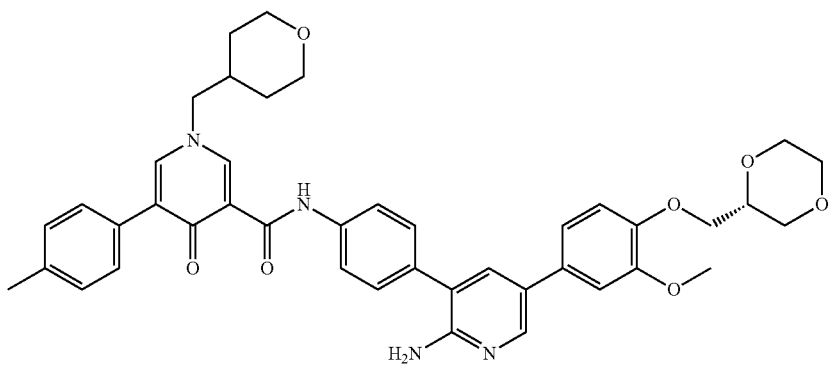 [SMILES: COc1cc(-c2cnc(N)c(-c3ccc(NC(=O)c4cn(CC5CCOCC5)cc(-c5ccc(C)cc5)c4=O)cc3)c2)ccc1OC[C@H]1COCCO1]

Example 129

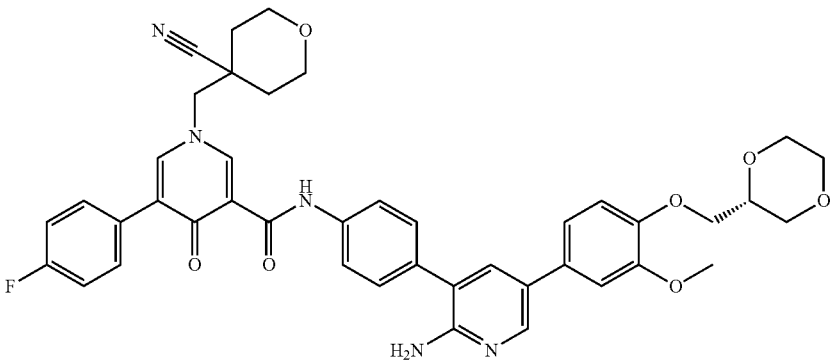 [SMILES: COc1cc(-c2cnc(N)c(-c3ccc(NC(=O)c4cn(CC5(C#N)CCOCC5)cc(-c5ccc(F)cc5)c4=O)cc3)c2)ccc1OC[C@H]1COCCO1]

Hereinafter, N-[4-(2-amino-5-{4-[(2R)-1,4-dioxan-2-yl-methoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide is the compound of Example 1, and N-[4-(2-amino-5-{4-[(2R)-1,4-dioxan-2-yl-methoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide is the compound of Example 34.

(Example 130) N-[4-(2-Amino-5-{4-[(2R)-1,4-di-oxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide methanesulfonate hydrate

[Formula 82]

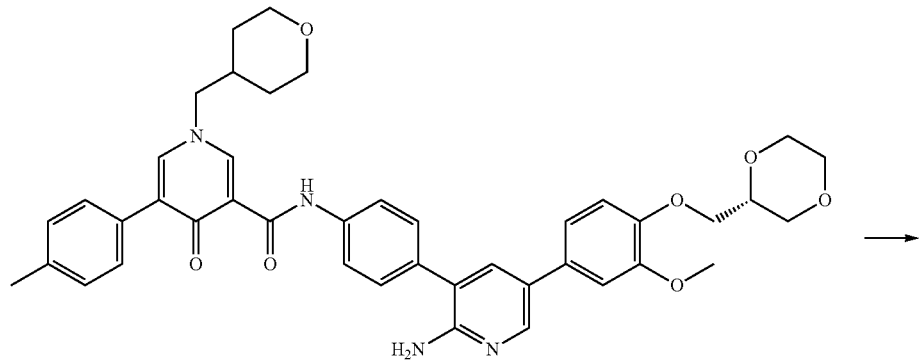

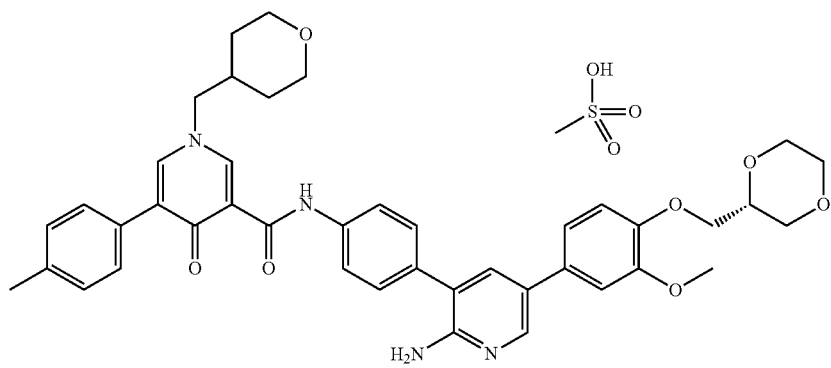

N-[4-(2-Amino-5-{4-[(2R)-1,4-dioxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydro-pyridine-3-carboxamide (46.3 g, 62.6 mmol) was suspended in acetone (244 ml). To the suspension, water (27.0 ml) was added. Methanesulfonic acid (4.27 ml, 65.8 mmol) was added in small portions to the mixture. The reaction mixture was stirred at room temperature for 30 hours and then suction-filtered with a Buchner funnel. The solid collected by filtration was washed with a water/acetone mixture (water/acetone=1/9) to obtain the title compound (47.5 g, yield: 87.5%) as a crystalline solid.

$^1$H-NMR (DMSO-D$_6$) δ: 13.22 (1H, s), 8.72 (1H, d, J=2.0 Hz), 8.28 (1H, d, J=2.0 Hz), 8.21 (1H, d, J=2.0 Hz), 8.19 (1H, d, J=2.0 Hz), 7.90 (2H, d, J=8.5 Hz), 7.60-7.52 (6H, m), 7.32 (1H, d, J=2.0 Hz), 7.27 (3H, d, J=8.5 Hz), 7.06 (1H, d, J=8.5 Hz), 4.11 (2H, d, J=7.5 Hz), 4.01-3.93 (2H, m), 3.89-3.22 (14H, m), 2.36 (3H, s), 2.32 (3H, s), 2.17-2.04 (1H, m), 1.46 (2H, d, J=11.0 Hz), 1.37-1.25 (2H, m).

MS (APCI) m/z: 717 [(M+H)$^+$].

Elemental analysis values for $C_{42}H_{44}N_4O_7 \cdot 1.0CH_3SO_3H \cdot 3.0H_2O$
Calcd: C, 59.57; H, 6.28; N, 6.46; S, 3.70.
Found: C, 59.75; H, 6.29; N, 6.48; S, 3.76.

The powder X-ray diffraction (CuKα, λ=1.54 angstroms, scanning rate=20°/min) pattern is shown in FIG. 1, and peaks having a relative intensity of 22 or more with the maximum peak intensity defined as 100 are shown in Table 26.

TABLE 26

| Peak No. | 2θ | d value | Relative intensity |
|---|---|---|---|
| 1 | 3.74 | 23.61 | 42 |
| 2 | 7.56 | 11.68 | 49 |
| 3 | 8.96 | 9.86 | 30 |
| 4 | 11.38 | 7.77 | 100 |
| 5 | 12.36 | 7.16 | 24 |
| 6 | 14.78 | 5.99 | 24 |
| 7 | 15.60 | 5.68 | 22 |
| 8 | 16.16 | 5.48 | 23 |
| 9 | 18.70 | 4.74 | 45 |
| 10 | 24.10 | 3.69 | 35 |

(Example 131) N-[4-(2-Amino-5-{4-[(2R)-1,4-di-oxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide hydrobromide hydrate

[Formula 83]

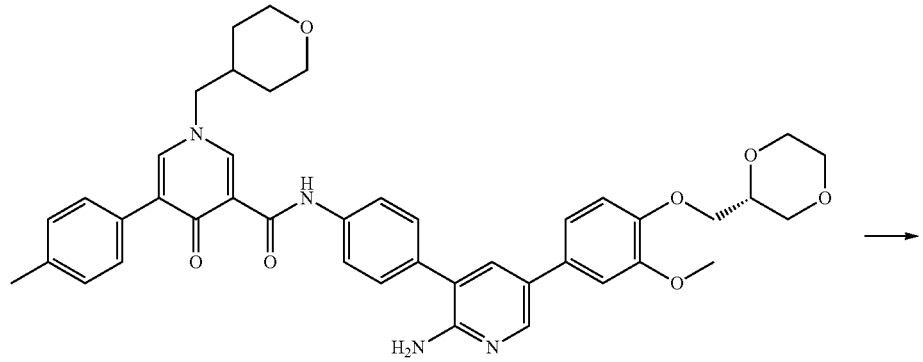

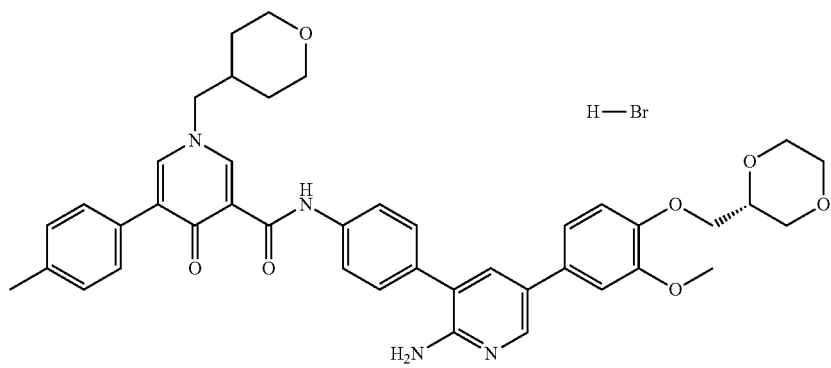

To N-[4-(2-amino-5-{4-[(2R)-1,4-dioxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide (250 mg, 349 μmol), methanol (3.99 ml) and water (633 μl) were added. Then, a 1.00 mol/L aqueous hydrobromic acid solution (365 μl, 365 μmol) was added thereto. The mixture was stirred at 40° C. for approximately 21 hours and subsequently at room temperature for approximately 30 minutes and suction-filtered with a Kiriyama funnel, and the deposited solid was collected by filtration. Then, the solid was dried in air to obtain the title compound (243 mg, yield: 81.4%) as a crystalline solid.

$^1$H-NMR (DMSO-D$_6$) δ: 13.22 (1H, s), 8.72 (1H, d, J=2.5 Hz), 8.28 (1H, d, J=2.5 Hz), 8.21 (1H, d, J=2.5 Hz), 8.19 (1H, d, J=2.5 Hz), 7.90 (2H, d, J=8.8 Hz), 7.60-7.55 (4H, m), 7.50 (2H, br s), 7.31 (1H, d, J=2.5 Hz), 7.29-7.23 (3H, m), 7.06 (1H, d, J=8.8 Hz), 4.12 (2H, d, J=7.5 Hz), 4.01-3.93 (2H, m), 3.89-3.24 (14H, m), 2.36 (3H, s), 2.16-2.05 (1H, m), 1.46 (2H, d, J=12.5 Hz), 1.37-1.25 (2H, m).

Elemental analysis values for C$_{42}$H$_{44}$N$_4$O$_7$.1HBr.3.3H$_2$O
Calcd: C, 58.85; H, 6.07; N, 6.53; Br, 9.32.
Found: C, 58.91; H, 5.98; N, 6.58; Br, 9.42.

The powder X-ray diffraction (CuKα, λ=1.54 angstroms, scanning rate=20°/min) pattern is shown in FIG. 2, and peaks having a relative intensity of 19 or more with the maximum peak intensity defined as 100 are shown in Table 27.

TABLE 27

| Peak No. | 2θ | d value | Relative intensity |
|---|---|---|---|
| 1 | 3.84 | 22.99 | 61 |
| 2 | 7.72 | 11.44 | 99 |
| 3 | 9.40 | 9.40 | 60 |
| 4 | 11.62 | 7.61 | 100 |
| 5 | 14.92 | 5.93 | 19 |
| 6 | 15.48 | 5.72 | 49 |
| 7 | 16.70 | 5.30 | 50 |
| 8 | 18.88 | 4.70 | 34 |
| 9 | 19.32 | 4.59 | 22 |
| 10 | 24.40 | 3.65 | 32 |

(Example 132) N-[4-(2-Amino-5-{4-[(2R)-1,4-di-oxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide nitrate hydrate Elemental analysis values for $C_{42}H_{44}N_4O_7 \cdot 1HNO_3 \cdot 3H_2O$
Calcd: C, 60.49; H, 6.16; N, 8.40.
Found: C, 60.58; H, 6.15; N, 8.43.

The powder X-ray diffraction (CuKα, λ=1.54 angstroms, scanning rate=20°/min) pattern is shown in FIG. 3, and peaks having a relative intensity of 34 or more with the maximum peak intensity defined as 100 are shown in Table 28.

[Formula 84]

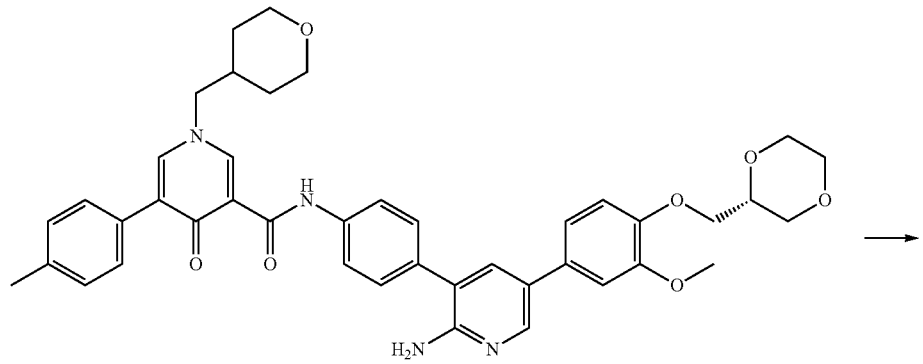

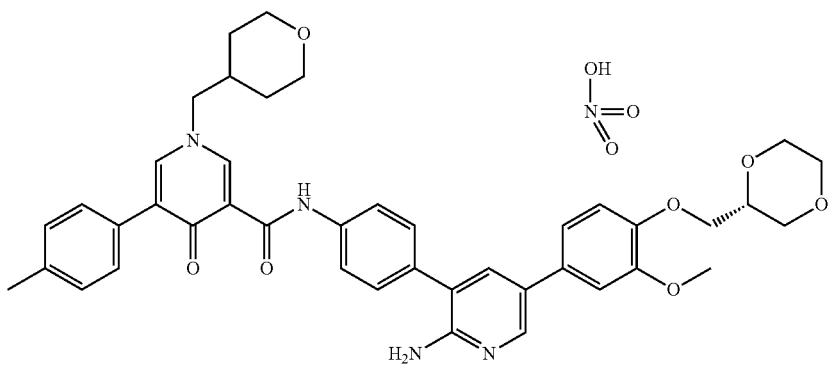

To N-[4-(2-amino-5-{4-[(2R)-1,4-dioxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide (249 mg, 347 μmol), methanol (1.49 ml) and water (9.10 μl) were added. Then, a 1.00 mol/L aqueous nitric acid solution (364 μl, 364 μmol) was added thereto. The mixture was stirred at 40° C. for approximately 21 hours and subsequently at room temperature for approximately 30 minutes and suction-filtered with a Kiriyama funnel, and the deposited solid was collected by filtration. Then, the solid was dried in air to obtain the title compound (252 mg, yield: 87.0%) as a crystalline solid.

$^1$H-NMR (DMSO-D$_6$) δ: 13.22 (1H, s), 8.72 (1H, d, J=2.5 Hz), 8.27 (1H, d, J=2.5 Hz), 8.21 (1H, d, J=2.5 Hz), 8.19 (1H, d, J=2.5 Hz), 7.90 (2H, d, J=8.8 Hz), 7.60-7.55 (4H, m), 7.49 (2H, br s), 7.31 (1H, d, J=2.4 Hz), 7.29-7.24 (3H, m), 7.06 (1H, d, J=8.8 Hz), 4.11 (2H, d, J=7.5 Hz), 4.01-3.93 (2H, m), 3.90-3.22 (14H, m), 2.36 (3H, s), 2.17-2.04 (1H, m), 1.46 (2H, d, J=12.5 Hz), 1.38-1.26 (2H, m).

TABLE 28

| Peak No. | 2θ | d value | Relative intensity |
|---|---|---|---|
| 1 | 3.82 | 23.11 | 52 |
| 2 | 7.66 | 11.53 | 82 |
| 3 | 9.28 | 9.52 | 77 |
| 4 | 9.52 | 9.28 | 44 |
| 5 | 11.54 | 7.66 | 100 |
| 6 | 15.26 | 5.80 | 38 |
| 7 | 15.54 | 5.70 | 44 |
| 8 | 16.62 | 5.33 | 37 |
| 9 | 19.24 | 4.61 | 34 |
| 10 | 24.56 | 3.62 | 72 |

(Example 133) N-[4-(2-Amino-5-{4-[(2R)-1,4-di-oxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide sulfate hydrate

[Formula 85]

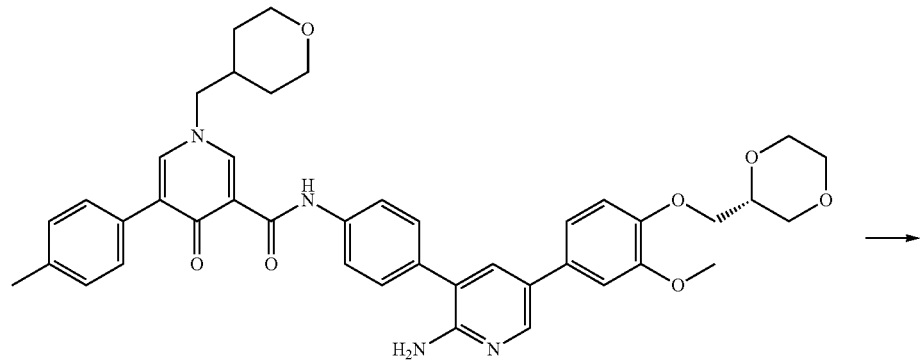

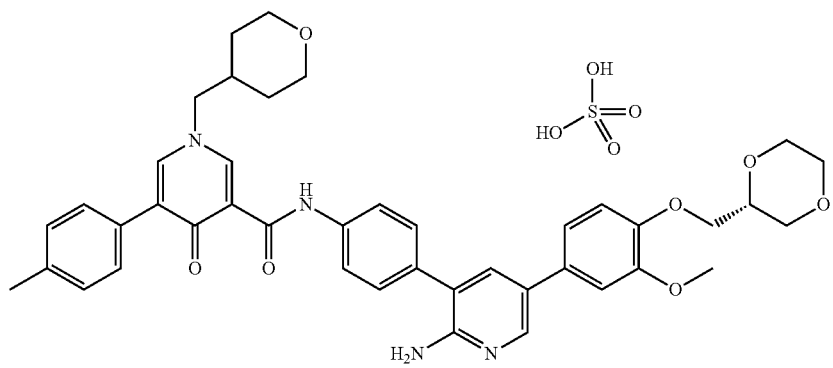

To N-[4-(2-amino-5-{4-[(2R)-1,4-dioxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide (249 mg, 347 μmol), methanol (3.98 ml) and water (632 μl) were added. Then, a 1.00 mol/L aqueous sulfuric acid solution (363 μl, 363 μmol) was added thereto. The mixture was stirred at 40° C. for approximately 21 hours and subsequently at room temperature for approximately 30 minutes and suction-filtered with a Kiriyama funnel, and the deposited solid was collected by filtration. Then, the solid was dried in air to obtain the title compound (271 mg, yield: 90.4%) as a crystalline solid.

$^1$H-NMR (DMSO-D$_6$) δ: 13.20 (1H, s), 8.72 (1H, d, J=2.4 Hz), 8.27 (1H, d, J=2.4 Hz), 8.18 (1H, d, J=2.4 Hz), 8.08 (1H, s), 7.88 (2H, d, J=8.5 Hz), 7.57 (4H, t, J=8.5 Hz), 7.30-7.03 (7H, m), 4.11 (2H, d, J=7.5 Hz), 4.01-3.92 (2H, m), 3.91-3.21 (14H, m), 2.36 (3H, s), 2.16-2.05 (1H, m), 1.46 (2H, d, J=12.5 Hz), 1.37-1.25 (2H, m).

Elemental analysis values for C$_{42}$H$_{44}$N$_4$O$_7$·0.75H$_2$SO$_4$·4H$_2$O
Calcd: C, 58.49; H, 6.25; N, 6.50; S, 2.79.
Found: C, 58.53; H, 6.13; N, 6.52; S, 2.80.
The powder X-ray diffraction (CuKα, λ=1.54 angstroms, scanning rate=20°/min) pattern is shown in FIG. 4, and peaks having a relative intensity of 13 or more with the maximum peak intensity defined as 100 are shown in Table 29.

TABLE 29

| Peak No. | 2θ | d value | Relative intensity |
|---|---|---|---|
| 1 | 3.74 | 23.61 | 72 |
| 2 | 7.56 | 11.68 | 100 |
| 3 | 8.92 | 9.91 | 38 |
| 4 | 9.58 | 9.22 | 50 |
| 5 | 11.36 | 7.78 | 54 |
| 6 | 12.38 | 7.14 | 13 |
| 7 | 14.68 | 6.03 | 25 |
| 8 | 15.64 | 5.66 | 41 |
| 9 | 16.06 | 5.51 | 21 |
| 10 | 24.38 | 3.65 | 16 |

(Example 134) N-[4-(2-Amino-5-{4-[(2R)-1,4-di-oxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide phosphate hydrate

[Formula 86]

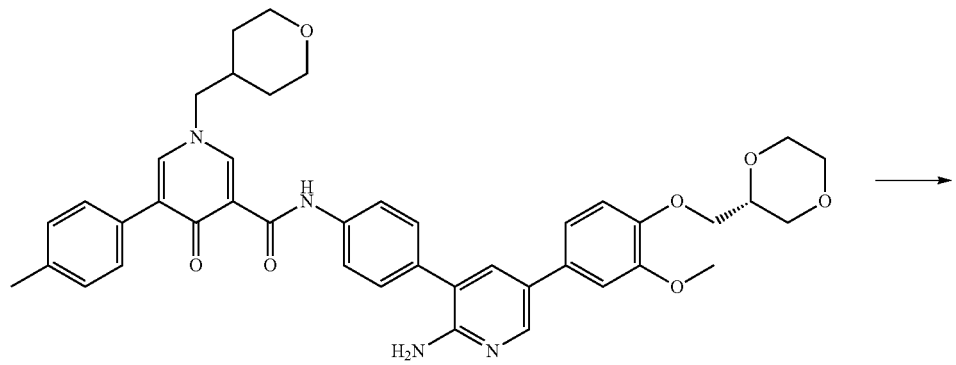

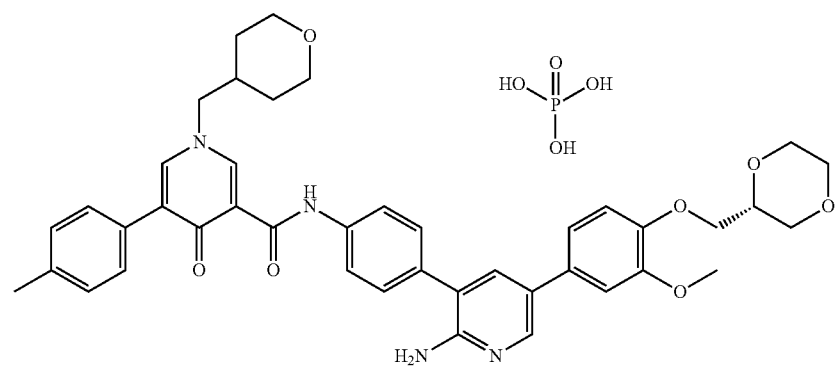

To N-[4-(2-amino-5-{4-[(2R)-1,4-dioxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide (251 mg, 350 μmol), methanol (501 μL) and water (1.28 ml) were added. Then, a 0.504 mol/L aqueous phosphoric acid solution (729 μl, 367 μmol) was added thereto. The mixture was stirred at 40° C. for approximately 24 hours and subsequently at room temperature for approximately 30 minutes and suction-filtered with a Kiriyama funnel, and the deposited solid was collected by filtration. Then, the solid was dried in air to obtain the title compound (254 mg, yield: 82.8%) as a crystalline solid.

$^1$H-NMR (DMSO-D$_6$) δ: 13.11 (1H, s), 8.72 (1H, d, J=2.5 Hz), 8.25 (1H, d, J=2.5 Hz), 8.17 (1H, d, J=2.5 Hz), 7.82 (2H, d, J=8.5 Hz), 7.62 (1H, d, J=2.5 Hz), 7.58 (2H, d, J=8.5 Hz), 7.53 (2H, d, J=8.5 Hz), 7.26 (2H, d, J=8.5 Hz), 7.20 (1H, d, J=2.0 Hz), 7.13 (1H, dd, J=8.5, 2.0 Hz), 6.99 (1H, d, J=8.5 Hz), 5.73 (2H, br s), 4.11 (2H, d, J=7.5 Hz), 3.98-3.90 (2H, m), 3.89-3.22 (14H, m), 2.36 (3H, s), 2.16-2.04 (1H, m), 1.46 (2H, d, J=11.5 Hz), 1.37-1.25 (2H, m).

Elemental analysis values for C$_{42}$H$_{44}$N$_4$O$_7$·1.0H$_3$PO$_4$·3.5H$_2$O
Calcd: C, 57.46; H, 6.20; N, 6.38; P, 3.53.
Found: C, 57.41; H, 6.20; N, 6.41; P, 3.41.
The powder X-ray diffraction (CuKα, λ=1.54 angstroms, scanning rate=20°/min) pattern is shown in FIG. 5, and peaks having a relative intensity of 20 or more with the maximum peak intensity defined as 100 are shown in Table 30.

TABLE 30

| Peak No. | 2θ | d value | Relative intensity |
|---|---|---|---|
| 1 | 3.74 | 23.61 | 76 |
| 2 | 7.56 | 11.68 | 90 |
| 3 | 8.80 | 10.04 | 57 |
| 4 | 9.56 | 9.24 | 100 |
| 5 | 11.34 | 7.80 | 22 |
| 6 | 14.56 | 6.08 | 59 |
| 7 | 15.74 | 5.63 | 59 |
| 8 | 23.68 | 3.75 | 20 |
| 9 | 24.34 | 3.65 | 21 |
| 10 | 24.68 | 3.60 | 23 |

(Example 135) N-[4-(2-Amino-5-{4-[(2R)-1,4-dioxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide ethanesulfonate hydrate

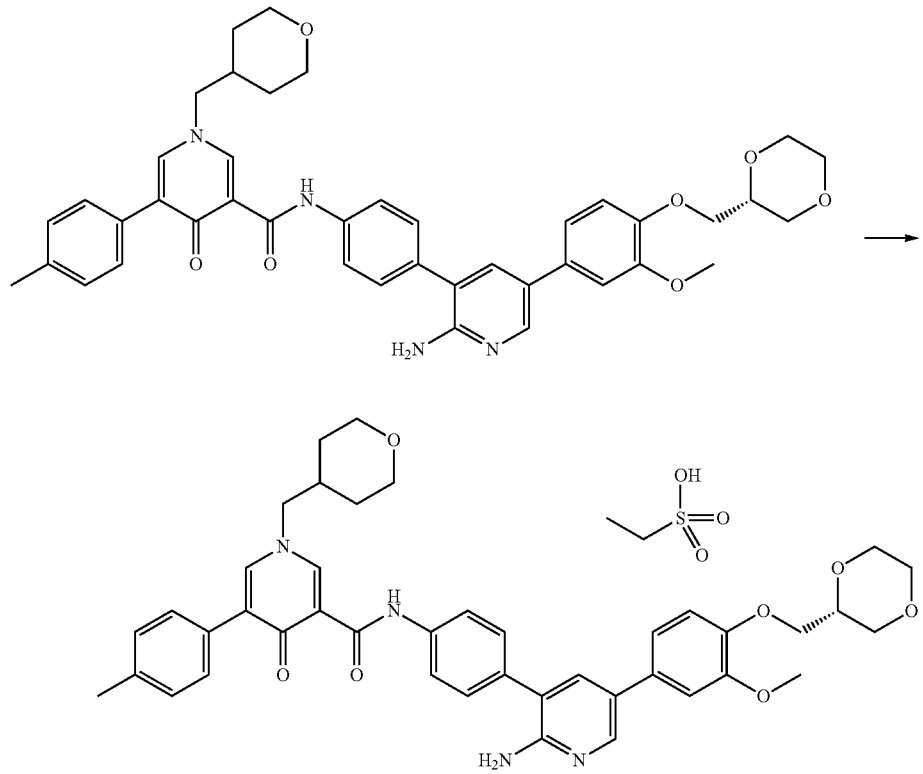

[Formula 87]

To N-[4-(2-amino-5-{4-[(2R)-1,4-dioxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide (251 mg, 350 µmol), methanol (1.00 ml) and water (3.65 ml) were added. Then, a 1.00 mol/L aqueous ethanesulfonic acid solution (368 µl, 368 µmol) was added thereto. A small amount of seed crystal obtained by the method given below was added to the mixture. The mixture was stirred at 40° C. for approximately 21 hours and subsequently at room temperature for approximately 30 minutes and suction-filtered with a Kiriyama funnel, and the deposited solid was collected by filtration. Then, the solid was dried in air to obtain the title compound (265 mg, yield: 81.8%) as a crystalline solid.

Method for Obtaining Seed Crystal

To N-[4-(2-amino-5-{4-[(2R)-1,4-dioxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide (10.4 mg, 14.5 µmol), methanol (41.6 µL) and water (151 µl) were added. Then, a 1.00 mol/L aqueous ethanesulfonic acid solution (15.2 µl, 15.2 µmol) was added thereto. The mixture was stirred at 40° C. for approximately 24 hours and subsequently at room temperature for approximately 30 minutes and suction-filtered with a Kiriyama funnel, and the deposited solid was collected by filtration. Then, the solid was dried in air to obtain a seed crystal (10.9 mg).

$^1$H-NMR (DMSO-D$_6$) δ: 13.22 (1H, s), 8.72 (1H, d, J=2.0 Hz), 8.28 (1H, d, J=2.0 Hz), 8.20 (2H, dd, J=8.5, 2.0 Hz), 7.90 (2H, d, J=8.5 Hz), 7.61-7.49 (6H, m), 7.32 (1H, d, J=2.0 Hz), 7.29-7.24 (3H, m), 7.06 (1H, d, J=8.5 Hz), 4.11 (2H, d, J=7.5 Hz), 4.01-3.93 (2H, m), 3.87-3.24 (14H, m), 2.41-2.31 (5H, m), 2.16-2.04 (1H, m), 1.46 (2H, d, J=11.5 Hz), 1.37-1.25 (2H, m), 1.06 (3H, t, J=7.5 Hz).

Elemental analysis values for C$_{42}$H$_{44}$N$_4$O$_7$·1.0C$_2$H$_5$SO$_3$H·5.5H$_2$O Calcd: C, 57.07; H, 6.64; N, 6.05; S, 3.46.

Found: C, 57.13; H, 6.78; N, 6.08; S, 3.60.

The powder X-ray diffraction (CuKα, λ=1.54 angstroms, scanning rate=20°/min) pattern is shown in FIG. 6, and peaks having a relative intensity of 5 or more with the maximum peak intensity defined as 100 are shown in Table 31.

TABLE 31

| Peak No. | 2θ | d value | Relative intensity |
| --- | --- | --- | --- |
| 1 | 6.72 | 13.14 | 6 |
| 2 | 7.90 | 11.18 | 100 |
| 3 | 12.02 | 7.36 | 42 |
| 4 | 13.40 | 6.60 | 10 |
| 5 | 16.90 | 5.24 | 13 |
| 6 | 17.88 | 4.96 | 5 |
| 7 | 19.00 | 4.67 | 5 |
| 8 | 19.80 | 4.48 | 9 |
| 9 | 21.26 | 4.18 | 9 |
| 10 | 24.18 | 3.68 | 6 |

(Example 136) N-[4-(2-Amino-5-{4-[(2R)-1,4-di-oxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide benzenesulfonate hydrate

[Formula 88]

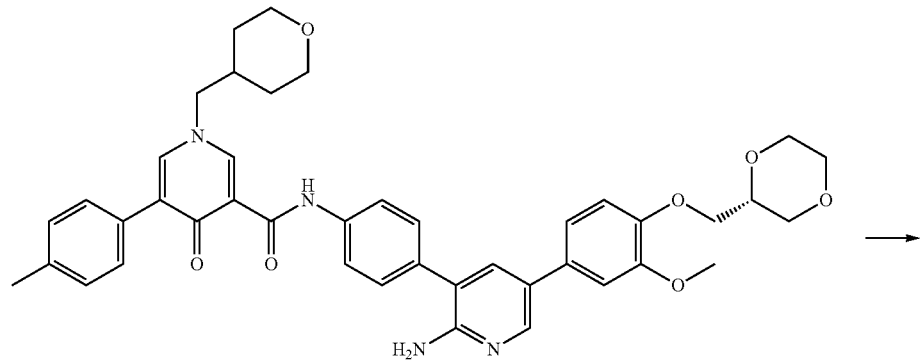

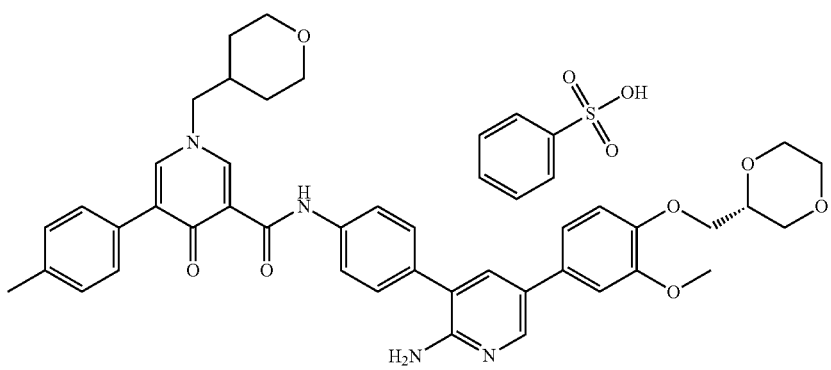

To N-[4-(2-amino-5-{4-[(2R)-1,4-dioxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide (250 mg, 349 μmol), methanol (1.00 ml) and water (3.64 ml) were added. Then, a 1.00 mol/L aqueous benzenesulfonic acid solution (366 μl, 366 μmol) was added thereto. A suspension was prepared therefrom using an ultrasonic washing machine, then stirred at 40° C. for approximately 21 hours and subsequently at room temperature for approximately 30 minutes, and suction-filtered with a Kiriyama funnel, and the deposited solid was collected by filtration. Then, the solid was dried in air to obtain the title compound (287 mg, yield: 88.3%) as a crystalline solid.

$^1$H-NMR (DMSO-D$_6$) δ: 13.22 (1H, s), 8.72 (1H, d, J=2.0 Hz), 8.27 (1H, d, J=2.0 Hz), 8.19 (2H, d, J=2.0 Hz), 7.90 (2H, d, J=8.5 Hz), 7.61-7.55 (6H, m), 7.44 (2H, br s), 7.35-7.24 (7H, m), 7.06 (1H, d, J=8.5 Hz), 4.11 (2H, d, J=7.5 Hz), 4.01-3.93 (2H, m), 3.90-3.22 (14H, m), 2.36 (3H, s), 2.17-2.04 (1H, m), 1.46 (2H, d, J=11.6 Hz), 1.31 (2H, td, J=12.2, 8.5 Hz).

Elemental analysis values for C$_{42}$H$_{44}$N$_4$O$_7$·1.0C$_6$H$_5$SO$_3$H·3H$_2$O
Calcd: C, 62.05; H, 6.08; N, 6.03; S, 3.45.
Found: C, 62.18; H, 6.07; N, 6.08; S, 3.46.

The powder X-ray diffraction (CuKα, λ=1.54 angstroms, scanning rate=20°/min) pattern is shown in FIG. 7, and peaks having a relative intensity of 29 or more with the maximum peak intensity defined as 100 are shown in Table 32.

TABLE 32

| Peak No. | 2θ | d value | Relative intensity |
|---|---|---|---|
| 1 | 9.22 | 9.58 | 82 |
| 2 | 10.60 | 8.34 | 29 |
| 3 | 10.82 | 8.17 | 35 |
| 4 | 11.10 | 7.96 | 42 |
| 5 | 13.40 | 6.60 | 52 |
| 6 | 15.78 | 5.61 | 30 |
| 7 | 17.50 | 5.06 | 46 |
| 8 | 18.66 | 4.75 | 48 |
| 9 | 21.02 | 4.22 | 100 |
| 10 | 26.10 | 3.41 | 37 |

(Example 137) N-[4-(2-Amino-5-{4-[(2R)-1,4-di-oxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide p-toluenesulfonate ¹H-NMR (DMSO-D₆) δ: 13.22 (1H, s), 8.73 (1H, d, J=2.0 Hz), 8.28 (1H, d, J=2.0 Hz), 8.21 (1H, d, J=2.0 Hz), 8.19 (1H, d, J=2.0 Hz), 7.90 (2H, d, J=8.0 Hz), 7.60-7.45 (8H, m), 7.31 (1H, d, J=2.0 Hz), 7.29-7.24 (3H, m), 7.11 (2H, d, J=8.0 Hz), 7.06 (1H, d, J=8.0 Hz), 4.11 (2H, d, J=7.5 Hz),

[Formula 89]

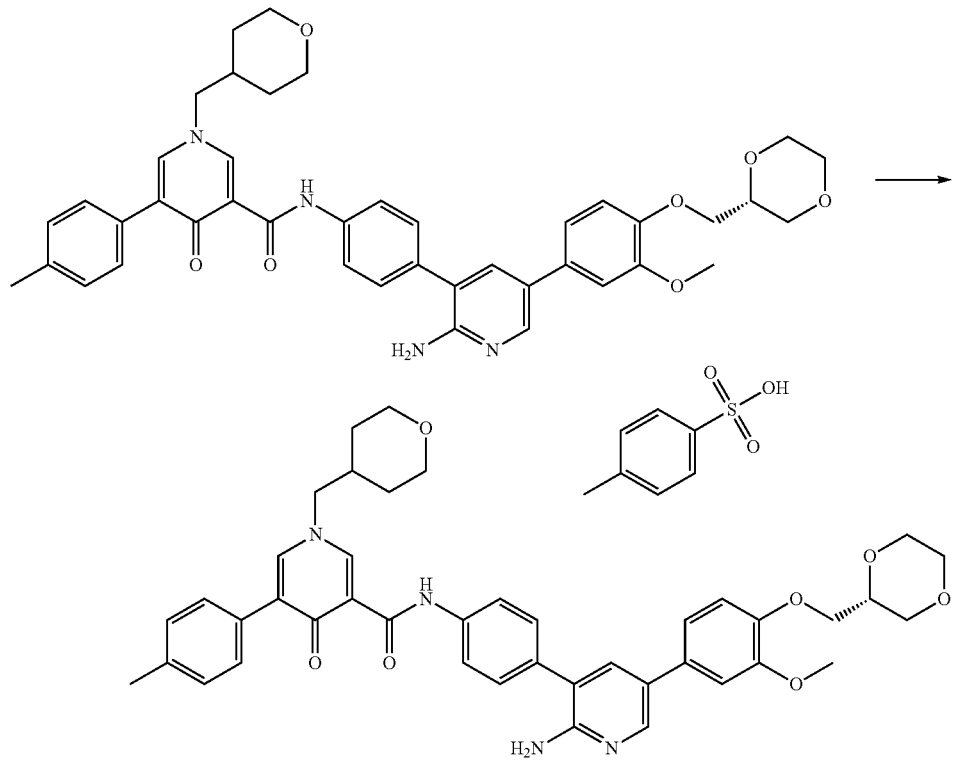

To N-[4-(2-amino-5-{4-[(2R)-1,4-dioxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide (268 mg, 373 µmol), methanol (2.14 ml) and water (145 µl) were added. Then, a 1.00 mol/L aqueous p-toluenesulfonic acid solution (390 µl, 390 µmol) were added thereto. A small amount of seed crystal obtained by the method given below was added to the mixture. The mixture was stirred at 40° C. for approximately 21 hours and subsequently at room temperature for approximately 30 minutes and suction-filtered with a Kiriyama funnel, and the deposited solid was collected by filtration. Then, the solid was dried in air to obtain the title compound (255 mg, yield: 77.0%) as a crystalline solid.

Method for Obtaining Seed Crystal

To N-[4-(2-amino-5-{4-[(2R)-1,4-dioxan-2-ylmethoxy]-3-methoxyphenyl}pyridin-3-yl)phenyl]-5-(4-methylphenyl)-4-oxo-1-(tetrahydro-2H-pyran-4-ylmethyl)-1,4-dihydropyridine-3-carboxamide (10.3 mg, 14.4 µmol), methanol (165 µL) and water (26.2 µl) were added. Then, a 1.00 mol/L aqueous p-toluenesulfonic acid solution (15.0 µl, 15.0 µmol) was added thereto. The mixture was stirred at 40° C. for approximately 24 hours and subsequently at room temperature for approximately 30 minutes and suction-filtered with a Kiriyama funnel, and the deposited solid was collected by filtration. Then, the solid was dried in air to obtain a seed crystal (10.7 mg).

4.02-3.93 (2H, m), 3.90-3.22 (14H, m), 2.36 (3H, s), 2.29 (3H, s), 2.16-2.04 (1H, m), 1.46 (2H, d, J=11.5 Hz), 1.37-1.25 (2H, m).

Elemental analysis values for $C_{42}H_{44}N_4O_7 \cdot 1.0 C_7H_7SO_3H$

Calcd: C, 66.19; H, 5.89; N, 6.30; S, 3.61.

Found: C, 65.91; H, 5.97; N, 6.26; S, 3.59.

The powder X-ray diffraction (CuKα, λ=1.54 angstroms, scanning rate=20°/min) pattern is shown in FIG. 8, and peaks having a relative intensity of 23 or more with the maximum peak intensity defined as 100 are shown in Table 33.

TABLE 33

| Peak No. | 2θ | d value | Relative intensity |
|---|---|---|---|
| 1 | 4.18 | 21.12 | 61 |
| 2 | 5.12 | 17.25 | 100 |
| 3 | 13.44 | 6.58 | 26 |
| 4 | 14.98 | 5.91 | 28 |
| 5 | 16.96 | 5.22 | 31 |
| 6 | 17.44 | 5.08 | 40 |
| 7 | 18.92 | 4.67 | 36 |
| 8 | 19.72 | 4.50 | 23 |
| 9 | 20.16 | 4.40 | 24 |
| 10 | 23.04 | 3.86 | 30 |

(Example 138) N-[4-(2-Amino-5-{4-[(2R)-1,4-di-oxan-2-ylmethoxy]-3-methoxyphenyl}pyridin-3-yl)-3-fluorophenyl]-5-methyl-4-oxo-1'-(tetrahydro-2H-pyran-4-ylmethyl)-1',4-dihydro-2,3'-bipyridine-5'-carboxamide phosphate hydrate

[Formula 90]

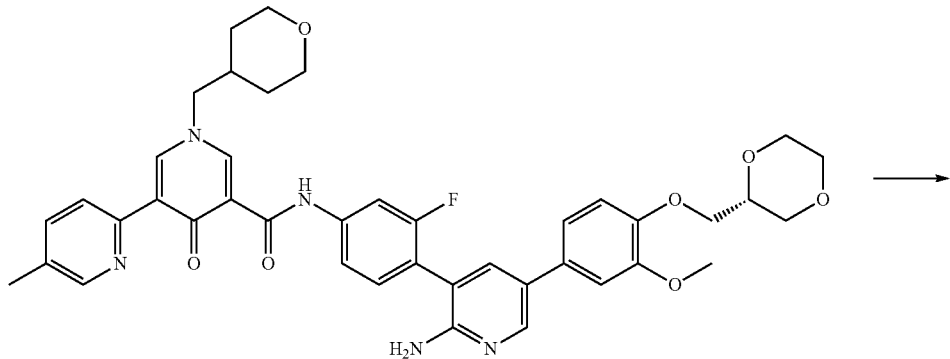

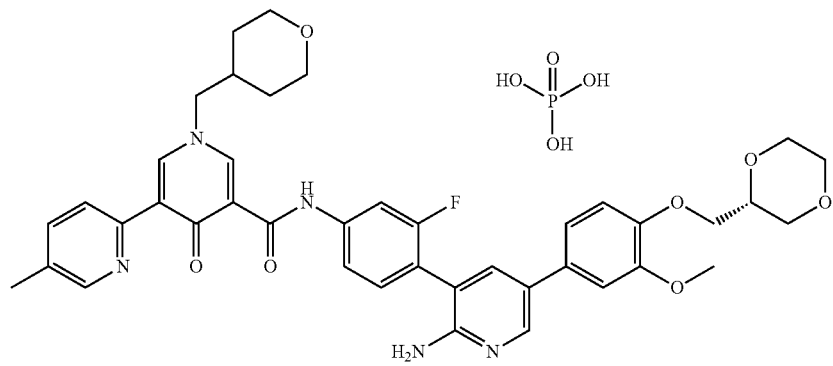

N-[4-(2-Amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide (50.0 mg, 67.9 μmol) was suspended in acetone (400 μl). To the suspension, water (64.4 μl) was added. Then, a 4.00 mol/L aqueous phosphoric acid solution (35.7 μl, 143 μmol) was added thereto, and the mixture was stirred at 40° C. for 3 hours. Then, 20% aqueous acetone (500 μl) was added thereto, and the mixture was further stirred for approximately 21 hours. Then, the reaction mixture was stirred at room temperature for approximately 30 minutes and then suction-filtered with a Kiriyama funnel to obtain the title compound (42.5 mg, yield: 69.7%) as a crystalline solid.

$^1$H-NMR (DMSO-D$_6$) δ: 13.22 (1H, s), 8.77 (1H, d, J=2.0 Hz), 8.69 (1H, d, J=2.0 Hz), 8.51 (1H, d, J=2.0 Hz), 8.47 (1H, d, J=8.5 Hz), 8.30 (1H, d, J=2.0 Hz), 7.93 (1H, dd, J=12.5, 2.0 Hz), 7.71 (1H, dd, J=8.5, 2.0 Hz), 7.64 (1H, d, J=2.0 Hz), 7.49-7.41 (2H, m), 7.19 (1H, d, J=2.0 Hz), 7.12 (1H, dd, J=8.5, 2.0 Hz), 6.99 (1H, d, J=8.5 Hz), 5.77 (2H, br s), 4.21 (2H, d, J=7.5 Hz), 3.98-3.24 (16H, m), 2.36 (3H, s), 2.13-2.01 (1H, m), 1.46 (2H, d, J=12.0 Hz), 1.38-1.26 (2H, m).

MS (APCI) m/z: 736 [(M+H)$^+$].

Elemental analysis values for $C_{41}H_{42}FN_5O_7 \cdot 1.0H_3PO_4 \cdot 3.5H_2O$ Calcd: C, 54.91; H, 5.84; N, 7.81; F, 2.12; P, 3.45.
Found: C, 54.95; H, 5.54; N, 7.86; F, 2.20; P, 3.19.

The powder X-ray diffraction (CuKα, λ=1.54 angstroms, scanning rate=20°/min) pattern is shown in FIG. 9, and peaks having a relative intensity of 18 or more with the maximum peak intensity defined as 100 are shown in Table 34.

TABLE 34

| Peak No. | 2θ | d value | Relative intensity |
|---|---|---|---|
| 1 | 4.28 | 20.63 | 100 |
| 2 | 8.42 | 10.49 | 40 |
| 3 | 8.64 | 10.23 | 35 |
| 4 | 10.54 | 8.39 | 19 |
| 5 | 12.72 | 6.95 | 28 |
| 6 | 13.48 | 6.56 | 24 |
| 7 | 15.90 | 5.57 | 23 |
| 8 | 17.00 | 5.21 | 19 |
| 9 | 17.46 | 5.08 | 18 |
| 10 | 21.26 | 4.18 | 31 |

(Example 139) N-[4-(2-Amino-5-{4-[(2R)-1,4-di-oxan-2-ylmethoxy]-3-methoxyphenyl}pyridin-3-yl)-3-fluorophenyl]-5-methyl-4-oxo-1'-(tetrahydro-2H-pyran-4-ylmethyl)-1',4'-dihydro-2,3'-bipyridine-5'-carboxamide sulfate hydrate The powder X-ray diffraction (CuKα, λ=1.54 angstroms, scanning rate=20°/min) pattern is shown in FIG. 10, and peaks having a relative intensity of 6 or more with the maximum peak intensity defined as 100 are shown in Table 35.

[Formula 91]

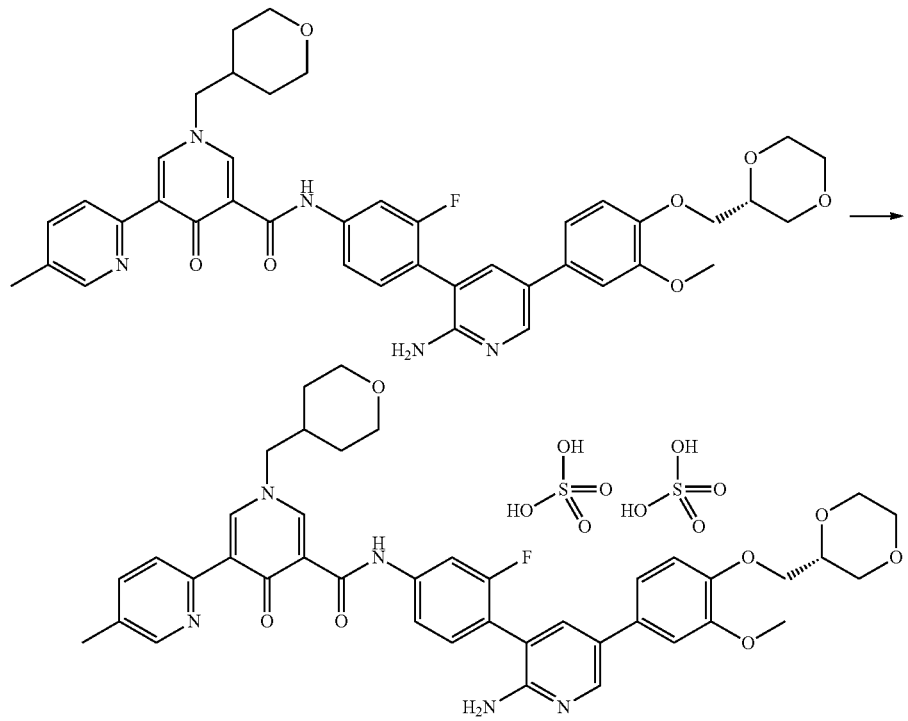

N-[4-(2-Amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide (80.0 g, 109 mmol) was suspended in acetone (1.28 L). To the suspension, water (247 ml) was added. 6.00 mol/L sulfuric acid (71.7 ml, 430 mmol) was added dropwise thereto at 40° C. The reaction mixture was stirred at 40° C. for 3 days and then suction-filtered with a Buchner funnel, and the deposited solid was collected by filtration. The solid was washed with a water/acetone mixture (water/acetone=1/9) to obtain the title compound (92.3 g, yield: 88.3%) as a crystalline solid.

$^1$H-NMR (DMSO-D$_6$) δ: 13.04 (1H, br s), 8.83 (2H, d, J=9.5 Hz), 8.63 (1H, s), 8.44 (1H, d, J=8.0 Hz), 8.34 (2H, s), 8.05-7.98 (2H, m), 7.72 (1H, br s), 7.59-7.52 (2H, m), 7.32 (1H, d, J=2.0 Hz), 7.26 (1H, dd, J=8.0, 2.0 Hz), 7.07 (1H, d, J=8.0 Hz), 4.22 (2H, d, J=7.5 Hz), 4.01-3.93 (2H, m), 3.90-3.74 (8H, m), 3.70-3.59 (2H, m), 3.53-3.45 (1H, m), 3.40 (1H, dd, J=11.0, 10.0 Hz), 3.27 (2H, t, J=11.0 Hz), 2.43 (3H, s), 2.16-2.05 (1H, m), 1.51-1.43 (2H, m), 1.39-1.26 (2H, m).

MS (APCI) m/z: 736 [(M+H)$^+$].

Elemental analysis values for C$_{41}$H$_{42}$FN$_5$O$_7$·1.8H$_2$SO$_4$·3.0H$_2$O Calcd: C, 50.96; H, 5.38; N, 7.25; F, 1.97; S, 5.97.
Found: C, 50.98; H, 5.36; N, 7.23; F, 1.97; S, 6.19.

TABLE 35

| Peak No. | 2θ | d value | Relative intensity |
|---|---|---|---|
| 1 | 3.66 | 24.12 | 100 |
| 2 | 6.42 | 13.76 | 12 |
| 3 | 7.32 | 12.07 | 68 |
| 4 | 9.76 | 9.05 | 15 |
| 5 | 11.00 | 8.04 | 6 |
| 6 | 12.88 | 6.87 | 6 |
| 7 | 18.42 | 4.81 | 23 |
| 8 | 19.62 | 4.52 | 17 |
| 9 | 20.54 | 4.32 | 18 |
| 10 | 24.22 | 3.67 | 8 |

(Example 140) N-[4-(2-Amino-5-{4-[(2R)-1,4-di-oxan-2-ylmethoxy]-3-methoxyphenyl}pyridin-3-yl)-3-fluorophenyl]-5-methyl-4-oxo-1'-(tetrahydro-2H-pyran-4-ylmethyl)-1',4'-dihydro-2,3'-bipyridine-5'-carboxamide sulfate hydrate To N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide (39.8 mg, 54.1 µmol), acetone (637 µL) and water (78.3 µl) were added. Then, a 1.00 mol/L aqueous sulfuric acid solution (80.9 µl, 80.9 µmol) was added thereto. The mixture was stirred at 40° C. for approximately 24 hours and subsequently at room temperature for approximately 30 minutes and suction-filtered with a Kiriyama funnel, and the deposited solid was collected by filtration. Then, the solid was dried in air to obtain the title compound (36.7 mg, yield: 71.6%) as a crystalline solid.

Elemental analysis values for $C_{41}H_{42}FN_5O_7 \cdot 1.60H_2SO_4 \cdot 3.0H_2O$ Calcd: C, 52.01; H, 5.45; N, 7.40; F, 2.01; S, 5.42.

Found: C, 52.07; H, 5.24; N, 7.25; F, 2.09; S, 5.50.

The powder X-ray diffraction (CuKα, λ=1.54 angstroms, scanning rate=20°/min) pattern is shown in FIG. 11, and peaks having a relative intensity of 12 or more with the maximum peak intensity defined as 100 are shown in Table 36.

TABLE 36

| Peak No. | 2θ | d value | Relative intensity |
|---|---|---|---|
| 1 | 3.64 | 24.25 | 100 |
| 2 | 6.40 | 13.80 | 19 |
| 3 | 7.32 | 12.07 | 84 |
| 4 | 9.76 | 9.05 | 19 |
| 5 | 17.38 | 5.10 | 12 |
| 6 | 18.42 | 4.81 | 31 |
| 7 | 19.64 | 4.52 | 22 |
| 8 | 20.56 | 4.32 | 25 |
| 9 | 22.90 | 3.88 | 14 |
| 10 | 24.20 | 3.67 | 12 |

(Example 141) N-[4-(2-Amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide sulfate hydrate To N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide (40.5 mg, 55.0 μmol), acetone (648 μL) and water (24.8 μl) were added. Then, a 1.00 mol/L aqueous sulfuric acid solution (137 μl, 137 μmol) was added thereto. The mixture was stirred at 40° C. for approximately 24 hours and subsequently at room temperature for approximately 30 minutes and suction-filtered with a Kiriyama funnel, and the deposited solid was collected by filtration. Then, the solid was dried in air to obtain the title compound (47.2 mg, yield: 88.8%) as a crystalline solid.

Elemental analysis values for $C_{41}H_{42}FN_5O_7 \cdot 1.80H_2SO_4 \cdot 3.0H_2O$ Calcd: C, 50.96; H, 5.38; N, 7.25; F, 1.97; S, 5.97.

Found: C, 50.85; H, 5.20; N, 7.06; F, 2.09; S, 5.99.

The powder X-ray diffraction (CuKα, λ=1.54 angstroms, scanning rate=20°/min) pattern is shown in FIG. 12, and peaks having a relative intensity of 7 or more with the maximum peak intensity defined as 100 are shown in Table 37.

TABLE 37

| Peak No. | 2θ | d value | Relative intensity |
|---|---|---|---|
| 1 | 3.64 | 24.25 | 100 |
| 2 | 6.40 | 13.80 | 13 |
| 3 | 7.30 | 12.10 | 50 |
| 4 | 9.76 | 9.05 | 11 |
| 5 | 17.34 | 5.11 | 9 |
| 6 | 18.38 | 4.82 | 18 |
| 7 | 19.34 | 4.59 | 12 |
| 8 | 20.56 | 4.32 | 15 |

TABLE 37-continued

| Peak No. | 2θ | d value | Relative intensity |
|---|---|---|---|
| 9 | 21.52 | 4.13 | 7 |
| 10 | 22.94 | 3.87 | 9 |

(Example 142) N-[4-(2-Amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide sulfate hydrate To N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide (39.8 mg, 54.0 μmol), acetone (636 μL) and water (112 μl) were added. Then, a 5.79 mol/L aqueous sulfuric acid solution (46.7 μl, 270 μmol) was added thereto. The mixture was stirred at 40° C. for approximately 24 hours and subsequently at room temperature for approximately 30 minutes and suction-filtered with a Kiriyama funnel, and the deposited solid was collected by filtration. Then, the solid was dried in air to obtain the title compound (47.5 mg, yield: 89.2%) as a crystalline solid.

Elemental analysis values for $C_{41}H_{42}FN_5O_7 \cdot 2.00H_2SO_4 \cdot 3.0H_2O$ Calcd: C, 49.94; H, 5.32; N, 7.10; F, 1.93; S, 6.50.

Found: C, 49.75; H, 5.08; N, 6.91; F, 2.20; S, 6.69.

The powder X-ray diffraction (CuKα, λ=1.54 angstroms, scanning rate=20°/min) pattern is shown in FIG. 13, and peaks having a relative intensity of 11 or more with the maximum peak intensity defined as 100 are shown in Table 38.

TABLE 38

| Peak No. | 2θ | d value | Relative intensity |
|---|---|---|---|
| 1 | 3.62 | 24.39 | 100 |
| 2 | 6.38 | 13.84 | 11 |
| 3 | 7.28 | 12.13 | 56 |
| 4 | 9.74 | 9.07 | 15 |
| 5 | 17.30 | 5.12 | 11 |
| 6 | 18.36 | 4.83 | 28 |
| 7 | 19.54 | 4.54 | 20 |
| 8 | 20.52 | 4.32 | 25 |
| 9 | 22.86 | 3.89 | 13 |
| 10 | 24.14 | 3.68 | 11 |

(Example 143) N-[4-(2-Amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide sulfate hydrate To N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide (40.2 mg, 54.6 μmol), acetone (643 μL) and water (51.8 μl) were added. Then, a 1.00 mol/L aqueous sulfuric acid solution (109 μl, 109 μmol) was added thereto. The mixture was stirred at 40° C. for approximately 24 hours and subsequently at room temperature for approximately 30 minutes and suction-filtered with a Kiriyama funnel, and the deposited solid was collected by filtration. Then, the solid was dried in air to obtain the title compound (44.4 mg, yield: 84.6%) as a crystalline solid.

Elemental analysis values for $C_{41}H_{42}FN_5O_7 \cdot 1.75H_2SO_4 \cdot 3.0H_2O$ Calcd: C, 51.22; H, 5.40; N, 7.28; F, 1.98; S, 5.84.

Found: C, 50.92; H, 5.19; N, 7.11; F, 2.25; S, 5.81.

The powder X-ray diffraction (CuKα, λ=1.54 angstroms, scanning rate=20°/min) pattern is shown in FIG. 14, and peaks having a relative intensity of 11 or more with the maximum peak intensity defined as 100 are shown in Table 39.

TABLE 39

| Peak No. | 2θ | d value | Relative intensity |
|---|---|---|---|
| 1 | 3.64 | 24.25 | 100 |
| 2 | 6.40 | 13.80 | 19 |
| 3 | 7.30 | 12.10 | 71 |
| 4 | 9.76 | 9.05 | 16 |
| 5 | 12.86 | 6.88 | 11 |
| 6 | 18.40 | 4.82 | 34 |
| 7 | 19.62 | 4.52 | 21 |
| 8 | 20.54 | 4.32 | 25 |
| 9 | 22.92 | 3.88 | 13 |
| 10 | 24.20 | 3.67 | 11 |

(Example 144) N-{4-[2-Amino-5-(4-{[(2R)-1,4-dioxan-2-yl]methoxy}-3-methoxyphenyl)-3-pyridyl]-3-fluorophenyl}-5-(5-methyl-2-pyridyl)-4-oxo-1-(tetrahydropyran-4-ylmethyl)pyridine-3-carboxamide sulfate hydrate To N-{4-[2-amino-5-(4-{[(2R)-1,4-dioxan-2-yl]methoxy}-3-methoxyphenyl)-3-pyridyl]-3-fluorophenyl}-5-(5-methyl-2-pyridyl)-4-oxo-1-(tetrahydropyran-4-ylmethyl)pyridine-3-carboxamide (2.11 g, 2.88 mmol), methanol (12.7 ml) and water (2.72 ml) were added, and 1.00 mol/L sulfuric acid (5.72 ml, 5.72 mmol) was added dropwise. The reaction mixture was stirred at 25° C. for approximately 21 hours, and then, the deposited solid was collected by filtration. The solid was dried under reduced pressure at room temperature for approximately 18 hours to obtain the title compound (2.39 g, yield: 85.8%).

Elemental analysis values for $C_{41}H_{42}N_5O_7F \cdot 1.75H_2SO_4 \cdot 3.5H_2O$ Calcd: C, 50.74; H, 5.45; N, 7.22; F, 1.96; S, 5.78.

Found: C, 50.70; H, 5.33; N, 7.13; F, 2.01; S, 5.82.

The powder X-ray diffraction (CuKα, λ=1.54 angstroms, scanning rate=20°/min) pattern is shown in FIG. 15, and peaks having a relative intensity of 18 or more with the maximum peak intensity defined as 100 are shown in Table 40.

TABLE 40

| Peak No. | 2θ | d value | Relative intensity |
|---|---|---|---|
| 1 | 3.64 | 24.25 | 100 |
| 2 | 6.36 | 13.89 | 18 |
| 3 | 7.30 | 12.10 | 50 |
| 4 | 18.36 | 4.83 | 18 |
| 5 | 19.04 | 4.66 | 24 |
| 6 | 19.42 | 4.57 | 22 |
| 7 | 19.70 | 4.50 | 23 |
| 8 | 20.12 | 4.41 | 22 |
| 9 | 20.42 | 4.35 | 21 |
| 10 | 21.32 | 4.16 | 21 |

[Formula 92]

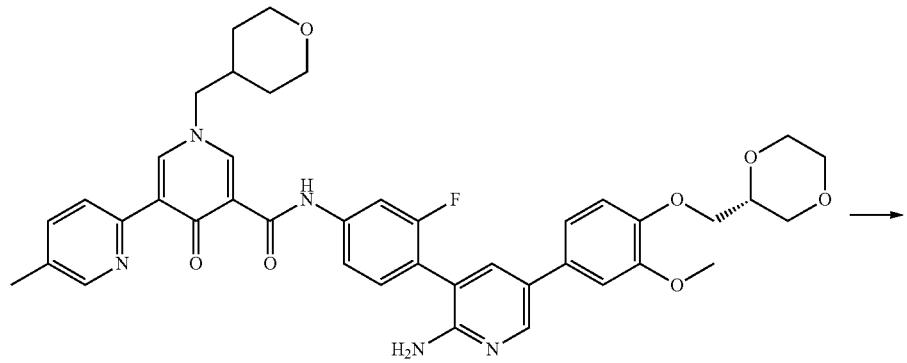

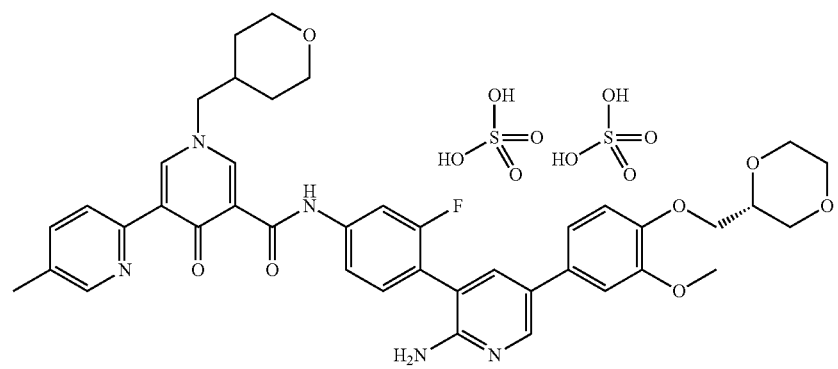

(Example 145) N-{4-[2-Amino-5-(4-{[(2R)-1,4-dioxan-2-yl]methoxy}-3-methoxyphenyl)-3-pyridyl]-3-fluorophenyl}-5-(5-methyl-2-pyridyl)-4-oxo-1-(tetrahydropyran-4-ylmethyl)pyridine-3-carboxamide sulfate hydrate

[Formula 93]

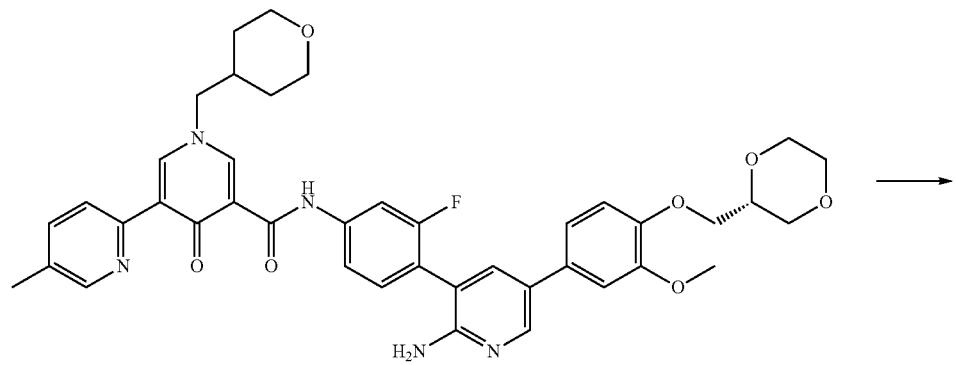

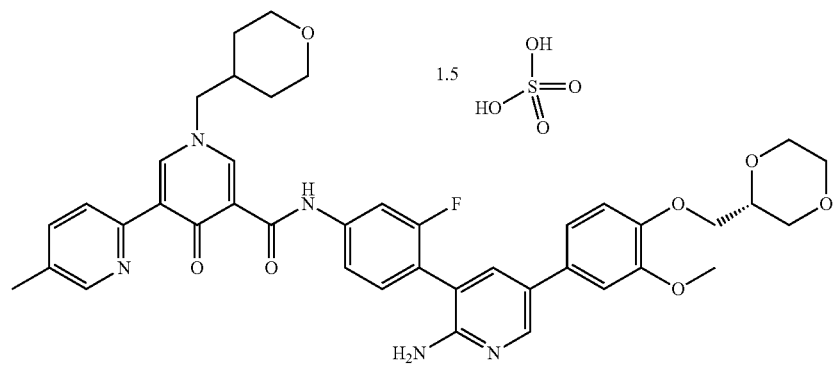

To the sulfate hydrate (2.44 g) described in Example 139, 20% aqueous methanol (24.4 ml) was added, and the mixture was stirred at 5° C. for approximately 27 hours. The solid was collected by filtration and then dried under reduced pressure at room temperature for 4.5 hours to obtain the title compound (2.30 g, yield: 93.5%).

Elemental analysis values for $C_{41}H_{42}N_5O_7F \cdot 1.5H_2SO_4 \cdot 5.0H_2O$ Calcd: C, 50.61; H, 5.70; N, 7.20; F, 1.95; S, 4.94.

Found: C, 50.59; H, 5.55; N, 7.24; F, 2.04; S, 5.09.

The powder X-ray diffraction (CuKα, λ=1.54 angstroms, scanning rate=20°/min) pattern is shown in FIG. 16, and peaks having a relative intensity of 13 or more with the maximum peak intensity defined as 100 are shown in Table 41.

TABLE 41

| Peak No. | 2θ | d value | Relative intensity |
|---|---|---|---|
| 1 | 5.62 | 15.71 | 55 |
| 2 | 7.18 | 12.30 | 100 |
| 3 | 9.22 | 9.58 | 13 |
| 4 | 10.36 | 8.53 | 15 |
| 5 | 15.56 | 5.69 | 22 |
| 6 | 16.40 | 5.40 | 26 |
| 7 | 20.86 | 4.25 | 23 |

(Example 146) N-{4-[2-Amino-5-(4-{[(2R)-1,4-dioxan-2-yl]methoxy}-3-methoxyphenyl)-3-pyridyl]-3-fluorophenyl}-5-(5-methyl-2-pyridyl)-4-oxo-1-(tetrahydropyran-4-ylmethyl)pyridine-3-carboxamide naphthalene-1,5-disulfonate hydrate MS (APCI) m/z: 736 [(M+H)+].
Elemental analysis values for $C_{41}H_{42}N_5O_7F·1.0C_{10}H_8O_6S_2·5.0H_2O$
Calcd: C, 54.98; H, 5.43; N, 6.29; F, 1.71; S, 5.76.
Found: C, 54.74; H, 5.37; N, 6.24; F, 1.92; S, 5.82.

[Formula 94]

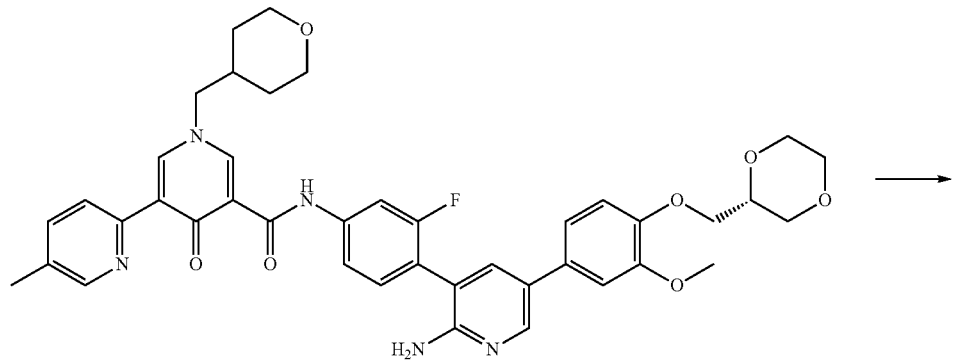

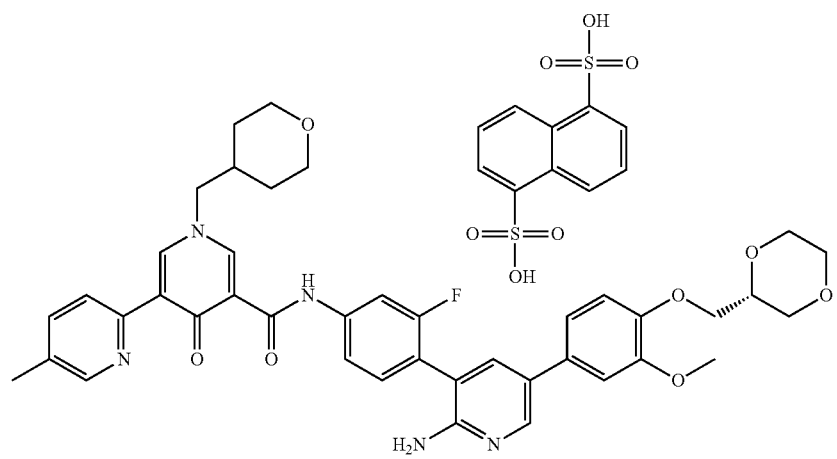

To N-{4-[2-amino-5-(4-{[(2R)-1,4-dioxan-2-yl]methoxy}-3-methoxyphenyl)-3-pyridyl]-3-fluorophenyl}-5-(5-methyl-2-pyridyl)-4-oxo-1-(tetrahydropyran-4-ylmethyl)pyridine-3-carboxamide (199.34 mg, 271 μmol), methanol (3.19 ml), a 1 mol/L aqueous naphthalene-1,5-disulfonic acid solution (285 μl, 284 μmol), and water (513 μl) were added. The reaction mixture was stirred at 40° C. for approximately 26 hours and then at room temperature for approximately 0.5 hours. The solid was collected by filtration and then dried in air overnight to obtain the title compound (285.7 mg, yield: 94.6%).

$^1$H-NMR (DMSO-D$_6$) δ: 12.97 (1H, br s), 8.90-8.80 (4H, m), 8.64 (1H, s), 8.42 (1H, d, J=8.5 Hz), 8.33 (2H, s), 8.11-7.97 (2H, m), 7.92 (2H, d, J=7.0 Hz), 7.71 (2H, br s), 7.59-7.52 (2H, m), 7.40 (2H, dd, J=8.5, 7.0 Hz), 7.31 (1H, d, J=2.5 Hz), 7.26 (1H, dd, J=8.5, 2.5 Hz), 7.06 (1H, d, J=8.5 Hz), 4.22 (2H, d, J=7.0 Hz), 3.99-3.24 (16H, m), 2.43 (3H, s), 2.18-2.05 (1H, m), 1.47 (2H, d, J=10.5 Hz), 1.39-1.26 (2H, m).

The powder X-ray diffraction (CuKα, λ=1.54 angstroms, scanning rate=20°/min) pattern is shown in FIG. 17, and peaks having a relative intensity of 45 or more with the maximum peak intensity defined as 100 are shown in Table 42.

TABLE 42

| Peak No. | 2θ | d value | Relative intensity |
|---|---|---|---|
| 1 | 6.14 | 14.38 | 100 |
| 2 | 6.98 | 12.65 | 48 |
| 3 | 11.24 | 7.87 | 62 |
| 4 | 14.84 | 5.96 | 62 |
| 5 | 17.48 | 5.07 | 63 |
| 6 | 19.54 | 4.54 | 72 |
| 7 | 20.94 | 4.24 | 53 |
| 8 | 22.38 | 3.97 | 45 |
| 9 | 23.20 | 3.83 | 48 |
| 10 | 24.70 | 3.60 | 90 |

(Example 147) N-{4-[2-Amino-5-(4-{[(2R)-1,4-dioxan-2-yl]methoxy}-3-methoxyphenyl)-3-pyridyl]-3-fluorophenyl}-5-(5-methyl-2-pyridyl)-4-oxo-1-(tetrahydropyran-4-ylmethyl)pyridine-3-carboxamide naphthalene-1,5-disulfonate hydrate

[Formula 95]

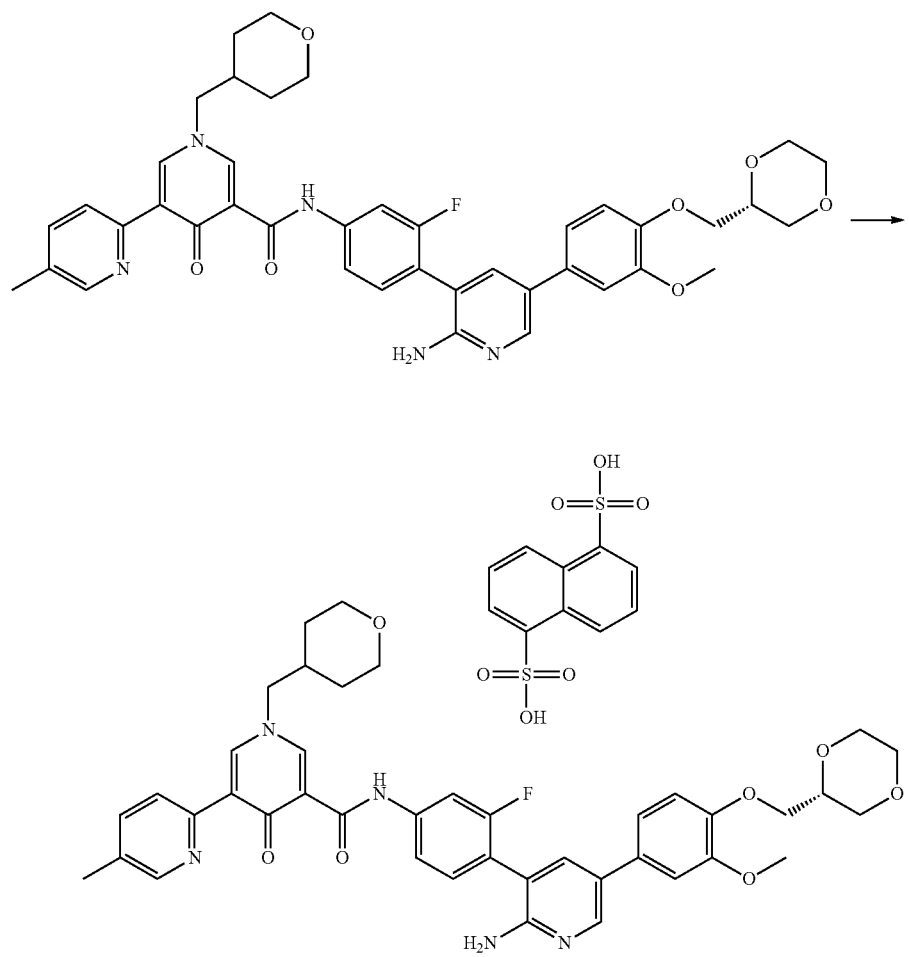

To N-{4-[2-amino-5-(4-{[(2R)-1,4-dioxan-2-yl]methoxy}-3-methoxyphenyl)-3-pyridyl]-3-fluorophenyl}-5-(5-methyl-2-pyridyl)-4-oxo-1-(tetrahydropyran-4-ylmethyl)pyridine-3-carboxamide (199.50 mg, 271 μmol), acetone (3.19 ml), a 1 mol/L aqueous naphthalene-1,5-disulfonic acid solution (285 μl, 284 mol), and water (513 μl) were added. The reaction mixture was stirred at 40° C. for approximately 26 hours and then at room temperature for approximately 0.5 hours. The solid was collected by filtration and then dried in air to obtain the title compound (290.9 mg, yield: 97.9%).

Elemental analysis values for $C_{41}H_{42}N_5O_7F \cdot 1.0 C_{10}H_8O_6S_2 \cdot 4.0H_2O$ Calcd: C, 55.88; H, 5.33; N, 6.39; F, 1.73; S, 5.85.

Found: C, 55.71; H, 5.45; N, 6.18; F, 1.82; S, 5.62.

The powder X-ray diffraction (CuKα, λ=1.54 angstroms, scanning rate=20°/min) pattern is shown in FIG. 18, and peaks having a relative intensity of 42 or more with the maximum peak intensity defined as 100 are shown in Table 43.

TABLE 43

| Peak No. | 2θ | d value | Relative intensity |
|---|---|---|---|
| 1 | 9.24 | 9.56 | 42 |
| 2 | 9.58 | 9.22 | 100 |
| 3 | 14.00 | 6.32 | 45 |
| 4 | 14.46 | 6.12 | 45 |
| 5 | 16.70 | 5.30 | 59 |
| 6 | 17.02 | 5.21 | 70 |
| 7 | 18.22 | 4.87 | 68 |
| 8 | 20.24 | 4.38 | 62 |
| 9 | 21.64 | 4.10 | 75 |
| 10 | 25.52 | 3.49 | 74 |

Test Example 1 Cell-Free Axl Kinase Inhibitory Activity

A kinase dilution solution containing 170 ng/ml AXL (the 464th to 885th amino acids of the intracellular domain of human AXL expressed as a fusion protein with glutathione transferase in a baculovirus expression system and purified by glutathione Sepharose chromatography; Carna Biosciences, Inc., catalog No. 08-107) was prepared using a kinase reaction buffer solution (100 mM HEPES (pH 7.4), 0.003% Brij-35, 0.004% Tween-20, 1 mM DTT, and 10 mM MgCl$_2$) and added at 19 µl/well to a 384-well plate.

Next, each test compound was diluted with DMSO, and this dilution solution was added at 1 µl/well to the plate.

After preincubation at room temperature for 30 minutes, a solution containing a substrate peptide (FL-Peptide 30 (5FAM-KKKKEEIYFFF-CONH$_2$), Caliper Life Sciences, catalog No. 760430) and ATP at 1.5 µM and 10 µM, respectively, was prepared and added at 5 µl/well to the plate to start kinase reaction. The plate was incubated at 28° C. for 1.5 hours, and the reaction was terminated by the addition of a termination buffer solution (100 mM HEPES (pH 7.4), 0.015% Brij-35, 40 mM EDTA, and 0.1% Coating Reagent 3) at 40 µl/well.

The substrate peptide and the phosphorylated peptide in the reaction mixture were separated and quantified using EZ Reader II (Caliper Life Sciences).

The kinase reaction was evaluated on the basis of a product ratio (P/(P+S)) calculated from the peak height (S) of the substrate peptide and the peak height (P) of the phosphorylated peptide.

The rate of inhibition (Inhibition) was determined according to the following expression (automatically calculated using the software of the EZ Reader II system).

Inhibition (%)=100×(1−$C_i$/$C_0$)

wherein $C_i$ represents the product ratio when the test compound was added, and $C_0$ represents the product ratio when DMSO was added instead of the test compound.

$IC_{50}$ was determined from the data on the rates of inhibition at 12 test compound concentrations by nonlinear regression (4-parameter logistic regression) according to the following expression:

Inhibition (%)=Bottom+(Top−Bottom)/(1+([Compound]/$IC_{50}$)$^{slope}$)

Test Example 2 Cell-Free Mer Kinase Inhibitory Activity

A kinase dilution solution containing 20 ng/ml Mer (the 528th to 999th amino acids of the intracellular domain of human MER expressed as a fusion protein with glutathione transferase in a baculovirus expression system and purified by glutathione Sepharose chromatography and ion-exchange chromatography; Carna Biosciences, Inc., catalog No. 08-108) was prepared using a kinase reaction buffer solution (100 mM HEPES (pH 7.4), 0.003% Brij-35, 0.004% Tween-20, 1 mM DTT, and 10 mM MgCl$_2$) and added at 19 µl/well to a 384-well plate.

Next, each test compound was diluted with DMSO, and this dilution solution was added at 1 µl/well to the plate.

After preincubation at room temperature for 20 minutes, a solution containing a substrate peptide (FL-Peptide 27 (5FAM-EFPIYDFLPAKKK-CONH$_2$), Caliper Life Sciences, catalog No. 760424) and ATP at 5 mM was prepared and added at 5 µl/well to the plate to start kinase reaction. The plate was incubated at 28° C. for 45 minutes, and the reaction was terminated by the addition of a termination buffer solution (100 mM HEPES (pH 7.4), 0.015% Brij-35, 40 mM EDTA, and 0.1% Coating Reagent 3) at 40 µl/well.

The substrate peptide and the phosphorylated peptide in the reaction mixture were separated and quantified using EZ Reader II (Caliper Life Sciences).

The kinase reaction was evaluated on the basis of a product ratio (P/(P+S)) calculated from the peak height (S) of the substrate peptide and the peak height (P) of the phosphorylated peptide.

The rate of inhibition (Inhibition) was determined according to the following expression (automatically calculated using the software of the EZ Reader II system).

Inhibition (%)=100×(1−$C_i$/$C_0$)

wherein $C_i$ represents the product ratio when the test compound was added, and $C_0$ represents the product ratio when DMSO was added instead of the test compound.

$IC_{50}$ was determined from the data on the rates of inhibition at 12 test compound concentrations by nonlinear regression (4-parameter logistic regression) according to the following expression:

Inhibition (%)=Bottom+(Top−Bottom)/(1+([Compound]/$IC_{50}$)$^{slope}$)

Table 44 shows Axl kinase inhibitory activity as $IC_{50}$ (nM) and Mer kinase inhibition $IC_{50}$ (nM) under conditions involving an ATP concentration of 1 mM, and further, Axl kinase selectivity (fold) relative to Mer kinase.

TABLE 44

| Example No. | Axl kinase $IC_{50}$ (nM) | Mer kinase $IC_{50}$ (nM) | Axl kinase selectivity (fold) |
|---|---|---|---|
| WO2013/115280 Example No. 9 (Compound A) | 2.3 | 5.1 | 2.2 |
| Example 1 | 1.0 | 101 | 101 |
| Example 2 | 0.9 | 102 | 113 |
| Example 3 | 0.9 | 551 | 612 |
| Example 4 | 3.3 | 649 | 197 |
| Example 5 | 0.7 | 21 | 30 |
| Example 6 | 3.6 | 271 | 75 |
| Example 7 | 11 | >4000 | >364 |
| Example 8 | 1.8 | 219 | 122 |
| Example 9 | 1.5 | 186 | 124 |
| Example 10 | 3.0 | 406 | 135 |
| Example 11 | 1.1 | 199 | 181 |
| Example 12 | 4.3 | 331 | 77 |
| Example 13 | 3.0 | 1176 | 392 |
| Example 14 | 0.8 | 104 | 130 |
| Example 15 | 2.8 | 189 | 68 |
| Example 16 | 1.5 | 712 | 475 |
| Example 17 | 1.2 | 526 | 438 |
| Example 18 | 1.2 | 130 | 108 |
| Example 19 | 1.5 | 59 | 39 |
| Example 20 | 3.5 | 594 | 170 |
| Example 21 | 1.9 | 128 | 67 |
| Example 22 | 1.2 | 41 | 34 |
| Example 23 | 2.3 | 133 | 58 |
| Example 24 | 3.1 | 190 | 61 |
| Example 25 | 1.3 | 39 | 30 |
| Example 26 | 2.7 | 361 | 134 |
| Example 27 | 2.0 | 140 | 70 |
| Example 28 | 1.9 | 202 | 106 |
| Example 29 | 0.7 | 78 | 111 |
| Example 30 | 0.8 | 180 | 225 |
| Example 31 | 0.9 | 36 | 40 |
| Example 32 | 0.6 | 39 | 65 |
| Example 33 | 0.7 | 144 | 206 |
| Example 34 | 0.4 | 53 | 133 |
| Example 35 | 0.5 | 196 | 392 |
| Example 36 | 1.0 | 127 | 127 |
| Example 37 | 2.3 | 126 | 55 |
| Example 38 | 4.9 | 230 | 47 |
| Example 39 | 2.4 | 136 | 57 |
| Example 40 | 7.3 | 1066 | 146 |
| Example 41 | 0.7 | 101 | 144 |
| Example 42 | 1.3 | 188 | 145 |
| Example 43 | 3.0 | 112 | 37 |
| Example 44 | 5.1 | 208 | 41 |

TABLE 44-continued

| Example No. | Axl kinase IC$_{50}$ (nM) | Mer kinase IC$_{50}$ (nM) | Axl kinase selectivity (fold) |
|---|---|---|---|
| Example 45 | 1.2 | 89 | 74 |
| Example 46 | 1.4 | 304 | 217 |
| Example 47 | 1.0 | 232 | 232 |
| Example 48 | 2.2 | 90 | 41 |
| Example 49 | 2.9 | 99 | 34 |
| Example 50 | 8.3 | 582 | 70 |
| Example 51 | 22 | 3066 | 139 |
| Example 52 | 27 | 1770 | 66 |
| Example 53 | 0.5 | 74 | 148 |
| Example 54 | 13 | 1392 | 107 |
| Example 55 | 7.2 | 728 | 101 |
| Example 56 | 7.0 | 649 | 93 |
| Example 57 | 1.4 | 163 | 116 |
| Example 58 | 0.6 | 46 | 77 |
| Example 59 | 7.3 | 446 | 61 |
| Example 60 | 1.7 | 171 | 101 |
| Example 61 | 4.7 | 113 | 24 |
| Example 62 | 4.3 | 130 | 30 |
| Example 63 | 0.7 | 48 | 69 |
| Example 64 | 4.8 | 216 | 45 |
| Example 65 | 2.2 | 97 | 44 |
| Example 66 | 2.0 | 458 | 230 |
| Example 67 | 2.4 | 313 | 131 |
| Example 68 | 0.6 | 38 | 63 |
| Example 69 | 7.7 | 2801 | 364 |
| Example 70 | 1.6 | 132 | 83 |
| Example 71 | 0.6 | 64 | 107 |
| Example 72 | 6.3 | 249 | 40 |
| Example 73 | 21 | 580 | 28 |
| Example 74 | 3.1 | 242 | 78 |
| Example 75 | 15 | 522 | 35 |
| Example 76 | 0.6 | 44 | 73 |
| Example 77 | 3.0 | 160 | 53 |
| Example 78 | 1.0 | 125 | 125 |
| Example 79 | 1.8 | 220 | 122 |
| Example 80 | 1.0 | 108 | 108 |
| Example 81 | 2.4 | 171 | 71 |
| Example 82 | 2.8 | 192 | 69 |
| Example 83 | 2.9 | 225 | 78 |
| Example 84 | 0.3 | 39 | 130 |
| Example 85 | 0.4 | 51 | 128 |
| Example 86 | 0.4 | 68 | 170 |
| Example 87 | 0.7 | 29 | 41 |
| Example 88 | 1.8 | 889 | 494 |
| Example 89 | 0.8 | >4000 | >5000 |
| Example 90 | 0.6 | 107 | 178 |
| Example 91 | 1.8 | 829 | 461 |
| Example 92 | 4.4 | 1278 | 290 |
| Example 93 | 2.4 | 164 | 68 |
| Example 94 | 6.2 | >4000 | >645 |
| Example 95 | 1.2 | 429 | 358 |
| Example 96 | 2.7 | >4000 | >1481 |
| Example 97 | 2.7 | 1644 | 609 |
| Example 98 | 0.5 | 101 | 202 |
| Example 99 | 14 | 3249 | 232 |
| Example 100 | 0.3 | 1569 | 5230 |
| Example 101 | 0.7 | 1065 | 1521 |
| Example 102 | 2.7 | >4000 | >1481 |
| Example 103 | 1.0 | >4000 | >4000 |
| Example 104 | 0.5 | 129 | 257 |
| Example 105 | 1.2 | >4000 | >3333 |
| Example 106 | 0.5 | >4000 | >8000 |
| Example 107 | 1.2 | 1659 | 1383 |
| Example 108 | 4.2 | >4000 | >952 |
| Example 109 | 1.3 | >4000 | >3077 |
| Example 110 | 0.2 | >4000 | >20000 |
| Example 111 | 0.1 | 198 | 1980 |
| Example 112 | 7.1 | >4000 | >563 |
| Example 113 | 1.3 | 1083 | 833 |
| Example 114 | 1.7 | 121 | 71 |
| Example 115 | 0.9 | 133 | 148 |
| Example 116 | 2.5 | 726 | 290 |
| Example 117 | 16 | 3277 | 205 |
| Example 118 | 3.2 | 91 | 28 |
| Example 119 | 1.9 | 289 | 152 |
| Example 120 | 37 | 1384 | 37 |
| Example 121 | 0.8 | 93 | 116 |
| Example 122 | 16 | 1755 | 110 |
| Example 123 | 5.7 | 489 | 86 |

Test Example 3 Intracellular Axl Phosphorylation Inhibitory Activity

A phosphorylated Axl (hereinafter, referred to as pAxl) inhibition test was conducted using a human non-small cell lung cancer-derived cell line NCI-H1299.

The NCI-H1299 cells were suspended in a medium (RPMI1640 medium containing 10% fetal bovine serum), then inoculated at 15000 cells/100 μl/well to each 96-well multiwall plate, and cultured at 37° C. for 1 day in the presence of 5% $CO_2$. On the next day, the medium was discarded, and a medium was added at 100 μl/well to the plate, followed by culture at 37° C. for 1 day in the presence of 5% $CO_2$. Each test compound was dissolved in DMSO and diluted with an FBS-free medium to prepare a sample solution (DMSO concentration: 2%). A medium or a medium supplemented with the sample was added at 25 μl/well (DMSO concentration: 0.4%) to the plate and incubated at 37° C. for 1 hour in the presence of 5% $CO_2$.

GAS6 (R&D Systems Inc., model: 885-GS) was diluted into 6 μg/ml with an FBS-free medium, then added at 25 μl/well to the plate, and incubated at 37° C. for 10 minutes in the presence of 5% $CO_2$ after stirring.

The supernatant was discarded, and a solution of a 37% formalin solution diluted to 4% with phosphate-buffered saline (PBS) (hereinafter, a 4% formalin solution) was added at 0.1 ml/well to the plate, which was then left standing at room temperature for 10 minutes. Next, the 4% formalin solution was discarded, and a solution of Triton X-100 diluted to 0.1% with PBS (hereinafter, referred to as a wash buffer) was added at 0.2 ml/well to the plate and discarded by decantation. An excess of water was removed on paper towel.

Subsequently, 10% $NaN_3$ and 110 μl of $H_2O_2$ were added to 10.7 mL of a wash buffer (hereinafter, referred to as a quenching buffer), and this quenching buffer was added at 0.1 ml/well to the plate, which was then left standing at room temperature for 15 minutes.

The quenching buffer was discarded, and a wash buffer was added at 0.2 ml/well to the plate and discarded by decantation. An excess of water was removed on a paper towel. Skimmed milk (WAKO #198-10605) was added (final concentration 5%) to a wash buffer (hereinafter, referred to as a blocking buffer), and this blocking buffer was added at 0.25 ml/well to the plate, which was then left standing at room temperature for 1 hour.

The blocking buffer was discarded, and Anti-phospho-Axl (Y702) (D12B2) rabbit monoclonal antibody (Cell Signaling Technology, Inc., catalog No. 5724) was reacted at a concentration of 1/1000 with the plate, which was then left standing overnight at 4° C. Each well was repetitively washed with a wash buffer five times, and Peroxidase AffiniPure Donkey Anti-Rabbit IgG (H+L) (Jackson ImmunoResearch Inc., catalog No. 711-035-152) was reacted at a concentration of 1/2000 with the plate at room temperature for 1 hour. A similar washing operation was carried out, and Super Signal ELISA pico chemiluminescent substrate (Thermo Fisher Scientific, Inc., catalog No. 37069) was added at 0.05 ml/well to the plate and gently stirred, followed by incubation for 20 minutes. Then, developed light was measured using ARVO sx (PerkinElmer Inc.) to measure the pAxl (Y702) level.

The pAxl inhibitory activity was determined according to the following expression:

Inhibition %=100−(A−B)×100/(T−B)

A: Measurement value of the test compound
B: Light intensity of the reaction mixture supplemented with a positive control compound having a concentration that inhibited almost 100% phosphorylation (e.g., light intensity of the reaction mixture supplemented with 1 μM BMS-777607)
T: Light intensity of the reaction mixture unsupplemented with the compound The 50% inhibition concentration ($IC_{50}$) was determined from the data on the pAxl inhibitory activity at a plurality of concentrations using GraphPad Prism 4.

Table 45 shows intracellular Axl phosphorylation inhibitory activity as $IC_{50}$ (nM)

TABLE 45

| Example No. | pAxl IC50 (nM) |
| --- | --- |
| Compound A | 13 |
| Example 1 | 10 |
| Example 2 | 15 |
| Example 34 | 8 |
| Example 36 | 14 |
| Example 41 | 9 |
| Example 53 | 13 |
| Example 58 | 13 |
| Example 63 | 7 |
| Example 76 | 14 |
| Example 85 | 7 |
| Example 86 | 10 |
| Example 90 | 11 |
| Example 98 | 9 |
| Example 100 | 6 |
| Example 101 | 7 |
| Example 103 | 13 |
| Example 104 | 10 |
| Example 106 | 4 |
| Example 107 | 15 |
| Example 110 | 7 |
| Example 111 | 7 |
| Example 121 | 16 |

Test Example 4 Ophthalmic Histopathological Examination

1. Animal: Female NOG mice
2. Drug:
   Compound A monohydrochloride dihydrate
   Compound of Example 124
   Compound of Example 128
   Compound of Example 129
3. Preparation of dosing solution:
   Compound A, the compound of Example 124, the compound of Example 128, and the compound of Example 129 were each suspended in a 0.5% methylcellulose solution (0.5% MC, Wako Pure Chemical Industries, Ltd.).
4. Administration method:
   Four continuous doses, 1 drug holiday, 5 continuous doses, 2 drug holidays, 5 continuous doses, 2 drug holidays, 5 continuous doses, 2 drug holidays, and 4 continuous doses.

5. Pathological examination
   On the day following the termination date of the administration period, the mice were euthanized by blood letting under isoflurane anesthesia. Then, their eyeballs were collected, fixed in Davidson's solutions, then embedded in paraffin, and stained with hematoxylin eosin to prepare preparations, which were then histopathologically examined.

Mild to moderate degeneration and thinning of the outer nuclear layer and the rod and cone cell layer in the retina were found in all of the mice (n=8) in the group given 100 mg/kg Compound A monohydrochloride dihydrate.

No histological change in the retinal was found in any of the mice (n=8) in the groups 100 or 200 mg/kg compound of Example 124, Example 128, or Example 129.

Test Example 5: Antitumor Test

NIH-3T3-Axl #7 (cells prepared by the transfection of NIH3T3 cells with pLXSN retrovirus having an insert of full-length Axl cDNA) was block-transplanted into female NOG mice. When their estimated tumor volumes reached approximately 500 mm³, Compound A monohydrochloride dihydrate (25, 4.2, or 0.7 mg/kg), the compound of Example 124 (50, 12.5, 3.1, or 0.8 mg/kg), and the compound of Example 128 (50, 12.5, 3.1, or 0.8 mg/kg) were each administered through an oral route twice a day (bid) at 5 continuous doses. Compound A administered at 25 and 4.2 mg/kg exhibited a distinct tumor regression effect. The compounds of Example 124 and Example 128 administered at 3.1 mg/kg almost completely inhibited tumor growth during the administration period, and these compounds administered at 50 and 12.5 mg/kg exhibited a distinct tumor regression effect.

Test Example 6: Study on In Vivo Effect Brought about by Combined Use with Erlotinib HCC827 lung cancer cells having a deletion mutation in EGFR gene exon 19 and exhibiting high sensitivity to EGFR inhibitors were suspended at $5 \times 10^7$ cells/mL in phosphate-buffered saline. 0.1 mL of the prepared cell suspension was subcutaneously transplanted to each nude mouse (female, 5 weeks old). When the estimated tumor volumes of most of the mice reached approximately 450 mm³ (52 days after tumor transplantation), the mice were grouped according to their tumor volumes and forced to orally receive 25 mg/kg erlotinib (LC Laboratories) once a day (qd) or 50 mg/kg N-[4-(2-amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide (Compound B) sulfate hydrate twice a day (bid) (these agents were administered alone or in combination). The administration was started on the day (Day 1) following the grouping date and carried out five times a week (Saturday and Sunday were set to drug holidays). The administration was continued to Day 46 for the groups given a vehicle or Compound B sulfate hydrate alone, Day 86 for the group given erlotinib alone, and Day 106 for the group given these agents in combination. The major axis (mm) and minor axis (mm) of each tumor were measured over time using an electronic digital caliper. The estimated tumor volume was calculated according to the expression (1) given below, and plotted. Also, the body weight was measured over time using an automatic balance for small animals. The rate of change in body weight (Body weight change %) was calculated according to the expression (2) given below. In this way, the influence of drug administration on the body weight was studied, while the results of last body weight measurement were used in dose calculation.

$$\text{Estimated tumor volume (mm}^3\text{)=Mean estimated tumor volume of individuals} \quad (1)$$

$$\text{Estimated tumor volume of each individual}=An \times Bn^2/2$$

An: Major axis of the tumor at Day n
Bn: Minor axis of the tumor at Day n $$\text{Body weight change (\%)=Mean rate of change in body weights of individuals} \quad (2)$$

$$\text{Rate of change in body weight of each individual}= (1-BWn/BWs) \times 100$$

BWn: Body weight at Day n
BWs: Body weight at the initial day of administration

Erlotinib administered alone was confirmed to have a tumor regression effect immediately after administration. However, the tumor then acquired resistance and became bigger than its size at the start of administration at Day 77. By contrast, the tumor size in the group given erlotinib and Compound B sulfate hydrate in combination did not reach that at the start of administration even at Day 107 (FIG. 19-1). No significant weight loss was found in the group given erlotinib and Compound B sulfate hydrate in combination (FIG. 19-2).

Test Example 7: Study on Elevation of AXL Expression by Erlotinib Administration HCC827 lung cancer cells were suspended at $5 \times 10^7$ cells/mL in phosphate-buffered saline. 0.1 mL of the prepared cell suspension was subcutaneously transplanted to each nude mouse (female, 5 weeks old). When the estimated tumor volumes of most of the mice reached approximately 450 mm³ (52 days after tumor transplantation), the mice were grouped according to their tumor volumes (Day 0) and forced to orally receive 25 mg/kg, 12.5 mg/kg, or 6.25 mg/kg erlotinib (LC Laboratories) five days a week (Saturday and Sunday were set to drug holidays). The administration was continued to Day 46 for a vehicle administration group and Day 86 for the erlotinib administration groups. The major axis (mm) and minor axis (mm) of each tumor were measured over time using an electronic digital caliper. The estimated tumor volume was calculated according to the expression (1) given below, and plotted (FIG. 20-1). A cell lysate was prepared from the tumor masses of 2 to 6 mice in each group and examined for the expression of AXL by Western blot, and each individual band was quantified using ImageQuant LAS4000 (GE Healthcare Japan Corp.) (FIG. 20-2). The cell lysate preparation and the Western blot were carried out as follows: approximately 100 mg of the tumor masses was homogenized in Lysis Buffer (Cell Signaling Technology, Inc., 9803) containing a phosphatase inhibitor (Roche Diagnostics., 04 906 837 001) and a protease inhibitor (Roche Diagnostics, 11 836 153 001), and the supernatant was used as a lysate sample. Proteins in this sample were fixed using buffers (Life Technologies Corp, NP0008 and NP0009) and thermal denaturation and subjected to Western blot. 15 g of the sample was subjected to electrophoresis and transferred to a nitrocellulose membrane. The membrane was blocked for 1 hour and then reacted overnight with a rabbit anti-AXL antibody (Cell Signaling Technology, Inc., 9803, 1/1000) or a rabbit anti-Actin antibody (Santa Cruz Biotechnology, Inc., SC-1616, 1/2000) under refrigeration. The membrane was washed with tris-buffered saline and then reacted with an HRP-labeled anti-rabbit IgG antibody (Cell Signaling Technology, Inc., 7074, 1/2000) at room temperature for 1 hour. The membrane was washed with tris-buffered saline and then allowed to develop light with an HRP substrate (Merck Millipore Corp., WBLUF0500).

The expression of AXL was confirmed by Western blot, and each individual band was quantified using ImageQuant LAS4000. As a result, the significant elevation of the expression of AXL in the erlotinib administration groups was confirmed by the Welch test.

Test Example 8: Study on In Vivo Effect Brought about by Combined Use with Erlotinib—2

HCC827 lung cancer cells were suspended at $4 \times 10^7$ cells/mL in phosphate-buffered saline. 0.1 mL of the prepared cell suspension was subcutaneously transplanted to each nude mouse (female, 5 weeks old). 52 days after tumor cell transplantation, mice having an estimated tumor volume of 200 mm³ or larger and smaller than 700 mm³ (86 mice/129 mice) were forced to orally receive 25 mg/kg erlotinib (LC Laboratories) once a day (qd). The administration was started on the day (53 days after transplantation) following the grouping date and carried out five times a week (Saturday and Sunday were set to drug holidays). Cancer-bearing mice confirmed to have temporal regression and distinct regrowth of a tumor were grouped (6 mice/group, 115 days after transplantation) into 3 groups: group 1: erlotinib+vehicle administration group (mean estimated tumor volume: 275 mm³), group 2: erlotinib+50 mg/kg Compound B sulfate hydrate (mean estimated tumor volume: 284 mm³), and group 3: erlotinib+25 mg/kg Compound B sulfate hydrate (mean estimated tumor volume: 268 mm³). A study was made on whether the combined use with Compound B sulfate hydrate would restore the effect of erlotinib on erlotinib-resistant tumors. The Compound B sulfate hydrate was administered twice a day (bid) from 116 days after transplantation, and this administration was continued five times a week (Saturday and Sunday were set to drug holidays). The tumor grew to the estimated tumor volume at the same level as the original volume at the time of transplantation in group 1, whereas the distinct growth inhibitory effect of erlotinib was confirmed in group 2 and group 3. In group 2, the estimated tumor volume at 116 days after transplantation when the combined administration was started was maintained even at 140 days after transplantation.

The invention claimed is:
1. A compound of formula (I):

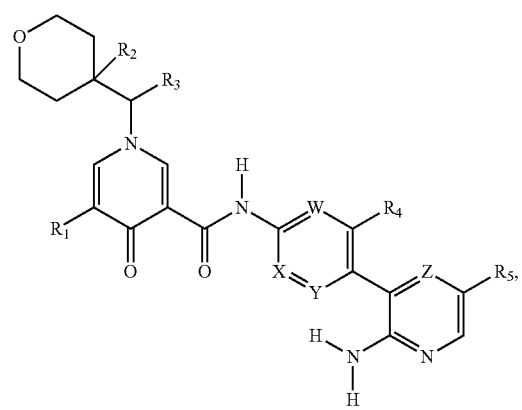

or a pharmaceutically acceptable salt thereof,
wherein
W, X, and Y are each independently C—H, C—F, or C—Cl,
Z is C—H, C—F, C—Cl, C—$C_1$-$C_6$ alkyl group, or C—$C_1$-$C_6$ alkoxy group,
$R_1$ is formula (II-1):

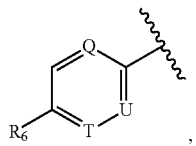

(II-1)

Q is C—H, or C—F,
T is C—H,
U is a nitrogen atom,
$R_6$ is a halogen atom, a $C_1$-$C_6$ alkyl group, a $C_3$-$C_6$ cycloalkyl group, a cyano group, or a trifluoromethoxy group,
$R_2$ is a hydrogen atom, a halogen atom, a $C_1$-$C_6$ alkyl group, a $C_1$-$C_6$ alkoxy group, or a cyano group,
$R_3$ is a hydrogen atom or a $C_1$-$C_6$ alkyl group,
$R_4$ is a hydrogen atom, a halogen atom, or a $C_1$-$C_6$ alkyl group, $R_5$ is a group of formula (III-1):

(III-1)

$R_8$ and $R_{12}$ are each independently a hydrogen atom or a deuterium atom,
$R_9$ is a hydrogen atom, a halogen atom, or a $C_1$-$C_6$ alkoxy group,
$R_{10}$ is 1,4-dioxan-2-ylmethoxy, and
$R_{11}$ is a hydrogen atom, a $C_1$-$C_6$ alkoxy group, or a deuterium-substituted $C_1$-$C_6$ alkoxy group.

2. The compound or salt of claim 1, wherein the compound is N-[4-(2-Amino-5-{4-[(2R)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide of the following formula:

or a pharmaceutically acceptable salt thereof.

3. The compound or salt of claim 1, wherein the compound is N-[4-(2-Amino-5-{4-[(2S)-1,4-dioxan-2-ylmethoxy]-3-methoxyphenyl}pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide of the following formula:

or a pharmaceutically acceptable salt thereof.

4. A methanesulfonate, phosphate, naphthalene-1,5-disulfonate, or sulfate of the compound of claim 2.

5. A pharmaceutical composition comprising the compound of claim 1 or a pharmaceutically acceptable salt thereof and a pharmaceutically acceptable carrier.

* * * * *